United States Patent
Gronenberg et al.

(10) Patent No.: US 10,696,992 B2
(45) Date of Patent: Jun. 30, 2020

(54) GENETICALLY MODIFIED BACTERIAL CELL FACTORY FOR THIAMINE PRODUCTION

(71) Applicant: BIOSYNTIA APS, Copenhagen Ø (DK)

(72) Inventors: Luisa Gronenberg, Copenhagen (DK); Bo Salomonsen, Frederiksberg (DK); Matteo Ferla, Gentofte (DK); Hans Jasper Genee, Copenhagen (DK)

(73) Assignee: BIOSYNTHIA APS, Copenhagen Ø (DK)

( * ) Notice: Subject to any disclaimer, the term of this patent is extended or adjusted under 35 U.S.C. 154(b) by 0 days.

(21) Appl. No.: 16/063,373

(22) PCT Filed: Dec. 16, 2016

(86) PCT No.: PCT/EP2016/081598
§ 371 (c)(1),
(2) Date: Jun. 18, 2018

(87) PCT Pub. No.: WO2017/103221
PCT Pub. Date: Jun. 22, 2017

(65) Prior Publication Data
US 2019/0382815 A1 Dec. 19, 2019

(30) Foreign Application Priority Data
Dec. 18, 2015 (EP) .................................... 15201200

(51) Int. Cl.
| | | |
|---|---|---|
| C12N 15/52 | (2006.01) | |
| C12P 17/16 | (2006.01) | |
| C12N 9/06 | (2006.01) | |
| C12N 9/10 | (2006.01) | |
| C12N 9/12 | (2006.01) | |
| C12N 9/16 | (2006.01) | |
| C12N 9/88 | (2006.01) | |

(52) U.S. Cl.
CPC .......... *C12P 17/165* (2013.01); *C12N 9/0022* (2013.01); *C12N 9/1085* (2013.01); *C12N 9/1229* (2013.01); *C12N 9/1241* (2013.01); *C12N 9/13* (2013.01); *C12N 9/16* (2013.01); *C12N 9/88* (2013.01); *C12Y 104/03019* (2013.01); *C12Y 205/01003* (2013.01); *C12Y 207/01089* (2013.01); *C12Y 207/04007* (2013.01); *C12Y 207/07073* (2013.01); *C12Y 208/0101* (2013.01); *C12Y 301/03* (2013.01); *C12Y 401/99017* (2013.01); *C12Y 401/99019* (2013.01)

(58) Field of Classification Search
CPC ........ C12N 15/52; C12P 17/167; C12R 1/185
See application file for complete search history.

(56) References Cited

U.S. PATENT DOCUMENTS

2012/0107888 A1* 5/2012 Schmalisch ............ C12N 15/52
435/155

FOREIGN PATENT DOCUMENTS

| EP | 0417953 A1 | 3/1991 |
|---|---|---|
| WO | 2004/106557 A2 | 12/2004 |

OTHER PUBLICATIONS

Du et al. 2011; Thiamin (Vitamin B1) biosynthesis and regulation: A rich source of anti-microbial drug targets? Int. J. Biol. 7: 41-52.*
Leonardi et al. 2004; Thiamine biosynthesis in *Escherichia coli*. J. Biol. Chem. 279(17): 17054-17062.*
Baba, et al., "Construction of *Escherichia coli* K-12 in-frame, single-gene knockout mutants: the Keio collection." Mol Syst Biol. 2(1) (2006).
Burroughs et al., "Evolutionary Genomics of the HAD Superfamily: Understanding the Structural Adaptations and Catalytic Diversity in a Superfamily of Phosphoesterases and Allied Enzymes." J. Mol. Biol. 361(5), 1003-1034 (2006).
Datsenko et al., One-step inactivation of chromosomal genes in *Escherichia coli* K-12 using PCR products. Proc Natl Acad Sci USA. 97(12):6640-5 (2000).
Gibson et al., "Enzymatic assembly of DNA molecules up to several hundred kilobases." Nat Methods. 6(5):343-5 (2009).
Guzman et al., "Tight Regulation, Modulation, and High-Level Expression by Vectors Containing the Arabinose P BAD Promoter." Journal of bacteriology, 177(14):4121-4130 (1995).
Hsanain et al., "Bacterial and plant HAFD enzymes catalyze a missing phosphatase step in thiamine diphosphatase biosynthesis." Biochemical Journal, 473(2): 157-166 (2016).
Komeda et al., "A th-1 Mutant of *Arabidopsis thaliana* is Defective for a Thiamin-Phosphate-Synthesizing Enzyme: Thiamin Phosphate Pyrophosphorylase." Plant Physiol. 88(2):248-50 (1988).
Lennen et al., "Transient overexpression of DNA adenine methylase enables efficient and mobile genome engineering with reduced off-target effects." Nucleic acids research. 44(4): 1-14 (2015).
Melnick et al., "Identification of the two missing bacterial genes involved in thiamine salvage: thiamine pyrophosphokinase and thiamine kinase." J Bacteriol.: 186(11): 3660-2 (2004).
Norrander et al., "Construction of improved M13 vectors using oligodeoxynucleotide-directed mutagenesis." Gene: 26(1): 101-106 (1983).

(Continued)

*Primary Examiner* — Karen Cochrane Carlson
(74) *Attorney, Agent, or Firm* — Nixon Peabody LLP

(57) ABSTRACT

The invention provides a genetically modified bacterium for production of thiamine; where the bacterium is characterized by a transgene encoding a thiamine monophosphate phosphatase (TMP phosphatase having EC 3.1.3.-) as well as transgenes encoding polypeptides that catalyze steps in the thiamine pathway. The genetically modified bacterium is characterized by enhanced synthesis and release of thiamine into the extracellular environment. The invention further provides a method for producing thiamine using the genetically modified bacterium of the invention; as well as the use of the genetically modified bacterium for extracellular thiamine production.

16 Claims, 11 Drawing Sheets

Specification includes a Sequence Listing.

(56) References Cited

OTHER PUBLICATIONS

Paglia et al., Development of a Metabolomic Assay for the Analysis of Polar Metabolites Using HILIC UPLC/QTof MS, Waters Application Note: Library No. APNT134726984 (2013) http://www.waters.com/waters/library.htm?lid=134726984&locale=en_DK.

Schyns et al., "Isolation and Characterization of New Thiamine-Deregulated Mutants of Bacillus subtilis." J Bacteriol.; 187(23):8127-8136 (2005).

Webb et al., "Characterization of thiL, Encoding Thiamin-monophosphate Kinase, in *Salmonella typhimurium*." J Biol Chem.; 272(25): 15702-15707 (1997).

Begley et al., "Thiamin biosynthesis in prokaryotes", Arch Microbiol 171(5) 293-300 (1999).

Goyer et al., "A cross-kingdom Nudix enzyme that pre-empts damage in thiamin metabolism", Biochem J 454(3) 533-542 (2013).

Rapala-Kozik et al., "Enzymes that control the thiamine diphosphate pool in plant tissues. Properties of thiamine pyrophosphokinase and thiamine-(di)phosphate phosphatase purified from *Zea mays* seedlings", Plant Physiol Biochem 47(4) 237-242 (2009).

Rapala-Kozik et al., "Modulation of thiamine metabolism in *Zea mays* seedlings under conditions of abiotic stress", J Ex Bot 59(15) 4133-4143 (2008).

Sanemori et al., "Pathway of thiamine pyrophosphate synthesis in Micrococcus denitrificans", J Bacteriol 126(3) 1030-1036 (1976).

Kawasaki et al., "Specific thiamine monophosphate phosphohydrolase in Micrococcus denitrificans", J Bacteriol 130(1) 542-544 (1977).

Pourcel et al., "Examining strategies to facilitate vitamin B1 biofortification of plants by genetic engineering", Front Plant Sci 4: 160 (2013).

Siddavattam et al., "Genome of a novel isolate of Paracoccus denitrificans capable of degrading N,N-dimethylformamide", J Bacteriol 193(19) 5598-5599 (2011).

\* cited by examiner

Clade 1

Clade 3

Figure 5

1. A. thaliana
2. B. napus
3. C. sinensis
4. G. max
5. J. curcas
6. N. tomentosiformis
7. O. sativa
8. P. bretschneideri
9. P. persica
10. P. trichocarpa
11. Z. mays

```
            1         10        20        30        40        50
            |         |         |         |         |         |
1              MRFLFPTRLINNSSLGLLRSPHTTAPIRSLWFRTKSPVFRSATTP----IMTAVA
2                 MRILNNSLALLRSPRAAAPIRSLLFGSKKSSVSRS--------AAAFSS
3            MRFLFTNPIKTPLLSSILFHCPNSPRLGLLDSVRVNSPSSLTT------QRSSLS
4                     MRMRWFLRSPIIKTSLLNLSPPISFRPHWARRTFTSSRLS
5                                             MAIPPKLASSSSSM
6            MRFSLLSPLVLNPVIRFSNSNALFGLRFQLYPRYSRYLRSPVTMA----SAKPKP
7                 MRGLLRRVYLRLPPFPPATSLYYWSRTRPAAAGP=---NHPIPRR
8                     MRILFPPNPIKTPTLFNSLRLRFNSLRSHC--ANSMAVPP
9                                                         MA
10         MRLLLFTSPNPIKTSSSLYFLNSLRSNLTKRTLPTRRSFIPARMAIPPRSIASAPSC
11             MLVLRRLRLRLPLPRPLLVSSFSSTSPSSSPSTSSSSSCWSSTG--ESRRAMAS 60        70        80        90        100       110
            |         |         |         |         |         |
1          FSSSLSIPPTSE-EALPGKLWI-KFNRECLFSIYSPFAVCLAAGNLKIDT-FRQYIA
2          AMSIPPPSISTSEEALAGRLWI-KFNRECLFSMYSPFAVSLAAGNLKIET-FRQYIA
3          MAAIPPKSPSPEEEGLARRLWI-KFKRESVFAMYSPFTVCLASGNLKLET-FRHYIA
4          MAAIHNHSNSNSETGLARRFWI-KFTRESIFAMYTPFAIALASGNLHIDS-FHHYIA
5          AASPTSAGGTNE-EGLASKFWI-KFRRESVLAMYTPFVVSFAAGNLKIES-FRHYIA
6          AAAVNKFPVEEECVGIARKCWI-KFKRESTFALYTPFVVSLASGTLNLDT-FRHYIA
7          MSTSSTAAAVVAEGSAARRFWIAAASREAAFAAYTPFLVSLAAGALRLDS-FRQYIA
8          PKSAMASAVVGNEVGLARRFWI-KFKRESIFAMYTPFTLCLAAGNLKIET-FRDYIA
9          ALARHSIVRLNHEGGLARRLWF-KFRDDSVFSLYTPFFVGLASATLHSETTFRHFIS
10         TTTSGRSNININIE-EGLASKFWI-KFRRESVFAMYTPFVISLASGTLKIDS-FRHYIS
11         SPSPDSAAVVAE=GSAARRFWIAASTREAAFAAYTPFLLSLAAGNLRLNV-FRHYIA 120       130       140       150       160       170
            |         |         |         |         |         |
1          QDVHFLKAFAHAYELAADCADDDDDKLAISDLRKSVMEELKMHDSFVQDWDLD-INK
2          QDVHFLKAFAHAYELAAECADDDDDKLAISDLRKSVMDELKMHNSFVQDWDLD-ISK
3          QDFHFLKAFAQAYELAEECADDDDAKLSISELRKGVLEELKMHDSFVKEWGTD-LAK
4          QDVHFLRAFAQAYELAEECADDDDAKLGICELRKAVLEELKMHNLLVQERELD-LAK
5          QDFHFLKAFAHAYELAEECADDDDAKLAIAALRKGVLEELKLHKSFVQEWGMD-PSK
6          QDVHFLKSFAQAYEAAEECTDDDDAKVGISELRKNVIEELKMHDAVLKEWGID-LVK
7          QDAYFLHAFARAYEMAEECADDDDDKATIVVLRKAILRELNLHASVLQEWGVD-PNK
8          QDVHFLKAFAHAYELAEDCADDDDAKPVISELRRAVLQELKMHDSFVKEWGLQG-AK
9          QDLHFLKAFVLAYELAEDCADDEDDKNGLRDLRKRAVGRLQMHDTFVREWGFEFPNE
10         QDSHFLKSFAHAFELAEECADDDEAKLAISELRKGVLEELKMHNSFVQEWGID-PGK
11         QDAHFLHAFARAYEMAEDCADDDDDMATIAALRKAILQELNLHSSVLKEWGVD-PTK
```

Figure 5 continued

```
          180        190        200        210        220
1   EVSVNSATLRYTNFLLATASGKVEGCKAP-GNLDTPFEKTKVAAYTLGAVTPCMRLY
2   EVSVNSATLRYTNFLLATSSGKVEGLKAP-GNLDTPFEKTKVAAYTLGAVTPCMRLY
3   NATVNSATVKYTNFLLATASGKVEGVKGP-GKLATPFEKTKVAAYTLGANSPCMRLY
4   ENGINSATVKYTNFLLATASGKIEGLKGP-GKLATPFEKTKIAAYTLGAMTPCMRLY
5   EVTINSATAKYTDFLLATASGKVEGVKGP-GKLATPFERTKVAAYTLGTMTPCNRLY
6   ESSLNPATAKYTDFLSATASGKVEGVKAA--KLATPFENTKLAAYTLGAMTPCMRLY
7   EIPPIPATTKYTDFLLATSTGKVDGGKGS-DKNVTPFRKTKIAAYTVGAMTPCMRLY
8   ETPINSAAVKYTDFLLATASGKVEGVKGP-GKLATPFENTKVAAYTLGAMTPCMRLY
9   DINKDIATTKYTDFLLATASGKIEGENSVLDKIATPFEKTKVAAYTLAALAPCMRLY
10  EGTINSATVKYTDFLLATASGKVEGVKGL-GKLATPFENTKVAAYTLGAMTPCMRLY
11  EIPPSAATTKYTDFLLATAAGKVDGTKGS-DKNVTPFRKTKIAAYTVGAMTPCMRLY 230        240        250        260        270        280
1   APLGKEFGSLLDLS-DVNHPYKKWIDNYSSDAFQASAKQTEDLLNKLSVSNTGENLD
2   APLGKEFGALLDSS-NANHPYKKWINHYSDAFQASAKQTEDLLNKLSVCNTGENLD
3   APLGKEFNGLLNAN-NGNHPYKKWIDNYSSNSFQASALQNEDLLDKLSVSLTGENLD
4   AVNGKEFQELLDSN-NSTHPYNKWINHYSSDGFQATTLQTEDLLDKLSVSLTGENLD
5   APLAKELQALIDAN-AGIHPYQKWIDNYSSNSFQASALQTEDLLDKLSVPLTGENLD
6   AYIGKELQVFLNGN--KIHPYKKWIDSYASNSFQASALQTEDLLDKLSVPLTGENLD
7   AYLGKELAVFLKQD--NNHPYKKWINTYASSDFNNNALQINNLLDKLSVSLTGENLN
8   APLGKEFKALLDPS-NGSHPYLKWIDSYSSNSFQASAVQIENLLDKLSVSLTGENLD
9   AFINTNIQGIINPDQDSTHIYKNWINNYSSQVFNNIALQNEDNLDKLSVSLTGENLN
10  SPLGKELQAVLDPN-NDGHPYKKWIDNYSSNSFQASALQTEDLLDKLSVSLTGENLD
11  AYLGKELKVFLKQD--NNHPYKKWINTYASSDFNDTTLQIENLLDKLSVSLTGENLN 290        300        310        320        330        340
1   IINKLYQQAMKLEVEFFNAQPL-AQPTIVPLLKNHN---NDDLVIFSDFDLTCTVVDS
2   IINKLYQQAMKLEVEFFSAQPF-AQPTIVPLLKNHS---NDNLNIFSDFDLTCTVVDS
3   IINKLYNQAMKLEVEFFCAQPL-AQPTVVPLIKGHNPAGDNLIIFSDFDLTCTIVDS
4   VINKLYYQAMKLEIEFPSAQPL-FQPTIVPLTKGHNPVNDNLIIPSDFDLTCTVVDS
5   IINKLYNQAMKLEIEFFNAQPL-DQPTVVPLTKNHNPLDDNLVIFSDFDLTCTVVDS
6   IINKLYNQAMKLEIDFFLTQPL-VQKAVIPLNKDHNPANNRLTIFSDFDLTCTVVDS
7   IINKLYQQAMNLEVEFFSAQPY-DQPVVAPLSNYCGP-KDNLLIFCDFDLTCTVVDS
8   IINKLYNQAMKLEIEFPSAQSL-VQPTVVPLINNHNPANDNLNIFSDFDLTCTVVDS
9   IINKLYNQAMKLQVDFIAAQPY SDQQNVVPLSNVHDFSKNNLTILCDFDLACTAFDS
10  IINKLYNQAMKLEIEFFIAQPI-AQTTLAPLTKGHNPNNDNLVIFSDFDLTCTVVDS
11  IINKLYQQAMKLEVEFFSSQLI-DQPVVAPLSNYCDP-KYNLLIFSDFDLTCTIVDS 350        360        370        380        390
1   SAILAEIAIVTAPKDNQSNSGQ-QINRMLSNDLNNTWNLLSKQYTENYNNCINSILN
2   SAILAEIAIVTAPKDDQGQ----QINRMLSADLNNTWSLLSKQYTENYNNCINSILN
3   SAILAEIAIVTAPKSDQNQPNN-QLGRMSSGNLRNTWGLLSKQYTENYNQCINSFNP
4   SAILAEIAIVTAPKSDQNQPND-QIVRMLSSDLRNTWGFLSKQYTENYNQCINSINP
5   SAILAEIAILTASKSDQSQNDN-QNARMSSYNLRNTWVLLSGQYTENYNQCINSILP
6   SAILAEIAIITAPRNSDQNNPNN-QIARMLSADLRNTWGDLSKQYTENYNQCINNNLL
7   SAILAEIAILSNQRASQGGADS-SLDNTKSADLRNSWNNLSNQYMENYNQCIASLLP
8   SAILAEIAIVTAPKSDQNQPNN-QIARMSSADLRNTWGLLSNQYTENYNQCINSIVP
9   AAILAEIAIITAPKADNDGSDQTQIARMPSADLRNTWDVLSTQYTNQFNQCVNSIVA
10  SAILAEIAILTAPKSDVVQPNT-QIARMSSADLRNTWGLLSGQYTENYNQCINSINP
11  SAILAEIAILSFOKANQSGIDN-NLDRAKSGDLRNSWNNLSKQYNENYNCCNNRLLP
```

Figure 5 continued

[Sequence alignment figure - sequences 1-11 aligned across positions ~400-680]

SEQUENCE LISTING

<160> NUMBER OF SEQ ID NOS: 157

<210> SEQ ID NO 1
<211> LENGTH: 1854
<212> TYPE: DNA
<213> ORGANISM: Arabidopsis thaliana
<220> FEATURE:
<221> NAME/KEY: CDS
<222> LOCATION: (1)..(1851)
<223> OTHER INFORMATION: Arabidopsis thaliana gene encoding TMP
      phosphatase [AT5G32470.1]

<400> SEQUENCE: 1

```
atg cgc ttc ctc ttc ccc acg cgc ctc atc aac aac tca tct ctc ggt      48
Met Arg Phe Leu Phe Pro Thr Arg Leu Ile Asn Asn Ser Ser Leu Gly
1               5                   10                  15 ctc ctc cga tct cca cac acc acc gcg ccg atc cgt tct ctc tgg ttt      96
Leu Leu Arg Ser Pro His Thr Thr Ala Pro Ile Arg Ser Leu Trp Phe
            20                  25                  30 cgc acc aag tct ccg gtc ttc cga tcg gcg act act cca ata atg acg     144
Arg Thr Lys Ser Pro Val Phe Arg Ser Ala Thr Thr Pro Ile Met Thr
        35                  40                  45 gcg gtc gct ttc tct tca tcg ttg tcg att ccc cct acc tcg gaa gaa     192
Ala Val Ala Phe Ser Ser Ser Leu Ser Ile Pro Pro Thr Ser Glu Glu
    50                  55                  60 gca ctt cca ggg aag cta tgg atc aag ttt aac aga gag tgt ctc ttc     240
Ala Leu Pro Gly Lys Leu Trp Ile Lys Phe Asn Arg Glu Cys Leu Phe
65                  70                  75                  80 tct atc tat agc ccc ttc gcc gtc tgt tta gcc gcc gga aat ctc aag     288
Ser Ile Tyr Ser Pro Phe Ala Val Cys Leu Ala Ala Gly Asn Leu Lys
                85                  90                  95 atc gac aca ttt cgt cag tat att gca cag gat gtt cat ttc ctt aag     336
Ile Asp Thr Phe Arg Gln Tyr Ile Ala Gln Asp Val His Phe Leu Lys
            100                 105                 110 gcc ttt gct cac gcg tat gaa ctg gcc gca gat tgt gct gat gac gat     384
Ala Phe Ala His Ala Tyr Glu Leu Ala Ala Asp Cys Ala Asp Asp Asp
        115                 120                 125 gat gat aaa ttg gca att tct gat ttg agg aaa agc gtg atg gaa gaa     432
Asp Asp Lys Leu Ala Ile Ser Asp Leu Arg Lys Ser Val Met Glu Glu
    130                 135                 140 ttg aaa atg cac gac tca ttt gta cag gat tgg gat tta gac atc aac     480
Leu Lys Met His Asp Ser Phe Val Gln Asp Trp Asp Leu Asp Ile Asn
145                 150                 155                 160 aaa gaa gta agt gtt aac tca gca act ttg aga tac act gag ttc ttg     528
Lys Glu Val Ser Val Asn Ser Ala Thr Leu Arg Tyr Thr Glu Phe Leu
                165                 170                 175 tta gct aca gca tcc gga aaa gta gaa gga tgc aaa gct ccc ggc atg     576
Leu Ala Thr Ala Ser Gly Lys Val Glu Gly Cys Lys Ala Pro Gly Met
            180                 185                 190 ctt gat act cca ttt gaa aaa aca aaa gtt gct gcc tac acg ctt ggt     624
Leu Asp Thr Pro Phe Glu Lys Thr Lys Val Ala Ala Tyr Thr Leu Gly
        195                 200                 205 gct gtg aca cct tgc atg cgg ttg tat gcc ttt ctc ggt aag gag ttt     672
Ala Val Thr Pro Cys Met Arg Leu Tyr Ala Phe Leu Gly Lys Glu Phe
    210                 215                 220 gga tca ctt ctt gat ctg agt gat gtg aac cat ccc tac aag aaa tgg     720
Gly Ser Leu Leu Asp Leu Ser Asp Val Asn His Pro Tyr Lys Lys Trp
```

|  |  |  |  |  |  |  |  |  |  |  |  |  |  |  |  |
|---|---|---|---|---|---|---|---|---|---|---|---|---|---|---|---|
| 225 |  |  |  |  | 230 |  |  |  |  | 235 |  |  |  |  | 240 |

```
atc gat aat tat tct agt gat gct ttc cag gca tca gcc aag caa act      768
Ile Asp Asn Tyr Ser Ser Asp Ala Phe Gln Ala Ser Ala Lys Gln Thr
                245                 250                 255 gaa gac ttg ctt gag aag ctt agt gtc tct atg act ggt gaa gaa ttg      816
Glu Asp Leu Leu Glu Lys Leu Ser Val Ser Met Thr Gly Glu Glu Leu
            260                 265                 270 gac ata att gaa aaa ttg tat caa cag gct atg aaa ctt gaa gta gag      864
Asp Ile Ile Glu Lys Leu Tyr Gln Gln Ala Met Lys Leu Glu Val Glu
        275                 280                 285 ttc ttc cat gcc cag cca ctt gcc cag cct acc ata gtt cca ctg ctc      912
Phe Phe His Ala Gln Pro Leu Ala Gln Pro Thr Ile Val Pro Leu Leu
    290                 295                 300 aag aac cac tca aaa gat gat ctg gtg atc ttt tct gat ttt gat ctg      960
Lys Asn His Ser Lys Asp Asp Leu Val Ile Phe Ser Asp Phe Asp Leu
305                 310                 315                 320 act tgc acc gtt gtg gat tct tct gct att tta gcg gaa ata gca att     1008
Thr Cys Thr Val Val Asp Ser Ser Ala Ile Leu Ala Glu Ile Ala Ile
                325                 330                 335 gta act gcc cca aaa gat gaa caa agt cga tct gga caa caa att cat     1056
Val Thr Ala Pro Lys Asp Glu Gln Ser Arg Ser Gly Gln Gln Ile His
            340                 345                 350 cgg atg ctc tca tct gac ctt aag aac acc tgg aat cta ctt tct aaa     1104
Arg Met Leu Ser Ser Asp Leu Lys Asn Thr Trp Asn Leu Leu Ser Lys
        355                 360                 365 caa tac aca gag cat tat gaa gaa tgc ata gag agt att ctg aat aaa     1152
Gln Tyr Thr Glu His Tyr Glu Glu Cys Ile Glu Ser Ile Leu Asn Lys
    370                 375                 380 aag aaa gcg gac aag ttt gac tat gaa ggt tta tgt aaa gca cta gag     1200
Lys Lys Ala Asp Lys Phe Asp Tyr Glu Gly Leu Cys Lys Ala Leu Glu
385                 390                 395                 400 cag ctt tca gat ttt gag aaa gag gca aat aat cga gtg att gag tct     1248
Gln Leu Ser Asp Phe Glu Lys Glu Ala Asn Asn Arg Val Ile Glu Ser
                405                 410                 415 ggt gta ctc aaa ggc ctg aat ctt gaa gac att aag cgc gct ggg gaa     1296
Gly Val Leu Lys Gly Leu Asn Leu Glu Asp Ile Lys Arg Ala Gly Glu
            420                 425                 430 agg tta atc ctt caa gat gga tgc atc aat gtc ttc cag aaa att tta     1344
Arg Leu Ile Leu Gln Asp Gly Cys Ile Asn Val Phe Gln Lys Ile Leu
        435                 440                 445 aag act gag aat ctg aat gca gaa ctt cat gtg ctt tcc tat tgt tgg     1392
Lys Thr Glu Asn Leu Asn Ala Glu Leu His Val Leu Ser Tyr Cys Trp
    450                 455                 460 tgt ggt gac ctc atc agg gca gcc ttt tct gca ggc gga gta gat gca     1440
Cys Gly Asp Leu Ile Arg Ala Ala Phe Ser Ala Gly Gly Val Asp Ala
465                 470                 475                 480 gtg gaa gta cat gca aat gaa ttc aca ttt gag gaa tcc atc tcg act     1488
Val Glu Val His Ala Asn Glu Phe Thr Phe Glu Glu Ser Ile Ser Thr
                485                 490                 495 ggt gag atc gaa aga aag gtg gaa tcc cca att aac aaa gct caa cag     1536
Gly Glu Ile Glu Arg Lys Val Glu Ser Pro Ile Asn Lys Ala Gln Gln
            500                 505                 510 ttc aaa agt atc cta caa aac aga aag aat gag aac aat aag aaa agt     1584
Phe Lys Ser Ile Leu Gln Asn Arg Lys Asn Glu Asn Asn Lys Lys Ser
        515                 520                 525 ttc ttg agt gtg tat att gga gat tcg gta ggt gac ttg ctg tgt ctc     1632
Phe Leu Ser Val Tyr Ile Gly Asp Ser Val Gly Asp Leu Leu Cys Leu
    530                 535                 540 ctc gaa gca gat ata gga ata gtg gtt agc tct agc tcg agt ctc agg     1680
```

```
Leu Glu Ala Asp Ile Gly Ile Val Val Ser Ser Ser Ser Leu Arg
545                 550                 555                 560 aga gtt gga agc cat ttt ggg gtc tca ttt gtg cct ttg ttt tct gga      1728
Arg Val Gly Ser His Phe Gly Val Ser Phe Val Pro Leu Phe Ser Gly
            565                 570                 575 atc gtc cag aaa cag aaa caa cac act gaa gaa tca tca tca gca          1776
Ile Val Gln Lys Gln Lys Gln His Thr Glu Glu Ser Ser Ser Ala
            580                 585                 590 tgg aaa gga ctc tct ggc aca ctt tac aca gtt tca agc tgg gcc gaa      1824
Trp Lys Gly Leu Ser Gly Thr Leu Tyr Thr Val Ser Ser Trp Ala Glu
            595                 600                 605 att cat tca ttc gct ctt gga tgg gag taa                              1854
Ile His Ser Phe Ala Leu Gly Trp Glu
            610                 615

<210> SEQ ID NO 2
<211> LENGTH: 617
<212> TYPE: PRT
<213> ORGANISM: Arabidopsis thaliana

<400> SEQUENCE: 2

Met Arg Phe Leu Phe Pro Thr Arg Leu Ile Asn Asn Ser Ser Leu Gly
1               5                   10                  15

Leu Leu Arg Ser Pro His Thr Thr Ala Pro Ile Arg Ser Leu Trp Phe
                20                  25                  30

Arg Thr Lys Ser Pro Val Phe Arg Ser Ala Thr Thr Pro Ile Met Thr
            35                  40                  45

Ala Val Ala Phe Ser Ser Ser Leu Ser Ile Pro Pro Thr Ser Glu Glu
50                  55                  60

Ala Leu Pro Gly Lys Leu Trp Ile Lys Phe Asn Arg Glu Cys Leu Phe
65                  70                  75                  80

Ser Ile Tyr Ser Pro Phe Ala Val Cys Leu Ala Ala Gly Asn Leu Lys
                85                  90                  95

Ile Asp Thr Phe Arg Gln Tyr Ile Ala Gln Asp Val His Phe Leu Lys
            100                 105                 110

Ala Phe Ala His Ala Tyr Glu Leu Ala Ala Asp Cys Ala Asp Asp Asp
        115                 120                 125

Asp Asp Lys Leu Ala Ile Ser Asp Leu Arg Lys Ser Val Met Glu Glu
130                 135                 140

Leu Lys Met His Asp Ser Phe Val Gln Asp Trp Asp Leu Asp Ile Asn
145                 150                 155                 160

Lys Glu Val Ser Val Asn Ser Ala Thr Leu Arg Tyr Thr Glu Phe Leu
                165                 170                 175

Leu Ala Thr Ala Ser Gly Lys Val Glu Gly Cys Lys Ala Pro Gly Met
            180                 185                 190

Leu Asp Thr Pro Phe Glu Lys Thr Lys Val Ala Ala Tyr Thr Leu Gly
        195                 200                 205

Ala Val Thr Pro Cys Met Arg Leu Tyr Ala Phe Leu Gly Lys Glu Phe
210                 215                 220

Gly Ser Leu Leu Asp Leu Ser Asp Val Asn His Pro Tyr Lys Lys Trp
225                 230                 235                 240

Ile Asp Asn Tyr Ser Ser Asp Ala Phe Gln Ala Ser Ala Lys Gln Thr
                245                 250                 255

Glu Asp Leu Leu Glu Lys Leu Ser Val Ser Met Thr Gly Glu Glu Leu
            260                 265                 270

Asp Ile Ile Glu Lys Leu Tyr Gln Gln Ala Met Lys Leu Glu Val Glu
```

```
                275                 280                 285
Phe Phe His Ala Gln Pro Leu Ala Gln Pro Thr Ile Val Pro Leu Leu
290                 295                 300
Lys Asn His Ser Lys Asp Asp Leu Val Ile Phe Ser Asp Phe Asp Leu
305                 310                 315                 320
Thr Cys Thr Val Val Asp Ser Ser Ala Ile Leu Ala Glu Ile Ala Ile
                325                 330                 335
Val Thr Ala Pro Lys Asp Glu Gln Ser Arg Ser Gly Gln Gln Ile His
                340                 345                 350
Arg Met Leu Ser Ser Asp Leu Lys Asn Thr Trp Asn Leu Leu Ser Lys
                355                 360                 365
Gln Tyr Thr Glu His Tyr Glu Glu Cys Ile Glu Ser Ile Leu Asn Lys
370                 375                 380
Lys Lys Ala Asp Lys Phe Asp Tyr Glu Gly Leu Cys Lys Ala Leu Glu
385                 390                 395                 400
Gln Leu Ser Asp Phe Glu Lys Glu Ala Asn Asn Arg Val Ile Glu Ser
                405                 410                 415
Gly Val Leu Lys Gly Leu Asn Leu Glu Asp Ile Lys Arg Ala Gly Glu
                420                 425                 430
Arg Leu Ile Leu Gln Asp Gly Cys Ile Asn Val Phe Gln Lys Ile Leu
                435                 440                 445
Lys Thr Glu Asn Leu Asn Ala Glu Leu His Val Leu Ser Tyr Cys Trp
450                 455                 460
Cys Gly Asp Leu Ile Arg Ala Ala Phe Ser Ala Gly Val Asp Ala
465                 470                 475                 480
Val Glu Val His Ala Asn Glu Phe Thr Phe Glu Ser Ile Ser Thr
                485                 490                 495
Gly Glu Ile Glu Arg Lys Val Glu Ser Pro Ile Asn Lys Ala Gln Gln
                500                 505                 510
Phe Lys Ser Ile Leu Gln Asn Arg Lys Asn Glu Asn Lys Lys Ser
                515                 520                 525
Phe Leu Ser Val Tyr Ile Gly Asp Ser Val Gly Asp Leu Leu Cys Leu
530                 535                 540
Leu Glu Ala Asp Ile Gly Ile Val Val Ser Ser Ser Ser Leu Arg
545                 550                 555                 560
Arg Val Gly Ser His Phe Gly Val Ser Phe Val Pro Leu Phe Ser Gly
                565                 570                 575
Ile Val Gln Lys Gln Lys Gln His Thr Glu Glu Ser Ser Ser Ser Ala
                580                 585                 590
Trp Lys Gly Leu Ser Gly Thr Leu Tyr Thr Val Ser Ser Trp Ala Glu
                595                 600                 605
Ile His Ser Phe Ala Leu Gly Trp Glu
610                 615

<210> SEQ ID NO 3
<211> LENGTH: 1806
<212> TYPE: DNA
<213> ORGANISM: Pyrus x bretschneideri
<220> FEATURE:
<221> NAME/KEY: CDS
<222> LOCATION: (1)..(1803)
<223> OTHER INFORMATION: Pyrus x bretschneideri gene encoding TMP
      phosphatase [XP_009379735.1]

<400> SEQUENCE: 3 atg cgc ata ctc ttc ccc cca aac cca atc aaa acc cca act ctc ttc      48
```

```
Met Arg Ile Leu Phe Pro Pro Asn Pro Ile Lys Thr Pro Thr Leu Phe
1               5                   10                  15 aac tcc ctc cgt ctg cga ttc aac tcg ctc cga tcc cac tgt gcc aac        96
Asn Ser Leu Arg Leu Arg Phe Asn Ser Leu Arg Ser His Cys Ala Asn
                20                  25                  30 tca atg gcc gta cct ccg ccg aag tca gcc atg gct tcc gcc gtc gtc       144
Ser Met Ala Val Pro Pro Pro Lys Ser Ala Met Ala Ser Ala Val Val
            35                  40                  45 ggc aac gag gtg ggt ctc gcc cgc cgc ttc tgg atc aag ttc aag cga       192
Gly Asn Glu Val Gly Leu Ala Arg Arg Phe Trp Ile Lys Phe Lys Arg
50                  55                  60 gaa tcg att ttc gct atg tac act ccc ttc acg ctc tgt ttg gct gct       240
Glu Ser Ile Phe Ala Met Tyr Thr Pro Phe Thr Leu Cys Leu Ala Ala
65                  70                  75                  80 ggg aat ctc aag att gaa act ttc cgc gat tat att gcc caa gat gtt       288
Gly Asn Leu Lys Ile Glu Thr Phe Arg Asp Tyr Ile Ala Gln Asp Val
            85                  90                  95 cac ttt ctc aag gcc ttc gct cac gcg tat gaa ttg gca gaa gat tgt       336
His Phe Leu Lys Ala Phe Ala His Ala Tyr Glu Leu Ala Glu Asp Cys
            100                 105                 110 gca gac gat gat gat gca aag ccc gtg att tct gag ttg agg agg gca       384
Ala Asp Asp Asp Asp Ala Lys Pro Val Ile Ser Glu Leu Arg Arg Ala
            115                 120                 125 gtt ctg cag gag ctg aaa atg cat gat tca ttt gtg aag gaa tgg ggg       432
Val Leu Gln Glu Leu Lys Met His Asp Ser Phe Val Lys Glu Trp Gly
130                 135                 140 tta cag ggt gct aaa gag acc cct atc aac tcc gct gcg gtg aag tac       480
Leu Gln Gly Ala Lys Glu Thr Pro Ile Asn Ser Ala Ala Val Lys Tyr
145                 150                 155                 160 aca gat ttc tta ttg gca aca gcc tct gga aaa gtt gaa gga gtc aag       528
Thr Asp Phe Leu Leu Ala Thr Ala Ser Gly Lys Val Glu Gly Val Lys
                165                 170                 175 gga cct ggt aaa ctt gca act cca ttt gaa aga acc aaa gtg gct gct       576
Gly Pro Gly Lys Leu Ala Thr Pro Phe Glu Arg Thr Lys Val Ala Ala
            180                 185                 190 tac acc ctt ggc gct atg act cct tgc atg aga ctg tat gcc ttt ctt       624
Tyr Thr Leu Gly Ala Met Thr Pro Cys Met Arg Leu Tyr Ala Phe Leu
            195                 200                 205 ggt aag gag ttc aag gca ctt cta gat ccc agc gaa ggc agt cac ccg       672
Gly Lys Glu Phe Lys Ala Leu Leu Asp Pro Ser Glu Gly Ser His Pro
210                 215                 220 tac ttg aag tgg att gac agt tat tct tct aaa agt ttt cag gca tca       720
Tyr Leu Lys Trp Ile Asp Ser Tyr Ser Ser Lys Ser Phe Gln Ala Ser
225                 230                 235                 240 gct gtg caa atc gaa gag ttg ctg gat aaa cta agt gtc tct ttg aca       768
Ala Val Gln Ile Glu Glu Leu Leu Asp Lys Leu Ser Val Ser Leu Thr
                245                 250                 255 ggc gag gag ctt gac atc atc gaa aag ctt tac cac caa gca atg aaa       816
Gly Glu Glu Leu Asp Ile Ile Glu Lys Leu Tyr His Gln Ala Met Lys
            260                 265                 270 ctt gag atc gag ttc ttc tct gct cag tct ctt gtt cag cca act gta       864
Leu Glu Ile Glu Phe Phe Ser Ala Gln Ser Leu Val Gln Pro Thr Val
            275                 280                 285 gtt cct ctg atc aga gaa cat aac cct gca gaa gat cgg ctc atg ata       912
Val Pro Leu Ile Arg Glu His Asn Pro Ala Glu Asp Arg Leu Met Ile
            290                 295                 300 ttt tct gat ttt gat ttg act tgt aca gtc gtt gat tca tct gcc att       960
Phe Ser Asp Phe Asp Leu Thr Cys Thr Val Val Asp Ser Ser Ala Ile
305                 310                 315                 320
```

```
ttg gct gaa att gca ata gta aca gca cca aaa tct gat caa cat caa       1008
Leu Ala Glu Ile Ala Ile Val Thr Ala Pro Lys Ser Asp Gln His Gln
                325                 330                 335 ccc gaa aat cag att gct cgg atg tct tcg gct gat ctc agg aat aca       1056
Pro Glu Asn Gln Ile Ala Arg Met Ser Ser Ala Asp Leu Arg Asn Thr
            340                 345                 350 tgg ggt ctt ctt tcc agg cag tac aca gaa gag tat gag caa tgc ata       1104
Trp Gly Leu Leu Ser Arg Gln Tyr Thr Glu Glu Tyr Glu Gln Cys Ile
        355                 360                 365 gaa agc att gtt ccc act gaa aaa gca gtg ttt gac tat gaa aat ttg       1152
Glu Ser Ile Val Pro Thr Glu Lys Ala Val Phe Asp Tyr Glu Asn Leu
    370                 375                 380 ctt aaa gca cta gag aaa ctt tca gat ttt gag agg aag gca aac aat       1200
Leu Lys Ala Leu Glu Lys Leu Ser Asp Phe Glu Arg Lys Ala Asn Asn
385                 390                 395                 400 aga gtc acg aag tct gaa gta ctc aag ggt ctt aat ctc gaa gat ata       1248
Arg Val Thr Lys Ser Glu Val Leu Lys Gly Leu Asn Leu Glu Asp Ile
                405                 410                 415 aaa aga gct ggt gaa cgt ctc att ctt caa gat ggc tgt att aat ttc       1296
Lys Arg Ala Gly Glu Arg Leu Ile Leu Gln Asp Gly Cys Ile Asn Phe
            420                 425                 430 ttt cag aaa att gcc aag agt gaa aac ttg aat gca aat gtt cat gtt       1344
Phe Gln Lys Ile Ala Lys Ser Glu Asn Leu Asn Ala Asn Val His Val
        435                 440                 445 ctt tca tac tgt tgg tgt ggt gat ctc ata aga tcg gcc ttt tca tca       1392
Leu Ser Tyr Cys Trp Cys Gly Asp Leu Ile Arg Ser Ala Phe Ser Ser
    450                 455                 460 ggg ggt tta aac gag ctg gat gta cat gca aat gag ttt acc ttc gag       1440
Gly Gly Leu Asn Glu Leu Asp Val His Ala Asn Glu Phe Thr Phe Glu
465                 470                 475                 480 gaa tcc atc tcc aca ggt gat att gtt aag aag gtg gag tcc cct att       1488
Glu Ser Ile Ser Thr Gly Asp Ile Val Lys Lys Val Glu Ser Pro Ile
                485                 490                 495 gac aag gtt aaa tct ttt aaa gat att ttg aaa aat tgc agc aat gac       1536
Asp Lys Val Lys Ser Phe Lys Asp Ile Leu Lys Asn Cys Ser Asn Asp
            500                 505                 510 aga aag aac ttg act gtt tac att gga gac tcg gtg ggt gac tta ctt       1584
Arg Lys Asn Leu Thr Val Tyr Ile Gly Asp Ser Val Gly Asp Leu Leu
        515                 520                 525 tgt ctg ctg gag gcg gat att gga atc gta att ggg tca agt tca agc       1632
Cys Leu Leu Glu Ala Asp Ile Gly Ile Val Ile Gly Ser Ser Ser Ser
    530                 535                 540 ctt agg aga gtg gcg act cag ttt ggg gta tct ttt gtt ccg ttg ttc       1680
Leu Arg Arg Val Ala Thr Gln Phe Gly Val Ser Phe Val Pro Leu Phe
545                 550                 555                 560 ccg ggt tta gtt aag aaa cag aaa gaa tgc aca gat gga agg tct cct       1728
Pro Gly Leu Val Lys Lys Gln Lys Glu Cys Thr Asp Gly Arg Ser Pro
                565                 570                 575 agt tgg aaa ggg tta act ggt att ctt tac aca gtg aat agt tgg gcg       1776
Ser Trp Lys Gly Leu Thr Gly Ile Leu Tyr Thr Val Asn Ser Trp Ala
            580                 585                 590 gaa ata cat gcc ttc att ttg ggg tgt taa                                1806
Glu Ile His Ala Phe Ile Leu Gly Cys
        595                 600

<210> SEQ ID NO 4
<211> LENGTH: 601
<212> TYPE: PRT
<213> ORGANISM: Pyrus x bretschneideri

<400> SEQUENCE: 4
```

-continued

```
Met Arg Ile Leu Phe Pro Pro Asn Pro Ile Lys Thr Pro Thr Leu Phe
1               5                   10                  15

Asn Ser Leu Arg Leu Arg Phe Asn Ser Leu Arg Ser His Cys Ala Asn
            20                  25                  30

Ser Met Ala Val Pro Pro Lys Ser Ala Met Ala Ser Ala Val Val
        35                  40                  45

Gly Asn Glu Val Gly Leu Ala Arg Arg Phe Trp Ile Lys Phe Lys Arg
        50                  55                  60

Glu Ser Ile Phe Ala Met Tyr Thr Pro Phe Thr Leu Cys Leu Ala Ala
65                      70                  75                  80

Gly Asn Leu Lys Ile Glu Thr Phe Arg Asp Tyr Ile Ala Gln Asp Val
                85                  90                  95

His Phe Leu Lys Ala Phe Ala His Ala Tyr Glu Leu Ala Glu Asp Cys
            100                 105                 110

Ala Asp Asp Asp Ala Lys Pro Val Ile Ser Glu Leu Arg Arg Ala
            115                 120                 125

Val Leu Gln Glu Leu Lys Met His Asp Ser Phe Val Lys Glu Trp Gly
        130                 135                 140

Leu Gln Gly Ala Lys Glu Thr Pro Ile Asn Ser Ala Ala Val Lys Tyr
145                 150                 155                 160

Thr Asp Phe Leu Leu Ala Thr Ala Ser Gly Lys Val Glu Gly Val Lys
                165                 170                 175

Gly Pro Gly Lys Leu Ala Thr Pro Phe Glu Arg Thr Lys Val Ala Ala
            180                 185                 190

Tyr Thr Leu Gly Ala Met Thr Pro Cys Met Arg Leu Tyr Ala Phe Leu
        195                 200                 205

Gly Lys Glu Phe Lys Ala Leu Leu Asp Pro Ser Glu Gly Ser His Pro
210                 215                 220

Tyr Leu Lys Trp Ile Asp Ser Tyr Ser Ser Lys Ser Phe Gln Ala Ser
225                 230                 235                 240

Ala Val Gln Ile Glu Glu Leu Leu Asp Lys Leu Ser Val Ser Leu Thr
                245                 250                 255

Gly Glu Glu Leu Asp Ile Ile Glu Lys Leu Tyr His Gln Ala Met Lys
            260                 265                 270

Leu Glu Ile Glu Phe Phe Ser Ala Gln Ser Leu Val Gln Pro Thr Val
        275                 280                 285

Val Pro Leu Ile Arg Glu His Asn Pro Ala Glu Asp Arg Leu Met Ile
        290                 295                 300

Phe Ser Asp Phe Asp Leu Thr Cys Thr Val Val Asp Ser Ser Ala Ile
305                 310                 315                 320

Leu Ala Glu Ile Ala Ile Val Thr Ala Pro Lys Ser Asp Gln His Gln
                325                 330                 335

Pro Glu Asn Gln Ile Ala Arg Met Ser Ser Ala Asp Leu Arg Asn Thr
            340                 345                 350

Trp Gly Leu Leu Ser Arg Gln Tyr Thr Glu Glu Tyr Glu Gln Cys Ile
        355                 360                 365

Glu Ser Ile Val Pro Thr Glu Lys Ala Val Phe Asp Tyr Glu Asn Leu
370                 375                 380

Leu Lys Ala Leu Glu Lys Leu Ser Asp Phe Glu Arg Lys Ala Asn Asn
385                 390                 395                 400

Arg Val Thr Lys Ser Glu Val Leu Lys Gly Leu Asn Leu Glu Asp Ile
                405                 410                 415
```

```
Lys Arg Ala Gly Glu Arg Leu Ile Leu Gln Asp Gly Cys Ile Asn Phe
            420                 425                 430

Phe Gln Lys Ile Ala Lys Ser Glu Asn Leu Asn Ala Asn Val His Val
        435                 440                 445

Leu Ser Tyr Cys Trp Cys Gly Asp Leu Ile Arg Ser Ala Phe Ser Ser
    450                 455                 460

Gly Gly Leu Asn Glu Leu Asp Val His Ala Asn Glu Phe Thr Phe Glu
465                 470                 475                 480

Glu Ser Ile Ser Thr Gly Asp Ile Val Lys Val Glu Ser Pro Ile
                485                 490                 495

Asp Lys Val Lys Ser Phe Lys Asp Ile Leu Lys Asn Cys Ser Asn Asp
            500                 505                 510

Arg Lys Asn Leu Thr Val Tyr Ile Gly Asp Ser Val Gly Asp Leu Leu
        515                 520                 525

Cys Leu Leu Glu Ala Asp Ile Gly Ile Val Ile Gly Ser Ser Ser Ser
    530                 535                 540

Leu Arg Arg Val Ala Thr Gln Phe Gly Val Ser Phe Val Pro Leu Phe
545                 550                 555                 560

Pro Gly Leu Val Lys Lys Gln Lys Glu Cys Thr Asp Gly Arg Ser Pro
            565                 570                 575

Ser Trp Lys Gly Leu Thr Gly Ile Leu Tyr Thr Val Asn Ser Trp Ala
        580                 585                 590

Glu Ile His Ala Phe Ile Leu Gly Cys
    595                 600

<210> SEQ ID NO 5
<211> LENGTH: 1797
<212> TYPE: DNA
<213> ORGANISM: Brassica napus
<220> FEATURE:
<221> NAME/KEY: CDS
<222> LOCATION: (1)..(1794)
<223> OTHER INFORMATION: Brassica napus gene encoding TMP phosphatase
      [CDY62623.1]

<400> SEQUENCE: 5 atg cgc atc ctc aac aac tcg ctc gcc ctt ctc cga tcg ccc cgc gcc      48
Met Arg Ile Leu Asn Asn Ser Leu Ala Leu Leu Arg Ser Pro Arg Ala
1               5                   10                  15 gcc gcc ccg atc cgt tct cta ctg ttc ggc agc aag aag tct tcc gtc      96
Ala Ala Pro Ile Arg Ser Leu Leu Phe Gly Ser Lys Lys Ser Ser Val
            20                  25                  30 tcc cga tcg gcg gcc gcc ttc tct tcg gcg atg tcg att cct cct cct     144
Ser Arg Ser Ala Ala Ala Phe Ser Ser Ala Met Ser Ile Pro Pro Pro
        35                  40                  45 agc ata tcc acc tcg gaa gaa gct ctg gcg ggg agg ctg tgg atc aag     192
Ser Ile Ser Thr Ser Glu Glu Ala Leu Ala Gly Arg Leu Trp Ile Lys
    50                  55                  60 ttc aac aga gag tgc ctc ttc tct atg tac agc ccc ttc gcc gtt tct     240
Phe Asn Arg Glu Cys Leu Phe Ser Met Tyr Ser Pro Phe Ala Val Ser
65                  70                  75                  80 ttg gcc gcc ggc aat ctc aag atc gag acc ttc cgg cag tat att gct     288
Leu Ala Ala Gly Asn Leu Lys Ile Glu Thr Phe Arg Gln Tyr Ile Ala
                85                  90                  95 cag gat gtt cat ttc ctc aag gcc ttt gct cac gcg tat gag ttg gcc     336
Gln Asp Val His Phe Leu Lys Ala Phe Ala His Ala Tyr Glu Leu Ala
            100                 105                 110 gca gag tgt gct gat gat gat gat gat aag ttg gca att tct gac ttg     384
Ala Glu Cys Ala Asp Asp Asp Asp Asp Lys Leu Ala Ile Ser Asp Leu
```

```
              115                 120                 125
agg aaa agc gtc atg gat gag ttg aaa atg cac aac tca ttt gta cag     432
Arg Lys Ser Val Met Asp Glu Leu Lys Met His Asn Ser Phe Val Gln
    130                 135                 140 gat tgg gat tta gac atc agc aaa gaa gta agt gtt aac tca gca aca     480
Asp Trp Asp Leu Asp Ile Ser Lys Glu Val Ser Val Asn Ser Ala Thr
145                 150                 155                 160 ttg aga tac acc gag ttc tta tta gct aca tca tcc gga aaa gta gaa     528
Leu Arg Tyr Thr Glu Phe Leu Leu Ala Thr Ser Ser Gly Lys Val Glu
                165                 170                 175 gga ctc aaa gct ccc ggc atg ctt gat act cca ttt gag aaa acc aaa     576
Gly Leu Lys Ala Pro Gly Met Leu Asp Thr Pro Phe Glu Lys Thr Lys
        180                 185                 190 gtg gcc gcc tac acg ctt ggt gct gtg aca cct tgc atg aag ctg tat     624
Val Ala Ala Tyr Thr Leu Gly Ala Val Thr Pro Cys Met Lys Leu Tyr
            195                 200                 205 gcc ttt ctt ggt aag gag ttt gga gcg ctt cta gat tcg agt gaa gcg     672
Ala Phe Leu Gly Lys Glu Phe Gly Ala Leu Leu Asp Ser Ser Glu Ala
    210                 215                 220 aac cat ccc tac aag aaa tgg atc gaa aat tat tct agt gat gca ttc     720
Asn His Pro Tyr Lys Lys Trp Ile Glu Asn Tyr Ser Ser Asp Ala Phe
225                 230                 235                 240 cag gca tca gct aag caa act gaa gac ttg ctt gag aag ctt agt gtg     768
Gln Ala Ser Ala Lys Gln Thr Glu Asp Leu Leu Glu Lys Leu Ser Val
                245                 250                 255 tgt atg act ggc gaa gag ctg gac atc att gaa aaa ctg tat caa cag     816
Cys Met Thr Gly Glu Glu Leu Asp Ile Ile Glu Lys Leu Tyr Gln Gln
        260                 265                 270 gca atg aaa ctt gaa gta gag ttc ttc cac gca caa ccg ttt gct cag     864
Ala Met Lys Leu Glu Val Glu Phe Phe His Ala Gln Pro Phe Ala Gln
            275                 280                 285 cct acc ata gtt ccg ctg ctg aag aac cat tca aaa gat gag ctg atg     912
Pro Thr Ile Val Pro Leu Leu Lys Asn His Ser Lys Asp Glu Leu Met
    290                 295                 300 ata ttt tct gat ttt gat ctg act tgc acc gtt gtt gat tct tct gct     960
Ile Phe Ser Asp Phe Asp Leu Thr Cys Thr Val Val Asp Ser Ser Ala
305                 310                 315                 320 att tta gcc gaa att gca atc gta act gcc ccg aaa gat gat cag ggt    1008
Ile Leu Ala Glu Ile Ala Ile Val Thr Ala Pro Lys Asp Asp Gln Gly
                325                 330                 335 caa caa att aat cgg atg ctt tcg gct gac ttg aag aac acc tgg agt    1056
Gln Gln Ile Asn Arg Met Leu Ser Ala Asp Leu Lys Asn Thr Trp Ser
        340                 345                 350 cta ctt tcc aaa cag tat aca gag cac tat gaa gag tgc ata gag agt    1104
Leu Leu Ser Lys Gln Tyr Thr Glu His Tyr Glu Glu Cys Ile Glu Ser
            355                 360                 365 att ctg aat aag gaa aaa gcg gac aag ttt gac tac gag ggt ttg tgt    1152
Ile Leu Asn Lys Glu Lys Ala Asp Lys Phe Asp Tyr Glu Gly Leu Cys
    370                 375                 380 gaa gca cta gag cag ctg tca gag ttt gag aag aaa gca aac gac cga    1200
Glu Ala Leu Glu Gln Leu Ser Glu Phe Glu Lys Lys Ala Asn Asp Arg
385                 390                 395                 400 gtg ata gag tct ggt gta ctc aag ggc ctg aat ctc gat gac atc aag    1248
Val Ile Glu Ser Gly Val Leu Lys Gly Leu Asn Leu Asp Asp Ile Lys
                405                 410                 415 cga gct ggg gaa agg ttg att ctt caa gat ggc tgc atc aat gtc ttc    1296
Arg Ala Gly Glu Arg Leu Ile Leu Gln Asp Gly Cys Ile Asn Val Phe
        420                 425                 430 cag aaa att ttg aag act cag gat gtg aat gca aaa ctc cac gtg ctt    1344
```

```
Gln Lys Ile Leu Lys Thr Gln Asp Val Asn Ala Lys Leu His Val Leu
            435                 440                 445 tcg tat tgt tgg tgt ggt gac ctc atc aga gca gcc ttt tct gca cgg      1392
Ser Tyr Cys Trp Cys Gly Asp Leu Ile Arg Ala Ala Phe Ser Ala Arg
    450                 455                 460 gga gta gat gca gtg gaa gta cat gca aat gaa ttc aca ttc gag gaa      1440
Gly Val Asp Ala Val Glu Val His Ala Asn Glu Phe Thr Phe Glu Glu
465                 470                 475                 480 tcc atc tct act gga gaa ata gaa aga aaa gtg gaa tcc cca atc gac      1488
Ser Ile Ser Thr Gly Glu Ile Glu Arg Lys Val Glu Ser Pro Ile Asp
                485                 490                 495 aag gct caa cag ttc aag agc atc cta caa aac aga aag aag gat gag      1536
Lys Ala Gln Gln Phe Lys Ser Ile Leu Gln Asn Arg Lys Lys Asp Glu
            500                 505                 510 gag aaa agc atc ctc act gtt tac att gga gat tca gta ggt gac ttg      1584
Glu Lys Ser Ile Leu Thr Val Tyr Ile Gly Asp Ser Val Gly Asp Leu
        515                 520                 525 ctc tgt ctc ctg gag gca gac att gga ata gtg gtc gcc tct agc tcg      1632
Leu Cys Leu Leu Glu Ala Asp Ile Gly Ile Val Val Ala Ser Ser Ser
530                 535                 540 agc ctc agg aga gtg gga agc cat ttc ggg gtc tca ttt gtg cct ttg      1680
Ser Leu Arg Arg Val Gly Ser His Phe Gly Val Ser Phe Val Pro Leu
545                 550                 555                 560 ttc tct gga att gtg caa aaa cag aaa caa gaa gaa acc tgg aag ggg      1728
Phe Ser Gly Ile Val Gln Lys Gln Lys Gln Glu Glu Thr Trp Lys Gly
                565                 570                 575 ctc tct ggc aca ctt tac acg gta tca agc tgg gct gaa ata cat tcc      1776
Leu Ser Gly Thr Leu Tyr Thr Val Ser Ser Trp Ala Glu Ile His Ser
            580                 585                 590 ttc gct ctt gga tgg gag taa                                           1797
Phe Ala Leu Gly Trp Glu
        595

<210> SEQ ID NO 6
<211> LENGTH: 598
<212> TYPE: PRT
<213> ORGANISM: Brassica napus

<400> SEQUENCE: 6

Met Arg Ile Leu Asn Asn Ser Leu Ala Leu Leu Arg Ser Pro Arg Ala
1               5                   10                  15

Ala Ala Pro Ile Arg Ser Leu Leu Phe Gly Ser Lys Lys Ser Ser Val
                20                  25                  30

Ser Arg Ser Ala Ala Ala Phe Ser Ser Ala Met Ser Ile Pro Pro Pro
            35                  40                  45

Ser Ile Ser Thr Ser Glu Glu Ala Leu Ala Gly Arg Leu Trp Ile Lys
        50                  55                  60

Phe Asn Arg Glu Cys Leu Phe Ser Met Tyr Ser Pro Phe Ala Val Ser
65                  70                  75                  80

Leu Ala Ala Gly Asn Leu Lys Ile Glu Thr Phe Arg Gln Tyr Ile Ala
                85                  90                  95

Gln Asp Val His Phe Leu Lys Ala Phe Ala His Ala Tyr Glu Leu Ala
            100                 105                 110

Ala Glu Cys Ala Asp Asp Asp Lys Leu Ala Ile Ser Asp Leu
        115                 120                 125

Arg Lys Ser Val Met Asp Glu Leu Lys Met His Asn Ser Phe Val Gln
130                 135                 140

Asp Trp Asp Leu Asp Ile Ser Lys Glu Val Ser Val Asn Ser Ala Thr
```

```
            145                 150                 155                 160
Leu Arg Tyr Thr Glu Phe Leu Leu Ala Thr Ser Ser Gly Lys Val Glu
                165                 170                 175
Gly Leu Lys Ala Pro Gly Met Leu Asp Thr Pro Phe Glu Lys Thr Lys
                180                 185                 190
Val Ala Ala Tyr Thr Leu Gly Ala Val Thr Pro Cys Met Lys Leu Tyr
                195                 200                 205
Ala Phe Leu Gly Lys Glu Phe Gly Ala Leu Leu Asp Ser Ser Glu Ala
        210                 215                 220
Asn His Pro Tyr Lys Lys Trp Ile Glu Asn Tyr Ser Ser Asp Ala Phe
225                 230                 235                 240
Gln Ala Ser Ala Lys Gln Thr Glu Asp Leu Leu Glu Lys Leu Ser Val
                245                 250                 255
Cys Met Thr Gly Glu Glu Leu Asp Ile Ile Glu Lys Leu Tyr Gln Gln
                260                 265                 270
Ala Met Lys Leu Glu Val Glu Phe Phe His Ala Gln Pro Phe Ala Gln
        275                 280                 285
Pro Thr Ile Val Pro Leu Leu Lys Asn His Ser Lys Asp Glu Leu Met
        290                 295                 300
Ile Phe Ser Asp Phe Asp Leu Thr Cys Thr Val Asp Ser Ser Ala
305                 310                 315                 320
Ile Leu Ala Glu Ile Ala Ile Val Thr Ala Pro Lys Asp Asp Gln Gly
                325                 330                 335
Gln Gln Ile Asn Arg Met Leu Ser Ala Asp Leu Lys Asn Thr Trp Ser
                340                 345                 350
Leu Leu Ser Lys Gln Tyr Thr Glu His Tyr Glu Glu Cys Ile Glu Ser
                355                 360                 365
Ile Leu Asn Lys Glu Lys Ala Asp Lys Phe Asp Tyr Glu Gly Leu Cys
                370                 375                 380
Glu Ala Leu Glu Gln Leu Ser Glu Phe Glu Lys Lys Ala Asn Asp Arg
385                 390                 395                 400
Val Ile Glu Ser Gly Val Leu Lys Gly Leu Asn Leu Asp Asp Ile Lys
                405                 410                 415
Arg Ala Gly Glu Arg Leu Ile Leu Gln Asp Gly Cys Ile Asn Val Phe
                420                 425                 430
Gln Lys Ile Leu Lys Thr Gln Asp Val Asn Ala Lys Leu His Val Leu
                435                 440                 445
Ser Tyr Cys Trp Cys Gly Asp Leu Ile Arg Ala Ala Phe Ser Ala Arg
        450                 455                 460
Gly Val Asp Ala Val Glu Val His Ala Asn Glu Phe Thr Phe Glu Glu
465                 470                 475                 480
Ser Ile Ser Thr Gly Glu Ile Glu Arg Lys Val Glu Ser Pro Ile Asp
                485                 490                 495
Lys Ala Gln Gln Phe Lys Ser Ile Leu Gln Asn Arg Lys Lys Asp Glu
                500                 505                 510
Glu Lys Ser Ile Leu Thr Val Tyr Ile Gly Asp Ser Val Gly Asp Leu
                515                 520                 525
Leu Cys Leu Leu Glu Ala Asp Ile Gly Ile Val Val Ala Ser Ser Ser
        530                 535                 540
Ser Leu Arg Arg Val Gly Ser His Phe Gly Val Ser Phe Val Pro Leu
545                 550                 555                 560
Phe Ser Gly Ile Val Gln Lys Gln Lys Gln Glu Glu Thr Trp Lys Gly
                565                 570                 575
```

```
Leu Ser Gly Thr Leu Tyr Thr Val Ser Ser Trp Ala Glu Ile His Ser
            580                 585                 590

Phe Ala Leu Gly Trp Glu
        595

<210> SEQ ID NO 7
<211> LENGTH: 1815
<212> TYPE: DNA
<213> ORGANISM: Glycine max
<220> FEATURE:
<221> NAME/KEY: CDS
<222> LOCATION: (1)..(1812)
<223> OTHER INFORMATION: Glycine max gene encoding TMP phosphatase
      [XP_003536133.1]

<400> SEQUENCE: 7 atg cgc atg cgg tgg ttc ctc cga agc cca atc atc aaa acc tcg ctg      48
Met Arg Met Arg Trp Phe Leu Arg Ser Pro Ile Ile Lys Thr Ser Leu
1               5                   10                  15 ctg aat ctg agc cct cca att tcg ttt aga cct cac tgg gcg agg agg      96
Leu Asn Leu Ser Pro Pro Ile Ser Phe Arg Pro His Trp Ala Arg Arg
            20                  25                  30 acc ttc act tct tcg aga ttg tca atg gcg gcc atc cac aac cac agc     144
Thr Phe Thr Ser Ser Arg Leu Ser Met Ala Ala Ile His Asn His Ser
        35                  40                  45 aac agc aac agc gaa acc gga ctc gcg aga cgg ttt tgg atc aag ttc     192
Asn Ser Asn Ser Glu Thr Gly Leu Ala Arg Arg Phe Trp Ile Lys Phe
    50                  55                  60 act cgt gaa tcc atc ttc gcc atg tac act ccc ttc gcc atc gcc ttg     240
Thr Arg Glu Ser Ile Phe Ala Met Tyr Thr Pro Phe Ala Ile Ala Leu
65                  70                  75                  80 gcc tcc ggt aat ttg cac att gat tcc ttc cac cat tac atc gcc caa     288
Ala Ser Gly Asn Leu His Ile Asp Ser Phe His His Tyr Ile Ala Gln
                85                  90                  95 gac gtt cat ttc cta cgc gcc ttt gct caa gcg tat gag ttg gct gaa     336
Asp Val His Phe Leu Arg Ala Phe Ala Gln Ala Tyr Glu Leu Ala Glu
            100                 105                 110 gag tgt gct gat gac gac gat gcg aaa ctt gga atc tgt gag ttg agg     384
Glu Cys Ala Asp Asp Asp Asp Ala Lys Leu Gly Ile Cys Glu Leu Arg
        115                 120                 125 aag gca gtt cta gag gag ctg aag atg cac aac ttg ctg gta cag gaa     432
Lys Ala Val Leu Glu Glu Leu Lys Met His Asn Leu Leu Val Gln Glu
    130                 135                 140 cgg gag ttg gac ctt gcc aaa gag cat ggt att aat tct gca act gtt     480
Arg Glu Leu Asp Leu Ala Lys Glu His Gly Ile Asn Ser Ala Thr Val
145                 150                 155                 160 aag tac aca gag ttc ctg ctg gct aca gcc tct ggg aag att gaa gga     528
Lys Tyr Thr Glu Phe Leu Leu Ala Thr Ala Ser Gly Lys Ile Glu Gly
                165                 170                 175 cta aaa ggt cct ggt aaa ctt gct aca cca ttt gag aaa aca aaa att     576
Leu Lys Gly Pro Gly Lys Leu Ala Thr Pro Phe Glu Lys Thr Lys Ile
            180                 185                 190 gct gct tat act tta ggt gcc atg act cct tgc atg agg ctt tat gcc     624
Ala Ala Tyr Thr Leu Gly Ala Met Thr Pro Cys Met Arg Leu Tyr Ala
        195                 200                 205 gtt atg gga aag aag ttc cag gaa ctt ttg gat tcc aat gaa agt act     672
Val Met Gly Lys Lys Phe Gln Glu Leu Leu Asp Ser Asn Glu Ser Thr
    210                 215                 220 cac cca tat aac aag tgg atc aac aac tat tcc tct gat ggt ttc cag     720
His Pro Tyr Asn Lys Trp Ile Asn Asn Tyr Ser Ser Asp Gly Phe Gln
225                 230                 235                 240
```

```
gct act act ctg caa act gaa gat ttg ctc gac aaa cta agt gtc tct    768
Ala Thr Thr Leu Gln Thr Glu Asp Leu Leu Asp Lys Leu Ser Val Ser
            245                 250                 255 ttg act ggt gaa gaa ctt gat gtc att gaa aag ctt tat tac caa gca    816
Leu Thr Gly Glu Glu Leu Asp Val Ile Glu Lys Leu Tyr Tyr Gln Ala
            260                 265                 270 atg aag ctt gaa ata gag ttc ttc tct gct cag cca ctc ttc cag cca    864
Met Lys Leu Glu Ile Glu Phe Phe Ser Ala Gln Pro Leu Phe Gln Pro
        275                 280                 285 act ata gta ccc ttg act aaa gga cat aag cct gtg gaa gat cat ctc    912
Thr Ile Val Pro Leu Thr Lys Gly His Lys Pro Val Glu Asp His Leu
        290                 295                 300 att att ttt tct gat ttt gat tta aca tgc acc gta gtt gat tcg tcc    960
Ile Ile Phe Ser Asp Phe Asp Leu Thr Cys Thr Val Val Asp Ser Ser
305                 310                 315                 320 gcc atc ttg gct gaa att gcc ata gtg acg gca cca aaa tct gat cag   1008
Ala Ile Leu Ala Glu Ile Ala Ile Val Thr Ala Pro Lys Ser Asp Gln
            325                 330                 335 aat cag cct gaa gat caa att gtt cgg atg tta tct tct gac ctc agg   1056
Asn Gln Pro Glu Asp Gln Ile Val Arg Met Leu Ser Ser Asp Leu Arg
            340                 345                 350 aat aca tgg ggt ttt cta tct aaa cag tat acg gag gag tat gag caa   1104
Asn Thr Trp Gly Phe Leu Ser Lys Gln Tyr Thr Glu Glu Tyr Glu Gln
            355                 360                 365 tgt ata gaa agc att atg cct ccc gat aga ttg aac aat ttc gat tac   1152
Cys Ile Glu Ser Ile Met Pro Pro Asp Arg Leu Asn Asn Phe Asp Tyr
        370                 375                 380 aaa gaa ttg tcg atg gcc ctt gag caa ctt tca aaa ttt gag aac act   1200
Lys Glu Leu Ser Met Ala Leu Glu Gln Leu Ser Lys Phe Glu Asn Thr
385                 390                 395                 400 gca aat aat agg gtt atc gag tca ggg gta ctc aag ggt ata agt cta   1248
Ala Asn Asn Arg Val Ile Glu Ser Gly Val Leu Lys Gly Ile Ser Leu
            405                 410                 415 gaa gat ata aag cgt gct gga gag cgt ctg ata cta caa gat ggt tgc   1296
Glu Asp Ile Lys Arg Ala Gly Glu Arg Leu Ile Leu Gln Asp Gly Cys
            420                 425                 430 cct aac ttc ttt cag agc att gtt aag aat gaa aat ttg aat gcc aac   1344
Pro Asn Phe Phe Gln Ser Ile Val Lys Asn Glu Asn Leu Asn Ala Asn
            435                 440                 445 gtg cat gtt ctt tca tac tgc tgg tgt ggt gac ctc att agg tct act   1392
Val His Val Leu Ser Tyr Cys Trp Cys Gly Asp Leu Ile Arg Ser Thr
        450                 455                 460 ttc tct tcc gct gat tta aat gag ttg aat gtt cat gct aat gag ttc   1440
Phe Ser Ser Ala Asp Leu Asn Glu Leu Asn Val His Ala Asn Glu Phe
465                 470                 475                 480 act tat gag gga tct gtt tcc acg ggt gaa att gtt aag aaa gtg gag   1488
Thr Tyr Glu Gly Ser Val Ser Thr Gly Glu Ile Val Lys Lys Val Glu
            485                 490                 495 tct ccc att gac aag gtt gaa gct ttt cgt aac ata ttg aaa aat tgc   1536
Ser Pro Ile Asp Lys Val Glu Ala Phe Arg Asn Ile Leu Lys Asn Cys
        500                 505                 510 aat gat gac aaa aag aaa tta act gtt tac att ggc gat tca gtg ggt   1584
Asn Asp Asp Lys Lys Lys Leu Thr Val Tyr Ile Gly Asp Ser Val Gly
        515                 520                 525 gat tta ctt tgc cta ctt gaa gct gat gta gga att gtg att ggt tca   1632
Asp Leu Leu Cys Leu Leu Glu Ala Asp Val Gly Ile Val Ile Gly Ser
        530                 535                 540 agt tca agc ctt aga agt gta ggg acg cag ttt ggt att tca ttt gtc   1680
Ser Ser Ser Leu Arg Ser Val Gly Thr Gln Phe Gly Ile Ser Phe Val
```

```
                     545                 550                 555                 560
cca ttg tat tct ggc ttg gtt aag aaa cag aaa gaa tat gtt gaa gga       1728
Pro Leu Tyr Ser Gly Leu Val Lys Lys Gln Lys Glu Tyr Val Glu Gly
                565                 570                 575 agc act tct gat tgg aag ggt tta tct ggc att ctt tac aca gtc tct       1776
Ser Thr Ser Asp Trp Lys Gly Leu Ser Gly Ile Leu Tyr Thr Val Ser
                580                 585                 590 agt tgg gct gaa gtg cat gct ttt att ttg ggt tgc tag                   1815
Ser Trp Ala Glu Val His Ala Phe Ile Leu Gly Cys
                595                 600
```

<210> SEQ ID NO 8
<211> LENGTH: 604
<212> TYPE: PRT
<213> ORGANISM: Glycine max

<400> SEQUENCE: 8

```
Met Arg Met Arg Trp Phe Leu Arg Ser Pro Ile Ile Lys Thr Ser Leu
1               5                   10                  15

Leu Asn Leu Ser Pro Pro Ile Ser Phe Arg Pro His Trp Ala Arg Arg
                20                  25                  30

Thr Phe Thr Ser Ser Arg Leu Ser Met Ala Ala Ile His Asn His Ser
            35                  40                  45

Asn Ser Asn Ser Glu Thr Gly Leu Ala Arg Arg Phe Trp Ile Lys Phe
        50                  55                  60

Thr Arg Glu Ser Ile Phe Ala Met Tyr Thr Pro Phe Ala Ile Ala Leu
65                  70                  75                  80

Ala Ser Gly Asn Leu His Ile Asp Ser Phe His His Tyr Ile Ala Gln
                85                  90                  95

Asp Val His Phe Leu Arg Ala Phe Ala Gln Ala Tyr Glu Leu Ala Glu
            100                 105                 110

Glu Cys Ala Asp Asp Asp Ala Lys Leu Gly Ile Cys Glu Leu Arg
        115                 120                 125

Lys Ala Val Leu Glu Glu Leu Lys Met His Asn Leu Leu Val Gln Glu
130                 135                 140

Arg Glu Leu Asp Leu Ala Lys Glu His Gly Ile Asn Ser Ala Thr Val
145                 150                 155                 160

Lys Tyr Thr Glu Phe Leu Leu Ala Thr Ala Ser Gly Lys Ile Glu Gly
                165                 170                 175

Leu Lys Gly Pro Gly Lys Leu Ala Thr Pro Phe Glu Lys Thr Lys Ile
            180                 185                 190

Ala Ala Tyr Thr Leu Gly Ala Met Thr Pro Cys Met Arg Leu Tyr Ala
        195                 200                 205

Val Met Gly Lys Lys Phe Gln Glu Leu Leu Asp Ser Asn Glu Ser Thr
210                 215                 220

His Pro Tyr Asn Lys Trp Ile Asn Asn Tyr Ser Ser Asp Gly Phe Gln
225                 230                 235                 240

Ala Thr Thr Leu Gln Thr Glu Asp Leu Leu Asp Lys Leu Ser Val Ser
                245                 250                 255

Leu Thr Gly Glu Glu Leu Asp Val Ile Glu Lys Leu Tyr Tyr Gln Ala
            260                 265                 270

Met Lys Leu Glu Ile Glu Phe Phe Ser Ala Gln Pro Leu Phe Gln Pro
        275                 280                 285

Thr Ile Val Pro Leu Thr Lys Gly His Lys Pro Val Glu Asp His Leu
            290                 295                 300
```

```
Ile Ile Phe Ser Asp Phe Asp Leu Thr Cys Thr Val Val Asp Ser Ser
305                 310                 315                 320

Ala Ile Leu Ala Glu Ile Ala Ile Val Thr Ala Pro Lys Ser Asp Gln
            325                 330                 335

Asn Gln Pro Glu Asp Gln Ile Val Arg Met Leu Ser Ser Asp Leu Arg
        340                 345                 350

Asn Thr Trp Gly Phe Leu Ser Lys Gln Tyr Thr Glu Glu Tyr Glu Gln
    355                 360                 365

Cys Ile Glu Ser Ile Met Pro Pro Asp Arg Leu Asn Asn Phe Asp Tyr
370                 375                 380

Lys Glu Leu Ser Met Ala Leu Glu Gln Leu Ser Lys Phe Glu Asn Thr
385                 390                 395                 400

Ala Asn Asn Arg Val Ile Glu Ser Gly Val Leu Lys Gly Ile Ser Leu
                405                 410                 415

Glu Asp Ile Lys Arg Ala Gly Glu Arg Leu Ile Leu Gln Asp Gly Cys
            420                 425                 430

Pro Asn Phe Phe Gln Ser Ile Val Lys Asn Glu Asn Leu Asn Ala Asn
        435                 440                 445

Val His Val Leu Ser Tyr Cys Trp Cys Gly Asp Leu Ile Arg Ser Thr
    450                 455                 460

Phe Ser Ser Ala Asp Leu Asn Glu Leu Asn Val His Ala Asn Glu Phe
465                 470                 475                 480

Thr Tyr Glu Gly Ser Val Ser Thr Gly Glu Ile Val Lys Lys Val Glu
                485                 490                 495

Ser Pro Ile Asp Lys Val Glu Ala Phe Arg Asn Ile Leu Lys Asn Cys
            500                 505                 510

Asn Asp Asp Lys Lys Leu Thr Val Tyr Ile Gly Asp Ser Val Gly
        515                 520                 525

Asp Leu Leu Cys Leu Leu Glu Ala Asp Val Gly Ile Val Ile Gly Ser
    530                 535                 540

Ser Ser Ser Leu Arg Ser Val Gly Thr Gln Phe Gly Ile Ser Phe Val
545                 550                 555                 560

Pro Leu Tyr Ser Gly Leu Val Lys Lys Gln Lys Glu Tyr Val Glu Gly
                565                 570                 575

Ser Thr Ser Asp Trp Lys Gly Leu Ser Gly Ile Leu Tyr Thr Val Ser
            580                 585                 590

Ser Trp Ala Glu Val His Ala Phe Ile Leu Gly Cys
    595                 600
```

<210> SEQ ID NO 9
<211> LENGTH: 1845
<212> TYPE: DNA
<213> ORGANISM: Nicotiana tomentosiformis
<220> FEATURE:
<221> NAME/KEY: CDS
<222> LOCATION: (1)..(1842)
<223> OTHER INFORMATION: Nicotiana tomentosiformi gene encoding TMP phosphatase [XP_009615535.1]

<400> SEQUENCE: 9

```
atg cgc ttc tca tta tta tcg ccc ctt gtt ctt aac cca gtc atc aga    48
Met Arg Phe Ser Leu Leu Ser Pro Leu Val Leu Asn Pro Val Ile Arg
1               5                   10                  15 ttc tcc aat tcc aac gcg ctt ttt ggg tta cga ttc aa tta tac cct    96
Phe Ser Asn Ser Asn Ala Leu Phe Gly Leu Arg Phe Gln Leu Tyr Pro
            20                  25                  30 cgt tac tct cgg tat tta cga tcg ccc gtt aca atg gcg tcg gcg aaa   144
Arg Tyr Ser Arg Tyr Leu Arg Ser Pro Val Thr Met Ala Ser Ala Lys
```

-continued

```
                Arg Tyr Ser Arg Tyr Leu Arg Ser Pro Val Thr Met Ala Ser Ala Lys
                            35                  40                  45 cca aag ccg gcg gcg gcg gtg aac aag ttt ccg gta gag gag gaa tgt         192
Pro Lys Pro Ala Ala Ala Val Asn Lys Phe Pro Val Glu Glu Glu Cys
        50                  55                  60 gtg ggt ata gcg agg aag tgt tgg atc aag ttc aag aga gag tct act         240
Val Gly Ile Ala Arg Lys Cys Trp Ile Lys Phe Lys Arg Glu Ser Thr
65                  70                  75                  80 ttc gct ctg tac act ccg ttt gtg gtt agt ttg gca tca gga acc cta         288
Phe Ala Leu Tyr Thr Pro Phe Val Val Ser Leu Ala Ser Gly Thr Leu
                85                  90                  95 aat ctg gac act ttc cgc cat tac att gct cag gat gtt cac ttc ctc         336
Asn Leu Asp Thr Phe Arg His Tyr Ile Ala Gln Asp Val His Phe Leu
            100                 105                 110 aaa tcc ttc gct caa gcg tat gaa gct gca gaa gag tgt act gac gat         384
Lys Ser Phe Ala Gln Ala Tyr Glu Ala Ala Glu Glu Cys Thr Asp Asp
        115                 120                 125 gac gat gcg aag gtt ggc att agt gag ttg cgg aag aat gtt att gaa         432
Asp Asp Ala Lys Val Gly Ile Ser Glu Leu Arg Lys Asn Val Ile Glu
130                 135                 140 gaa ctt aaa atg cat gat gca gtt tta aaa gag tgg ggc att gat ctg         480
Glu Leu Lys Met His Asp Ala Val Leu Lys Glu Trp Gly Ile Asp Leu
145                 150                 155                 160 gtc aaa gag tcc agt ctt aac cct gca acg gcc aag tac aca gat ttt         528
Val Lys Glu Ser Ser Leu Asn Pro Ala Thr Ala Lys Tyr Thr Asp Phe
                165                 170                 175 tta tca gct aca gct tca gga aag gtg gaa gga gta aaa gct gct aaa         576
Leu Ser Ala Thr Ala Ser Gly Lys Val Glu Gly Val Lys Ala Ala Lys
            180                 185                 190 ctt gcc aca cca ttt gag aga acg aag ttg gca gct tat act cta ggt         624
Leu Ala Thr Pro Phe Glu Arg Thr Lys Leu Ala Ala Tyr Thr Leu Gly
        195                 200                 205 gct atg act cct tgc atg agg ctt tac gcc tac att ggt aag gag ctg         672
Ala Met Thr Pro Cys Met Arg Leu Tyr Ala Tyr Ile Gly Lys Glu Leu
210                 215                 220 caa gtg ttc ctc gag gga gag aaa att cat cca tac aag aag tgg att         720
Gln Val Phe Leu Glu Gly Glu Lys Ile His Pro Tyr Lys Lys Trp Ile
225                 230                 235                 240 gac agt tat gcc tct gaa agt ttc cag gca tca gct ctt caa acc gag         768
Asp Ser Tyr Ala Ser Glu Ser Phe Gln Ala Ser Ala Leu Gln Thr Glu
                245                 250                 255 gac ttg ttg gat aaa ctg agt gtc cct ttg aca ggc gag gag ctt gac         816
Asp Leu Leu Asp Lys Leu Ser Val Pro Leu Thr Gly Glu Glu Leu Asp
            260                 265                 270 atc att gaa aag ctt tat cat caa gca atg aaa ctt gaa att gat ttc         864
Ile Ile Glu Lys Leu Tyr His Gln Ala Met Lys Leu Glu Ile Asp Phe
        275                 280                 285 ttc tta acc cag cca ctt gtt cag aaa gct gtc atc cct ttg tca aaa         912
Phe Leu Thr Gln Pro Leu Val Gln Lys Ala Val Ile Pro Leu Ser Lys
290                 295                 300 gat cac aac cct gct gaa cac cgg ctt aca ata ttt tct gat ttc gat         960
Asp His Asn Pro Ala Glu His Arg Leu Thr Ile Phe Ser Asp Phe Asp
305                 310                 315                 320 ttg acg tgc act gtt gtt gat tct tct gcc atc ttg gct gaa att gca        1008
Leu Thr Cys Thr Val Val Asp Ser Ser Ala Ile Leu Ala Glu Ile Ala
                325                 330                 335 att ata aca gca ccg aga tct gat caa aat cga cca gag aat caa att        1056
Ile Ile Thr Ala Pro Arg Ser Asp Gln Asn Arg Pro Glu Asn Gln Ile
            340                 345                 350
```

| | | |
|---|---|---|
| gcg cgg atg ttg tcg gct gat ttg agg aat aca tgg gga gat ctc tct<br>Ala Arg Met Leu Ser Ala Asp Leu Arg Asn Thr Trp Gly Asp Leu Ser<br>355 360 365 | | 1104 |
| aag cag tac act gaa gag tat gag caa tgt ata gag aag atg tta ctt<br>Lys Gln Tyr Thr Glu Glu Tyr Glu Gln Cys Ile Glu Lys Met Leu Leu<br>370 375 380 | | 1152 |
| act gaa aaa gcg gaa aaa ttt gat tat gaa aga ctg cat aaa aca ctt<br>Thr Glu Lys Ala Glu Lys Phe Asp Tyr Glu Arg Leu His Lys Thr Leu<br>385 390 395 400 | | 1200 |
| gag gaa ctt tct gat ttt gag aaa aga gca aat act agg gtg act gaa<br>Glu Glu Leu Ser Asp Phe Glu Lys Arg Ala Asn Thr Arg Val Thr Glu<br>405 410 415 | | 1248 |
| tct ggg gta ctg aaa ggt tta aac ctt gaa gac ata aaa cga gct ggg<br>Ser Gly Val Leu Lys Gly Leu Asn Leu Glu Asp Ile Lys Arg Ala Gly<br>420 425 430 | | 1296 |
| cag cga ttg att ctc cag gat ggt tgc acc aac ttc ttc cag agc ata<br>Gln Arg Leu Ile Leu Gln Asp Gly Cys Thr Asn Phe Phe Gln Ser Ile<br>435 440 445 | | 1344 |
| ata aga aat gaa aat ctg aac gca gac att cat gtc ctc tcc tat tgc<br>Ile Arg Asn Glu Asn Leu Asn Ala Asp Ile His Val Leu Ser Tyr Cys<br>450 455 460 | | 1392 |
| tgg tgt ggc gac ctt att agg tct tcc ttt tca tca ggg ggt ata gac<br>Trp Cys Gly Asp Leu Ile Arg Ser Ser Phe Ser Ser Gly Gly Ile Asp<br>465 470 475 480 | | 1440 |
| gct ctg aat gtg cat gcc aat gag ttt atg ttt caa gaa tct cta tcc<br>Ala Leu Asn Val His Ala Asn Glu Phe Met Phe Gln Glu Ser Leu Ser<br>485 490 495 | | 1488 |
| act ggt gaa att gtt aag aaa gtt gaa tcc ccc att gac aag gtt caa<br>Thr Gly Glu Ile Val Lys Lys Val Glu Ser Pro Ile Asp Lys Val Gln<br>500 505 510 | | 1536 |
| gca ttc agt aaa att cga atg aac tgt ggc aat gac caa aaa aat ctg<br>Ala Phe Ser Lys Ile Arg Met Asn Cys Gly Asn Asp Gln Lys Asn Leu<br>515 520 525 | | 1584 |
| act ctt tat att ggg gat tca gtc ggc gac tta ctt tgc ttg ctt gaa<br>Thr Leu Tyr Ile Gly Asp Ser Val Gly Asp Leu Leu Cys Leu Leu Glu<br>530 535 540 | | 1632 |
| gca gat gtt ggc ata gtg ctt ggt acg agc tca agt cta agg acg gtg<br>Ala Asp Val Gly Ile Val Leu Gly Thr Ser Ser Ser Leu Arg Thr Val<br>545 550 555 560 | | 1680 |
| ggg aat cat ttt ggt gtt tct ttt gtt cct ctg ttt cca ggt gtt gtc<br>Gly Asn His Phe Gly Val Ser Phe Val Pro Leu Phe Pro Gly Val Val<br>565 570 575 | | 1728 |
| cag aaa cag aag atg tgc act ggg gta gac tcg tca agt tgt tgg aag<br>Gln Lys Gln Lys Met Cys Thr Gly Val Asp Ser Ser Ser Cys Trp Lys<br>580 585 590 | | 1776 |
| gga cta tct ggt gtt ctc tat act gcc tct agc tgg gct gag ata cat<br>Gly Leu Ser Gly Val Leu Tyr Thr Ala Ser Ser Trp Ala Glu Ile His<br>595 600 605 | | 1824 |
| gct ttt gta ttg ggg tca tga<br>Ala Phe Val Leu Gly Ser<br>610 | | 1845 |

<210> SEQ ID NO 10
<211> LENGTH: 614
<212> TYPE: PRT
<213> ORGANISM: Nicotiana tomentosiformis

<400> SEQUENCE: 10

Met Arg Phe Ser Leu Leu Ser Pro Leu Val Leu Asn Pro Val Ile Arg
1               5                   10                  15

```
Phe Ser Asn Ser Asn Ala Leu Phe Gly Leu Arg Phe Gln Leu Tyr Pro
            20                  25                  30

Arg Tyr Ser Arg Tyr Leu Arg Ser Pro Val Thr Met Ala Ser Ala Lys
        35                  40                  45

Pro Lys Pro Ala Ala Ala Val Asn Lys Phe Pro Val Glu Glu Glu Cys
    50                  55                  60

Val Gly Ile Ala Arg Lys Cys Trp Ile Lys Phe Lys Arg Glu Ser Thr
65                  70                  75                  80

Phe Ala Leu Tyr Thr Pro Phe Val Val Ser Leu Ala Ser Gly Thr Leu
                85                  90                  95

Asn Leu Asp Thr Phe Arg His Tyr Ile Ala Gln Asp Val His Phe Leu
            100                 105                 110

Lys Ser Phe Ala Gln Ala Tyr Glu Ala Ala Glu Glu Cys Thr Asp Asp
        115                 120                 125

Asp Asp Ala Lys Val Gly Ile Ser Glu Leu Arg Lys Asn Val Ile Glu
    130                 135                 140

Glu Leu Lys Met His Asp Ala Val Leu Lys Glu Trp Gly Ile Asp Leu
145                 150                 155                 160

Val Lys Glu Ser Ser Leu Asn Pro Ala Thr Ala Lys Tyr Thr Asp Phe
                165                 170                 175

Leu Ser Ala Thr Ala Ser Gly Lys Val Glu Gly Val Lys Ala Ala Lys
            180                 185                 190

Leu Ala Thr Pro Phe Glu Arg Thr Lys Leu Ala Ala Tyr Thr Leu Gly
        195                 200                 205

Ala Met Thr Pro Cys Met Arg Leu Tyr Ala Tyr Ile Gly Lys Glu Leu
    210                 215                 220

Gln Val Phe Leu Glu Gly Glu Lys Ile His Pro Tyr Lys Lys Trp Ile
225                 230                 235                 240

Asp Ser Tyr Ala Ser Glu Ser Phe Gln Ala Ser Ala Leu Gln Thr Glu
                245                 250                 255

Asp Leu Leu Asp Lys Leu Ser Val Pro Leu Thr Gly Glu Glu Leu Asp
            260                 265                 270

Ile Ile Glu Lys Leu Tyr His Gln Ala Met Lys Leu Glu Ile Asp Phe
        275                 280                 285

Phe Leu Thr Gln Pro Leu Val Gln Lys Ala Val Ile Pro Leu Ser Lys
    290                 295                 300

Asp His Asn Pro Ala Glu His Arg Leu Thr Ile Phe Ser Asp Phe Asp
305                 310                 315                 320

Leu Thr Cys Thr Val Val Asp Ser Ser Ala Ile Leu Ala Glu Ile Ala
                325                 330                 335

Ile Ile Thr Ala Pro Arg Ser Asp Gln Asn Arg Pro Glu Asn Gln Ile
            340                 345                 350

Ala Arg Met Leu Ser Ala Asp Leu Arg Asn Thr Trp Gly Asp Leu Ser
        355                 360                 365

Lys Gln Tyr Thr Glu Glu Tyr Glu Gln Cys Ile Glu Lys Met Leu Leu
    370                 375                 380

Thr Glu Lys Ala Glu Lys Phe Asp Tyr Glu Arg Leu His Lys Thr Leu
385                 390                 395                 400

Glu Glu Leu Ser Asp Phe Glu Lys Arg Ala Asn Thr Arg Val Thr Glu
                405                 410                 415

Ser Gly Val Leu Lys Gly Leu Asn Leu Glu Asp Ile Lys Arg Ala Gly
            420                 425                 430

Gln Arg Leu Ile Leu Gln Asp Gly Cys Thr Asn Phe Phe Gln Ser Ile
```

-continued

```
                435                 440                 445
Ile Arg Asn Glu Asn Leu Asn Ala Asp Ile His Val Leu Ser Tyr Cys
    450                 455                 460

Trp Cys Gly Asp Leu Ile Arg Ser Ser Phe Ser Gly Gly Ile Asp
465                 470                 475                 480

Ala Leu Asn Val His Ala Asn Glu Phe Met Phe Gln Glu Ser Leu Ser
                485                 490                 495

Thr Gly Glu Ile Val Lys Lys Val Glu Ser Pro Ile Asp Lys Val Gln
            500                 505                 510

Ala Phe Ser Lys Ile Arg Met Asn Cys Gly Asn Asp Gln Lys Asn Leu
        515                 520                 525

Thr Leu Tyr Ile Gly Asp Ser Val Gly Asp Leu Leu Cys Leu Leu Glu
    530                 535                 540

Ala Asp Val Gly Ile Val Leu Gly Thr Ser Ser Ser Leu Arg Thr Val
545                 550                 555                 560

Gly Asn His Phe Gly Val Ser Phe Val Pro Leu Phe Pro Gly Val Val
                565                 570                 575

Gln Lys Gln Lys Met Cys Thr Gly Val Asp Ser Ser Ser Cys Trp Lys
            580                 585                 590

Gly Leu Ser Gly Val Leu Tyr Thr Ala Ser Ser Trp Ala Glu Ile His
        595                 600                 605

Ala Phe Val Leu Gly Ser
    610
```

<210> SEQ ID NO 11
<211> LENGTH: 1779
<212> TYPE: DNA
<213> ORGANISM: Populus trichocarpa
<220> FEATURE:
<221> NAME/KEY: CDS
<222> LOCATION: (1)..(1776)
<223> OTHER INFORMATION: Populus trichocarpa gene encoding TMP
      phosphatase [XP_002325785.2]

<400> SEQUENCE: 11

```
atg cgc cta ctc ttg ttt act tct cca aac cca atc aaa acc tct tca      48
Met Arg Leu Leu Leu Phe Thr Ser Pro Asn Pro Ile Lys Thr Ser Ser
1               5                   10                  15 tca cta tat ttc ctc aac tcg ctc cga tcc aac tta acc aaa cgc acc      96
Ser Leu Tyr Phe Leu Asn Ser Leu Arg Ser Asn Leu Thr Lys Arg Thr
            20                  25                  30 ttg cca act cgg aga tct ttc atc cct gca aga atg gca atc cct cca     144
Leu Pro Thr Arg Arg Ser Phe Ile Pro Ala Arg Met Ala Ile Pro Pro
        35                  40                  45 cga tca ata gca tca gcg cca tct tgc act aca aca tca ggc aga agt     192
Arg Ser Ile Ala Ser Ala Pro Ser Cys Thr Thr Thr Ser Gly Arg Ser
    50                  55                  60 aac atc aac att gaa gag ggt ctt gct agt aaa ttc tgg atc aag ttt     240
Asn Ile Asn Ile Glu Glu Gly Leu Ala Ser Lys Phe Trp Ile Lys Phe
65                  70                  75                  80 aga aga gaa tcc gtt ttt gct atg tac act cct ttt gtc atc tct ttg     288
Arg Arg Glu Ser Val Phe Ala Met Tyr Thr Pro Phe Val Ile Ser Leu
                85                  90                  95 gct tct ggc act ctc aag att gat tct ttc agg cat tat atc tct caa     336
Ala Ser Gly Thr Leu Lys Ile Asp Ser Phe Arg His Tyr Ile Ser Gln
            100                 105                 110 gat tct cac ttt ctc aaa tct ttt gct cat gcg ttt gaa tta gcg gaa     384
Asp Ser His Phe Leu Lys Ser Phe Ala His Ala Phe Glu Leu Ala Glu
        115                 120                 125
```

```
gag tgt gct gat gat gat gaa gca aag cta gca atc tcc gag ttg agg       432
Glu Cys Ala Asp Asp Asp Glu Ala Lys Leu Ala Ile Ser Glu Leu Arg
    130                 135                 140 aag ggt gtc tta gag gag ctg aag atg cac aat tca ttt gta cag gaa       480
Lys Gly Val Leu Glu Glu Leu Lys Met His Asn Ser Phe Val Gln Glu
145                 150                 155                 160 tgg ggt ata gac cca ggt aaa gag ggg act atc aat tct gct act gta       528
Trp Gly Ile Asp Pro Gly Lys Glu Gly Thr Ile Asn Ser Ala Thr Val
                165                 170                 175 aaa tac aca gat ttc ttg ttg gct aca gct tct ggg aag gtt gaa gga       576
Lys Tyr Thr Asp Phe Leu Leu Ala Thr Ala Ser Gly Lys Val Glu Gly
            180                 185                 190 gtg aaa ggt ctt ggt aaa ctt gca act cct ttt gaa aga aca aaa gtt       624
Val Lys Gly Leu Gly Lys Leu Ala Thr Pro Phe Glu Arg Thr Lys Val
        195                 200                 205 gca gcc tat act ctg ggt gcc atg aca cct tgc atg cgg ctg tat tcc       672
Ala Ala Tyr Thr Leu Gly Ala Met Thr Pro Cys Met Arg Leu Tyr Ser
    210                 215                 220 ttt cta ggc aag gaa ctc cag gca gtt tta gat ccg gag gaa gat ggg       720
Phe Leu Gly Lys Glu Leu Gln Ala Val Leu Asp Pro Glu Glu Asp Gly
225                 230                 235                 240 cac cct tac aag aag tgg att gac agt tat tcg tct gag agt ttt cag       768
His Pro Tyr Lys Lys Trp Ile Asp Ser Tyr Ser Ser Glu Ser Phe Gln
                245                 250                 255 gca tca gct ctg caa act gaa gac ttg ctg gat aaa ctt agt gtc tcc       816
Ala Ser Ala Leu Gln Thr Glu Asp Leu Leu Asp Lys Leu Ser Val Ser
            260                 265                 270 ttg aca ggc gag gag ctt gac atc att gaa aag ctt tat cac cag gcc       864
Leu Thr Gly Glu Glu Leu Asp Ile Ile Glu Lys Leu Tyr His Gln Ala
        275                 280                 285 atg aaa ctt gaa ata gaa ttc ttc ctt gct cag cca att gct cag aca       912
Met Lys Leu Glu Ile Glu Phe Phe Leu Ala Gln Pro Ile Ala Gln Thr
    290                 295                 300 act tta gct ccc ctg aca aaa ggg cat aac cct gaa gaa gac cgg ctt       960
Thr Leu Ala Pro Leu Thr Lys Gly His Asn Pro Glu Glu Asp Arg Leu
305                 310                 315                 320 gtc ata ttt tct gat ttt gat ttg aca tgc act gtt gtt gac tct tct      1008
Val Ile Phe Ser Asp Phe Asp Leu Thr Cys Thr Val Val Asp Ser Ser
                325                 330                 335 gcc att ttg gca gaa att gca ata cta aca gca cca aaa tct gat gtg      1056
Ala Ile Leu Ala Glu Ile Ala Ile Leu Thr Ala Pro Lys Ser Asp Val
            340                 345                 350 gtt caa cct gag act caa att gct cga atg tca tca gct gat ctg agg      1104
Val Gln Pro Glu Thr Gln Ile Ala Arg Met Ser Ser Ala Asp Leu Arg
        355                 360                 365 aac aca tgg ggt ctt ctt tct gga cag tac acg gaa gag tat gaa caa      1152
Asn Thr Trp Gly Leu Leu Ser Gly Gln Tyr Thr Glu Glu Tyr Glu Gln
    370                 375                 380 tgt att gaa agc att atg cca tct gca aaa gtg gaa ttc aac tat gaa      1200
Cys Ile Glu Ser Ile Met Pro Ser Ala Lys Val Glu Phe Asn Tyr Glu
385                 390                 395                 400 gct ctt tgt aaa gca ctt gaa caa ctt tca gac ttt gag cga agg gca      1248
Ala Leu Cys Lys Ala Leu Glu Gln Leu Ser Asp Phe Glu Arg Arg Ala
                405                 410                 415 aat tct aga gtg att gat tct gga gtt ctc aaa ggt ttg aat ctt gaa      1296
Asn Ser Arg Val Ile Asp Ser Gly Val Leu Lys Gly Leu Asn Leu Glu
            420                 425                 430 gat gta aaa cga gcg ggt gaa cgt ttg att ctt cag gat ggt tgc att      1344
Asp Val Lys Arg Ala Gly Glu Arg Leu Ile Leu Gln Asp Gly Cys Ile
```

```
                      435                 440                 445
ggt ttc ttt cag aaa att gtg aag aat gaa aat ttg aac act aat gtc      1392
Gly Phe Phe Gln Lys Ile Val Lys Asn Glu Asn Leu Asn Thr Asn Val
    450                 455                 460 cat gtg ctc tca tac tgc tgg tgt ggt gat ctc atc aga tca gct ttc      1440
His Val Leu Ser Tyr Cys Trp Cys Gly Asp Leu Ile Arg Ser Ala Phe
465                 470                 475                 480 tcc tca ggg ggt ttg gat gct cta aat att cat gca aat gag tta att      1488
Ser Ser Gly Gly Leu Asp Ala Leu Asn Ile His Ala Asn Glu Leu Ile
                485                 490                 495 ttt gaa gaa tca atc tcc acg gga gag att aac ttg act gtt tac att      1536
Phe Glu Glu Ser Ile Ser Thr Gly Glu Ile Asn Leu Thr Val Tyr Ile
            500                 505                 510 gga gat tca gtt ggt gac ttg ctt tgt cta ctt cag gca gat att ggt      1584
Gly Asp Ser Val Gly Asp Leu Leu Cys Leu Leu Gln Ala Asp Ile Gly
        515                 520                 525 att gta gtt gga tct agt gca agc tta agg agc gtg gga agt caa tat      1632
Ile Val Val Gly Ser Ser Ala Ser Leu Arg Ser Val Gly Ser Gln Tyr
    530                 535                 540 ggt gtt tct ttt gta cca ctg ttc cct ggc ttg gta aga aaa cag aaa      1680
Gly Val Ser Phe Val Pro Leu Phe Pro Gly Leu Val Arg Lys Gln Lys
545                 550                 555                 560 gaa tct gat gga gaa tct cct aat tgg aaa ggg cta tct ggc ata cta      1728
Glu Ser Asp Gly Glu Ser Pro Asn Trp Lys Gly Leu Ser Gly Ile Leu
                565                 570                 575 tat aca gtc tcc agt tgg tca gaa ata cat gcc ttc att ttg ggg tgg      1776
Tyr Thr Val Ser Ser Trp Ser Glu Ile His Ala Phe Ile Leu Gly Trp
            580                 585                 590 tag                                                                  1779

<210> SEQ ID NO 12
<211> LENGTH: 592
<212> TYPE: PRT
<213> ORGANISM: Populus trichocarpa

<400> SEQUENCE: 12

Met Arg Leu Leu Leu Phe Thr Ser Pro Asn Pro Ile Lys Thr Ser Ser
1               5                   10                  15

Ser Leu Tyr Phe Leu Asn Ser Leu Arg Ser Asn Leu Thr Lys Arg Thr
            20                  25                  30

Leu Pro Thr Arg Arg Ser Phe Ile Pro Ala Arg Met Ala Ile Pro Pro
        35                  40                  45

Arg Ser Ile Ala Ser Ala Pro Ser Cys Thr Thr Thr Ser Gly Arg Ser
    50                  55                  60

Asn Ile Asn Ile Glu Glu Gly Leu Ala Ser Lys Phe Trp Ile Lys Phe
65                  70                  75                  80

Arg Arg Glu Ser Val Phe Ala Met Tyr Thr Pro Phe Val Ile Ser Leu
                85                  90                  95

Ala Ser Gly Thr Leu Lys Ile Asp Ser Phe Arg His Tyr Ile Ser Gln
            100                 105                 110

Asp Ser His Phe Leu Lys Ser Phe Ala His Ala Phe Glu Leu Ala Glu
        115                 120                 125

Glu Cys Ala Asp Asp Glu Ala Lys Leu Ala Ile Ser Glu Leu Arg
    130                 135                 140

Lys Gly Val Leu Glu Glu Leu Lys Met His Asn Ser Phe Val Gln Glu
145                 150                 155                 160

Trp Gly Ile Asp Pro Gly Lys Glu Gly Thr Ile Asn Ser Ala Thr Val
```

```
            165                 170                 175
Lys Tyr Thr Asp Phe Leu Leu Ala Thr Ala Ser Gly Lys Val Glu Gly
            180                 185                 190

Val Lys Gly Leu Gly Lys Leu Ala Thr Pro Phe Glu Arg Thr Lys Val
            195                 200                 205

Ala Ala Tyr Thr Leu Gly Ala Met Thr Pro Cys Met Arg Leu Tyr Ser
            210                 215                 220

Phe Leu Gly Lys Glu Leu Gln Ala Val Leu Asp Pro Glu Glu Asp Gly
225                 230                 235                 240

His Pro Tyr Lys Lys Trp Ile Asp Ser Tyr Ser Ser Glu Ser Phe Gln
            245                 250                 255

Ala Ser Ala Leu Gln Thr Glu Asp Leu Leu Asp Lys Leu Ser Val Ser
            260                 265                 270

Leu Thr Gly Glu Glu Leu Asp Ile Ile Glu Lys Leu Tyr His Gln Ala
            275                 280                 285

Met Lys Leu Glu Ile Glu Phe Phe Leu Ala Gln Pro Ile Ala Gln Thr
            290                 295                 300

Thr Leu Ala Pro Leu Thr Lys Gly His Asn Pro Glu Glu Asp Arg Leu
305                 310                 315                 320

Val Ile Phe Ser Asp Phe Asp Leu Thr Cys Thr Val Val Asp Ser Ser
            325                 330                 335

Ala Ile Leu Ala Glu Ile Ala Ile Leu Thr Ala Pro Lys Ser Asp Val
            340                 345                 350

Val Gln Pro Glu Thr Gln Ile Ala Arg Met Ser Ser Ala Asp Leu Arg
            355                 360                 365

Asn Thr Trp Gly Leu Leu Ser Gly Gln Tyr Thr Glu Glu Tyr Glu Gln
            370                 375                 380

Cys Ile Glu Ser Ile Met Pro Ser Ala Lys Val Glu Phe Asn Tyr Glu
385                 390                 395                 400

Ala Leu Cys Lys Ala Leu Glu Gln Leu Ser Asp Phe Glu Arg Arg Ala
            405                 410                 415

Asn Ser Arg Val Ile Asp Ser Gly Val Leu Lys Gly Leu Asn Leu Glu
            420                 425                 430

Asp Val Lys Arg Ala Gly Glu Arg Leu Ile Leu Gln Asp Gly Cys Ile
            435                 440                 445

Gly Phe Phe Gln Lys Ile Val Lys Asn Glu Asn Leu Asn Thr Asn Val
            450                 455                 460

His Val Leu Ser Tyr Cys Trp Cys Gly Asp Leu Ile Arg Ser Ala Phe
465                 470                 475                 480

Ser Ser Gly Gly Leu Asp Ala Leu Asn Ile His Ala Asn Glu Leu Ile
            485                 490                 495

Phe Glu Glu Ser Ile Ser Thr Gly Glu Ile Asn Leu Thr Val Tyr Ile
            500                 505                 510

Gly Asp Ser Val Gly Asp Leu Leu Cys Leu Leu Gln Ala Asp Ile Gly
            515                 520                 525

Ile Val Val Gly Ser Ser Ala Ser Leu Arg Ser Val Gly Ser Gln Tyr
            530                 535                 540

Gly Val Ser Phe Val Pro Leu Phe Pro Gly Leu Val Arg Lys Gln Lys
545                 550                 555                 560

Glu Ser Asp Gly Glu Ser Pro Asn Trp Lys Gly Leu Ser Gly Ile Leu
            565                 570                 575

Tyr Thr Val Ser Ser Trp Ser Glu Ile His Ala Phe Ile Leu Gly Trp
            580                 585                 590
```

```
<210> SEQ ID NO 13
<211> LENGTH: 1860
<212> TYPE: DNA
<213> ORGANISM: Jatropha curcas
<220> FEATURE:
<221> NAME/KEY: CDS
<222> LOCATION: (1)..(1857)
<223> OTHER INFORMATION: Jatropha curcas gene encoding TMP phosphatase
      [KDP23738.1]

<400> SEQUENCE: 13
```

| | | | | | | | | | | | | | | | | |
|---|---|---|---|---|---|---|---|---|---|---|---|---|---|---|---|---|
| atg | gcg | atc | cct | cca | aag | cta | gct | tcc | tca | tcg | tct | tcc | atg | gcc | gcc | 48 |
| Met | Ala | Ile | Pro | Pro | Lys | Leu | Ala | Ser | Ser | Ser | Ser | Ser | Met | Ala | Ala | |
| 1 | | | | 5 | | | | | 10 | | | | | 15 | | |
| tcc | cct | act | tct | gct | ggt | gga | acc | aac | gag | gaa | ggc | ctc | gct | agt | aaa | 96 |
| Ser | Pro | Thr | Ser | Ala | Gly | Gly | Thr | Asn | Glu | Glu | Gly | Leu | Ala | Ser | Lys | |
| | | | 20 | | | | | 25 | | | | | 30 | | | |
| ttc | tgg | atc | aag | ttt | cgc | cga | gaa | tcg | gtt | ctc | gct | atg | tac | act | cct | 144 |
| Phe | Trp | Ile | Lys | Phe | Arg | Arg | Glu | Ser | Val | Leu | Ala | Met | Tyr | Thr | Pro | |
| | 35 | | | | | 40 | | | | | 45 | | | | | |
| ttc | gtc | gtc | tct | ttt | gcc | gcc | ggc | aac | ctc | aag | att | gag | agt | ttt | agg | 192 |
| Phe | Val | Val | Ser | Phe | Ala | Ala | Gly | Asn | Leu | Lys | Ile | Glu | Ser | Phe | Arg | |
| 50 | | | | | 55 | | | | | 60 | | | | | | |
| cat | tac | atc | gct | cag | gat | ttt | cac | ttc | ctc | aaa | gcc | ttc | gct | cac | gcg | 240 |
| His | Tyr | Ile | Ala | Gln | Asp | Phe | His | Phe | Leu | Lys | Ala | Phe | Ala | His | Ala | |
| 65 | | | | | 70 | | | | | 75 | | | | | 80 | |
| tat | gaa | ttg | gca | gaa | gag | tgt | gct | gat | gat | gat | gat | gcc | aag | cta | gct | 288 |
| Tyr | Glu | Leu | Ala | Glu | Glu | Cys | Ala | Asp | Asp | Asp | Asp | Ala | Lys | Leu | Ala | |
| | | | | 85 | | | | | 90 | | | | | 95 | | |
| att | gcc | gcg | ttg | agg | aag | ggg | gtc | tta | gag | gag | ctg | aag | ttg | cat | aaa | 336 |
| Ile | Ala | Ala | Leu | Arg | Lys | Gly | Val | Leu | Glu | Glu | Leu | Lys | Leu | His | Lys | |
| | | | 100 | | | | | 105 | | | | | 110 | | | |
| tca | ttt | gta | cag | gaa | tgg | ggt | atg | gac | cct | tcc | aaa | gag | gtg | act | atc | 384 |
| Ser | Phe | Val | Gln | Glu | Trp | Gly | Met | Asp | Pro | Ser | Lys | Glu | Val | Thr | Ile | |
| | 115 | | | | | 120 | | | | | 125 | | | | | |
| aat | tct | gca | act | gca | aaa | tac | aca | gat | ttc | ttg | ttg | gct | aca | gct | tct | 432 |
| Asn | Ser | Ala | Thr | Ala | Lys | Tyr | Thr | Asp | Phe | Leu | Leu | Ala | Thr | Ala | Ser | |
| 130 | | | | | 135 | | | | | 140 | | | | | | |
| gga | aag | gtt | gaa | gga | gtg | aaa | ggt | cct | ggt | aaa | ctt | gca | act | cct | ttt | 480 |
| Gly | Lys | Val | Glu | Gly | Val | Lys | Gly | Pro | Gly | Lys | Leu | Ala | Thr | Pro | Phe | |
| 145 | | | | | 150 | | | | | 155 | | | | | 160 | |
| gaa | aga | aca | aaa | gtt | gca | gct | tac | act | ctt | ggt | acc | atg | aca | ccc | tgt | 528 |
| Glu | Arg | Thr | Lys | Val | Ala | Ala | Tyr | Thr | Leu | Gly | Thr | Met | Thr | Pro | Cys | |
| | | | | 165 | | | | | 170 | | | | | 175 | | |
| atg | agg | ttg | tat | gcc | ttt | cta | gct | aag | gag | ctg | caa | gca | cta | ata | gat | 576 |
| Met | Arg | Leu | Tyr | Ala | Phe | Leu | Ala | Lys | Glu | Leu | Gln | Ala | Leu | Ile | Asp | |
| | | | 180 | | | | | 185 | | | | | 190 | | | |
| gca | gaa | gct | ggt | att | cat | cct | tac | cag | aag | tgg | att | gac | aat | tac | tca | 624 |
| Ala | Glu | Ala | Gly | Ile | His | Pro | Tyr | Gln | Lys | Trp | Ile | Asp | Asn | Tyr | Ser | |
| | 195 | | | | | 200 | | | | | 205 | | | | | |
| tct | gag | agt | ttt | cag | gca | tca | gct | ctg | caa | act | gaa | gac | ttg | ctg | gat | 672 |
| Ser | Glu | Ser | Phe | Gln | Ala | Ser | Ala | Leu | Gln | Thr | Glu | Asp | Leu | Leu | Asp | |
| 210 | | | | | 215 | | | | | 220 | | | | | | |
| aaa | ctt | agt | gtc | cct | ttg | aca | ggc | gaa | gag | ctt | gac | atc | att | gaa | aag | 720 |
| Lys | Leu | Ser | Val | Pro | Leu | Thr | Gly | Glu | Glu | Leu | Asp | Ile | Ile | Glu | Lys | |
| 225 | | | | | 230 | | | | | 235 | | | | | 240 | |
| ctt | tat | cac | caa | gcc | atg | aaa | ctt | gaa | ata | gag | ttc | ttc | aat | gcg | cag | 768 |
| Leu | Tyr | His | Gln | Ala | Met | Lys | Leu | Glu | Ile | Glu | Phe | Phe | Asn | Ala | Gln | |
| | | | | 245 | | | | | 250 | | | | | 255 | | |
| cca | ctt | gat | cag | ccc | act | gtg | gtt | cct | ctg | aca | aaa | gag | cat | aac | cct | 816 |

```
                Pro Leu Asp Gln Pro Thr Val Val Pro Leu Thr Lys Glu His Asn Pro
                                260                 265                 270 cta gaa gat cgc ctc gtg ata ttt tct gat ttt gat ttg aca tgc aca          864
Leu Glu Asp Arg Leu Val Ile Phe Ser Asp Phe Asp Leu Thr Cys Thr
            275                 280                 285 gtt gtt gat tcc tct gcc att ttg gca gag att gca att tta aca gca          912
Val Val Asp Ser Ser Ala Ile Leu Ala Glu Ile Ala Ile Leu Thr Ala
        290                 295                 300 tca aaa tct gat cag tca caa tct gat aat caa aat gct agg atg tca          960
Ser Lys Ser Asp Gln Ser Gln Ser Asp Asn Gln Asn Ala Arg Met Ser
305                 310                 315                 320 tca act gag cta agg aac aca tgg gtt ctt ctc tct gga cag tat act         1008
Ser Thr Glu Leu Arg Asn Thr Trp Val Leu Leu Ser Gly Gln Tyr Thr
                325                 330                 335 gaa gaa tat gag caa tgc att gaa agc att ctg ccc tct gaa aaa atg         1056
Glu Glu Tyr Glu Gln Cys Ile Glu Ser Ile Leu Pro Ser Glu Lys Met
            340                 345                 350 gag ttc aac ttt gaa gct ttg tgt aaa gca ctc gaa caa ctc tca gac         1104
Glu Phe Asn Phe Glu Ala Leu Cys Lys Ala Leu Glu Gln Leu Ser Asp
        355                 360                 365 ttt gag cga agg gca aat gct aga gtt atc aaa tct gga gtt ctt aag         1152
Phe Glu Arg Arg Ala Asn Ala Arg Val Ile Lys Ser Gly Val Leu Lys
370                 375                 380 ggt ttg aat ctt gaa gac ata aaa cga gct gtg gag ttc aac ttt gaa         1200
Gly Leu Asn Leu Glu Asp Ile Lys Arg Ala Val Glu Phe Asn Phe Glu
385                 390                 395                 400 gct ttg tgt aaa gca ctc gaa caa ctc tca gac ttt gag cga agg gca         1248
Ala Leu Cys Lys Ala Leu Glu Gln Leu Ser Asp Phe Glu Arg Arg Ala
                405                 410                 415 aat gct aga gtt atc aaa tct gga gtt ctt aag ggt ttg aat ctt gaa         1296
Asn Ala Arg Val Ile Lys Ser Gly Val Leu Lys Gly Leu Asn Leu Glu
            420                 425                 430 gac ata aaa cga gct ggt gaa aga ctg att ctt caa gat ggc tgc acc         1344
Asp Ile Lys Arg Ala Gly Glu Arg Leu Ile Leu Gln Asp Gly Cys Thr
        435                 440                 445 agt ttt ttt cag aaa atc tcg aag aat gaa aat ctg aat gct aat ata         1392
Ser Phe Phe Gln Lys Ile Ser Lys Asn Glu Asn Leu Asn Ala Asn Ile
450                 455                 460 cat ttc ctc tca tat tgt tgg tgt gct gat ctg atc aga tct gct ttc         1440
His Phe Leu Ser Tyr Cys Trp Cys Ala Asp Leu Ile Arg Ser Ala Phe
465                 470                 475                 480 tca tca ggg ggt ttg gat gtt ctg aat ata cat gcg aat gag ttt gat         1488
Ser Ser Gly Gly Leu Asp Val Leu Asn Ile His Ala Asn Glu Phe Asp
                485                 490                 495 ttc gta gaa tca att tca acg ggt gag att att atg aag gtg gaa acc         1536
Phe Val Glu Ser Ile Ser Thr Gly Glu Ile Ile Met Lys Val Glu Thr
            500                 505                 510 cct aca gac aaa gcc caa gct ttt aat aat att tta atg aac tac agc         1584
Pro Thr Asp Lys Ala Gln Ala Phe Asn Asn Ile Leu Met Asn Tyr Ser
        515                 520                 525 cct gac aaa aag aat ttg act gtt tat att gga gac tca gtt ggg gac         1632
Pro Asp Lys Lys Asn Leu Thr Val Tyr Ile Gly Asp Ser Val Gly Asp
530                 535                 540 ttg ctt tgt ctg ctt gcg gca gat ata ggc atc gtg atc gga tca agc         1680
Leu Leu Cys Leu Leu Ala Ala Asp Ile Gly Ile Val Ile Gly Ser Ser
545                 550                 555                 560 tcc agc cta agg aga gtc gga agt cag ttt ggt gta aca ttt tta cca         1728
Ser Ser Leu Arg Arg Val Gly Ser Gln Phe Gly Val Thr Phe Leu Pro
                565                 570                 575
```

```
ttg tat cct ggc ttg gtt aaa aaa cag aga gag tat act gaa gga agc    1776
Leu Tyr Pro Gly Leu Val Lys Lys Gln Arg Glu Tyr Thr Glu Gly Ser
        580                 585                 590 tct tgg aat tgg aag ggt caa tct ggc gtt ctg tac aca gtt tct agt    1824
Ser Trp Asn Trp Lys Gly Gln Ser Gly Val Leu Tyr Thr Val Ser Ser
        595                 600                 605 tgg gct gaa ata cat tcc ttc gtt ttg gga tgg tag                    1860
Trp Ala Glu Ile His Ser Phe Val Leu Gly Trp
        610                 615
```

<210> SEQ ID NO 14
<211> LENGTH: 619
<212> TYPE: PRT
<213> ORGANISM: Jatropha curcas

<400> SEQUENCE: 14

```
Met Ala Ile Pro Pro Lys Leu Ala Ser Ser Ser Ser Met Ala Ala
1               5                   10                  15

Ser Pro Thr Ser Ala Gly Gly Thr Asn Glu Glu Gly Leu Ala Ser Lys
            20                  25                  30

Phe Trp Ile Lys Phe Arg Arg Glu Ser Val Leu Ala Met Tyr Thr Pro
        35                  40                  45

Phe Val Val Ser Phe Ala Ala Gly Asn Leu Lys Ile Glu Ser Phe Arg
    50                  55                  60

His Tyr Ile Ala Gln Asp Phe His Phe Leu Lys Ala Phe Ala His Ala
65                  70                  75                  80

Tyr Glu Leu Ala Glu Glu Cys Ala Asp Asp Asp Ala Lys Leu Ala
                85                  90                  95

Ile Ala Ala Leu Arg Lys Gly Val Leu Glu Glu Leu Lys Leu His Lys
            100                 105                 110

Ser Phe Val Gln Glu Trp Gly Met Asp Pro Ser Lys Val Thr Ile
        115                 120                 125

Asn Ser Ala Thr Ala Lys Tyr Thr Asp Phe Leu Leu Ala Thr Ala Ser
    130                 135                 140

Gly Lys Val Glu Gly Val Lys Gly Pro Gly Lys Leu Ala Thr Pro Phe
145                 150                 155                 160

Glu Arg Thr Lys Val Ala Ala Tyr Thr Leu Gly Thr Met Thr Pro Cys
                165                 170                 175

Met Arg Leu Tyr Ala Phe Leu Ala Lys Glu Leu Gln Ala Leu Ile Asp
            180                 185                 190

Ala Glu Ala Gly Ile His Pro Tyr Gln Lys Trp Ile Asp Asn Tyr Ser
        195                 200                 205

Ser Glu Ser Phe Gln Ala Ser Ala Leu Gln Thr Glu Asp Leu Leu Asp
    210                 215                 220

Lys Leu Ser Val Pro Leu Thr Gly Glu Glu Leu Asp Ile Ile Glu Lys
225                 230                 235                 240

Leu Tyr His Gln Ala Met Lys Leu Glu Ile Glu Phe Phe Asn Ala Gln
                245                 250                 255

Pro Leu Asp Gln Pro Thr Val Val Pro Leu Thr Lys Glu His Asn Pro
            260                 265                 270

Leu Glu Asp Arg Leu Val Ile Phe Ser Asp Phe Asp Leu Thr Cys Thr
        275                 280                 285

Val Val Asp Ser Ser Ala Ile Leu Ala Glu Ile Ala Ile Leu Thr Ala
    290                 295                 300

Ser Lys Ser Asp Gln Ser Gln Asp Asn Gln Asn Ala Arg Met Ser
305                 310                 315                 320
```

```
Ser Thr Glu Leu Arg Asn Thr Trp Val Leu Ser Gly Gln Tyr Thr
            325                 330                 335

Glu Glu Tyr Glu Gln Cys Ile Glu Ser Ile Leu Pro Ser Glu Lys Met
                340                 345                 350

Glu Phe Asn Phe Glu Ala Leu Cys Lys Ala Leu Glu Gln Leu Ser Asp
            355                 360                 365

Phe Glu Arg Arg Ala Asn Ala Arg Val Ile Lys Ser Gly Val Leu Lys
        370                 375                 380

Gly Leu Asn Leu Glu Asp Ile Lys Arg Ala Val Glu Phe Asn Phe Glu
385                 390                 395                 400

Ala Leu Cys Lys Ala Leu Glu Gln Leu Ser Asp Phe Glu Arg Arg Ala
                405                 410                 415

Asn Ala Arg Val Ile Lys Ser Gly Val Leu Lys Gly Leu Asn Leu Glu
            420                 425                 430

Asp Ile Lys Arg Ala Gly Glu Arg Leu Ile Leu Gln Asp Gly Cys Thr
        435                 440                 445

Ser Phe Phe Gln Lys Ile Ser Lys Asn Glu Asn Leu Asn Ala Asn Ile
    450                 455                 460

His Phe Leu Ser Tyr Cys Trp Cys Ala Asp Leu Ile Arg Ser Ala Phe
465                 470                 475                 480

Ser Ser Gly Gly Leu Asp Val Leu Asn Ile His Ala Asn Glu Phe Asp
                485                 490                 495

Phe Val Glu Ser Ile Ser Thr Gly Glu Ile Ile Met Lys Val Glu Thr
            500                 505                 510

Pro Thr Asp Lys Ala Gln Ala Phe Asn Asn Ile Leu Met Asn Tyr Ser
        515                 520                 525

Pro Asp Lys Lys Asn Leu Thr Val Tyr Ile Gly Asp Ser Val Gly Asp
    530                 535                 540

Leu Leu Cys Leu Leu Ala Ala Asp Ile Gly Ile Val Ile Gly Ser Ser
545                 550                 555                 560

Ser Ser Leu Arg Arg Val Gly Ser Gln Phe Gly Val Thr Phe Leu Pro
                565                 570                 575

Leu Tyr Pro Gly Leu Val Lys Lys Gln Arg Glu Tyr Thr Glu Gly Ser
            580                 585                 590

Ser Trp Asn Trp Lys Gly Gln Ser Gly Val Leu Tyr Thr Val Ser Ser
        595                 600                 605

Trp Ala Glu Ile His Ser Phe Val Leu Gly Trp
    610                 615

<210> SEQ ID NO 15
<211> LENGTH: 1842
<212> TYPE: DNA
<213> ORGANISM: Citrus sinensis
<220> FEATURE:
<221> NAME/KEY: CDS
<222> LOCATION: (1)..(1839)
<223> OTHER INFORMATION: Citrus sinensi gene encoding TMP phosphatase
      [XP_006484613.1]

<400> SEQUENCE: 15 atg cgc ttc ctt ttc aca aac cca atc aaa acc cca tta ctc tct tct       48
Met Arg Phe Leu Phe Thr Asn Pro Ile Lys Thr Pro Leu Leu Ser Ser
1               5                   10                  15 att ctt ttc cat tgt ccc aac tcg ccc cga ctc ggc ctt ctt gac tca       96
Ile Leu Phe His Cys Pro Asn Ser Pro Arg Leu Gly Leu Leu Asp Ser
            20                  25                  30
```

| | | |
|---|---|---|
| gtc cga gtc aac tca cct tct tct ttg aca act caa aga tcg tca ctt<br>Val Arg Val Asn Ser Pro Ser Ser Leu Thr Thr Gln Arg Ser Ser Leu<br>35                         40                     45 | | 144 |
| tcg atg gcg gcg att ccc cca aaa tcg ccg agc cct gag gag gag gga<br>Ser Met Ala Ala Ile Pro Pro Lys Ser Pro Ser Pro Glu Glu Glu Gly<br>50                         55                     60 | | 192 |
| ctc gcg agg agg ttg tgg atc aag ttt aag aga gaa tct gtg ttt gcc<br>Leu Ala Arg Arg Leu Trp Ile Lys Phe Lys Arg Glu Ser Val Phe Ala<br>65                         70                     75                     80 | | 240 |
| atg tac tcc ccg ttt acg gtt tgt ttg gct tct ggg aac cta aag ctt<br>Met Tyr Ser Pro Phe Thr Val Cys Leu Ala Ser Gly Asn Leu Lys Leu<br>                     85                     90                     95 | | 288 |
| gaa acc ttc agg cat tac atc gcc caa gat ttt cat ttt ctc aaa gct<br>Glu Thr Phe Arg His Tyr Ile Ala Gln Asp Phe His Phe Leu Lys Ala<br>                    100                  105                  110 | | 336 |
| ttc gcc caa gcg tat gaa ctg gcg gaa gaa tgt gct gat gat gat gat<br>Phe Ala Gln Ala Tyr Glu Leu Ala Glu Glu Cys Ala Asp Asp Asp Asp<br>                    115                  120                  125 | | 384 |
| gca aag tta tct atc tct gaa ttg agg aag ggt gta ctt gag gag tta<br>Ala Lys Leu Ser Ile Ser Glu Leu Arg Lys Gly Val Leu Glu Glu Leu<br>130                       135                  140 | | 432 |
| aaa atg cat gat tcc ttt gtg aag gag tgg ggt aca gat ctt gct aaa<br>Lys Met His Asp Ser Phe Val Lys Glu Trp Gly Thr Asp Leu Ala Lys<br>145                       150                  155                  160 | | 480 |
| atg gct act gtt aac tct gca act gta aag tat aca gag ttc ttg ttg<br>Met Ala Thr Val Asn Ser Ala Thr Val Lys Tyr Thr Glu Phe Leu Leu<br>                    165                  170                  175 | | 528 |
| gca aca gct tcc ggg aag gtc gaa ggt gtt aaa ggt cct gga aaa ctt<br>Ala Thr Ala Ser Gly Lys Val Glu Gly Val Lys Gly Pro Gly Lys Leu<br>                    180                  185                  190 | | 576 |
| gca acc cca ttt gag aaa act aaa gtt gcc gct tac aca ttg ggt gcc<br>Ala Thr Pro Phe Glu Lys Thr Lys Val Ala Ala Tyr Thr Leu Gly Ala<br>                    195                  200                  205 | | 624 |
| atg tca cct tgt atg agg ctc tat gct ttc ctt gga aag gaa ttc cat<br>Met Ser Pro Cys Met Arg Leu Tyr Ala Phe Leu Gly Lys Glu Phe His<br>210                       215                  220 | | 672 |
| ggc ctc cta aat gct aat gaa ggc aat cat cct tac aag aag tgg att<br>Gly Leu Leu Asn Ala Asn Glu Gly Asn His Pro Tyr Lys Lys Trp Ile<br>225                       230                  235                  240 | | 720 |
| gac aat tat tct tct gaa agt ttt cag gcc tca gct ctg caa aat gag<br>Asp Asn Tyr Ser Ser Glu Ser Phe Gln Ala Ser Ala Leu Gln Asn Glu<br>                    245                  250                  255 | | 768 |
| gac ttg ctg gat aaa ctt agt gtc tct ttg aca ggc gaa gaa cta gac<br>Asp Leu Leu Asp Lys Leu Ser Val Ser Leu Thr Gly Glu Glu Leu Asp<br>                    260                  265                  270 | | 816 |
| ata ata gaa aag ctc tat cac caa gcc atg aaa ctt gaa gta gag ttc<br>Ile Ile Glu Lys Leu Tyr His Gln Ala Met Lys Leu Glu Val Glu Phe<br>                    275                  280                  285 | | 864 |
| ttc tgt gct cag cca ctt gct cag ccc act gta gtt cct ctg att aaa<br>Phe Cys Ala Gln Pro Leu Ala Gln Pro Thr Val Val Pro Leu Ile Lys<br>290                       295                  300 | | 912 |
| ggg cat aat cct gca gga gac cgt cta att ata ttt tct gat ttc gat<br>Gly His Asn Pro Ala Gly Asp Arg Leu Ile Ile Phe Ser Asp Phe Asp<br>305                       310                  315                  320 | | 960 |
| ttg act tgc acc att gtt gat tcc tct gcc att ttg gca gag atc gca<br>Leu Thr Cys Thr Ile Val Asp Ser Ser Ala Ile Leu Ala Glu Ile Ala<br>                    325                  330                  335 | | 1008 |
| ata gtg aca gca cca aaa tct gac cag aat caa cct gaa aat caa ctt<br>Ile Val Thr Ala Pro Lys Ser Asp Gln Asn Gln Pro Glu Asn Gln Leu<br>340                       345                  350 | | 1056 |

```
ggt cgg atg tca tca ggt gag ctg agg aac aca tgg ggt ctt ctt tcc     1104
Gly Arg Met Ser Ser Gly Glu Leu Arg Asn Thr Trp Gly Leu Leu Ser
            355                 360                 365 aaa cag tac aca gag gag tac gaa caa tgc att gaa agc ttc atg ccc     1152
Lys Gln Tyr Thr Glu Glu Tyr Glu Gln Cys Ile Glu Ser Phe Met Pro
370                 375                 380 tct gag aaa gtg gag aat ttc aac tat gaa act ttg cat aaa gca ctt     1200
Ser Glu Lys Val Glu Asn Phe Asn Tyr Glu Thr Leu His Lys Ala Leu
385                 390                 395                 400 gag caa ctc tca cac ttt gag aag agg gca aat tct aga gtg atc gaa     1248
Glu Gln Leu Ser His Phe Glu Lys Arg Ala Asn Ser Arg Val Ile Glu
            405                 410                 415 tct gga gtt ctc aag ggt ata aat ctt gaa gat att aaa aaa gct ggt     1296
Ser Gly Val Leu Lys Gly Ile Asn Leu Glu Asp Ile Lys Lys Ala Gly
        420                 425                 430 gaa cgc ctg agt ctt caa gat ggt tgc act acc ttc ttt cag aaa gtt     1344
Glu Arg Leu Ser Leu Gln Asp Gly Cys Thr Thr Phe Phe Gln Lys Val
435                 440                 445 gta aag aat gaa aat ttg aat gct aat gtc cat gtg ctt tca tac tgt     1392
Val Lys Asn Glu Asn Leu Asn Ala Asn Val His Val Leu Ser Tyr Cys
450                 455                 460 tgg tgt ggt gat ctc atc aga gca tct ttt tct tca gca ggt tta aat     1440
Trp Cys Gly Asp Leu Ile Arg Ala Ser Phe Ser Ser Ala Gly Leu Asn
465                 470                 475                 480 gca ctg aat gta cat gcg aat gag ttc tca ttc aaa gaa tct att tca     1488
Ala Leu Asn Val His Ala Asn Glu Phe Ser Phe Lys Glu Ser Ile Ser
                485                 490                 495 acg ggt gaa att att gag aaa gtg gag tcc ccc att gac aaa gtt caa     1536
Thr Gly Glu Ile Ile Glu Lys Val Glu Ser Pro Ile Asp Lys Val Gln
            500                 505                 510 gct ttc aac aat act tta gag aaa tac gga act gac aga aag aac ttg     1584
Ala Phe Asn Asn Thr Leu Glu Lys Tyr Gly Thr Asp Arg Lys Asn Leu
        515                 520                 525 agt gtt tac att gga gac tct gtg ggt gac ttg ctt tgt ctg ctt gag     1632
Ser Val Tyr Ile Gly Asp Ser Val Gly Asp Leu Leu Cys Leu Leu Glu
530                 535                 540 gct gat ata ggc att gta atc ggg tct agc tca agc tta agg aga gtg     1680
Ala Asp Ile Gly Ile Val Ile Gly Ser Ser Ser Ser Leu Arg Arg Val
545                 550                 555                 560 gga tct caa ttt ggt gtt aca ttt atc ccg ttg tac cct ggc ttg gtt     1728
Gly Ser Gln Phe Gly Val Thr Phe Ile Pro Leu Tyr Pro Gly Leu Val
                565                 570                 575 aag aaa cag aag gag tac act gaa gga agc tct tct aac tgg aag gag     1776
Lys Lys Gln Lys Glu Tyr Thr Glu Gly Ser Ser Ser Asn Trp Lys Glu
            580                 585                 590 aaa tct ggc ata ctt tac aca gtc tca agt tgg gct gaa gta cat gcc     1824
Lys Ser Gly Ile Leu Tyr Thr Val Ser Ser Trp Ala Glu Val His Ala
        595                 600                 605 ttt atc ttg ggg tgg tag                                             1842
Phe Ile Leu Gly Trp
    610
```

<210> SEQ ID NO 16
<211> LENGTH: 613
<212> TYPE: PRT
<213> ORGANISM: Citrus sinensis

<400> SEQUENCE: 16

```
Met Arg Phe Leu Phe Thr Asn Pro Ile Lys Thr Pro Leu Leu Ser Ser
1               5                   10                  15
```

```
Ile Leu Phe His Cys Pro Asn Ser Pro Arg Leu Gly Leu Leu Asp Ser
             20                  25                  30

Val Arg Val Asn Ser Pro Ser Ser Leu Thr Thr Gln Arg Ser Ser Leu
         35                  40                  45

Ser Met Ala Ala Ile Pro Pro Lys Ser Pro Ser Pro Glu Glu Glu Gly
 50                  55                  60

Leu Ala Arg Arg Leu Trp Ile Lys Phe Lys Arg Glu Ser Val Phe Ala
 65                  70                  75                  80

Met Tyr Ser Pro Phe Thr Val Cys Leu Ala Ser Gly Asn Leu Lys Leu
                 85                  90                  95

Glu Thr Phe Arg His Tyr Ile Ala Gln Asp Phe His Phe Leu Lys Ala
             100                 105                 110

Phe Ala Gln Ala Tyr Glu Leu Ala Glu Cys Ala Asp Asp Asp Asp
         115                 120                 125

Ala Lys Leu Ser Ile Ser Glu Leu Arg Lys Gly Val Leu Glu Glu Leu
 130                 135                 140

Lys Met His Asp Ser Phe Val Lys Glu Trp Gly Thr Asp Leu Ala Lys
145                 150                 155                 160

Met Ala Thr Val Asn Ser Ala Thr Val Lys Tyr Thr Glu Phe Leu Leu
                 165                 170                 175

Ala Thr Ala Ser Gly Lys Val Glu Gly Val Lys Gly Pro Gly Lys Leu
             180                 185                 190

Ala Thr Pro Phe Glu Lys Thr Lys Val Ala Ala Tyr Thr Leu Gly Ala
         195                 200                 205

Met Ser Pro Cys Met Arg Leu Tyr Ala Phe Leu Gly Lys Glu Phe His
 210                 215                 220

Gly Leu Leu Asn Ala Asn Glu Gly Asn His Pro Tyr Lys Lys Trp Ile
225                 230                 235                 240

Asp Asn Tyr Ser Ser Glu Ser Phe Gln Ala Ser Ala Leu Gln Asn Glu
                 245                 250                 255

Asp Leu Leu Asp Lys Leu Ser Val Ser Leu Thr Gly Glu Glu Leu Asp
             260                 265                 270

Ile Ile Glu Lys Leu Tyr His Gln Ala Met Lys Leu Glu Val Glu Phe
         275                 280                 285

Phe Cys Ala Gln Pro Leu Ala Gln Pro Thr Val Val Pro Leu Ile Lys
 290                 295                 300

Gly His Asn Pro Ala Gly Asp Arg Leu Ile Ile Phe Ser Asp Phe Asp
305                 310                 315                 320

Leu Thr Cys Thr Ile Val Asp Ser Ser Ala Ile Leu Ala Glu Ile Ala
                 325                 330                 335

Ile Val Thr Ala Pro Lys Ser Asp Gln Asn Gln Pro Glu Asn Gln Leu
             340                 345                 350

Gly Arg Met Ser Ser Gly Glu Leu Arg Asn Thr Trp Gly Leu Leu Ser
         355                 360                 365

Lys Gln Tyr Thr Glu Glu Tyr Glu Gln Cys Ile Glu Ser Phe Met Pro
 370                 375                 380

Ser Glu Lys Val Glu Asn Phe Asn Tyr Glu Thr Leu His Lys Ala Leu
385                 390                 395                 400

Glu Gln Leu Ser His Phe Glu Lys Arg Ala Asn Ser Arg Val Ile Glu
                 405                 410                 415

Ser Gly Val Leu Lys Gly Ile Asn Leu Glu Asp Ile Lys Lys Ala Gly
             420                 425                 430
```

-continued

```
Glu Arg Leu Ser Leu Gln Asp Gly Cys Thr Thr Phe Phe Gln Lys Val
            435                 440                 445

Val Lys Asn Glu Asn Leu Asn Ala Asn Val His Val Leu Ser Tyr Cys
450                 455                 460

Trp Cys Gly Asp Leu Ile Arg Ala Ser Phe Ser Ser Ala Gly Leu Asn
465                 470                 475                 480

Ala Leu Asn Val His Ala Asn Glu Phe Ser Phe Lys Glu Ser Ile Ser
                485                 490                 495

Thr Gly Glu Ile Ile Glu Lys Val Glu Ser Pro Ile Asp Lys Val Gln
            500                 505                 510

Ala Phe Asn Asn Thr Leu Glu Lys Tyr Gly Thr Asp Arg Lys Asn Leu
        515                 520                 525

Ser Val Tyr Ile Gly Asp Ser Val Gly Asp Leu Leu Cys Leu Leu Glu
    530                 535                 540

Ala Asp Ile Gly Ile Val Ile Gly Ser Ser Ser Ser Leu Arg Arg Val
545                 550                 555                 560

Gly Ser Gln Phe Gly Val Thr Phe Ile Pro Leu Tyr Pro Gly Leu Val
                565                 570                 575

Lys Lys Gln Lys Glu Tyr Thr Glu Gly Ser Ser Ser Asn Trp Lys Glu
            580                 585                 590

Lys Ser Gly Ile Leu Tyr Thr Val Ser Ser Trp Ala Glu Val His Ala
        595                 600                 605

Phe Ile Leu Gly Trp
    610

<210> SEQ ID NO 17
<211> LENGTH: 1728
<212> TYPE: DNA
<213> ORGANISM: Prunus persica
<220> FEATURE:
<221> NAME/KEY: CDS
<222> LOCATION: (1)..(1725)
<223> OTHER INFORMATION: Prunus persica gene encoding TMP phosphatase
      [XP_007199656.1]

<400> SEQUENCE: 17 atg gcg gca ttg gct cgt cat agc att gtt aga ctc aat cac gaa gga       48
Met Ala Ala Leu Ala Arg His Ser Ile Val Arg Leu Asn His Glu Gly
1               5                   10                  15 ggc cta gcc aga cgg ctg tgg ttc aag ttc aga gac gac tct gtt ttc       96
Gly Leu Ala Arg Arg Leu Trp Phe Lys Phe Arg Asp Asp Ser Val Phe
            20                  25                  30 tct ctc tac act ccc ttc ttc gtt ggc tta gcc tct gct act ctg cac      144
Ser Leu Tyr Thr Pro Phe Phe Val Gly Leu Ala Ser Ala Thr Leu His
        35                  40                  45 tct gaa act acc ttt cgc cat ttc atc tct cag gac ctc cat ttt ctc      192
Ser Glu Thr Thr Phe Arg His Phe Ile Ser Gln Asp Leu His Phe Leu
    50                  55                  60 aaa gcc ttc gtt ctc gca tat gaa ttg gcg gaa gat tgt gct gat gat      240
Lys Ala Phe Val Leu Ala Tyr Glu Leu Ala Glu Asp Cys Ala Asp Asp
65                  70                  75                  80 gag gac gac aag aat ggt tta cgc gat ttg aga aaa cgt gcc gtc ggc      288
Glu Asp Asp Lys Asn Gly Leu Arg Asp Leu Arg Lys Arg Ala Val Gly
                85                  90                  95 agg ctt caa atg cac gac aca ttt gtc cga gaa tgg ggt ttt gaa ttc      336
Arg Leu Gln Met His Asp Thr Phe Val Arg Glu Trp Gly Phe Glu Phe
            100                 105                 110 cca aat gag gac att tct aaa gac att gca aca acc aaa tac aca gat      384
Pro Asn Glu Asp Ile Ser Lys Asp Ile Ala Thr Thr Lys Tyr Thr Asp
```

-continued

|     |     |     |     |     |     |     |     |     |     |     |     |     |     |     |     |     |
|---|---|---|---|---|---|---|---|---|---|---|---|---|---|---|---|---|
|     | 115 |     |     |     | 120 |     |     |     | 125 |     |     |     |     |     |     |     |
| ttc | ttg | ctt | gca | aca | gca | tca | ggg | aaa | att | gaa | gga | gaa | aga | tcg | gtt | 432 |
| Phe | Leu | Leu | Ala | Thr | Ala | Ser | Gly | Lys | Ile | Glu | Gly | Glu | Arg | Ser | Val |     |
|     | 130 |     |     |     | 135 |     |     |     | 140 |     |     |     |     |     |     |     |
| ctg | gac | aaa | atc | gca | acc | cct | ttc | gaa | aag | acc | aag | gtt | gct | gca | tat | 480 |
| Leu | Asp | Lys | Ile | Ala | Thr | Pro | Phe | Glu | Lys | Thr | Lys | Val | Ala | Ala | Tyr |     |
| 145 |     |     |     |     | 150 |     |     |     | 155 |     |     |     |     |     | 160 |     |
| aca | ctt | gct | gct | ctg | gct | cct | tgt | atg | aga | ctc | tat | gcc | ttc | atc | agt | 528 |
| Thr | Leu | Ala | Ala | Leu | Ala | Pro | Cys | Met | Arg | Leu | Tyr | Ala | Phe | Ile | Ser |     |
|     |     |     |     | 165 |     |     |     |     | 170 |     |     |     |     | 175 |     |     |
| act | gag | atc | caa | ggc | att | ata | aat | cct | gat | caa | gat | agc | act | cac | att | 576 |
| Thr | Glu | Ile | Gln | Gly | Ile | Ile | Asn | Pro | Asp | Gln | Asp | Ser | Thr | His | Ile |     |
|     |     |     | 180 |     |     |     |     | 185 |     |     |     |     | 190 |     |     |     |
| tac | aaa | agc | tgg | ata | gaa | aat | tat | tcg | tct | caa | gtt | ttc | gag | gaa | ata | 624 |
| Tyr | Lys | Ser | Trp | Ile | Glu | Asn | Tyr | Ser | Ser | Gln | Val | Phe | Glu | Glu | Ile |     |
|     |     | 195 |     |     |     |     | 200 |     |     |     |     | 205 |     |     |     |     |
| gcc | ctg | caa | aat | gaa | gac | atg | cta | gat | aaa | ctt | agt | gtt | tct | ttg | act | 672 |
| Ala | Leu | Gln | Asn | Glu | Asp | Met | Leu | Asp | Lys | Leu | Ser | Val | Ser | Leu | Thr |     |
|     | 210 |     |     |     |     | 215 |     |     |     |     | 220 |     |     |     |     |     |
| ggt | gag | gag | ctt | gag | att | ata | gag | aag | ctc | tat | cat | caa | gct | atg | aag | 720 |
| Gly | Glu | Glu | Leu | Glu | Ile | Ile | Glu | Lys | Leu | Tyr | His | Gln | Ala | Met | Lys |     |
| 225 |     |     |     |     | 230 |     |     |     | 235 |     |     |     |     |     | 240 |     |
| ctt | caa | gta | gat | ttt | att | gct | gct | caa | cca | att | tct | gat | cag | caa | tct | 768 |
| Leu | Gln | Val | Asp | Phe | Ile | Ala | Ala | Gln | Pro | Ile | Ser | Asp | Gln | Gln | Ser |     |
|     |     |     |     | 245 |     |     |     |     | 250 |     |     |     |     | 255 |     |     |
| gta | gtt | cct | ttg | tct | cgg | gtg | cat | gac | ttt | agc | aaa | cgc | cat | ctt | acg | 816 |
| Val | Val | Pro | Leu | Ser | Arg | Val | His | Asp | Phe | Ser | Lys | Arg | His | Leu | Thr |     |
|     |     |     | 260 |     |     |     |     | 265 |     |     |     |     | 270 |     |     |     |
| ata | ctt | tgt | gac | ttt | gat | ttg | gca | tgc | act | gct | ttt | gat | tct | gct | gcc | 864 |
| Ile | Leu | Cys | Asp | Phe | Asp | Leu | Ala | Cys | Thr | Ala | Phe | Asp | Ser | Ala | Ala |     |
|     |     | 275 |     |     |     |     | 280 |     |     |     |     | 285 |     |     |     |     |
| ata | ttg | gct | gag | att | gcg | atc | ata | aca | gca | cca | aag | gct | gat | atg | gat | 912 |
| Ile | Leu | Ala | Glu | Ile | Ala | Ile | Ile | Thr | Ala | Pro | Lys | Ala | Asp | Met | Asp |     |
|     | 290 |     |     |     |     | 295 |     |     |     |     | 300 |     |     |     |     |     |
| gga | tct | gat | caa | acc | caa | ctt | gct | cgg | atg | cca | tca | gca | gac | tta | agg | 960 |
| Gly | Ser | Asp | Gln | Thr | Gln | Leu | Ala | Arg | Met | Pro | Ser | Ala | Asp | Leu | Arg |     |
| 305 |     |     |     |     | 310 |     |     |     |     | 315 |     |     |     |     | 320 |     |
| agc | aca | tgg | gat | gtt | ctt | tca | acc | caa | tac | act | gaa | caa | ttt | gaa | caa | 1008 |
| Ser | Thr | Trp | Asp | Val | Leu | Ser | Thr | Gln | Tyr | Thr | Glu | Gln | Phe | Glu | Gln |     |
|     |     |     |     | 325 |     |     |     |     | 330 |     |     |     |     | 335 |     |     |
| tgt | gta | gaa | agc | att | gtg | gcc | agt | gag | aga | gtg | gaa | gaa | ttc | gat | tat | 1056 |
| Cys | Val | Glu | Ser | Ile | Val | Ala | Ser | Glu | Arg | Val | Glu | Glu | Phe | Asp | Tyr |     |
|     |     |     | 340 |     |     |     |     | 345 |     |     |     |     | 350 |     |     |     |
| gaa | cgt | ctg | tgt | agc | gcg | ctt | gaa | caa | ctt | gcg | gag | ttt | gag | aga | aag | 1104 |
| Glu | Arg | Leu | Cys | Ser | Ala | Leu | Glu | Gln | Leu | Ala | Glu | Phe | Glu | Arg | Lys |     |
|     |     | 355 |     |     |     |     | 360 |     |     |     |     | 365 |     |     |     |     |
| gca | aat | gaa | agg | gtg | gtt | cag | tca | gga | gtg | ttg | aag | ggt | tta | aat | gcg | 1152 |
| Ala | Asn | Glu | Arg | Val | Val | Gln | Ser | Gly | Val | Leu | Lys | Gly | Leu | Asn | Ala |     |
|     | 370 |     |     |     |     | 375 |     |     |     |     | 380 |     |     |     |     |     |
| gag | gat | ata | aaa | agg | gct | gga | cag | agc | ctc | att | ctg | caa | gat | ggt | tgc | 1200 |
| Glu | Asp | Ile | Lys | Arg | Ala | Gly | Gln | Ser | Leu | Ile | Leu | Gln | Asp | Gly | Cys |     |
| 385 |     |     |     |     | 390 |     |     |     |     | 395 |     |     |     |     | 400 |     |
| aga | agc | ttc | ttt | cag | aag | att | gtg | aaa | aat | aaa | aat | ctg | aaa | act | gat | 1248 |
| Arg | Ser | Phe | Phe | Gln | Lys | Ile | Val | Lys | Asn | Lys | Asn | Leu | Lys | Thr | Asp |     |
|     |     |     |     | 405 |     |     |     |     | 410 |     |     |     |     | 415 |     |     |
| gtt | cat | gtg | ctt | tca | tac | tgc | tgg | tgt | aat | gac | ctc | att | gta | tca | gct | 1296 |
| Val | His | Val | Leu | Ser | Tyr | Cys | Trp | Cys | Asn | Asp | Leu | Ile | Val | Ser | Ala |     |
|     |     |     || 420 |     |     |     |     | 425 |     |     |     |     | 430 |     |     |     |
| ttc | tct | tca | gga | gat | ttg | aat | gtc | ttg | aat | gta | cat | tca | aat | gag | ttg | 1344 |

```
Phe Ser Ser Gly Asp Leu Asn Val Leu Asn Val His Ser Asn Glu Leu
            435                 440                 445 gtt tat caa gaa tct gtc aca act ggt gaa att gta aag aag atg gag     1392
Val Tyr Gln Glu Ser Val Thr Thr Gly Glu Ile Val Lys Lys Met Glu
450                 455                 460 tct ccc atg gaa aag ctt caa gtc ttc aac gac gtc cta atc gac cgc     1440
Ser Pro Met Glu Lys Leu Gln Val Phe Asn Asp Val Leu Ile Asp Arg
465                 470                 475                 480 agg ggc gaa ggc aat aaa cac ttg aca gtt tac att gga ggc tca gtg     1488
Arg Gly Glu Gly Asn Lys His Leu Thr Val Tyr Ile Gly Gly Ser Val
                485                 490                 495 ggt gac ttg ctt tgc ctg ctt gaa gca gat ata ggc att gta gtt ggt     1536
Gly Asp Leu Leu Cys Leu Leu Glu Ala Asp Ile Gly Ile Val Val Gly
            500                 505                 510 tca agt tca agc cta agg aga cta ggt gat cat ttt ggt gtt tcc ttt     1584
Ser Ser Ser Ser Leu Arg Arg Leu Gly Asp His Phe Gly Val Ser Phe
        515                 520                 525 gtc cca ttg ttc tct ggc ttg gtg aag agg cag aaa gaa ctt gct gat     1632
Val Pro Leu Phe Ser Gly Leu Val Lys Arg Gln Lys Glu Leu Ala Asp
530                 535                 540 caa gat tgt gcc tct aat tgg tgg aaa cca ttg tct ggt gtt ctt tat     1680
Gln Asp Cys Ala Ser Asn Trp Trp Lys Pro Leu Ser Gly Val Leu Tyr
545                 550                 555                 560 acg gtg tct agt tgg gct gaa ata cag gca ttc att ttg ggt aca tag     1728
Thr Val Ser Ser Trp Ala Glu Ile Gln Ala Phe Ile Leu Gly Thr
                565                 570                 575

<210> SEQ ID NO 18
<211> LENGTH: 575
<212> TYPE: PRT
<213> ORGANISM: Prunus persica

<400> SEQUENCE: 18

Met Ala Ala Leu Ala Arg His Ser Ile Val Arg Leu Asn His Glu Gly
1               5                   10                  15

Gly Leu Ala Arg Arg Leu Trp Phe Lys Phe Arg Asp Asp Ser Val Phe
            20                  25                  30

Ser Leu Tyr Thr Pro Phe Phe Val Gly Leu Ala Ser Ala Thr Leu His
        35                  40                  45

Ser Glu Thr Thr Phe Arg His Phe Ile Ser Gln Asp Leu His Phe Leu
    50                  55                  60

Lys Ala Phe Val Leu Ala Tyr Glu Leu Ala Glu Asp Cys Ala Asp Asp
65                  70                  75                  80

Glu Asp Asp Lys Asn Gly Leu Arg Asp Leu Arg Lys Arg Ala Val Gly
                85                  90                  95

Arg Leu Gln Met His Asp Thr Phe Val Arg Glu Trp Gly Phe Glu Phe
            100                 105                 110

Pro Asn Glu Asp Ile Ser Lys Asp Ile Ala Thr Thr Lys Tyr Thr Asp
        115                 120                 125

Phe Leu Leu Ala Thr Ala Ser Gly Lys Ile Glu Gly Glu Arg Ser Val
    130                 135                 140

Leu Asp Lys Ile Ala Thr Pro Phe Glu Lys Thr Lys Val Ala Ala Tyr
145                 150                 155                 160

Thr Leu Ala Ala Leu Ala Pro Cys Met Arg Leu Tyr Ala Phe Ile Ser
                165                 170                 175

Thr Glu Ile Gln Gly Ile Ile Asn Pro Asp Gln Asp Ser Thr His Ile
            180                 185                 190
```

Tyr Lys Ser Trp Ile Glu Asn Tyr Ser Ser Gln Val Phe Glu Ile
            195                 200                 205

Ala Leu Gln Asn Glu Asp Met Leu Asp Lys Leu Ser Val Ser Leu Thr
210                 215                 220

Gly Glu Glu Leu Glu Ile Ile Glu Lys Leu Tyr His Gln Ala Met Lys
225                 230                 235                 240

Leu Gln Val Asp Phe Ile Ala Ala Gln Pro Ile Ser Asp Gln Gln Ser
                245                 250                 255

Val Val Pro Leu Ser Arg Val His Asp Phe Ser Lys Arg His Leu Thr
            260                 265                 270

Ile Leu Cys Asp Phe Asp Leu Ala Cys Thr Ala Phe Asp Ser Ala Ala
        275                 280                 285

Ile Leu Ala Glu Ile Ala Ile Ile Thr Ala Pro Lys Ala Asp Met Asp
290                 295                 300

Gly Ser Asp Gln Thr Gln Leu Ala Arg Met Pro Ser Ala Asp Leu Arg
305                 310                 315                 320

Ser Thr Trp Asp Val Leu Ser Thr Gln Tyr Thr Glu Gln Phe Glu Gln
                325                 330                 335

Cys Val Glu Ser Ile Val Ala Ser Glu Arg Val Glu Glu Phe Asp Tyr
            340                 345                 350

Glu Arg Leu Cys Ser Ala Leu Glu Gln Leu Ala Glu Phe Glu Arg Lys
        355                 360                 365

Ala Asn Glu Arg Val Val Gln Ser Gly Val Leu Lys Gly Leu Asn Ala
370                 375                 380

Glu Asp Ile Lys Arg Ala Gly Gln Ser Leu Ile Leu Gln Asp Gly Cys
385                 390                 395                 400

Arg Ser Phe Phe Gln Lys Ile Val Lys Asn Lys Asn Leu Lys Thr Asp
                405                 410                 415

Val His Val Leu Ser Tyr Cys Trp Cys Asn Asp Leu Ile Val Ser Ala
            420                 425                 430

Phe Ser Ser Gly Asp Leu Asn Val Leu Asn Val His Ser Asn Glu Leu
        435                 440                 445

Val Tyr Gln Glu Ser Val Thr Thr Gly Glu Ile Val Lys Lys Met Glu
450                 455                 460

Ser Pro Met Glu Lys Leu Gln Val Phe Asn Asp Val Leu Ile Asp Arg
465                 470                 475                 480

Arg Gly Glu Gly Asn Lys His Leu Thr Val Tyr Ile Gly Gly Ser Val
                485                 490                 495

Gly Asp Leu Leu Cys Leu Leu Glu Ala Asp Ile Gly Ile Val Val Gly
            500                 505                 510

Ser Ser Ser Ser Leu Arg Arg Leu Gly Asp His Phe Gly Val Ser Phe
        515                 520                 525

Val Pro Leu Phe Ser Gly Leu Val Lys Arg Gln Lys Glu Leu Ala Asp
530                 535                 540

Gln Asp Cys Ala Ser Asn Trp Trp Lys Pro Leu Ser Gly Val Leu Tyr
545                 550                 555                 560

Thr Val Ser Ser Trp Ala Glu Ile Gln Ala Phe Ile Leu Gly Thr
                565                 570                 575

<210> SEQ ID NO 19
<211> LENGTH: 1944
<212> TYPE: DNA
<213> ORGANISM: Phoenix dactylifera
<220> FEATURE:
<221> NAME/KEY: CDS
<222> LOCATION: (1)..(1941)
<223> OTHER INFORMATION: Phoenix_dactylifera gene encoding TMP
      phosphatase [XP_008796407]

<400> SEQUENCE: 19

| | | | | | | | | | | | | | | | | |
|---|---|---|---|---|---|---|---|---|---|---|---|---|---|---|---|---|
| atg | cga | ttc | ctc | tcc | cct | ctt | ctc | ccc | ctc | cgc | cga | aac | cca | aac | cct | 48 |
| Met | Arg | Phe | Leu | Ser | Pro | Leu | Leu | Pro | Leu | Arg | Arg | Asn | Pro | Asn | Pro | |
| 1 | | | | 5 | | | | | 10 | | | | | 15 | | |
| agc | cct | agg | ttc | ttc | tcg | ctc | tcc | cct | ccc | ata | tcc | ctc | gcc | tcc | gcc | 96 |
| Ser | Pro | Arg | Phe | Phe | Ser | Leu | Ser | Pro | Pro | Ile | Ser | Leu | Ala | Ser | Ala | |
| | | | 20 | | | | | 25 | | | | | 30 | | | |
| tgc | ccc | cga | ttc | ggt | ttc | ttg | aat | cga | gat | cgc | ccc | cgg | cgc | cgc | ctt | 144 |
| Cys | Pro | Arg | Phe | Gly | Phe | Leu | Asn | Arg | Asp | Arg | Pro | Arg | Arg | Arg | Leu | |
| | | 35 | | | | | 40 | | | | | 45 | | | | |
| cca | aag | ggg | ttc | cga | tcg | atc | gcc | gcg | gcg | aat | cag | cgg | gcg | tcg | cct | 192 |
| Pro | Lys | Gly | Phe | Arg | Ser | Ile | Ala | Ala | Ala | Asn | Gln | Arg | Ala | Ser | Pro | |
| | 50 | | | | | 55 | | | | | 60 | | | | | |
| cca | aga | ttg | gtg | ccg | gag | agg | gcg | gcc | gcc | acg | agt | tct | tgg | cct | tct | 240 |
| Pro | Arg | Leu | Val | Pro | Glu | Arg | Ala | Ala | Ala | Thr | Ser | Ser | Trp | Pro | Ser | |
| 65 | | | | | 70 | | | | | 75 | | | | | 80 | |
| tca | gcc | gga | cga | gcc | atg | gca | gtg | gtg | gcg | acg | gcg | gtt | gaa | gaa | ggc | 288 |
| Ser | Ala | Gly | Arg | Ala | Met | Ala | Val | Val | Ala | Thr | Ala | Val | Glu | Glu | Gly | |
| | | | | 85 | | | | | 90 | | | | | 95 | | |
| tcc | gcg | gcg | aag | cgg | ttc | tgg | atc | agg | tcc | cgg | aag | gag | gcg | gtg | ttc | 336 |
| Ser | Ala | Ala | Lys | Arg | Phe | Trp | Ile | Arg | Ser | Arg | Lys | Glu | Ala | Val | Phe | |
| | | | 100 | | | | | 105 | | | | | 110 | | | |
| gcg | gag | tac | acc | ccg | ttc | gtg | gtg | tgc | ctg | gcg | gcg | ggg | aga | ctg | gag | 384 |
| Ala | Glu | Tyr | Thr | Pro | Phe | Val | Val | Cys | Leu | Ala | Ala | Gly | Arg | Leu | Glu | |
| | | | 115 | | | | | 120 | | | | | 125 | | | |
| atg | gag | gcc | ttc | cgc | gac | tac | att | gct | cag | gac | gtg | cac | ttc | ctc | aat | 432 |
| Met | Glu | Ala | Phe | Arg | Asp | Tyr | Ile | Ala | Gln | Asp | Val | His | Phe | Leu | Asn | |
| | | 130 | | | | | 135 | | | | | 140 | | | | |
| act | ttt | gcc | caa | gcg | tat | gag | atg | gcg | gaa | gag | tgt | gct | gat | gat | gat | 480 |
| Thr | Phe | Ala | Gln | Ala | Tyr | Glu | Met | Ala | Glu | Glu | Cys | Ala | Asp | Asp | Asp | |
| 145 | | | | | 150 | | | | | 155 | | | | | 160 | |
| gat | gcg | aag | gct | gca | ata | act | gat | ctg | agg | aaa | gct | gtt | ttg | gag | gaa | 528 |
| Asp | Ala | Lys | Ala | Ala | Ile | Thr | Asp | Leu | Arg | Lys | Ala | Val | Leu | Glu | Glu | |
| | | | | 165 | | | | | 170 | | | | | 175 | | |
| ctg | aaa | atg | cat | agt | tca | ttt | gtc | caa | gaa | tgg | gga | ata | gac | ccc | act | 576 |
| Leu | Lys | Met | His | Ser | Ser | Phe | Val | Gln | Glu | Trp | Gly | Ile | Asp | Pro | Thr | |
| | | | 180 | | | | | 185 | | | | | 190 | | | |
| aaa | gaa | atc | att | cct | ttc | cct | gca | aca | gta | aag | tac | acc | gac | ttc | ctg | 624 |
| Lys | Glu | Ile | Ile | Pro | Phe | Pro | Ala | Thr | Val | Lys | Tyr | Thr | Asp | Phe | Leu | |
| | | | 195 | | | | | 200 | | | | | 205 | | | |
| ctt | gct | aca | gct | gca | gga | aaa | gtt | gaa | gga | ggg | aaa | gat | cct | ggg | aaa | 672 |
| Leu | Ala | Thr | Ala | Ala | Gly | Lys | Val | Glu | Gly | Gly | Lys | Asp | Pro | Gly | Lys | |
| | 210 | | | | | 215 | | | | | 220 | | | | | |
| att | gtc | act | cct | ttt | gag | aag | aca | aaa | att | gct | gct | tat | act | gta | ggt | 720 |
| Ile | Val | Thr | Pro | Phe | Glu | Lys | Thr | Lys | Ile | Ala | Ala | Tyr | Thr | Val | Gly | |
| 225 | | | | | 230 | | | | | 235 | | | | | 240 | |
| gcc | atg | gct | cct | tgc | atg | agg | ctt | tat | gca | ttc | ttg | gga | aaa | gag | ctc | 768 |
| Ala | Met | Ala | Pro | Cys | Met | Arg | Leu | Tyr | Ala | Phe | Leu | Gly | Lys | Glu | Leu | |
| | | | | 245 | | | | | 250 | | | | | 255 | | |
| cag | acg | tgt | ctg | caa | ctt | gac | gaa | aat | tgt | cat | ccc | tac | aaa | aag | tgg | 816 |
| Gln | Thr | Cys | Leu | Gln | Leu | Asp | Glu | Asn | Cys | His | Pro | Tyr | Lys | Lys | Trp | |
| | | | 260 | | | | | 265 | | | | | 270 | | | |
| att | gat | aat | tat | tcc | tct | gaa | agt | ttt | gag | aca | gct | gct | gtg | caa | ata | 864 |
| Ile | Asp | Asn | Tyr | Ser | Ser | Glu | Ser | Phe | Glu | Thr | Ala | Ala | Val | Gln | Ile | |
| | | 275 | | | | | 280 | | | | | 285 | | | | |
| gaa | gaa | ttg | ctt | gac | aaa | ttg | agt | gtt | tca | ttg | act | ggg | gag | gag | ctt | 912 |

```
                Glu Glu Leu Leu Asp Lys Leu Ser Val Ser Leu Thr Gly Glu Glu Leu
                    290                 295                 300 gaa gac ata gaa aag ctt tac cgc caa gct atg aaa ctt gaa att gaa            960
Glu Asp Ile Glu Lys Leu Tyr Arg Gln Ala Met Lys Leu Glu Ile Glu
305                 310                 315                 320 ttt ttt ctt gct cag cca att gtc cga cca gct gta gtt cct ttg aca           1008
Phe Phe Leu Ala Gln Pro Ile Val Arg Pro Ala Val Val Pro Leu Thr
                    325                 330                 335 aga ctg cat gat ccg gca aat tgc ctt gtc att ttt tct gat ttt gac           1056
Arg Leu His Asp Pro Ala Asn Cys Leu Val Ile Phe Ser Asp Phe Asp
                340                 345                 350 ttg aca tgc agt gta gtt gat tcc tct gcc att tta gca gag att gca           1104
Leu Thr Cys Ser Val Val Asp Ser Ser Ala Ile Leu Ala Glu Ile Ala
            355                 360                 365 ata tta agt gca cca aag act gat aag act ggg act gat aat tta gat           1152
Ile Leu Ser Ala Pro Lys Thr Asp Lys Thr Gly Thr Asp Asn Leu Asp
        370                 375                 380 gct cga agg tct tct tca gaa atg aga aac tca tgg gat gct ctt tct           1200
Ala Arg Arg Ser Ser Ser Glu Met Arg Asn Ser Trp Asp Ala Leu Ser
385                 390                 395                 400 aaa cag tat aca gaa gag tat gag cag tgc ata gaa agc tta ctt cca           1248
Lys Gln Tyr Thr Glu Glu Tyr Glu Gln Cys Ile Glu Ser Leu Leu Pro
                    405                 410                 415 tta gaa gaa gct aaa aca ttt gat tat gaa ggc ctt tgc aaa agt ttg           1296
Leu Glu Glu Ala Lys Thr Phe Asp Tyr Glu Gly Leu Cys Lys Ser Leu
                420                 425                 430 ggc cag ctc tct gag ttt gag aaa cga gca aat tcc agg gtt att gag           1344
Gly Gln Leu Ser Glu Phe Glu Lys Arg Ala Asn Ser Arg Val Ile Glu
            435                 440                 445 tct ggg gtg cta aag gga atg aat cta gat gac ata aaa aga gct ggg           1392
Ser Gly Val Leu Lys Gly Met Asn Leu Asp Asp Ile Lys Arg Ala Gly
        450                 455                 460 gaa cgt ttg atc ctc caa gat ggt tgt ata gat ttt ttt cag aag gtt           1440
Glu Arg Leu Ile Leu Gln Asp Gly Cys Ile Asp Phe Phe Gln Lys Val
465                 470                 475                 480 gta aag gaa aag gaa aat cta aat tta gat ctc cat gta ctt tct tat           1488
Val Lys Glu Lys Glu Asn Leu Asn Leu Asp Leu His Val Leu Ser Tyr
                    485                 490                 495 tgt tgg tgt gcg gat cta ata agg tca gct ttt tca tca gta ggt tgc           1536
Cys Trp Cys Ala Asp Leu Ile Arg Ser Ala Phe Ser Ser Val Gly Cys
                500                 505                 510 cta aat gat ttg aac ata cac tca aat gag ttc aac tat caa gaa tct           1584
Leu Asn Asp Leu Asn Ile His Ser Asn Glu Phe Asn Tyr Gln Glu Ser
            515                 520                 525 att tca acg ggt gaa att gtt agg aag atg gaa tca ccc atg gac aag           1632
Ile Ser Thr Gly Glu Ile Val Arg Lys Met Glu Ser Pro Met Asp Lys
        530                 535                 540 gtt gaa gca ttc aaa agt atc tta agc aac ctt gga agc aat gag aag           1680
Val Glu Ala Phe Lys Ser Ile Leu Ser Asn Leu Gly Ser Asn Glu Lys
545                 550                 555                 560 cgc tta tct gtg tac att gga gat tcg gtt ggt gac ttg ctt tgc ctg           1728
Arg Leu Ser Val Tyr Ile Gly Asp Ser Val Gly Asp Leu Leu Cys Leu
                    565                 570                 575 ttg gaa gca gat gtt ggt att gtg att gga tca agc act agc tta agg           1776
Leu Glu Ala Asp Val Gly Ile Val Ile Gly Ser Ser Thr Ser Leu Arg
                580                 585                 590 aga atc ggg aag cag ttt ggt gtt tct ttc att cca ctc ttc cgt ggt           1824
Arg Ile Gly Lys Gln Phe Gly Val Ser Phe Ile Pro Leu Phe Arg Gly
            595                 600                 605
```

```
ttg gta aac aag caa aga caa ctt aat gaa aaa gac tca tct atc tgg    1872
Leu Val Asn Lys Gln Arg Gln Leu Asn Glu Lys Asp Ser Ser Ile Trp
        610                 615                 620 aag ggg ttg tct ggt gtt ctt tat aca gca tca agc tgg tca gaa ata    1920
Lys Gly Leu Ser Gly Val Leu Tyr Thr Ala Ser Ser Trp Ser Glu Ile
625                 630                 635                 640 caa gct ttt att ttg ggg gca taa                                    1944
Gln Ala Phe Ile Leu Gly Ala
                645
```

<210> SEQ ID NO 20
<211> LENGTH: 647
<212> TYPE: PRT
<213> ORGANISM: Phoenix dactylifera

<400> SEQUENCE: 20

```
Met Arg Phe Leu Ser Pro Leu Pro Leu Arg Arg Asn Pro Asn Pro
1               5                   10                  15

Ser Pro Arg Phe Phe Ser Leu Ser Pro Pro Ile Ser Leu Ala Ser Ala
                20                  25                  30

Cys Pro Arg Phe Gly Phe Leu Asn Arg Asp Arg Pro Arg Arg Arg Leu
            35                  40                  45

Pro Lys Gly Phe Arg Ser Ile Ala Ala Ala Asn Gln Arg Ala Ser Pro
    50                  55                  60

Pro Arg Leu Val Pro Glu Arg Ala Ala Thr Ser Ser Trp Pro Ser
65                  70                  75                  80

Ser Ala Gly Arg Ala Met Ala Val Val Ala Thr Ala Val Glu Glu Gly
                85                  90                  95

Ser Ala Ala Lys Arg Phe Trp Ile Arg Ser Arg Lys Glu Ala Val Phe
            100                 105                 110

Ala Glu Tyr Thr Pro Phe Val Val Cys Leu Ala Ala Gly Arg Leu Glu
        115                 120                 125

Met Glu Ala Phe Arg Asp Tyr Ile Ala Gln Asp Val His Phe Leu Asn
    130                 135                 140

Thr Phe Ala Gln Ala Tyr Glu Met Ala Glu Glu Cys Ala Asp Asp Asp
145                 150                 155                 160

Asp Ala Lys Ala Ala Ile Thr Asp Leu Arg Lys Ala Val Leu Glu Glu
                165                 170                 175

Leu Lys Met His Ser Ser Phe Val Gln Glu Trp Gly Ile Asp Pro Thr
            180                 185                 190

Lys Glu Ile Ile Pro Phe Pro Ala Thr Val Lys Tyr Thr Asp Phe Leu
        195                 200                 205

Leu Ala Thr Ala Ala Gly Lys Val Glu Gly Gly Lys Asp Pro Gly Lys
    210                 215                 220

Ile Val Thr Pro Phe Glu Lys Thr Lys Ile Ala Ala Tyr Thr Val Gly
225                 230                 235                 240

Ala Met Ala Pro Cys Met Arg Leu Tyr Ala Phe Leu Gly Lys Glu Leu
                245                 250                 255

Gln Thr Cys Leu Gln Leu Asp Glu Asn Cys His Pro Tyr Lys Lys Trp
            260                 265                 270

Ile Asp Asn Tyr Ser Ser Glu Ser Phe Glu Thr Ala Ala Val Gln Ile
        275                 280                 285

Glu Glu Leu Leu Asp Lys Leu Ser Val Ser Leu Thr Gly Glu Glu Leu
    290                 295                 300

Glu Asp Ile Glu Lys Leu Tyr Arg Gln Ala Met Lys Leu Glu Ile Glu
305                 310                 315                 320
```

```
Phe Phe Leu Ala Gln Pro Ile Val Arg Pro Ala Val Pro Leu Thr
                325                 330                 335

Arg Leu His Asp Pro Ala Asn Cys Leu Val Ile Phe Ser Asp Phe Asp
                340                 345                 350

Leu Thr Cys Ser Val Val Asp Ser Ser Ala Ile Leu Ala Glu Ile Ala
                355                 360                 365

Ile Leu Ser Ala Pro Lys Thr Asp Lys Thr Gly Thr Asp Asn Leu Asp
                370                 375                 380

Ala Arg Arg Ser Ser Ser Glu Met Arg Asn Ser Trp Asp Ala Leu Ser
385                 390                 395                 400

Lys Gln Tyr Thr Glu Glu Tyr Glu Gln Cys Ile Glu Ser Leu Leu Pro
                405                 410                 415

Leu Glu Glu Ala Lys Thr Phe Asp Tyr Glu Gly Leu Cys Lys Ser Leu
                420                 425                 430

Gly Gln Leu Ser Glu Phe Glu Lys Arg Ala Asn Ser Arg Val Ile Glu
                435                 440                 445

Ser Gly Val Leu Lys Gly Met Asn Leu Asp Asp Ile Lys Arg Ala Gly
                450                 455                 460

Glu Arg Leu Ile Leu Gln Asp Gly Cys Ile Asp Phe Phe Gln Lys Val
465                 470                 475                 480

Val Lys Glu Lys Glu Asn Leu Asn Leu Asp Leu His Val Leu Ser Tyr
                485                 490                 495

Cys Trp Cys Ala Asp Leu Ile Arg Ser Ala Phe Ser Ser Val Gly Cys
                500                 505                 510

Leu Asn Asp Leu Asn Ile His Ser Asn Glu Phe Asn Tyr Gln Glu Ser
                515                 520                 525

Ile Ser Thr Gly Glu Ile Val Arg Lys Met Glu Ser Pro Met Asp Lys
                530                 535                 540

Val Glu Ala Phe Lys Ser Ile Leu Ser Asn Leu Gly Ser Asn Glu Lys
545                 550                 555                 560

Arg Leu Ser Val Tyr Ile Gly Asp Ser Val Gly Asp Leu Leu Cys Leu
                565                 570                 575

Leu Glu Ala Asp Val Gly Ile Val Ile Gly Ser Ser Thr Ser Leu Arg
                580                 585                 590

Arg Ile Gly Lys Gln Phe Gly Val Ser Phe Ile Pro Leu Phe Arg Gly
                595                 600                 605

Leu Val Asn Lys Gln Arg Gln Leu Asn Glu Lys Asp Ser Ser Ile Trp
                610                 615                 620

Lys Gly Leu Ser Gly Val Leu Tyr Thr Ala Ser Ser Trp Ser Glu Ile
625                 630                 635                 640

Gln Ala Phe Ile Leu Gly Ala
                645
```

<210> SEQ ID NO 21
<211> LENGTH: 1860
<212> TYPE: DNA
<213> ORGANISM: Zea mays
<220> FEATURE:
<221> NAME/KEY: CDS
<222> LOCATION: (1)..(1857)
<223> OTHER INFORMATION: Zea mays gene encoding TMP phosphatase
      [XP_008678418.1]

<400> SEQUENCE: 21

```
atg ctt gtt ctc cgc cgt ctc cgc ctc cgc ctc cca ctg cca cgc cct      48
Met Leu Val Leu Arg Arg Leu Arg Leu Arg Leu Pro Leu Pro Arg Pro
```

```
1               5                   10                  15
ctt ctc gtc tcc tcc ttc tcc tcc acc tcc ccc tcc tca ccc tcg        96
Leu Leu Val Ser Ser Phe Ser Ser Thr Ser Pro Ser Ser Pro Ser
             20                  25                  30 acc tct agc tcc tcc tcc tgt tgg tcg tcg aca ggc gaa agt aga agg   144
Thr Ser Ser Ser Ser Ser Cys Trp Ser Ser Thr Gly Glu Ser Arg Arg
         35                  40                  45 gcc atg gcg tca tct cct tct ccc gat tcg gcc gcg gtc gtt gcc gag   192
Ala Met Ala Ser Ser Pro Ser Pro Asp Ser Ala Ala Val Val Ala Glu
 50                  55                  60 ggc tcc gcg gct cgc cgc ttc tgg atc gct gcc tcc acg cgc gag gcc   240
Gly Ser Ala Ala Arg Arg Phe Trp Ile Ala Ala Ser Thr Arg Glu Ala
 65                  70                  75                  80 gcc ttc gcc gca tac acg ccc ttc ctc ctc tcc ctc gcc gcc ggc aat   288
Ala Phe Ala Ala Tyr Thr Pro Phe Leu Leu Ser Leu Ala Ala Gly Asn
                 85                  90                  95 ctg cgg ctc aac gtg ttt cgc cac tac atc gcg cag gac gcg cac ttc   336
Leu Arg Leu Asn Val Phe Arg His Tyr Ile Ala Gln Asp Ala His Phe
            100                 105                 110 ctt cac gcc ttc gct cgc gcg tac gaa atg gcc gag gac tgc gct gat   384
Leu His Ala Phe Ala Arg Ala Tyr Glu Met Ala Glu Asp Cys Ala Asp
            115                 120                 125 gat gac gac gac atg gcc acc ata gcc gcc ctc agg aag gcc atc ctc   432
Asp Asp Asp Asp Met Ala Thr Ile Ala Ala Leu Arg Lys Ala Ile Leu
130                 135                 140 caa gag ctc aac ctc cac tcc tcc gtt ctg aag gag tgg gga gtt gat   480
Gln Glu Leu Asn Leu His Ser Ser Val Leu Lys Glu Trp Gly Val Asp
145                 150                 155                 160 cct acc aaa gag ata cct cca agt gca gct aca acc aaa tat act gat   528
Pro Thr Lys Glu Ile Pro Pro Ser Ala Ala Thr Thr Lys Tyr Thr Asp
                165                 170                 175 ttc cta ctt gca act gcg gct gga aaa gtt gat ggc aca aaa ggt tct   576
Phe Leu Leu Ala Thr Ala Ala Gly Lys Val Asp Gly Thr Lys Gly Ser
            180                 185                 190 gac aaa atg gtt act cca ttt gag aag act aaa att gct gca tac act   624
Asp Lys Met Val Thr Pro Phe Glu Lys Thr Lys Ile Ala Ala Tyr Thr
            195                 200                 205 gtt ggg gcc atg act cca tgc atg agg ctt tat gca tat cta ggc aaa   672
Val Gly Ala Met Thr Pro Cys Met Arg Leu Tyr Ala Tyr Leu Gly Lys
            210                 215                 220 gaa ctc atg gtt ttc ctt aaa caa gat gaa aat cat cca tac aag aaa   720
Glu Leu Met Val Phe Leu Lys Gln Asp Glu Asn His Pro Tyr Lys Lys
225                 230                 235                 240 tgg att aac aca tat gca tcc agt gat ttt gag gac acc aca ctc caa   768
Trp Ile Asn Thr Tyr Ala Ser Ser Asp Phe Glu Asp Thr Thr Leu Gln
                245                 250                 255 ata gaa gaa ttg cta gac aaa cta agt gtc tca tta act ggt gag gaa   816
Ile Glu Glu Leu Leu Asp Lys Leu Ser Val Ser Leu Thr Gly Glu Glu
            260                 265                 270 ctt gag att att ggc aag ctc tac cag caa gct atg aaa ctg gaa gtg   864
Leu Glu Ile Ile Gly Lys Leu Tyr Gln Gln Ala Met Lys Leu Glu Val
            275                 280                 285 gag ttc ttt tct tct cag ctt ata gac caa cct gtt gta gct cca ctt   912
Glu Phe Phe Ser Ser Gln Leu Ile Asp Gln Pro Val Val Ala Pro Leu
            290                 295                 300 tca aga tac tgt gat cca aaa tat aaa ctc ttg atc ttt tct gat ttt   960
Ser Arg Tyr Cys Asp Pro Lys Tyr Lys Leu Leu Ile Phe Ser Asp Phe
305                 310                 315                 320 gat ttg acg tgc act att gtt gat tca tct gcc att ttg gcg gag att  1008
```

```
                Asp Leu Thr Cys Thr Ile Val Asp Ser Ser Ala Ile Leu Ala Glu Ile
                                325                 330                 335 gca att ttg tca ttc caa aag gca aat caa agt ggg att gat aat aac        1056
Ala Ile Leu Ser Phe Gln Lys Ala Asn Gln Ser Gly Ile Asp Asn Asn
            340                 345                 350 ctc gac cgt gca aaa tcg gga gac ctg aga agt tcg tgg aac atg ctc        1104
Leu Asp Arg Ala Lys Ser Gly Asp Leu Arg Ser Ser Trp Asn Met Leu
                355                 360                 365 tct aag caa tac atg gaa gag tat gag aaa tgc atg gaa aga cta ctt        1152
Ser Lys Gln Tyr Met Glu Glu Tyr Glu Lys Cys Met Glu Arg Leu Leu
            370                 375                 380 cct cca gaa gaa tcg aag tca cta gat tat gat aaa ctg tat aaa ggc        1200
Pro Pro Glu Glu Ser Lys Ser Leu Asp Tyr Asp Lys Leu Tyr Lys Gly
385                 390                 395                 400 ctg gag gtg cta gct gag ttt gag aag ctt gca aat tct agg gtt gtc        1248
Leu Glu Val Leu Ala Glu Phe Glu Lys Leu Ala Asn Ser Arg Val Val
                405                 410                 415 gac tct ggt gtg ctg agg gga atg aat ttg gaa gac atc agg aaa gct        1296
Asp Ser Gly Val Leu Arg Gly Met Asn Leu Glu Asp Ile Arg Lys Ala
            420                 425                 430 ggt gag cgt ctt att ctt caa ggt ggc tgt aaa aat ttc ttt cag aag        1344
Gly Glu Arg Leu Ile Leu Gln Gly Gly Cys Lys Asn Phe Phe Gln Lys
        435                 440                 445 att gta aaa aca agg gag aac ctc aat ttg gat gtc cat att ctt tcc        1392
Ile Val Lys Thr Arg Glu Asn Leu Asn Leu Asp Val His Ile Leu Ser
450                 455                 460 tat tgc tgg tgt gca gaa ctt ata aga tca gcc ttc tca tca gcc ggt        1440
Tyr Cys Trp Cys Ala Glu Leu Ile Arg Ser Ala Phe Ser Ser Ala Gly
465                 470                 475                 480 tgt cta gat ggt ttg aac ata cat tca aat gag ttt gcc ttt gag gat        1488
Cys Leu Asp Gly Leu Asn Ile His Ser Asn Glu Phe Ala Phe Glu Asp
                485                 490                 495 tct gtt tca act ggt gag atc gac aga aag atg cag tct ccg cta gac        1536
Ser Val Ser Thr Gly Glu Ile Asp Arg Lys Met Gln Ser Pro Leu Asp
            500                 505                 510 aaa gtt gaa aag ttc aag agc atc aga agt gac gtg gac agt aca gtg        1584
Lys Val Glu Lys Phe Lys Ser Ile Arg Ser Asp Val Asp Ser Thr Val
        515                 520                 525 cca ttc cta tct gtt tat att gga gac tcg gtt gga gat ttg ctc tgc        1632
Pro Phe Leu Ser Val Tyr Ile Gly Asp Ser Val Gly Asp Leu Leu Cys
    530                 535                 540 tta ttg gag gct gat att ggt ata gtc att ggg tca acc aca agt ttg        1680
Leu Leu Glu Ala Asp Ile Gly Ile Val Ile Gly Ser Thr Thr Ser Leu
545                 550                 555                 560 cgt agg gtg ggc aaa cag ttt ggt gtt tct ttt gtc cca ttg ttc cct        1728
Arg Arg Val Gly Lys Gln Phe Gly Val Ser Phe Val Pro Leu Phe Pro
                565                 570                 575 ggt cta gta gag aag cag agg caa ctg gcg gag gaa gat gca tcc gta        1776
Gly Leu Val Glu Lys Gln Arg Gln Leu Ala Glu Glu Asp Ala Ser Val
            580                 585                 590 ttc aag gca cgg tct gga gtc ctc tat acg gtt tct agc tgg tca gaa        1824
Phe Lys Ala Arg Ser Gly Val Leu Tyr Thr Val Ser Ser Trp Ser Glu
        595                 600                 605 ata cac gcc ttc gta ctg gga agt gat ttc agc tga                        1860
Ile His Ala Phe Val Leu Gly Ser Asp Phe Ser
    610                 615

<210> SEQ ID NO 22
<211> LENGTH: 619
<212> TYPE: PRT
```

-continued

<213> ORGANISM: Zea mays

<400> SEQUENCE: 22

Met Leu Val Leu Arg Leu Arg Leu Arg Leu Pro Leu Pro Arg Pro
1               5                   10                  15

Leu Leu Val Ser Ser Phe Ser Ser Thr Ser Pro Ser Ser Pro Ser
            20                  25                  30

Thr Ser Ser Ser Ser Ser Cys Trp Ser Ser Thr Gly Glu Ser Arg Arg
            35                  40                  45

Ala Met Ala Ser Ser Pro Ser Pro Asp Ser Ala Ala Val Val Ala Glu
    50                  55                  60

Gly Ser Ala Ala Arg Arg Phe Trp Ile Ala Ala Ser Thr Arg Glu Ala
65                  70                  75                  80

Ala Phe Ala Ala Tyr Thr Pro Phe Leu Leu Ser Leu Ala Ala Gly Asn
                85                  90                  95

Leu Arg Leu Asn Val Phe Arg His Tyr Ile Ala Gln Asp Ala His Phe
            100                 105                 110

Leu His Ala Phe Ala Arg Ala Tyr Glu Met Ala Glu Asp Cys Ala Asp
            115                 120                 125

Asp Asp Asp Met Ala Thr Ile Ala Ala Leu Arg Lys Ala Ile Leu
130                 135                 140

Gln Glu Leu Asn Leu His Ser Ser Val Leu Lys Glu Trp Gly Val Asp
145                 150                 155                 160

Pro Thr Lys Glu Ile Pro Pro Ser Ala Ala Thr Thr Lys Tyr Thr Asp
                165                 170                 175

Phe Leu Leu Ala Thr Ala Ala Gly Lys Val Asp Gly Thr Lys Gly Ser
            180                 185                 190

Asp Lys Met Val Thr Pro Phe Glu Lys Thr Lys Ile Ala Ala Tyr Thr
        195                 200                 205

Val Gly Ala Met Thr Pro Cys Met Arg Leu Tyr Ala Tyr Leu Gly Lys
210                 215                 220

Glu Leu Met Val Phe Leu Lys Gln Asp Glu Asn His Pro Tyr Lys Lys
225                 230                 235                 240

Trp Ile Asn Thr Tyr Ala Ser Ser Asp Phe Glu Asp Thr Thr Leu Gln
                245                 250                 255

Ile Glu Glu Leu Leu Asp Lys Leu Ser Val Ser Leu Thr Gly Glu Glu
            260                 265                 270

Leu Glu Ile Ile Gly Lys Leu Tyr Gln Gln Ala Met Lys Leu Glu Val
        275                 280                 285

Glu Phe Phe Ser Ser Gln Leu Ile Asp Gln Pro Val Val Ala Pro Leu
290                 295                 300

Ser Arg Tyr Cys Asp Pro Lys Tyr Lys Leu Leu Ile Phe Ser Asp Phe
305                 310                 315                 320

Asp Leu Thr Cys Thr Ile Val Asp Ser Ser Ala Ile Leu Ala Glu Ile
                325                 330                 335

Ala Ile Leu Ser Phe Gln Lys Ala Asn Gln Ser Gly Ile Asp Asn Asn
            340                 345                 350

Leu Asp Arg Ala Lys Ser Gly Asp Leu Arg Ser Ser Trp Asn Met Leu
        355                 360                 365

Ser Lys Gln Tyr Met Glu Glu Tyr Glu Lys Cys Met Glu Arg Leu Leu
370                 375                 380

Pro Pro Glu Glu Ser Lys Ser Leu Asp Tyr Asp Lys Leu Tyr Lys Gly
385                 390                 395                 400

```
Leu Glu Val Leu Ala Glu Phe Glu Lys Leu Ala Asn Ser Arg Val Val
                405                 410                 415

Asp Ser Gly Val Leu Arg Gly Met Asn Leu Glu Asp Ile Arg Lys Ala
            420                 425                 430

Gly Glu Arg Leu Ile Leu Gln Gly Gly Cys Lys Asn Phe Phe Gln Lys
        435                 440                 445

Ile Val Lys Thr Arg Glu Asn Leu Asn Leu Asp Val His Ile Leu Ser
    450                 455                 460

Tyr Cys Trp Cys Ala Glu Leu Ile Arg Ser Ala Phe Ser Ser Ala Gly
465                 470                 475                 480

Cys Leu Asp Gly Leu Asn Ile His Ser Asn Glu Phe Ala Phe Glu Asp
                485                 490                 495

Ser Val Ser Thr Gly Glu Ile Asp Arg Lys Met Gln Ser Pro Leu Asp
            500                 505                 510

Lys Val Glu Lys Phe Lys Ser Ile Arg Ser Asp Val Asp Ser Thr Val
        515                 520                 525

Pro Phe Leu Ser Val Tyr Ile Gly Asp Ser Val Gly Asp Leu Leu Cys
    530                 535                 540

Leu Leu Glu Ala Asp Ile Gly Ile Val Ile Gly Ser Thr Thr Ser Leu
545                 550                 555                 560

Arg Arg Val Gly Lys Gln Phe Gly Val Ser Phe Val Pro Leu Phe Pro
                565                 570                 575

Gly Leu Val Glu Lys Gln Arg Gln Leu Ala Glu Asp Ala Ser Val
            580                 585                 590

Phe Lys Ala Arg Ser Gly Val Leu Tyr Thr Val Ser Ser Trp Ser Glu
        595                 600                 605

Ile His Ala Phe Val Leu Gly Ser Asp Phe Ser
    610                 615

<210> SEQ ID NO 23
<211> LENGTH: 1830
<212> TYPE: DNA
<213> ORGANISM: Oryza sativa
<220> FEATURE:
<221> NAME/KEY: CDS
<222> LOCATION: (1)..(1827)
<223> OTHER INFORMATION: Oryza sativa gene encoding TMP phosphatase
      [NP_001062539.1]

<400> SEQUENCE: 23 atg cgc ggc ctc ctc cgc cgt gtc tac ctc cgc ctc ccc cct ttc cct    48
Met Arg Gly Leu Leu Arg Arg Val Tyr Leu Arg Leu Pro Pro Phe Pro
1               5                   10                  15 cct gcc acc tct ctt tat tat tgg tca aga aca aga cct gca gct gca    96
Pro Ala Thr Ser Leu Tyr Tyr Trp Ser Arg Thr Arg Pro Ala Ala Ala
            20                  25                  30 ggg ccc aac cac ccc atc cct agg cgc atg tcg acg tcc tct act gcc   144
Gly Pro Asn His Pro Ile Pro Arg Arg Met Ser Thr Ser Ser Thr Ala
        35                  40                  45 gcg gcg gtc gtt gcc gag ggc tcc gcc gct cgc cgc ttc tgg atc gcc   192
Ala Ala Val Val Ala Glu Gly Ser Ala Ala Arg Arg Phe Trp Ile Ala
    50                  55                  60 gcc gcc tcg agg gag gcc gcc ttc gcc gcc tac acg ccc ttc ctc gtc   240
Ala Ala Ser Arg Glu Ala Ala Phe Ala Ala Tyr Thr Pro Phe Leu Val
65                  70                  75                  80 tcc ctc gcc gcc ggg gcc ctc cgc ctg gat tcc ttc cgc caa tac atc   288
Ser Leu Ala Ala Gly Ala Leu Arg Leu Asp Ser Phe Arg Gln Tyr Ile
                85                  90                  95
```

```
gcc cag gat gcc tac ttc ctc cac gcc ttc gcc cgc gcc tat gag atg      336
Ala Gln Asp Ala Tyr Phe Leu His Ala Phe Ala Arg Ala Tyr Glu Met
            100                 105                 110 gcc gag gag tgc gcc gat gac gac gac aag gcc acc atc gtc gtc          384
Ala Glu Glu Cys Ala Asp Asp Asp Asp Lys Ala Thr Ile Val Val
        115                 120                 125 ctc agg aag gcc atc ctc cgc gag ctc aac ctc cac gct tcc gtc ctt      432
Leu Arg Lys Ala Ile Leu Arg Glu Leu Asn Leu His Ala Ser Val Leu
130                 135                 140 cag gaa tgg gga gtc gat ccc aac aaa gaa atc cct cca atc cca gcc      480
Gln Glu Trp Gly Val Asp Pro Asn Lys Glu Ile Pro Pro Ile Pro Ala
145                 150                 155                 160 aca act aag tac act gat ttc tta ctt gca act tcc act gga aag gtt      528
Thr Thr Lys Tyr Thr Asp Phe Leu Leu Ala Thr Ser Thr Gly Lys Val
                165                 170                 175 gat ggt ggg aaa ggt tct gat aaa atg gtc aca cca ttc gag aag acg      576
Asp Gly Gly Lys Gly Ser Asp Lys Met Val Thr Pro Phe Glu Lys Thr
            180                 185                 190 aaa att gct gca tac act gtt ggg gct atg acc cca tgc atg agg ctt      624
Lys Ile Ala Ala Tyr Thr Val Gly Ala Met Thr Pro Cys Met Arg Leu
        195                 200                 205 tat gcg tat ctg ggc aaa gaa ctt gca gtt ttc ttg aaa cag gat gaa      672
Tyr Ala Tyr Leu Gly Lys Glu Leu Ala Val Phe Leu Lys Gln Asp Glu
210                 215                 220 aat cac cca tac aag aaa tgg att gag act tat gca tcc agt gat ttt      720
Asn His Pro Tyr Lys Lys Trp Ile Glu Thr Tyr Ala Ser Ser Asp Phe
225                 230                 235                 240 gag aat aac gca ctc caa ata gaa gag ttg ctt gat aaa cta agt gtc      768
Glu Asn Asn Ala Leu Gln Ile Glu Glu Leu Leu Asp Lys Leu Ser Val
                245                 250                 255 tct cta act ggc gag gag ctt gag att att ggg aag ctc tac cag caa      816
Ser Leu Thr Gly Glu Glu Leu Glu Ile Ile Gly Lys Leu Tyr Gln Gln
            260                 265                 270 gct atg agg ctg gaa gtt gag ttc ttc tct gct cag cca gta gac caa      864
Ala Met Arg Leu Glu Val Glu Phe Phe Ser Ala Gln Pro Val Asp Gln
        275                 280                 285 cct gtt gta gct cca ctc tca aga tat tgt ggt ccg aaa gat aag ctc      912
Pro Val Val Ala Pro Leu Ser Arg Tyr Cys Gly Pro Lys Asp Lys Leu
    290                 295                 300 ttg ata ttt tgt gat ttt gat ttg aca tgc act gtt gtt gat tca tct      960
Leu Ile Phe Cys Asp Phe Asp Leu Thr Cys Thr Val Val Asp Ser Ser
305                 310                 315                 320 gcc att ttg gcg gag att gca atc ttg tca cac caa aag gct agt caa     1008
Ala Ile Leu Ala Glu Ile Ala Ile Leu Ser His Gln Lys Ala Ser Gln
                325                 330                 335 ggt ggg gct gat agt tcc ctt gat cgt aca aaa tca gcg gac ttg aga     1056
Gly Gly Ala Asp Ser Ser Leu Asp Arg Thr Lys Ser Ala Asp Leu Arg
            340                 345                 350 aat tca tgg aac atg ctc tca aat caa tac atg gaa gag tat gag caa     1104
Asn Ser Trp Asn Met Leu Ser Asn Gln Tyr Met Glu Glu Tyr Glu Gln
        355                 360                 365 tgc ata gca agc ttg ctt cct cca gaa gaa gca agg tca cta gac tat     1152
Cys Ile Ala Ser Leu Leu Pro Pro Glu Glu Ala Arg Ser Leu Asp Tyr
370                 375                 380 gat caa ctg tat aaa ggt ttg gag gtg cta tcg cag ttt gag aaa ctt     1200
Asp Gln Leu Tyr Lys Gly Leu Glu Val Leu Ser Gln Phe Glu Lys Leu
385                 390                 395                 400 gca aac tct agg gtg gtt gat tct ggt gtc ctg agg gga atg aat tta     1248
Ala Asn Ser Arg Val Val Asp Ser Gly Val Leu Arg Gly Met Asn Leu
                405                 410                 415
```

```
gat gac atc cga aaa gct gga gag agg ctt att ctg caa gat gga tgc    1296
Asp Asp Ile Arg Lys Ala Gly Glu Arg Leu Ile Leu Gln Asp Gly Cys
        420                 425                 430 aaa att ttt ttt caa aag att ggc aaa aca agg gag aac ctc aat tta    1344
Lys Ile Phe Phe Gln Lys Ile Gly Lys Thr Arg Glu Asn Leu Asn Leu
            435                 440                 445 gat gtc cat att ctt tcc tat tgc tgg tgc gca gat ctt ata agg tca    1392
Asp Val His Ile Leu Ser Tyr Cys Trp Cys Ala Asp Leu Ile Arg Ser
    450                 455                 460 gct ttt tca tca gtt ggt tgt cta gac ggg ctg aac ata cat tca aat    1440
Ala Phe Ser Ser Val Gly Cys Leu Asp Gly Leu Asn Ile His Ser Asn
465                 470                 475                 480 gag ttt gct ttt gag gga tct gtt tca act ggt cat att aac aga caa    1488
Glu Phe Ala Phe Glu Gly Ser Val Ser Thr Gly His Ile Asn Arg Gln
                485                 490                 495 atg gag tct cct ctg gac aaa gct gaa aag ttc aag agc atc aaa agc    1536
Met Glu Ser Pro Leu Asp Lys Ala Glu Lys Phe Lys Ser Ile Lys Ser
            500                 505                 510 gac gtg ggt agt aca ggg aca tta ttg tca gtc tat att ggg gac tcg    1584
Asp Val Gly Ser Thr Gly Thr Leu Leu Ser Val Tyr Ile Gly Asp Ser
    515                 520                 525 gtt gga gat ttg ctt tgc ttg ttg gag gca gat att ggt att gtt gtt    1632
Val Gly Asp Leu Leu Cys Leu Leu Glu Ala Asp Ile Gly Ile Val Val
530                 535                 540 gga tca agc aca acc ttg cgg aga gtg ggc aaa cag ttt ggt gtt tca    1680
Gly Ser Ser Thr Thr Leu Arg Arg Val Gly Lys Gln Phe Gly Val Ser
545                 550                 555                 560 ttt gtt cct ctg ttc act ggg ttg gta gag aag cag agg cga ata gaa    1728
Phe Val Pro Leu Phe Thr Gly Leu Val Glu Lys Gln Arg Arg Ile Glu
                565                 570                 575 aag gaa gaa tca tcc atc ttc aag gca cgg tct gga att ctt tat acg    1776
Lys Glu Glu Ser Ser Ile Phe Lys Ala Arg Ser Gly Ile Leu Tyr Thr
            580                 585                 590 gtt tct agc tgg tcg gag gta cag gct ttc atc ctg gga aat gat ttc    1824
Val Ser Ser Trp Ser Glu Val Gln Ala Phe Ile Leu Gly Asn Asp Phe
    595                 600                 605 agc tga                                                            1830
Ser

<210> SEQ ID NO 24
<211> LENGTH: 609
<212> TYPE: PRT
<213> ORGANISM: Oryza sativa

<400> SEQUENCE: 24

Met Arg Gly Leu Leu Arg Arg Val Tyr Leu Arg Leu Pro Pro Phe Pro
1               5                   10                  15

Pro Ala Thr Ser Leu Tyr Tyr Trp Ser Arg Thr Arg Pro Ala Ala Ala
            20                  25                  30

Gly Pro Asn His Pro Ile Pro Arg Met Ser Thr Ser Ser Thr Ala
        35                  40                  45

Ala Ala Val Val Ala Glu Gly Ser Ala Ala Arg Phe Trp Ile Ala
    50                  55                  60

Ala Ala Ser Arg Glu Ala Phe Ala Ala Tyr Thr Pro Phe Leu Val
65                  70                  75                  80

Ser Leu Ala Ala Gly Ala Leu Arg Leu Asp Ser Phe Arg Gln Tyr Ile
                85                  90                  95

Ala Gln Asp Ala Tyr Phe Leu His Ala Phe Ala Arg Ala Tyr Glu Met
```

```
                100             105             110
Ala Glu Glu Cys Ala Asp Asp Asp Asp Lys Ala Thr Ile Val Val
            115             120             125
Leu Arg Lys Ala Ile Leu Arg Glu Leu Asn Leu His Ala Ser Val Leu
        130             135             140
Gln Glu Trp Gly Val Asp Pro Asn Lys Glu Ile Pro Pro Ile Pro Ala
145             150             155             160
Thr Thr Lys Tyr Thr Asp Phe Leu Leu Ala Thr Ser Thr Gly Lys Val
                165             170             175
Asp Gly Gly Lys Gly Ser Asp Lys Met Val Thr Pro Phe Glu Lys Thr
            180             185             190
Lys Ile Ala Ala Tyr Thr Val Gly Ala Met Thr Pro Cys Met Arg Leu
        195             200             205
Tyr Ala Tyr Leu Gly Lys Glu Leu Ala Val Phe Leu Lys Gln Asp Glu
    210             215             220
Asn His Pro Tyr Lys Lys Trp Ile Glu Thr Tyr Ala Ser Ser Asp Phe
225             230             235             240
Glu Asn Asn Ala Leu Gln Ile Glu Glu Leu Leu Asp Lys Leu Ser Val
                245             250             255
Ser Leu Thr Gly Glu Glu Leu Glu Ile Ile Gly Lys Leu Tyr Gln Gln
            260             265             270
Ala Met Arg Leu Glu Val Glu Phe Phe Ser Ala Gln Pro Val Asp Gln
        275             280             285
Pro Val Val Ala Pro Leu Ser Arg Tyr Cys Gly Pro Lys Asp Lys Leu
    290             295             300
Leu Ile Phe Cys Asp Phe Asp Leu Thr Cys Thr Val Val Asp Ser Ser
305             310             315             320
Ala Ile Leu Ala Glu Ile Ala Ile Leu Ser His Gln Lys Ala Ser Gln
                325             330             335
Gly Gly Ala Asp Ser Ser Leu Asp Arg Thr Lys Ser Ala Asp Leu Arg
            340             345             350
Asn Ser Trp Asn Met Leu Ser Asn Gln Tyr Met Glu Glu Tyr Glu Gln
        355             360             365
Cys Ile Ala Ser Leu Leu Pro Pro Glu Glu Ala Arg Ser Leu Asp Tyr
    370             375             380
Asp Gln Leu Tyr Lys Gly Leu Glu Val Leu Ser Gln Phe Glu Lys Leu
385             390             395             400
Ala Asn Ser Arg Val Val Asp Ser Gly Val Leu Arg Gly Met Asn Leu
                405             410             415
Asp Asp Ile Arg Lys Ala Gly Glu Arg Leu Ile Leu Gln Asp Gly Cys
            420             425             430
Lys Ile Phe Phe Gln Lys Ile Gly Lys Thr Arg Glu Asn Leu Asn Leu
        435             440             445
Asp Val His Ile Leu Ser Tyr Cys Trp Cys Ala Asp Leu Ile Arg Ser
    450             455             460
Ala Phe Ser Ser Val Gly Cys Leu Asp Gly Leu Asn Ile His Ser Asn
465             470             475             480
Glu Phe Ala Phe Glu Gly Ser Val Ser Thr Gly His Ile Asn Arg Gln
                485             490             495
Met Glu Ser Pro Leu Asp Lys Ala Glu Lys Phe Lys Ser Ile Lys Ser
            500             505             510
Asp Val Gly Ser Thr Gly Thr Leu Leu Ser Val Tyr Ile Gly Asp Ser
        515             520             525
```

```
Val Gly Asp Leu Leu Cys Leu Leu Glu Ala Asp Ile Gly Ile Val Val
            530                 535                 540

Gly Ser Ser Thr Thr Leu Arg Arg Val Gly Lys Gln Phe Gly Val Ser
545                 550                 555                 560

Phe Val Pro Leu Phe Thr Gly Leu Val Glu Lys Gln Arg Arg Ile Glu
                565                 570                 575

Lys Glu Glu Ser Ser Ile Phe Lys Ala Arg Ser Gly Ile Leu Tyr Thr
            580                 585                 590

Val Ser Ser Trp Ser Glu Val Gln Ala Phe Ile Leu Gly Asn Asp Phe
        595                 600                 605

Ser
```

<210> SEQ ID NO 25
<211> LENGTH: 1683
<212> TYPE: DNA
<213> ORGANISM: Picea sitchensis
<220> FEATURE:
<221> NAME/KEY: CDS
<222> LOCATION: (1)..(1680)
<223> OTHER INFORMATION: Picea_sitchensis gene encoding TMP phosphatase [ABR16455]

<400> SEQUENCE: 25

```
atg ggg gtc gcc gat gaa gca gga gtc gcc aga agg cta tgg aca aag      48
Met Gly Val Ala Asp Glu Ala Gly Val Ala Arg Arg Leu Trp Thr Lys
1               5                   10                  15 ttc aag aaa gac acc gcg ctt gca cag tat aat tcc ttt gtt gtt gct      96
Phe Lys Lys Asp Thr Ala Leu Ala Gln Tyr Asn Ser Phe Val Val Ala
            20                  25                  30 ttg gcg gcc ggg acg ctc aac atg acg tct ttt cag cag tac atg gcg     144
Leu Ala Ala Gly Thr Leu Asn Met Thr Ser Phe Gln Gln Tyr Met Ala
        35                  40                  45 cag gat gct tat ttt ctc aaa gca ttt gct cag gcg tac aca atg gca     192
Gln Asp Ala Tyr Phe Leu Lys Ala Phe Ala Gln Ala Tyr Thr Met Ala
    50                  55                  60 gag gat tgc gca gat gat gac gac gac aaa gca tcg atc cgt gaa cta     240
Glu Asp Cys Ala Asp Asp Asp Asp Asp Lys Ala Ser Ile Arg Glu Leu
65                  70                  75                  80 cga aaa gcc gct gag gaa gag ctc aat ctg cac aat tcc ttg gct gag     288
Arg Lys Ala Ala Glu Glu Glu Leu Asn Leu His Asn Ser Leu Ala Glu
                85                  90                  95 gac tgg gac gtt gaa ttt gca aaa gag tgc tct ccc aat atg gca aca     336
Asp Trp Asp Val Glu Phe Ala Lys Glu Cys Ser Pro Asn Met Ala Thr
            100                 105                 110 gtc aag tac aca gaa ttt tta ttg gca aca gct gct ggc aag gtg gaa     384
Val Lys Tyr Thr Glu Phe Leu Leu Ala Thr Ala Ala Gly Lys Val Glu
        115                 120                 125 gga ggg aag gga cca agc aga agt gtg act cct ttt gag aaa aca aaa     432
Gly Gly Lys Gly Pro Ser Arg Ser Val Thr Pro Phe Glu Lys Thr Lys
    130                 135                 140 ata gca gca tac aca gtg ggt gcc atg acc ccg tgc atg agg ctt tat     480
Ile Ala Ala Tyr Thr Val Gly Ala Met Thr Pro Cys Met Arg Leu Tyr
145                 150                 155                 160 gct ttc ttg ggc caa gaa att gtc aaa gcc ctg gaa cct gat tgc agt     528
Ala Phe Leu Gly Gln Glu Ile Val Lys Ala Leu Glu Pro Asp Cys Ser
                165                 170                 175 aat cat cca tat aag cag tgg att gaa aca tac tct tct gca aag ttt     576
Asn His Pro Tyr Lys Gln Trp Ile Glu Thr Tyr Ser Ser Ala Lys Phe
            180                 185                 190
```

-continued

| | | |
|---|---|---|
| gag gca tcg gca tta caa act gaa gag ttg ctt gac aaa ctg gct att<br>Glu Ala Ser Ala Leu Gln Thr Glu Glu Leu Leu Asp Lys Leu Ala Ile<br>195                                  200                          205 | | 624 |
| tcg cta act ggg gaa gag ctt gaa gtg ctg cgg agg ttg tat tat cat<br>Ser Leu Thr Gly Glu Glu Leu Glu Val Leu Arg Arg Leu Tyr Tyr His<br>210                                  215                          220 | | 672 |
| gcc tta aaa cta gaa ata gaa ttc ttt tcc gct cag cct ttc tct cag<br>Ala Leu Lys Leu Glu Ile Glu Phe Phe Ser Ala Gln Pro Phe Ser Gln<br>225                                  230                          235                          240 | | 720 |
| aga aca tta gtt ccg atg ttg aaa ctg ggt gat tca gcc agc cgc cga<br>Arg Thr Leu Val Pro Met Leu Lys Leu Gly Asp Ser Ala Ser Arg Arg<br>                                 245                          250                          255 | | 768 |
| tat acc att gtc tca gat ttc gat ttg tct tgc act gtc ttg gat tct<br>Tyr Thr Ile Val Ser Asp Phe Asp Leu Ser Cys Thr Val Leu Asp Ser<br>                                 260                          265                          270 | | 816 |
| tca gca gta tta gca gaa att gca ata ttg act act ctc aaa act gag<br>Ser Ala Val Leu Ala Glu Ile Ala Ile Leu Thr Thr Leu Lys Thr Glu<br>275                                  280                          285 | | 864 |
| caa aat ggt gct gaa aac tta agt gat cac aag tca tca tcg gag ttg<br>Gln Asn Gly Ala Glu Asn Leu Ser Asp His Lys Ser Ser Ser Glu Leu<br>        290                          295                          300 | | 912 |
| aga aaa act tgg gat gca ctt tct agt caa tat tct gaa gaa tgt gaa<br>Arg Lys Thr Trp Asp Ala Leu Ser Ser Gln Tyr Ser Glu Glu Cys Glu<br>305                                  310                          315                          320 | | 960 |
| gaa tgc tta agg aag act ctg cca cct gaa gaa gtg ggc tct ttt gat<br>Glu Cys Leu Arg Lys Thr Leu Pro Pro Glu Glu Val Gly Ser Phe Asp<br>                                 325                          330                          335 | | 1008 |
| tat gaa ggc cta cac caa tct ctt gag cat ctg tct cag ttt gaa atg<br>Tyr Glu Gly Leu His Gln Ser Leu Glu His Leu Ser Gln Phe Glu Met<br>                                 340                          345                          350 | | 1056 |
| gag gca aac tct aaa gtt gtc gag tca ggt gtc ctt gag ggc att aat<br>Glu Ala Asn Ser Lys Val Val Glu Ser Gly Val Leu Glu Gly Ile Asn<br>                               355                          360                          365 | | 1104 |
| ata gat gac att aaa aag gca gga gag cgt ctt gca ttt cag gat gga<br>Ile Asp Asp Ile Lys Lys Ala Gly Glu Arg Leu Ala Phe Gln Asp Gly<br>370                                  375                          380 | | 1152 |
| tgc gca aac ttt ttt gaa caa atc cta acg aaa atg gac agc tta aat<br>Cys Ala Asn Phe Phe Glu Gln Ile Leu Thr Lys Met Asp Ser Leu Asn<br>385                                  390                          395                          400 | | 1200 |
| gtg gat gtg cac ata att tct gtt tgt tgg agt gga gat atc atc agg<br>Val Asp Val His Ile Ile Ser Val Cys Trp Ser Gly Asp Ile Ile Arg<br>                                 405                          410                          415 | | 1248 |
| gct gct ttt tca tca agc ggt ttg gat ggt tta cag gtt cat tca aat<br>Ala Ala Phe Ser Ser Ser Gly Leu Asp Gly Leu Gln Val His Ser Asn<br>                                 420                          425                          430 | | 1296 |
| gaa ctc acc ttt gtg gaa tca gtc tct act ggt ggt att gat agg cgt<br>Glu Leu Thr Phe Val Glu Ser Val Ser Thr Gly Gly Ile Asp Arg Arg<br>                                 435                          440                          445 | | 1344 |
| gtt gag tcc cca gtt gac aag ttg aaa atc ttc aat aat att tgg agt<br>Val Glu Ser Pro Val Asp Lys Leu Lys Ile Phe Asn Asn Ile Trp Ser<br>450                                  455                          460 | | 1392 |
| tct tca aag gac cag gac acg gaa cat atc tct ata tac att ggg gac<br>Ser Ser Lys Asp Gln Asp Thr Glu His Ile Ser Ile Tyr Ile Gly Asp<br>465                                  470                          475                          480 | | 1440 |
| ggt tta ggt gac ttg ctt tgt ctt ctt cag gca gat att gga ata gtg<br>Gly Leu Gly Asp Leu Leu Cys Leu Leu Gln Ala Asp Ile Gly Ile Val<br>                                 485                          490                          495 | | 1488 |
| att ggt aca agc tca acg cta aga agg gtt gga aaa cgt ttt gga gta<br>Ile Gly Thr Ser Ser Thr Leu Arg Arg Val Gly Lys Arg Phe Gly Val<br>                                 500                          505                          510 | | 1536 |

```
tcc ttt gtt cct ttg ttt tct ggt ctt ctc aaa cag gag aga gca tat       1584
Ser Phe Val Pro Leu Phe Ser Gly Leu Leu Lys Gln Glu Arg Ala Tyr
    515                 520                 525 gta gaa ggt tct agt tgt tgg aca aaa caa agt ggt att ctt tat acc       1632
Val Glu Gly Ser Ser Cys Trp Thr Lys Gln Ser Gly Ile Leu Tyr Thr
530                 535                 540 gtc tct agt tgg agt gaa ata cat gct ttt att ttg ggc tct tcc aat       1680
Val Ser Ser Trp Ser Glu Ile His Ala Phe Ile Leu Gly Ser Ser Asn
545                 550                 555                 560 tga                                                                    1683
```

<210> SEQ ID NO 26
<211> LENGTH: 560
<212> TYPE: PRT
<213> ORGANISM: Picea sitchensis

<400> SEQUENCE: 26

```
Met Gly Val Ala Asp Glu Ala Gly Val Ala Arg Arg Leu Trp Thr Lys
1               5                   10                  15

Phe Lys Lys Asp Thr Ala Leu Ala Gln Tyr Asn Ser Phe Val Val Ala
            20                  25                  30

Leu Ala Ala Gly Thr Leu Asn Met Thr Ser Phe Gln Gln Tyr Met Ala
        35                  40                  45

Gln Asp Ala Tyr Phe Leu Lys Ala Phe Ala Gln Ala Tyr Thr Met Ala
    50                  55                  60

Glu Asp Cys Ala Asp Asp Asp Lys Ala Ser Ile Arg Glu Leu
65                  70                  75                  80

Arg Lys Ala Ala Glu Glu Leu Asn Leu His Asn Ser Leu Ala Glu
                85                  90                  95

Asp Trp Asp Val Glu Phe Ala Lys Glu Cys Ser Pro Asn Met Ala Thr
            100                 105                 110

Val Lys Tyr Thr Glu Phe Leu Leu Ala Thr Ala Ala Gly Lys Val Glu
        115                 120                 125

Gly Gly Lys Gly Pro Ser Arg Ser Val Thr Pro Phe Glu Lys Thr Lys
    130                 135                 140

Ile Ala Ala Tyr Thr Val Gly Ala Met Thr Pro Cys Met Arg Leu Tyr
145                 150                 155                 160

Ala Phe Leu Gly Gln Glu Ile Val Lys Ala Leu Glu Pro Asp Cys Ser
                165                 170                 175

Asn His Pro Tyr Lys Gln Trp Ile Glu Thr Tyr Ser Ser Ala Lys Phe
            180                 185                 190

Glu Ala Ser Ala Leu Gln Thr Glu Glu Leu Leu Asp Lys Leu Ala Ile
        195                 200                 205

Ser Leu Thr Gly Glu Glu Leu Glu Val Leu Arg Arg Leu Tyr Tyr His
    210                 215                 220

Ala Leu Lys Leu Glu Ile Glu Phe Phe Ser Ala Gln Pro Phe Ser Gln
225                 230                 235                 240

Arg Thr Leu Val Pro Met Leu Lys Leu Gly Asp Ser Ala Ser Arg Arg
                245                 250                 255

Tyr Thr Ile Val Ser Asp Phe Asp Leu Ser Cys Thr Val Leu Asp Ser
            260                 265                 270

Ser Ala Val Leu Ala Glu Ile Ala Ile Leu Thr Thr Leu Lys Thr Glu
        275                 280                 285

Gln Asn Gly Ala Glu Asn Leu Ser Asp His Lys Ser Ser Glu Leu
    290                 295                 300
```

-continued

Arg Lys Thr Trp Asp Ala Leu Ser Ser Gln Tyr Ser Glu Glu Cys Glu
305                 310                 315                 320

Glu Cys Leu Arg Lys Thr Leu Pro Pro Glu Val Gly Ser Phe Asp
            325                 330                 335

Tyr Glu Gly Leu His Gln Ser Leu Glu His Leu Ser Gln Phe Glu Met
            340                 345                 350

Glu Ala Asn Ser Lys Val Val Glu Ser Gly Val Leu Glu Gly Ile Asn
            355                 360                 365

Ile Asp Asp Ile Lys Lys Ala Gly Glu Arg Leu Ala Phe Gln Asp Gly
        370                 375                 380

Cys Ala Asn Phe Phe Glu Gln Ile Leu Thr Lys Met Asp Ser Leu Asn
385                 390                 395                 400

Val Asp Val His Ile Ile Ser Val Cys Trp Ser Gly Asp Ile Ile Arg
                405                 410                 415

Ala Ala Phe Ser Ser Ser Gly Leu Asp Gly Leu Gln Val His Ser Asn
            420                 425                 430

Glu Leu Thr Phe Val Glu Ser Val Ser Thr Gly Gly Ile Asp Arg Arg
        435                 440                 445

Val Glu Ser Pro Val Asp Lys Leu Lys Ile Phe Asn Asn Ile Trp Ser
450                 455                 460

Ser Ser Lys Asp Gln Asp Thr Glu His Ile Ser Ile Tyr Ile Gly Asp
465                 470                 475                 480

Gly Leu Gly Asp Leu Leu Cys Leu Leu Gln Ala Asp Ile Gly Ile Val
            485                 490                 495

Ile Gly Thr Ser Ser Thr Leu Arg Arg Val Gly Lys Arg Phe Gly Val
        500                 505                 510

Ser Phe Val Pro Leu Phe Ser Gly Leu Leu Lys Gln Glu Arg Ala Tyr
            515                 520                 525

Val Glu Gly Ser Ser Cys Trp Thr Lys Gln Ser Gly Ile Leu Tyr Thr
530                 535                 540

Val Ser Ser Trp Ser Glu Ile His Ala Phe Ile Leu Gly Ser Ser Asn
545                 550                 555                 560

<210> SEQ ID NO 27
<211> LENGTH: 1641
<212> TYPE: DNA
<213> ORGANISM: Physcomitrella patens
<220> FEATURE:
<221> NAME/KEY: CDS
<222> LOCATION: (1)..(1638)
<223> OTHER INFORMATION: Physcomitrella patens gene encoding TMP
      phosphatase [XP_001769831]

<400> SEQUENCE: 27 atg aat ttg agc acg caa gct aac aca ggg ttg gcg aag agc ttc tgg       48
Met Asn Leu Ser Thr Gln Ala Asn Thr Gly Leu Ala Lys Ser Phe Trp
1               5                   10                  15 gct agt tgt aag aga gag gct tat gca tca ctc tac cat ccg ttt gtg       96
Ala Ser Cys Lys Arg Glu Ala Tyr Ala Ser Leu Tyr His Pro Phe Val
            20                  25                  30 gtt gcg tta gcg gct ggc acc ttg cca aaa caa act ttt caa cgt tac      144
Val Ala Leu Ala Ala Gly Thr Leu Pro Lys Gln Thr Phe Gln Arg Tyr
        35                  40                  45 atg gca cag gat gcc tat ttc ttg gag gcg ttc aag aat gcg tat caa      192
Met Ala Gln Asp Ala Tyr Phe Leu Glu Ala Phe Lys Asn Ala Tyr Gln
50                  55                  60 ctg gct atg gaa acc act aca gac gaa gag gca aag gcc atc att gag      240

```
                Leu Ala Met Glu Thr Thr Thr Asp Glu Glu Ala Lys Ala Ile Ile Glu
                65                  70                  75                  80 tcc ctt cag aga gat gtg cag gaa gag ctc aat ttg cac tcg tcg atc          288
Ser Leu Gln Arg Asp Val Gln Glu Glu Leu Asn Leu His Ser Ser Ile
                85                  90                  95 atg cag tct ttg gat gct acc gat cag aat tgc ttt gaa cca aac atg          336
Met Gln Ser Leu Asp Ala Thr Asp Gln Asn Cys Phe Glu Pro Asn Met
100                 105                 110 gca aca aca gcg tat tgt gat ttt ctg cta gcc aca gct aca gga agt          384
Ala Thr Thr Ala Tyr Cys Asp Phe Leu Leu Ala Thr Ala Thr Gly Ser
            115                 120                 125 aac gaa gca caa aaa ttt gga agc aca agt gct caa atc ata acc gct          432
Asn Glu Ala Gln Lys Phe Gly Ser Thr Ser Ala Gln Ile Ile Thr Ala
        130                 135                 140 atg act cct tgc atg cgg cta tat gca ttt ttg ggg cag gag ctc aaa          480
Met Thr Pro Cys Met Arg Leu Tyr Ala Phe Leu Gly Gln Glu Leu Lys
145                 150                 155                 160 aaa cac gtt gat cat gtt gct gac cat cct tac cag gag tgg att gat          528
Lys His Val Asp His Val Ala Asp His Pro Tyr Gln Glu Trp Ile Asp
            165                 170                 175 act tac tct gct gca gag ttc gag gct gca gct tcg aag att gag cag          576
Thr Tyr Ser Ala Ala Glu Phe Glu Ala Ala Ala Ser Lys Ile Glu Gln
        180                 185                 190 ctg cta gac aag tta act gct act ttg act gga aag cat gaa ata gca          624
Leu Leu Asp Lys Leu Thr Ala Thr Leu Thr Gly Lys His Glu Ile Ala
    195                 200                 205 ttc tta gaa agt ctc tat ctt caa gcc atg aac ttg gag gtg gat ttc          672
Phe Leu Glu Ser Leu Tyr Leu Gln Ala Met Asn Leu Glu Val Asp Phe
210                 215                 220 ttc ggt gct cag ctg tta ggg cct gtg ctc gta ccc ttc ctc aaa tgc          720
Phe Gly Ala Gln Leu Leu Gly Pro Val Leu Val Pro Phe Leu Lys Cys
225                 230                 235                 240 caa ccg gct cca gag agc tat ata tta ctt gcg tct gac ttt gat tcc          768
Gln Pro Ala Pro Glu Ser Tyr Ile Leu Leu Ala Ser Asp Phe Asp Ser
            245                 250                 255 acg tgc acg ata tct gat tca tgc ccc ata ttg gca gac ctg acc gtg          816
Thr Cys Thr Ile Ser Asp Ser Cys Pro Ile Leu Ala Asp Leu Thr Val
        260                 265                 270 caa act gcg cga aaa tct cac ggt ggt cgt tca gtt ggt gaa tca ggg          864
Gln Thr Ala Arg Lys Ser His Gly Gly Arg Ser Val Gly Glu Ser Gly
    275                 280                 285 gcc agc ttg ttg aaa aaa aga tgg gat gat ctc gtc atg cag tat atg          912
Ala Ser Leu Leu Lys Lys Arg Trp Asp Asp Leu Val Met Gln Tyr Met
290                 295                 300 gac gag tat gag gac gtt ctg aag cga agc ctg gtg aaa aaa gat aat          960
Asp Glu Tyr Glu Asp Val Leu Lys Arg Ser Leu Val Lys Lys Asp Asn
305                 310                 315                 320 ggc agt gtt aat gcg ctc agt gca gag aat ctc caa gag ttt ctg aag         1008
Gly Ser Val Asn Ala Leu Ser Ala Glu Asn Leu Gln Glu Phe Leu Lys
            325                 330                 335 gaa atg tcc aac ttc gaa cag aag gcc aat gcg agg gtc gaa gag gct         1056
Glu Met Ser Asn Phe Glu Gln Lys Ala Asn Ala Arg Val Glu Glu Ala
        340                 345                 350 gca gtt cta aaa ggc tta tct ctg gct tcg att caa gaa gct gga aaa         1104
Ala Val Leu Lys Gly Leu Ser Leu Ala Ser Ile Gln Glu Ala Gly Lys
    355                 360                 365 tcc atg cct ctt cgt gag ggc tgt tct gac ttt ttt aag cgt ctg gaa         1152
Ser Met Pro Leu Arg Glu Gly Cys Ser Asp Phe Phe Lys Arg Leu Glu
370                 375                 380
```

```
tca gga gag gtt ctt gtt gac aca tgt ata ttg tct gtg tgc tgg agc      1200
Ser Gly Glu Val Leu Val Asp Thr Cys Ile Leu Ser Val Cys Trp Ser
385                 390                 395                 400 aaa acc ttc atc gaa gct gtc ttg gaa aag gtt cgt att cca aac atc      1248
Lys Thr Phe Ile Glu Ala Val Leu Glu Lys Val Arg Ile Pro Asn Ile
            405                 410                 415 aat gcc aac gag ctc gtt ttc gaa gga cgc att tcc acc ggt gct att      1296
Asn Ala Asn Glu Leu Val Phe Glu Gly Arg Ile Ser Thr Gly Ala Ile
        420                 425                 430 atc aaa aac gtc gaa acg gct ctt gac aag caa aga cac ttc gtt cag      1344
Ile Lys Asn Val Glu Thr Ala Leu Asp Lys Gln Arg His Phe Val Gln
    435                 440                 445 ttg ctg gat aat cta aaa cca act caa gac gtg ctg tcc att tat gtt      1392
Leu Leu Asp Asn Leu Lys Pro Thr Gln Asp Val Leu Ser Ile Tyr Val
450                 455                 460 ggt gat agt ctg act gat ctt ctc tgc cta atc aga gca gac ctg ggt      1440
Gly Asp Ser Leu Thr Asp Leu Leu Cys Leu Ile Arg Ala Asp Leu Gly
465                 470                 475                 480 ata gtt ctc ggt gac agc agc gct ctg aag cag gtg tat ggg cca aaa      1488
Ile Val Leu Gly Asp Ser Ser Ala Leu Lys Gln Val Tyr Gly Pro Lys
            485                 490                 495 atg gcc ccc ctc ttc atg aaa gcc ata ctc ttg gag cag gca aac atg      1536
Met Ala Pro Leu Phe Met Lys Ala Ile Leu Leu Glu Gln Ala Asn Met
        500                 505                 510 cga ggc agg cag caa ccc aca ggt tac gtc ttc act gtc tcc agt tgg      1584
Arg Gly Arg Gln Gln Pro Thr Gly Tyr Val Phe Thr Val Ser Ser Trp
    515                 520                 525 tat gag gtg gaa gcc ttt ctg ttg ggt cct gct aga aac aga cct ttg      1632
Tyr Glu Val Glu Ala Phe Leu Leu Gly Pro Ala Arg Asn Arg Pro Leu
530                 535                 540 tac atc tag                                                          1641
Tyr Ile
545

<210> SEQ ID NO 28
<211> LENGTH: 546
<212> TYPE: PRT
<213> ORGANISM: Physcomitrella patens

<400> SEQUENCE: 28

Met Asn Leu Ser Thr Gln Ala Asn Thr Gly Leu Ala Lys Ser Phe Trp
1               5                   10                  15

Ala Ser Cys Lys Arg Glu Ala Tyr Ala Ser Leu Tyr His Pro Phe Val
            20                  25                  30

Val Ala Leu Ala Ala Gly Thr Leu Pro Lys Gln Thr Phe Gln Arg Tyr
        35                  40                  45

Met Ala Gln Asp Ala Tyr Phe Leu Glu Ala Phe Lys Asn Ala Tyr Gln
    50                  55                  60

Leu Ala Met Glu Thr Thr Thr Asp Glu Glu Ala Lys Ala Ile Ile Glu
65                  70                  75                  80

Ser Leu Gln Arg Asp Val Gln Glu Glu Leu Asn Leu His Ser Ser Ile
                85                  90                  95

Met Gln Ser Leu Asp Ala Thr Asp Gln Asn Cys Phe Glu Pro Asn Met
            100                 105                 110

Ala Thr Thr Ala Tyr Cys Asp Phe Leu Leu Ala Thr Ala Thr Gly Ser
        115                 120                 125

Asn Glu Ala Gln Lys Phe Gly Ser Thr Ser Ala Gln Ile Ile Thr Ala
    130                 135                 140
```

```
Met Thr Pro Cys Met Arg Leu Tyr Ala Phe Leu Gly Gln Glu Leu Lys
145                 150                 155                 160

Lys His Val Asp His Val Ala Asp His Pro Tyr Gln Glu Trp Ile Asp
            165                 170                 175

Thr Tyr Ser Ala Ala Glu Phe Glu Ala Ala Ser Lys Ile Glu Gln
            180                 185                 190

Leu Leu Asp Lys Leu Thr Ala Thr Leu Thr Gly Lys His Glu Ile Ala
            195                 200                 205

Phe Leu Glu Ser Leu Tyr Leu Gln Ala Met Asn Leu Glu Val Asp Phe
            210                 215                 220

Phe Gly Ala Gln Leu Leu Gly Pro Val Leu Val Pro Phe Leu Lys Cys
225                 230                 235                 240

Gln Pro Ala Pro Glu Ser Tyr Ile Leu Leu Ala Ser Asp Phe Asp Ser
            245                 250                 255

Thr Cys Thr Ile Ser Asp Ser Cys Pro Ile Leu Ala Asp Leu Thr Val
            260                 265                 270

Gln Thr Ala Arg Lys Ser His Gly Gly Arg Ser Val Gly Glu Ser Gly
            275                 280                 285

Ala Ser Leu Leu Lys Lys Arg Trp Asp Asp Leu Val Met Gln Tyr Met
290                 295                 300

Asp Glu Tyr Glu Asp Val Leu Lys Arg Ser Leu Val Lys Lys Asp Asn
305                 310                 315                 320

Gly Ser Val Asn Ala Leu Ser Ala Glu Asn Leu Gln Glu Phe Leu Lys
            325                 330                 335

Glu Met Ser Asn Phe Glu Gln Lys Ala Asn Ala Arg Val Glu Glu Ala
            340                 345                 350

Ala Val Leu Lys Gly Leu Ser Leu Ala Ser Ile Gln Glu Ala Gly Lys
            355                 360                 365

Ser Met Pro Leu Arg Glu Gly Cys Ser Asp Phe Phe Lys Arg Leu Glu
            370                 375                 380

Ser Gly Glu Val Leu Val Asp Thr Cys Ile Leu Ser Val Cys Trp Ser
385                 390                 395                 400

Lys Thr Phe Ile Glu Ala Val Leu Glu Lys Val Arg Ile Pro Asn Ile
            405                 410                 415

Asn Ala Asn Glu Leu Val Phe Glu Gly Arg Ile Ser Thr Gly Ala Ile
            420                 425                 430

Ile Lys Asn Val Glu Thr Ala Leu Asp Lys Gln Arg His Phe Val Gln
            435                 440                 445

Leu Leu Asp Asn Leu Lys Pro Thr Gln Asp Val Leu Ser Ile Tyr Val
            450                 455                 460

Gly Asp Ser Leu Thr Asp Leu Leu Cys Leu Ile Arg Ala Asp Leu Gly
465                 470                 475                 480

Ile Val Leu Gly Asp Ser Ser Ala Leu Lys Gln Val Tyr Gly Pro Lys
            485                 490                 495

Met Ala Pro Leu Phe Met Lys Ala Ile Leu Leu Glu Gln Ala Asn Met
            500                 505                 510

Arg Gly Arg Gln Gln Pro Thr Gly Tyr Val Phe Thr Val Ser Ser Trp
            515                 520                 525

Tyr Glu Val Glu Ala Phe Leu Leu Gly Pro Ala Arg Asn Arg Pro Leu
            530                 535                 540

Tyr Ile
545
```

```
<210> SEQ ID NO 29
<211> LENGTH: 1593
<212> TYPE: DNA
<213> ORGANISM: Selaginella moellendorffii
<220> FEATURE:
<221> NAME/KEY: CDS
<222> LOCATION: (1)..(1590)
<223> OTHER INFORMATION: Selaginella_moellendorffii gene encoding TMP
      phosphatase [XP_002990363]

<400> SEQUENCE: 29
```

| | | | | | | | | | | | | | | | | |
|---|---|---|---|---|---|---|---|---|---|---|---|---|---|---|---|---|
| atg | tcg | tgt | ttg | ctt | aga | aat | gta | gtg | gcc | aga | gga | ttg | agg | agc | ttg | 48 |
| Met | Ser | Cys | Leu | Leu | Arg | Asn | Val | Val | Ala | Arg | Gly | Leu | Arg | Ser | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gca | agc | gcc | cag | gcg | atg | gag | cca | tcc | att | tca | aag | cgc | ttg | tgg | cag | 96 |
| Ala | Ser | Ala | Gln | Ala | Met | Glu | Pro | Ser | Ile | Ser | Lys | Arg | Leu | Trp | Gln | |
| | | | 20 | | | | | 25 | | | | | 30 | | | |

| | | | | | | | | | | | | | | | | |
|---|---|---|---|---|---|---|---|---|---|---|---|---|---|---|---|---|
| caa | tcc | aag | cgc | gag | gca | atg | gta | tgt | ctg | tat | cat | cca | ttt | gtg | gtg | 144 |
| Gln | Ser | Lys | Arg | Glu | Ala | Met | Val | Cys | Leu | Tyr | His | Pro | Phe | Val | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| tcc | atc | gct | gct | ggg | acg | ctg | gat | ctt | cac | agc | ttc | cag | cga | ttc | ata | 192 |
| Ser | Ile | Ala | Ala | Gly | Thr | Leu | Asp | Leu | His | Ser | Phe | Gln | Arg | Phe | Ile | |
| 50 | | | | | 55 | | | | | 60 | | | | | | |

| | | | | | | | | | | | | | | | | |
|---|---|---|---|---|---|---|---|---|---|---|---|---|---|---|---|---|
| gcg | cag | gat | tcc | ttc | ttc | ctg | acg | gca | ttc | gcg | aaa | gcc | tat | ggt | ttg | 240 |
| Ala | Gln | Asp | Ser | Phe | Phe | Leu | Thr | Ala | Phe | Ala | Lys | Ala | Tyr | Gly | Leu | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| gcc | ata | gag | cgc | agc | gat | gat | cga | gaa | gtt | aaa | tct | gag | att | tgc | aag | 288 |
| Ala | Ile | Glu | Arg | Ser | Asp | Asp | Arg | Glu | Val | Lys | Ser | Glu | Ile | Cys | Lys | |
| | | | | 85 | | | | | 90 | | | | | 95 | | |

| | | | | | | | | | | | | | | | | |
|---|---|---|---|---|---|---|---|---|---|---|---|---|---|---|---|---|
| ctc | caa | cag | gct | gtg | tac | gag | gaa | ctt | gag | ctc | cat | tct | tcc | ctc | atg | 336 |
| Leu | Gln | Gln | Ala | Val | Tyr | Glu | Glu | Leu | Glu | Leu | His | Ser | Ser | Leu | Met | |
| | | | 100 | | | | | 105 | | | | | 110 | | | |

| | | | | | | | | | | | | | | | | |
|---|---|---|---|---|---|---|---|---|---|---|---|---|---|---|---|---|
| aag | gct | tgg | aac | ttc | gat | cat | aca | cca | cca | tcg | cca | gca | act | tgt | gct | 384 |
| Lys | Ala | Trp | Asn | Phe | Asp | His | Thr | Pro | Pro | Ser | Pro | Ala | Thr | Cys | Ala | |
| | | 115 | | | | | 120 | | | | | 125 | | | | |

| | | | | | | | | | | | | | | | | |
|---|---|---|---|---|---|---|---|---|---|---|---|---|---|---|---|---|
| tac | aca | gat | ttt | ctc | ctc | gca | gtg | gct | gct | ggg | aag | aaa | att | gaa | tgc | 432 |
| Tyr | Thr | Asp | Phe | Leu | Leu | Ala | Val | Ala | Ala | Gly | Lys | Lys | Ile | Glu | Cys | |
| | 130 | | | | | 135 | | | | | 140 | | | | | |

| | | | | | | | | | | | | | | | | |
|---|---|---|---|---|---|---|---|---|---|---|---|---|---|---|---|---|
| gag | aaa | act | aag | gtg | ccg | atg | ctc | gct | ctg | gca | gca | atg | gct | ccg | tgc | 480 |
| Glu | Lys | Thr | Lys | Val | Pro | Met | Leu | Ala | Leu | Ala | Ala | Met | Ala | Pro | Cys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| atg | cgt | ctc | tac | gct | ttc | cta | ggc | caa | gag | acg | aga | gtt | ttc | tct | cga | 528 |
| Met | Arg | Leu | Tyr | Ala | Phe | Leu | Gly | Gln | Glu | Thr | Arg | Val | Phe | Ser | Arg | |
| | | | | 165 | | | | | 170 | | | | | 175 | | |

| | | | | | | | | | | | | | | | | |
|---|---|---|---|---|---|---|---|---|---|---|---|---|---|---|---|---|
| gaa | aat | cat | cca | tat | cgc | gac | tgg | att | tcg | act | tac | tcg | tcg | cct | ggt | 576 |
| Glu | Asn | His | Pro | Tyr | Arg | Asp | Trp | Ile | Ser | Thr | Tyr | Ser | Ser | Pro | Gly | |
| | | | 180 | | | | | 185 | | | | | 190 | | | |

| | | | | | | | | | | | | | | | | |
|---|---|---|---|---|---|---|---|---|---|---|---|---|---|---|---|---|
| ttc | gag | act | gct | gct | act | cga | ctc | gag | cag | ctt | ctc | gat | agc | ctc | tcg | 624 |
| Phe | Glu | Thr | Ala | Ala | Thr | Arg | Leu | Glu | Gln | Leu | Leu | Asp | Ser | Leu | Ser | |
| | | 195 | | | | | 200 | | | | | 205 | | | | |

| | | | | | | | | | | | | | | | | |
|---|---|---|---|---|---|---|---|---|---|---|---|---|---|---|---|---|
| gaa | gct | caa | gag | act | acg | gca | gcg | gaa | ttt | cag | agt | atg | caa | agt | ttg | 672 |
| Glu | Ala | Gln | Glu | Thr | Thr | Ala | Ala | Glu | Phe | Gln | Ser | Met | Gln | Ser | Leu | |
| | 210 | | | | | 215 | | | | | 220 | | | | | |

| | | | | | | | | | | | | | | | | |
|---|---|---|---|---|---|---|---|---|---|---|---|---|---|---|---|---|
| tat | cac | cgt | gcc | ata | gcg | tac | gag | gtg | agc | ttc | ttc | gat | gcc | cag | gaa | 720 |
| Tyr | His | Arg | Ala | Ile | Ala | Tyr | Glu | Val | Ser | Phe | Phe | Asp | Ala | Gln | Glu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gtg | cgt | ggc | agc | aac | gct | ttt | gtc | ccg | ctg | cta | gag | agt | gta | gca | ctc | 768 |
| Val | Arg | Gly | Ser | Asn | Ala | Phe | Val | Pro | Leu | Leu | Glu | Ser | Val | Ala | Leu | |
| | | | | 245 | | | | | 250 | | | | | 255 | | |

| | | | | | | | | | | | | | | | | |
|---|---|---|---|---|---|---|---|---|---|---|---|---|---|---|---|---|
| aag | gat | cgc | aac | ttc | gtc | ctc | atc | tct | gat | ttt | gat | tct | act | tgc | acc | 816 |
| Lys | Asp | Arg | Asn | Phe | Val | Leu | Ile | Ser | Asp | Phe | Asp | Ser | Thr | Cys | Thr | |
| | | | | 260 | | | | | 265 | | | | | 270 | | |

```
gtc tct gat tca tcc cca gtt cta gcg gag ctg gct atg gcg gtc gat        864
Val Ser Asp Ser Ser Pro Val Leu Ala Glu Leu Ala Met Ala Val Asp
        275                 280                 285 cca aat gta agg agg aaa tgg agc agc ctc tcg gac gag tat ttc agg        912
Pro Asn Val Arg Arg Lys Trp Ser Ser Leu Ser Asp Glu Tyr Phe Arg
            290                 295                 300 gac tac tcc aaa ctc ctg gaa gaa gtt gtt ctt cgt gag tac gac tac        960
Asp Tyr Ser Lys Leu Leu Glu Glu Val Val Leu Arg Glu Tyr Asp Tyr
305                 310                 315                 320 gat gcg atc aaa gag gct ctc caa gtt ctt tcc gag ttt gag aag caa       1008
Asp Ala Ile Lys Glu Ala Leu Gln Val Leu Ser Glu Phe Glu Lys Gln
                325                 330                 335 ggg aac gcg aaa atc gac gcc tcc cgc gtt ttg caa ggc att aag atc       1056
Gly Asn Ala Lys Ile Asp Ala Ser Arg Val Leu Gln Gly Ile Lys Ile
            340                 345                 350 gat gat atc aag caa gcc gga caa aac atg gca ctt caa gct ggc tgt       1104
Asp Asp Ile Lys Gln Ala Gly Gln Asn Met Ala Leu Gln Ala Gly Cys
        355                 360                 365 gcc agt gtg ctt tgc agg cta agt tcc aaa atc tct tgt caa atc ctc       1152
Ala Ser Val Leu Cys Arg Leu Ser Ser Lys Ile Ser Cys Gln Ile Leu
370                 375                 380 tcg gtt tgc tgg agc cgg acc ttc atc gaa gca gct ttc tcc aaa gag       1200
Ser Val Cys Trp Ser Arg Thr Phe Ile Glu Ala Ala Phe Ser Lys Glu
385                 390                 395                 400 aat atc acc aat gtt cct gtc cat tcc aac gaa ctc gaa aac gat ggg       1248
Asn Ile Thr Asn Val Pro Val His Ser Asn Glu Leu Glu Asn Asp Gly
                405                 410                 415 aac ttt aca acc ggg agc ttg atc aga cgc gtc gag aca ccg att gac       1296
Asn Phe Thr Thr Gly Ser Leu Ile Arg Arg Val Glu Thr Pro Ile Asp
            420                 425                 430 aag gaa gag acg atg ttt cgt gag att cta cac gct ccg gac gac aag       1344
Lys Glu Glu Thr Met Phe Arg Glu Ile Leu His Ala Pro Asp Asp Lys
        435                 440                 445 ttt gtg att ttc att gga gac agc ctc acg gat ctg cta gcc ttg ctc       1392
Phe Val Ile Phe Ile Gly Asp Ser Leu Thr Asp Leu Leu Ala Leu Leu
    450                 455                 460 cga gct gac att gga att gtt cta gga acg agc tcc agc ctc gat cga       1440
Arg Ala Asp Ile Gly Ile Val Leu Gly Thr Ser Ser Ser Leu Asp Arg
465                 470                 475                 480 gcc tcc aaa gcc ttt gga gtg aag atc gtg cca ctc ttt tcc ggc ctc       1488
Ala Ser Lys Ala Phe Gly Val Lys Ile Val Pro Leu Phe Ser Gly Leu
                485                 490                 495 gtc cag cgg cag caa agc tct cga tca gcg tgg aga aaa gag gaa gga       1536
Val Gln Arg Gln Gln Ser Ser Arg Ser Ala Trp Arg Lys Glu Glu Gly
            500                 505                 510 gtt ttg tat cga gct tct gga tgg ctg gag ata gaa gcg ttt cta gct       1584
Val Leu Tyr Arg Ala Ser Gly Trp Leu Glu Ile Glu Ala Phe Leu Ala
        515                 520                 525 ggt aat tag                                                            1593
Gly Asn
    530
```

<210> SEQ ID NO 30
<211> LENGTH: 530
<212> TYPE: PRT
<213> ORGANISM: Selaginella moellendorffii

<400> SEQUENCE: 30

```
Met Ser Cys Leu Leu Arg Asn Val Val Ala Arg Gly Leu Arg Ser Leu
1               5                   10                  15
```

```
Ala Ser Ala Gln Ala Met Glu Pro Ser Ile Ser Lys Arg Leu Trp Gln
             20                  25                  30

Gln Ser Lys Arg Glu Ala Met Val Cys Leu Tyr His Pro Phe Val Val
         35                  40                  45

Ser Ile Ala Ala Gly Thr Leu Asp Leu His Ser Phe Gln Arg Phe Ile
 50                  55                  60

Ala Gln Asp Ser Phe Phe Leu Thr Ala Phe Ala Lys Ala Tyr Gly Leu
 65                  70                  75                  80

Ala Ile Glu Arg Ser Asp Asp Arg Glu Val Lys Ser Glu Ile Cys Lys
                 85                  90                  95

Leu Gln Gln Ala Val Tyr Glu Glu Leu Glu Leu His Ser Ser Leu Met
            100                 105                 110

Lys Ala Trp Asn Phe Asp His Thr Pro Pro Ser Pro Ala Thr Cys Ala
        115                 120                 125

Tyr Thr Asp Phe Leu Leu Ala Val Ala Ala Gly Lys Lys Ile Glu Cys
130                 135                 140

Glu Lys Thr Lys Val Pro Met Leu Ala Leu Ala Ala Met Ala Pro Cys
145                 150                 155                 160

Met Arg Leu Tyr Ala Phe Leu Gly Gln Glu Thr Arg Val Phe Ser Arg
                165                 170                 175

Glu Asn His Pro Tyr Arg Asp Trp Ile Ser Thr Tyr Ser Ser Pro Gly
            180                 185                 190

Phe Glu Thr Ala Ala Thr Arg Leu Glu Gln Leu Leu Asp Ser Leu Ser
        195                 200                 205

Glu Ala Gln Glu Thr Thr Ala Ala Glu Phe Gln Ser Met Gln Ser Leu
210                 215                 220

Tyr His Arg Ala Ile Ala Tyr Glu Val Ser Phe Phe Asp Ala Gln Glu
225                 230                 235                 240

Val Arg Gly Ser Asn Ala Phe Val Pro Leu Leu Glu Ser Val Ala Leu
                245                 250                 255

Lys Asp Arg Asn Phe Val Leu Ile Ser Asp Phe Asp Ser Thr Cys Thr
            260                 265                 270

Val Ser Asp Ser Ser Pro Val Leu Ala Glu Leu Ala Met Ala Val Asp
        275                 280                 285

Pro Asn Val Arg Arg Lys Trp Ser Ser Leu Ser Asp Glu Tyr Phe Arg
290                 295                 300

Asp Tyr Ser Lys Leu Leu Glu Glu Val Val Leu Arg Glu Tyr Asp Tyr
305                 310                 315                 320

Asp Ala Ile Lys Glu Ala Leu Gln Val Leu Ser Glu Phe Glu Lys Gln
                325                 330                 335

Gly Asn Ala Lys Ile Asp Ala Ser Arg Val Leu Gln Gly Ile Lys Ile
            340                 345                 350

Asp Asp Ile Lys Gln Ala Gly Gln Asn Met Ala Leu Gln Ala Gly Cys
        355                 360                 365

Ala Ser Val Leu Cys Arg Leu Ser Ser Lys Ile Ser Cys Gln Ile Leu
370                 375                 380

Ser Val Cys Trp Ser Arg Thr Phe Ile Glu Ala Ala Phe Ser Lys Glu
385                 390                 395                 400

Asn Ile Thr Asn Val Pro Val His Ser Asn Glu Leu Glu Asn Asp Gly
                405                 410                 415

Asn Phe Thr Thr Gly Ser Leu Ile Arg Arg Val Glu Thr Pro Ile Asp
            420                 425                 430
```

```
Lys Glu Glu Thr Met Phe Arg Glu Ile Leu His Ala Pro Asp Asp Lys
            435                 440                 445

Phe Val Ile Phe Ile Gly Asp Ser Leu Thr Asp Leu Leu Ala Leu Leu
        450                 455                 460

Arg Ala Asp Ile Gly Ile Val Leu Gly Thr Ser Ser Ser Leu Asp Arg
465                 470                 475                 480

Ala Ser Lys Ala Phe Gly Val Lys Ile Val Pro Leu Phe Ser Gly Leu
                485                 490                 495

Val Gln Arg Gln Gln Ser Ser Arg Ser Ala Trp Arg Lys Glu Glu Gly
            500                 505                 510

Val Leu Tyr Arg Ala Ser Gly Trp Leu Glu Ile Glu Ala Phe Leu Ala
        515                 520                 525

Gly Asn
    530

<210> SEQ ID NO 31
<211> LENGTH: 648
<212> TYPE: DNA
<213> ORGANISM: Anaerotruncus colihominis
<220> FEATURE:
<221> NAME/KEY: CDS
<222> LOCATION: (1)..(645)
<223> OTHER INFORMATION: Anaerotruncus colihominis gene encoding TMP
      phosphatase [WP_006874980]

<400> SEQUENCE: 31 atg atc aaa ggc gcg att ttt gat atg gac ggt acg ctg att gat tcc      48
Met Ile Lys Gly Ala Ile Phe Asp Met Asp Gly Thr Leu Ile Asp Ser
1               5                   10                  15 atg cct cta tgg gag gac tgc gga cgg gcc ttt tta tcc gcg cgc ggc      96
Met Pro Leu Trp Glu Asp Cys Gly Arg Ala Phe Leu Ser Ala Arg Gly
                20                  25                  30 att act gcg cgt gac gat ctg ggc gaa acg ctc aaa tcc ctg tcg atg     144
Ile Thr Ala Arg Asp Asp Leu Gly Glu Thr Leu Lys Ser Leu Ser Met
            35                  40                  45 gag caa acg gct aat tat ttg cgg gac gca tac ggt att tcc gag aca     192
Glu Gln Thr Ala Asn Tyr Leu Arg Asp Ala Tyr Gly Ile Ser Glu Thr
        50                  55                  60 acc tct gaa atc att gag atg atc aat gga atg gtt act gac gca tat     240
Thr Ser Glu Ile Ile Glu Met Ile Asn Gly Met Val Thr Asp Ala Tyr
65                  70                  75                  80 cag cgc acc atc ccg ctt aaa cgt gac att gcc gcg ttt ctc gag cgc     288
Gln Arg Thr Ile Pro Leu Lys Arg Asp Ile Ala Ala Phe Leu Glu Arg
                85                  90                  95 ctc agg cag gcg gat gtg cgc atg tgt gtc gca acg gca acg gac cgt     336
Leu Arg Gln Ala Asp Val Arg Met Cys Val Ala Thr Ala Thr Asp Arg
            100                 105                 110 cca ctg gtg gag gcg gcg ctt gga cgc ctt gac ctc ctg ccc ttt ttt     384
Pro Leu Val Glu Ala Ala Leu Gly Arg Leu Asp Leu Leu Pro Phe Phe
        115                 120                 125 gaa cgg att ttc acc tgt tcg gag gtg ggg gcc ggc aag gac cgc ccc     432
Glu Arg Ile Phe Thr Cys Ser Glu Val Gly Ala Gly Lys Asp Arg Pro
130                 135                 140 gat atc ttt gag cag gcg tgc gcc gcg ctt ggc acg ccg cgc ggc gaa     480
Asp Ile Phe Glu Gln Ala Cys Ala Ala Leu Gly Thr Pro Arg Gly Glu
145                 150                 155                 160 acc gtc atc ttt gag gat gct ctt tat gcg att gaa aca gct cgg cgc     528
Thr Val Ile Phe Glu Asp Ala Leu Tyr Ala Ile Glu Thr Ala Arg Arg
                165                 170                 175 gcc ggg ttc cgc gtt gtc gca atc gcg gac gac gcc tcc gcc ggc gac     576
```

```
Ala Gly Phe Arg Val Val Ala Ile Ala Asp Asp Ala Ser Ala Gly Asp
            180                 185                 190 gag gcg cgc ata gcc gca ctg tct gag caa tat ata cat aac tat gag    624
Glu Ala Arg Ile Ala Ala Leu Ser Glu Gln Tyr Ile His Asn Tyr Glu
        195                 200                 205 gaa tgc gag gta aac agt tta tga                                    648
Glu Cys Glu Val Asn Ser Leu
    210                 215
```

<210> SEQ ID NO 32
<211> LENGTH: 215
<212> TYPE: PRT
<213> ORGANISM: Anaerotruncus colihominis

<400> SEQUENCE: 32

```
Met Ile Lys Gly Ala Ile Phe Asp Met Asp Gly Thr Leu Ile Asp Ser
1               5                   10                  15

Met Pro Leu Trp Glu Asp Cys Gly Arg Ala Phe Leu Ser Ala Arg Gly
            20                  25                  30

Ile Thr Ala Arg Asp Asp Leu Gly Glu Thr Leu Lys Ser Leu Ser Met
        35                  40                  45

Glu Gln Thr Ala Asn Tyr Leu Arg Asp Ala Tyr Gly Ile Ser Glu Thr
    50                  55                  60

Thr Ser Glu Ile Ile Glu Met Ile Asn Gly Met Val Thr Asp Ala Tyr
65                  70                  75                  80

Gln Arg Thr Ile Pro Leu Lys Arg Asp Ile Ala Ala Phe Leu Glu Arg
                85                  90                  95

Leu Arg Gln Ala Asp Val Arg Met Cys Val Ala Thr Ala Thr Asp Arg
            100                 105                 110

Pro Leu Val Glu Ala Ala Leu Gly Arg Leu Asp Leu Leu Pro Phe Phe
        115                 120                 125

Glu Arg Ile Phe Thr Cys Ser Glu Val Gly Ala Gly Lys Asp Arg Pro
    130                 135                 140

Asp Ile Phe Glu Gln Ala Cys Ala Ala Leu Gly Thr Pro Arg Gly Glu
145                 150                 155                 160

Thr Val Ile Phe Glu Asp Ala Leu Tyr Ala Ile Glu Thr Ala Arg Arg
                165                 170                 175

Ala Gly Phe Arg Val Val Ala Ile Ala Asp Asp Ala Ser Ala Gly Asp
            180                 185                 190

Glu Ala Arg Ile Ala Ala Leu Ser Glu Gln Tyr Ile His Asn Tyr Glu
        195                 200                 205

Glu Cys Glu Val Asn Ser Leu
    210                 215
```

<210> SEQ ID NO 33
<211> LENGTH: 666
<212> TYPE: DNA
<213> ORGANISM: Eubacterium ventriosum
<220> FEATURE:
<221> NAME/KEY: CDS
<222> LOCATION: (1)..(663)
<223> OTHER INFORMATION: Eubacterium ventriosum gene encoding TMP
      phosphatase [WP_005362972]

<400> SEQUENCE: 33

```
atg tca aca gga ttt ata ttt gat gta gat gga aca ata cta gac tca    48
Met Ser Thr Gly Phe Ile Phe Asp Val Asp Gly Thr Ile Leu Asp Ser
1               5                   10                  15 atg gga ata tgg atg aac gta gga gaa cta tat cta aaa gat atg gga    96
```

```
                Met Gly Ile Trp Met Asn Val Gly Glu Leu Tyr Leu Lys Asp Met Gly
                             20                  25                  30 ata aag gcg gaa cca aat ctt gga gaa att cta ttc gaa atg aca atg         144
Ile Lys Ala Glu Pro Asn Leu Gly Glu Ile Leu Phe Glu Met Thr Met
             35                  40                  45 aat gaa ggt gca gaa tac ata caa aaa aag tat aat cta aac ctt aca         192
Asn Glu Gly Ala Glu Tyr Ile Gln Lys Lys Tyr Asn Leu Asn Leu Thr
 50                  55                  60 aca gaa gaa ata tgc acc gga ata aac aac cgt gta tac aaa ttc tac         240
Thr Glu Glu Ile Cys Thr Gly Ile Asn Asn Arg Val Tyr Lys Phe Tyr
 65                  70                  75                  80 gaa aaa gaa gca atg cca aaa cca aaa gtt atc gac ttt ata gaa caa         288
Glu Lys Glu Ala Met Pro Lys Pro Lys Val Ile Asp Phe Ile Glu Gln
                 85                  90                  95 gcc tac gag aac aaa atc cca atg aca ata gca acg tca aca gac aga         336
Ala Tyr Glu Asn Lys Ile Pro Met Thr Ile Ala Thr Ser Thr Asp Arg
                100                 105                 110 cca atg ata gaa gca gct ttc aaa aga ctg cac ata gac aaa tat ttt         384
Pro Met Ile Glu Ala Ala Phe Lys Arg Leu His Ile Asp Lys Tyr Phe
            115                 120                 125 aaa aaa ata ttt acc acg aca gag gtt ggg tat gga aaa gac aaa ccg         432
Lys Lys Ile Phe Thr Thr Thr Glu Val Gly Tyr Gly Lys Asp Lys Pro
        130                 135                 140 gac atc ttc ata aaa gca atg gaa gaa atg gga aca aca cca aag caa         480
Asp Ile Phe Ile Lys Ala Met Glu Glu Met Gly Thr Thr Pro Lys Gln
145                 150                 155                 160 aca tgg cta ttt gaa gat gga gca tac tca ata gaa aca gcc aaa caa         528
Thr Trp Leu Phe Glu Asp Gly Ala Tyr Ser Ile Glu Thr Ala Lys Gln
                165                 170                 175 cta gga ata aaa aca ata gga atc tac gat cct gca agc gaa aaa gac         576
Leu Gly Ile Lys Thr Ile Gly Ile Tyr Asp Pro Ala Ser Glu Lys Asp
            180                 185                 190 cag gaa aaa ata aga aac cta aca aac atc tac ata aaa aat tgg aca         624
Gln Glu Lys Ile Arg Asn Leu Thr Asn Ile Tyr Ile Lys Asn Trp Thr
        195                 200                 205 gaa cac aaa acc cta ctt aac caa ata caa aac aac aag tag               666
Glu His Lys Thr Leu Leu Asn Gln Ile Gln Asn Asn Lys
    210                 215                 220

<210> SEQ ID NO 34
<211> LENGTH: 221
<212> TYPE: PRT
<213> ORGANISM: Eubacterium ventriosum

<400> SEQUENCE: 34

Met Ser Thr Gly Phe Ile Phe Asp Val Asp Gly Thr Ile Leu Asp Ser
1               5                   10                  15

Met Gly Ile Trp Met Asn Val Gly Glu Leu Tyr Leu Lys Asp Met Gly
            20                  25                  30

Ile Lys Ala Glu Pro Asn Leu Gly Glu Ile Leu Phe Glu Met Thr Met
        35                  40                  45

Asn Glu Gly Ala Glu Tyr Ile Gln Lys Lys Tyr Asn Leu Asn Leu Thr
    50                  55                  60

Thr Glu Glu Ile Cys Thr Gly Ile Asn Asn Arg Val Tyr Lys Phe Tyr
65                  70                  75                  80

Glu Lys Glu Ala Met Pro Lys Pro Lys Val Ile Asp Phe Ile Glu Gln
                85                  90                  95

Ala Tyr Glu Asn Lys Ile Pro Met Thr Ile Ala Thr Ser Thr Asp Arg
            100                 105                 110
```

```
        Pro Met Ile Glu Ala Ala Phe Lys Arg Leu His Ile Asp Lys Tyr Phe
                115                 120                 125

Lys Lys Ile Phe Thr Thr Thr Glu Val Gly Tyr Gly Lys Asp Lys Pro
            130                 135                 140

Asp Ile Phe Ile Lys Ala Met Glu Glu Met Gly Thr Thr Pro Lys Gln
        145                 150                 155                 160

Thr Trp Leu Phe Glu Asp Gly Ala Tyr Ser Ile Glu Thr Ala Lys Gln
                        165                 170                 175

Leu Gly Ile Lys Thr Ile Gly Ile Tyr Asp Pro Ala Ser Glu Lys Asp
                    180                 185                 190

Gln Glu Lys Ile Arg Asn Leu Thr Asn Ile Tyr Ile Lys Asn Trp Thr
                    195                 200                 205

Glu His Lys Thr Leu Leu Asn Gln Ile Gln Asn Asn Lys
                    210                 215                 220

<210> SEQ ID NO 35
        <211> LENGTH: 1482
        <212> TYPE: DNA
        <213> ORGANISM: Coprococcus eutactus
        <220> FEATURE:
        <221> NAME/KEY: CDS
        <222> LOCATION: (1)..(1479)
        <223> OTHER INFORMATION: Coprococcus eutactus ATCC 27759 gene encoding
              TMP phosphatase [EDP27707]

<400> SEQUENCE: 35 atg aaa aag ata gtt atc agc gat ata aaa ggt gcg ata ttt gac atg       48
        Met Lys Lys Ile Val Ile Ser Asp Ile Lys Gly Ala Ile Phe Asp Met
        1               5                   10                  15 gat gga gtt ctg ctg gac tct atg ccg atg tgg gac cat gcg ggc gag       96
        Asp Gly Val Leu Leu Asp Ser Met Pro Met Trp Asp His Ala Gly Glu
                        20                  25                  30 atg tac ctt gca gga cag ggg ata gag gct gag cct gat ctt gaa aaa      144
        Met Tyr Leu Ala Gly Gln Gly Ile Glu Ala Glu Pro Asp Leu Glu Lys
                    35                  40                  45 gtc ttg ttt aca atg act atg caa aag ggc gct gaa tat ata cgt gat      192
        Val Leu Phe Thr Met Thr Met Gln Lys Gly Ala Glu Tyr Ile Arg Asp
                50                  55                  60 cat tat ggg tta aaa ctc acg gcg gat gag atc ata gat ggc ata aat      240
        His Tyr Gly Leu Lys Leu Thr Ala Asp Glu Ile Ile Asp Gly Ile Asn
        65                  70                  75                  80 gag act gtg aga gat ttc tat gca aat aag gtt gtg cct aag aat gga      288
        Glu Thr Val Arg Asp Phe Tyr Ala Asn Lys Val Val Pro Lys Asn Gly
                        85                  90                  95 gtc ctt aag ttc ctc agg ctg ttg aag agt cac aat ata cct gta acc      336
        Val Leu Lys Phe Leu Arg Leu Leu Lys Ser His Asn Ile Pro Val Thr
                    100                 105                 110 gtt gca act tcg acc gac aga tgc cat gtg gag gct gct ctt tca aga      384
        Val Ala Thr Ser Thr Asp Arg Cys His Val Glu Ala Ala Leu Ser Arg
                115                 120                 125 aat gga ctt atg gaa tat gta gac aag ata ttt acg tgt tcg gaa gtt      432
        Asn Gly Leu Met Glu Tyr Val Asp Lys Ile Phe Thr Cys Ser Glu Val
        130                 135                 140 ggc gtt gga aag gct gcc tct cca aag ata tat gag ctt gcg gcc gaa      480
        Gly Val Gly Lys Ala Ala Ser Pro Lys Ile Tyr Glu Leu Ala Ala Glu
        145                 150                 155                 160 ttt atg ggg acg aaa gtc ggc gag tca ttt gtg ttc gag gat gcc tat      528
        Phe Met Gly Thr Lys Val Gly Glu Ser Phe Val Phe Glu Asp Ala Tyr
                        165                 170                 175
```

```
cat gcg gcc gag aca gct cag aat gcg gga ttt aca gtt gta gga ctc      576
His Ala Ala Glu Thr Ala Gln Asn Ala Gly Phe Thr Val Val Gly Leu
            180                 185                 190 tat gac gag tca agc cgt gac atg caa gca gaa ctt aag gtt cac tgc      624
Tyr Asp Glu Ser Ser Arg Asp Met Gln Ala Glu Leu Lys Val His Cys
        195                 200                 205 aat tat tac tat ttg gga ttt gcc gag ctt ata gat gag ctg ctg cct      672
Asn Tyr Tyr Tyr Leu Gly Phe Ala Glu Leu Ile Asp Glu Leu Leu Pro
    210                 215                 220 gac aga agc cag ctt gca ccg gtt ctt acc atc gcg ggc agt gat tca      720
Asp Arg Ser Gln Leu Ala Pro Val Leu Thr Ile Ala Gly Ser Asp Ser
225                 230                 235                 240 tcg gga ggt gcg gga ata cag gca gat ctt aag acc atg cag gca aat      768
Ser Gly Gly Ala Gly Ile Gln Ala Asp Leu Lys Thr Met Gln Ala Asn
                245                 250                 255 gga gtg ttt ggc atg agc gca gta act gcc ttg acg gcg cag aat acc      816
Gly Val Phe Gly Met Ser Ala Val Thr Ala Leu Thr Ala Gln Asn Thr
            260                 265                 270 aca ggt gtg aca tcc atc atg aat gtg aca cct gac ata ctt gca gat      864
Thr Gly Val Thr Ser Ile Met Asn Val Thr Pro Asp Ile Leu Ala Asp
        275                 280                 285 cag ata gat gca gta ttt aca gat ata aga cca cag gcg gtc aag ata      912
Gln Ile Asp Ala Val Phe Thr Asp Ile Arg Pro Gln Ala Val Lys Ile
    290                 295                 300 ggt atg gtg tct gtg cca gaa ctt ata aat gtg atc gca gac aag ctt      960
Gly Met Val Ser Val Pro Glu Leu Ile Asn Val Ile Ala Asp Lys Leu
305                 310                 315                 320 gaa ttt tac agg gcg gag aat gtg gtg ctt gat cct gtg atg gtt gcg     1008
Glu Phe Tyr Arg Ala Glu Asn Val Val Leu Asp Pro Val Met Val Ala
                325                 330                 335 aca agc ggt gct aaa ctc ata agc gat gat gct gtg gac gtt ttg aca     1056
Thr Ser Gly Ala Lys Leu Ile Ser Asp Asp Ala Val Asp Val Leu Thr
            340                 345                 350 gga agg ctg ttc cca ctt gca aag ctg atc acc cca aat att cca gag     1104
Gly Arg Leu Phe Pro Leu Ala Lys Leu Ile Thr Pro Asn Ile Pro Glu
        355                 360                 365 aca gag gcc ctc aca ggt atg agt atc cgg tct aag gaa gat atg gaa     1152
Thr Glu Ala Leu Thr Gly Met Ser Ile Arg Ser Lys Glu Asp Met Glu
    370                 375                 380 agt gca gca agg aaa ata tat gaa aaa tat ggc tgc tca gtt ctt gtg     1200
Ser Ala Ala Arg Lys Ile Tyr Glu Lys Tyr Gly Cys Ser Val Leu Val
385                 390                 395                 400 aag ggc gga cat agc ata aac gat gcg aat gat atg ctg ttt gat gga     1248
Lys Gly Gly His Ser Ile Asn Asp Ala Asn Asp Met Leu Phe Asp Gly
                405                 410                 415 gag aat gta tca tgg ttt tca ggt gag aga ata gaa aat ccg aat acc     1296
Glu Asn Val Ser Trp Phe Ser Gly Glu Arg Ile Glu Asn Pro Asn Thr
            420                 425                 430 cat gga acg ggg tgt aca ctc tca agt gca ata gcc tcc aac ctt gca     1344
His Gly Thr Gly Cys Thr Leu Ser Ser Ala Ile Ala Ser Asn Leu Ala
        435                 440                 445 aag gga tat gat ata gaa act tct gtg cag aga gca aaa gcg tac atc     1392
Lys Gly Tyr Asp Ile Glu Thr Ser Val Gln Arg Ala Lys Ala Tyr Ile
    450                 455                 460 tca gga gcc ctg gct gcg atg ctt gat cta gga aga gga agc ggc ccg     1440
Ser Gly Ala Leu Ala Ala Met Leu Asp Leu Gly Arg Gly Ser Gly Pro
465                 470                 475                 480 tta aac cat ggc ttt gat ata gac agc aga ttc atg ata taa             1482
Leu Asn His Gly Phe Asp Ile Asp Ser Arg Phe Met Ile
                485                 490
```

```
<210> SEQ ID NO 36
<211> LENGTH: 493
<212> TYPE: PRT
<213> ORGANISM: Coprococcus eutactus

<400> SEQUENCE: 36
```

| | | | | | | | | | | | | | | |
|---|---|---|---|---|---|---|---|---|---|---|---|---|---|---|
| Met | Lys | Lys | Ile | Val | Ile | Ser | Asp | Ile | Lys | Gly | Ala | Ile | Phe | Asp | Met |
| 1 | | | | 5 | | | | | 10 | | | | | 15 | |

| Asp | Gly | Val | Leu | Leu | Asp | Ser | Met | Pro | Met | Trp | Asp | His | Ala | Gly | Glu |
| | | | 20 | | | | | 25 | | | | | 30 | | |

| Met | Tyr | Leu | Ala | Gly | Gln | Gly | Ile | Glu | Ala | Glu | Pro | Asp | Leu | Glu | Lys |
| | | | 35 | | | | | 40 | | | | | 45 | | |

| Val | Leu | Phe | Thr | Met | Thr | Met | Gln | Lys | Gly | Ala | Glu | Tyr | Ile | Arg | Asp |
| | 50 | | | | | 55 | | | | | 60 | | | | |

| His | Tyr | Gly | Leu | Lys | Leu | Thr | Ala | Asp | Glu | Ile | Ile | Asp | Gly | Ile | Asn |
| 65 | | | | | 70 | | | | | 75 | | | | | 80 |

| Glu | Thr | Val | Arg | Asp | Phe | Tyr | Ala | Asn | Lys | Val | Val | Pro | Lys | Asn | Gly |
| | | | | 85 | | | | | 90 | | | | | 95 | |

| Val | Leu | Lys | Phe | Leu | Arg | Leu | Leu | Lys | Ser | His | Asn | Ile | Pro | Val | Thr |
| | | | 100 | | | | | 105 | | | | | 110 | | |

| Val | Ala | Thr | Ser | Thr | Asp | Arg | Cys | His | Val | Glu | Ala | Ala | Leu | Ser | Arg |
| | | | 115 | | | | | 120 | | | | | 125 | | |

| Asn | Gly | Leu | Met | Glu | Tyr | Val | Asp | Lys | Ile | Phe | Thr | Cys | Ser | Glu | Val |
| | 130 | | | | | 135 | | | | | 140 | | | | |

| Gly | Val | Gly | Lys | Ala | Ala | Ser | Pro | Lys | Ile | Tyr | Glu | Leu | Ala | Ala | Glu |
| 145 | | | | | 150 | | | | | 155 | | | | | 160 |

| Phe | Met | Gly | Thr | Lys | Val | Gly | Glu | Ser | Phe | Val | Phe | Glu | Asp | Ala | Tyr |
| | | | | 165 | | | | | 170 | | | | | 175 | |

| His | Ala | Ala | Glu | Thr | Ala | Gln | Asn | Ala | Gly | Phe | Thr | Val | Val | Gly | Leu |
| | | | 180 | | | | | 185 | | | | | 190 | | |

| Tyr | Asp | Glu | Ser | Ser | Arg | Asp | Met | Gln | Ala | Glu | Leu | Lys | Val | His | Cys |
| | | | 195 | | | | | 200 | | | | | 205 | | |

| Asn | Tyr | Tyr | Tyr | Leu | Gly | Phe | Ala | Glu | Leu | Ile | Asp | Glu | Leu | Leu | Pro |
| | 210 | | | | | 215 | | | | | 220 | | | | |

| Asp | Arg | Ser | Gln | Leu | Ala | Pro | Val | Leu | Thr | Ile | Ala | Gly | Ser | Asp | Ser |
| 225 | | | | | 230 | | | | | 235 | | | | | 240 |

| Ser | Gly | Gly | Ala | Gly | Ile | Gln | Ala | Asp | Leu | Lys | Thr | Met | Gln | Ala | Asn |
| | | | | 245 | | | | | 250 | | | | | 255 | |

| Gly | Val | Phe | Gly | Met | Ser | Ala | Val | Thr | Ala | Leu | Thr | Ala | Gln | Asn | Thr |
| | | | 260 | | | | | 265 | | | | | 270 | | |

| Thr | Gly | Val | Thr | Ser | Ile | Met | Asn | Val | Thr | Pro | Asp | Ile | Leu | Ala | Asp |
| | | | 275 | | | | | 280 | | | | | 285 | | |

| Gln | Ile | Asp | Ala | Val | Phe | Thr | Asp | Ile | Arg | Pro | Gln | Ala | Val | Lys | Ile |
| | 290 | | | | | 295 | | | | | 300 | | | | |

| Gly | Met | Val | Ser | Val | Pro | Glu | Leu | Ile | Asn | Val | Ile | Ala | Asp | Lys | Leu |
| 305 | | | | | 310 | | | | | 315 | | | | | 320 |

| Glu | Phe | Tyr | Arg | Ala | Glu | Asn | Val | Val | Leu | Asp | Pro | Val | Met | Val | Ala |
| | | | | 325 | | | | | 330 | | | | | 335 | |

| Thr | Ser | Gly | Ala | Lys | Leu | Ile | Ser | Asp | Asp | Ala | Val | Asp | Val | Leu | Thr |
| | | | 340 | | | | | 345 | | | | | 350 | | |

| Gly | Arg | Leu | Phe | Pro | Leu | Ala | Lys | Leu | Ile | Thr | Pro | Asn | Ile | Pro | Glu |
| | | | 355 | | | | | 360 | | | | | 365 | | |

| Thr | Glu | Ala | Leu | Thr | Gly | Met | Ser | Ile | Arg | Ser | Lys | Glu | Asp | Met | Glu |

```
                370                 375                 380
Ser Ala Ala Arg Lys Ile Tyr Glu Lys Tyr Gly Cys Ser Val Leu Val
385                 390                 395                 400

Lys Gly Gly His Ser Ile Asn Asp Ala Asn Asp Met Leu Phe Asp Gly
                405                 410                 415

Glu Asn Val Ser Trp Phe Ser Gly Glu Arg Ile Glu Asn Pro Asn Thr
                420                 425                 430

His Gly Thr Gly Cys Thr Leu Ser Ser Ala Ile Ala Ser Asn Leu Ala
            435                 440                 445

Lys Gly Tyr Asp Ile Glu Thr Ser Val Gln Arg Ala Lys Ala Tyr Ile
        450                 455                 460

Ser Gly Ala Leu Ala Ala Met Leu Asp Leu Gly Arg Gly Ser Gly Pro
465                 470                 475                 480

Leu Asn His Gly Phe Asp Ile Asp Ser Arg Phe Met Ile
                485                 490
```

<210> SEQ ID NO 37
<211> LENGTH: 663
<212> TYPE: DNA
<213> ORGANISM: Ruminococcus bromii
<220> FEATURE:
<221> NAME/KEY: CDS
<222> LOCATION: (1)..(660)
<223> OTHER INFORMATION: Ruminococcus bromii L2-63 gene encoding TMP
      phosphatase [CBL14666]

<400> SEQUENCE: 37

```
atg att aaa tct gca ata ttt gat gtt gac ggc aca ctt ctc gat tca      48
Met Ile Lys Ser Ala Ile Phe Asp Val Asp Gly Thr Leu Leu Asp Ser
1               5                   10                  15 atg aag ata tgg gat gat gca gga gag cgt tac ctc tcg tct gtc ggc      96
Met Lys Ile Trp Asp Asp Ala Gly Glu Arg Tyr Leu Ser Ser Val Gly
                20                  25                  30 aaa aca gcc gaa aac gga ctt tcc gaa aag ctc tgt gat atg agt ctg     144
Lys Thr Ala Glu Asn Gly Leu Ser Glu Lys Leu Cys Asp Met Ser Leu
            35                  40                  45 acg gag ggt gcg gag tat atg aaa aag cag tat gct ctt tcc ttt tca     192
Thr Glu Gly Ala Glu Tyr Met Lys Lys Gln Tyr Ala Leu Ser Phe Ser
        50                  55                  60 act gat gaa ata gtt tcg ggt gtg ctg aaa atc att gaa gat ttt tac     240
Thr Asp Glu Ile Val Ser Gly Val Leu Lys Ile Ile Glu Asp Phe Tyr
65                  70                  75                  80 ttt tat gag gtc ggt tta aaa aac gat gca aaa gaa att ttg cag ttt     288
Phe Tyr Glu Val Gly Leu Lys Asn Asp Ala Lys Glu Ile Leu Gln Phe
                85                  90                  95 ttg gaa tcg aac aat atc aaa atg att att gca aca tca agc gac aaa     336
Leu Glu Ser Asn Asn Ile Lys Met Ile Ile Ala Thr Ser Ser Asp Lys
                100                 105                 110 acg cat att aaa aag gca ttt gaa agg ctc ggt att cta aaa tat ttt     384
Thr His Ile Lys Lys Ala Phe Glu Arg Leu Gly Ile Leu Lys Tyr Phe
            115                 120                 125 acg gat att gtg acc tgt tca caa gtc gga aaa ggc aaa aca agc ccc     432
Thr Asp Ile Val Thr Cys Ser Gln Val Gly Lys Gly Lys Thr Ser Pro
        130                 135                 140 gac att tac ctt gtc tgt gca gat aaa ctc gga aca gct ccg agt gaa     480
Asp Ile Tyr Leu Val Cys Ala Asp Lys Leu Gly Thr Ala Pro Ser Glu
145                 150                 155                 160 acg ctt gta ttc gag gac gct gtt ttt gcc gca gaa act gct cac aag     528
Thr Leu Val Phe Glu Asp Ala Val Phe Ala Ala Glu Thr Ala His Lys
                165                 170                 175
```

```
gca ggt ttc aaa acg gtg gga gtg tat gac gaa ttg agc agg aat aat      576
Ala Gly Phe Lys Thr Val Gly Val Tyr Asp Glu Leu Ser Arg Asn Asn
        180                 185                 190 aaa aac aga ata aaa gcc gtt tgc gat tac tac gca gac agc ttt gaa      624
Lys Asn Arg Ile Lys Ala Val Cys Asp Tyr Tyr Ala Asp Ser Phe Glu
        195                 200                 205 aaa gcg gca gat tgg ggg cac cac ctt ttg tcg ctg taa                  663
Lys Ala Ala Asp Trp Gly His His Leu Leu Ser Leu
        210                 215                 220
```

<210> SEQ ID NO 38
<211> LENGTH: 220
<212> TYPE: PRT
<213> ORGANISM: Ruminococcus bromii

<400> SEQUENCE: 38

```
Met Ile Lys Ser Ala Ile Phe Asp Val Asp Gly Thr Leu Leu Asp Ser
1               5                   10                  15

Met Lys Ile Trp Asp Asp Ala Gly Glu Arg Tyr Leu Ser Ser Val Gly
            20                  25                  30

Lys Thr Ala Glu Asn Gly Leu Ser Glu Lys Leu Cys Asp Met Ser Leu
        35                  40                  45

Thr Glu Gly Ala Glu Tyr Met Lys Lys Gln Tyr Ala Leu Ser Phe Ser
    50                  55                  60

Thr Asp Glu Ile Val Ser Gly Val Leu Lys Ile Ile Glu Asp Phe Tyr
65                  70                  75                  80

Phe Tyr Glu Val Gly Leu Lys Asn Asp Ala Lys Glu Ile Leu Gln Phe
                85                  90                  95

Leu Glu Ser Asn Asn Ile Lys Met Ile Ile Ala Thr Ser Ser Asp Lys
            100                 105                 110

Thr His Ile Lys Lys Ala Phe Glu Arg Leu Gly Ile Leu Lys Tyr Phe
        115                 120                 125

Thr Asp Ile Val Thr Cys Ser Gln Val Gly Lys Gly Lys Thr Ser Pro
    130                 135                 140

Asp Ile Tyr Leu Val Cys Ala Asp Lys Leu Gly Thr Ala Pro Ser Glu
145                 150                 155                 160

Thr Leu Val Phe Glu Asp Ala Val Phe Ala Ala Glu Thr Ala His Lys
                165                 170                 175

Ala Gly Phe Lys Thr Val Gly Val Tyr Asp Glu Leu Ser Arg Asn Asn
            180                 185                 190

Lys Asn Arg Ile Lys Ala Val Cys Asp Tyr Tyr Ala Asp Ser Phe Glu
        195                 200                 205

Lys Ala Ala Asp Trp Gly His His Leu Leu Ser Leu
    210                 215                 220
```

<210> SEQ ID NO 39
<211> LENGTH: 1434
<212> TYPE: DNA
<213> ORGANISM: Dorea longicatena
<220> FEATURE:
<221> NAME/KEY: CDS
<222> LOCATION: (1)..(1431)
<223> OTHER INFORMATION: Dorea longicatena DSM13814 gene encoding TMP
      phosphatase [EDM62146]

<400> SEQUENCE: 39

```
atg ata aaa gga gca ata ttt gat gta gac gga acc ctt ctg gat tcc       48
Met Ile Lys Gly Ala Ile Phe Asp Val Asp Gly Thr Leu Leu Asp Ser
1               5                   10                  15
```

```
atg gag atc tgg gaa gac gta gga gtc cgt tat ctg aac agt atc ggt      96
Met Glu Ile Trp Glu Asp Val Gly Val Arg Tyr Leu Asn Ser Ile Gly
         20                  25                  30 ata gag gca gag ccg gat ctt ggg acg gtg tta ttt aca atg agc atc     144
Ile Glu Ala Glu Pro Asp Leu Gly Thr Val Leu Phe Thr Met Ser Ile
     35                  40                  45 cag gaa ggt gca gca tat gta aaa gaa cat tat cat ctg tcc cag gag     192
Gln Glu Gly Ala Ala Tyr Val Lys Glu His Tyr His Leu Ser Gln Glu
 50                  55                  60 ccg gaa gaa att gtg cag gga gtt ctg gac atc atc agc aat tat tat     240
Pro Glu Glu Ile Val Gln Gly Val Leu Asp Ile Ile Ser Asn Tyr Tyr
 65                  70                  75                  80 aag aaa acc gca cta tta aag agt gga gtg aag gaa ctt ctg gaa aag     288
Lys Lys Thr Ala Leu Leu Lys Ser Gly Val Lys Glu Leu Leu Glu Lys
                 85                  90                  95 ctt gat aag cat aat atc cca atg acg gtt gca tca tcc aat aat aaa     336
Leu Asp Lys His Asn Ile Pro Met Thr Val Ala Ser Ser Asn Asn Lys
            100                 105                 110 aaa gag ata gag atg gca ttt gag cgt ctg gga att gca aaa tat ttt     384
Lys Glu Ile Glu Met Ala Phe Glu Arg Leu Gly Ile Ala Lys Tyr Phe
        115                 120                 125 gac cgg atc ttt acc tgt gaa gag gtc ggt gcg gga aag acg aag ccg     432
Asp Arg Ile Phe Thr Cys Glu Glu Val Gly Ala Gly Lys Thr Lys Pro
    130                 135                 140 gat att tat ctg cgg gca gca gaa tat ctc gga acc cgt ccg gag gag     480
Asp Ile Tyr Leu Arg Ala Ala Glu Tyr Leu Gly Thr Arg Pro Glu Glu
145                 150                 155                 160 acg gtt gta ttc gaa gat gtc att cat gca atc cgt act gca aag cag     528
Thr Val Val Phe Glu Asp Val Ile His Ala Ile Arg Thr Ala Lys Gln
                165                 170                 175 gca ggg ttc cag gtt gta gga atc tat gat gaa gca agt aag gat gac     576
Ala Gly Phe Gln Val Val Gly Ile Tyr Asp Glu Ala Ser Lys Asp Asp
            180                 185                 190 cag gaa gag gtt cag aga gaa gta gac tgg tat tgt aga gag tgg gca     624
Gln Glu Glu Val Gln Arg Glu Val Asp Trp Tyr Cys Arg Glu Trp Ala
        195                 200                 205 gaa ctt atg aaa aaa aag aca gca att aca atc gcc gga agt gat tca     672
Glu Leu Met Lys Lys Lys Thr Ala Ile Thr Ile Ala Gly Ser Asp Ser
210                 215                 220 agt gga ggt gca gga att cag gca gac atc aag acg atg cag gca aac     720
Ser Gly Gly Ala Gly Ile Gln Ala Asp Ile Lys Thr Met Gln Ala Asn
225                 230                 235                 240 gga gtc tac gca atg agt gca atc acc gca ctg aca gcc cag aat aca     768
Gly Val Tyr Ala Met Ser Ala Ile Thr Ala Leu Thr Ala Gln Asn Thr
                245                 250                 255 acc gga gta acc gga atc atg gaa gta tct ccg gaa ttt cta gaa caa     816
Thr Gly Val Thr Gly Ile Met Glu Val Ser Pro Glu Phe Leu Glu Gln
            260                 265                 270 cag ttg gac gca gtt atc aca gac atc cgt ccg gat gca gtg aaa atc     864
Gln Leu Asp Ala Val Ile Thr Asp Ile Arg Pro Asp Ala Val Lys Ile
        275                 280                 285 ggt atg gtg tca tca gaa gag tta ata aaa atg ata tca aag aaa cta     912
Gly Met Val Ser Ser Glu Glu Leu Ile Lys Met Ile Ser Lys Lys Leu
    290                 295                 300 aaa gag tac cat ctg gag aat atc gta gtt gat cca gtg atg gta gca     960
Lys Glu Tyr His Leu Glu Asn Ile Val Val Asp Pro Val Met Val Ala
305                 310                 315                 320 aca agc gga tcc aga ctg atc agt gaa acc gcg att gat aca tta aaa    1008
Thr Ser Gly Ser Arg Leu Ile Ser Glu Thr Ala Ile Asp Thr Leu Lys
```

```
                    325                 330                 335
aca cag ctg ctg cca atg gca act gtg atc aca ccg aat atc cca gag    1056
Thr Gln Leu Leu Pro Met Ala Thr Val Ile Thr Pro Asn Ile Pro Glu
            340                 345                 350 gca gaa gtt ctt gca gaa atg gag att aga tca gaa gat gat atg gtg    1104
Ala Glu Val Leu Ala Glu Met Glu Ile Arg Ser Glu Asp Asp Met Val
355                 360                 365 gaa gca gca aag aag att cat gaa atg tat cac tgt gca gtc tta tgc    1152
Glu Ala Ala Lys Lys Ile His Glu Met Tyr His Cys Ala Val Leu Cys
        370                 375                 380 aaa ggc gga cac agc ctg aat gat gcg aat gat ctc cta tac cag gat    1200
Lys Gly Gly His Ser Leu Asn Asp Ala Asn Asp Leu Leu Tyr Gln Asp
385                 390                 395                 400 gga gaa aca aca tgg ttc cac gga aaa aga atc aac aac ccg aac act    1248
Gly Glu Thr Thr Trp Phe His Gly Lys Arg Ile Asn Asn Pro Asn Thr
                405                 410                 415 cac gga acc ggc tgt acc tta tcc agc gca atc gca tcc aat ctg gca    1296
His Gly Thr Gly Cys Thr Leu Ser Ser Ala Ile Ala Ser Asn Leu Ala
            420                 425                 430 aaa gga tat tct ctg gaa gaa tct att cac cgc gcg aaa gag tat atc    1344
Lys Gly Tyr Ser Leu Glu Glu Ser Ile His Arg Ala Lys Glu Tyr Ile
                435                 440                 445 agc ggg gcg ttg gaa gcc atg tta gat ctg gga aaa gga agc gga ccg    1392
Ser Gly Ala Leu Glu Ala Met Leu Asp Leu Gly Lys Gly Ser Gly Pro
450                 455                 460 atg gat cat ggg ttt gag atg cgg ggg aga ttt tct att taa            1434
Met Asp His Gly Phe Glu Met Arg Gly Arg Phe Ser Ile
465                 470                 475

<210> SEQ ID NO 40
<211> LENGTH: 477
<212> TYPE: PRT
<213> ORGANISM: Dorea longicatena

<400> SEQUENCE: 40

Met Ile Lys Gly Ala Ile Phe Asp Val Asp Gly Thr Leu Leu Asp Ser
1               5                   10                  15

Met Glu Ile Trp Glu Asp Val Gly Val Arg Tyr Leu Asn Ser Ile Gly
                20                  25                  30

Ile Glu Ala Glu Pro Asp Leu Gly Thr Val Leu Phe Thr Met Ser Ile
            35                  40                  45

Gln Glu Gly Ala Ala Tyr Val Lys Glu His Tyr His Leu Ser Gln Glu
        50                  55                  60

Pro Glu Glu Ile Val Gln Gly Val Leu Asp Ile Ile Ser Asn Tyr Tyr
65                  70                  75                  80

Lys Lys Thr Ala Leu Leu Lys Ser Gly Val Lys Glu Leu Leu Glu Lys
                85                  90                  95

Leu Asp Lys His Asn Ile Pro Met Thr Val Ala Ser Ser Asn Asn Lys
            100                 105                 110

Lys Glu Ile Glu Met Ala Phe Glu Arg Leu Gly Ile Ala Lys Tyr Phe
        115                 120                 125

Asp Arg Ile Phe Thr Cys Glu Glu Val Gly Ala Gly Lys Thr Lys Pro
    130                 135                 140

Asp Ile Tyr Leu Arg Ala Ala Glu Tyr Leu Gly Thr Arg Pro Glu Glu
145                 150                 155                 160

Thr Val Val Phe Glu Asp Val Ile His Ala Ile Arg Thr Ala Lys Gln
                165                 170                 175
```

-continued

```
Ala Gly Phe Gln Val Val Gly Ile Tyr Asp Glu Ala Ser Lys Asp Asp
            180                 185                 190

Gln Glu Glu Val Gln Arg Glu Val Asp Trp Tyr Cys Arg Glu Trp Ala
        195                 200                 205

Glu Leu Met Lys Lys Lys Thr Ala Ile Thr Ile Ala Gly Ser Asp Ser
    210                 215                 220

Ser Gly Gly Ala Gly Ile Gln Ala Asp Ile Lys Thr Met Gln Ala Asn
225                 230                 235                 240

Gly Val Tyr Ala Met Ser Ala Ile Thr Ala Leu Thr Ala Gln Asn Thr
                245                 250                 255

Thr Gly Val Thr Gly Ile Met Glu Val Ser Pro Glu Phe Leu Glu Gln
            260                 265                 270

Gln Leu Asp Ala Val Ile Thr Asp Ile Arg Pro Asp Ala Val Lys Ile
        275                 280                 285

Gly Met Val Ser Ser Glu Glu Leu Ile Lys Met Ile Ser Lys Lys Leu
    290                 295                 300

Lys Glu Tyr His Leu Glu Asn Ile Val Val Asp Pro Val Met Val Ala
305                 310                 315                 320

Thr Ser Gly Ser Arg Leu Ile Ser Glu Thr Ala Ile Asp Thr Leu Lys
                325                 330                 335

Thr Gln Leu Leu Pro Met Ala Thr Val Ile Thr Pro Asn Ile Pro Glu
            340                 345                 350

Ala Glu Val Leu Ala Glu Met Glu Ile Arg Ser Glu Asp Met Val
        355                 360                 365

Glu Ala Ala Lys Lys Ile His Glu Met Tyr His Cys Ala Val Leu Cys
    370                 375                 380

Lys Gly His Ser Leu Asn Asp Ala Asn Asp Leu Leu Tyr Gln Asp
385                 390                 395                 400

Gly Glu Thr Thr Trp Phe His Gly Lys Arg Ile Asn Asn Pro Asn Thr
                405                 410                 415

His Gly Thr Gly Cys Thr Leu Ser Ala Ile Ala Ser Asn Leu Ala
            420                 425                 430

Lys Gly Tyr Ser Leu Glu Glu Ser Ile His Arg Ala Lys Glu Tyr Ile
        435                 440                 445

Ser Gly Ala Leu Glu Ala Met Leu Asp Leu Gly Lys Gly Ser Gly Pro
    450                 455                 460

Met Asp His Gly Phe Glu Met Arg Gly Arg Phe Ser Ile
465                 470                 475
```

<210> SEQ ID NO 41
<211> LENGTH: 1305
<212> TYPE: DNA
<213> ORGANISM: Unknown
<220> FEATURE:
<223> OTHER INFORMATION: Description of Unknown: Lachnospiraceae bacterium sequence
<220> FEATURE:
<221> NAME/KEY: CDS
<222> LOCATION: (1)..(1302)
<223> OTHER INFORMATION: Lachnospiraceae_bacterium_3_1_57FAA_CT1 gene encoding TMP phosphatase [EPC05128]

<400> SEQUENCE: 41

```
atg aaa tgt gac aga aag aca atg ctt ctt tat gcg gtg acc gat cgg    48
Met Lys Cys Asp Arg Lys Thr Met Leu Leu Tyr Ala Val Thr Asp Arg
1               5                   10                  15 gcc tgg aca gga gaa aag aca ctg ctt atg cag gtc gag gaa gcg ctg    96
Ala Trp Thr Gly Glu Lys Thr Leu Leu Met Gln Val Glu Glu Ala Leu
```

|  |  |  |  |  |  |  |  |  |  |  |  |  |  |  |  |
|---|---|---|---|---|---|---|---|---|---|---|---|---|---|---|---|
|  |  |  | 20 |  |  |  | 25 |  |  |  | 30 |  |  |  |  |
| gca | gga | ggt | gtg | acc | tgt | gtc | cag | ctt | cgt | gaa | aag | gat | atg | cca | aag | 144 |
| Ala | Gly | Gly | Val | Thr | Cys | Val | Gln | Leu | Arg | Glu | Lys | Asp | Met | Pro | Lys |  |
|  |  | 35 |  |  |  | 40 |  |  |  | 45 |  |  |  |  |  |
| gag | cag | ttc | ctg | gaa | gaa | gcg | gag | agt | ata | aaa | aga | ctt | tgt | cat | aaa | 192 |
| Glu | Gln | Phe | Leu | Glu | Glu | Ala | Glu | Ser | Ile | Lys | Arg | Leu | Cys | His | Lys |  |
| 50 |  |  |  | 55 |  |  |  | 60 |  |  |  |  |  |  |  |
| tat | ggg | atc | cct | ttt | ata | att | gac | gat | gat | gtg | gag | ctg | gcc | gta | cgc | 240 |
| Tyr | Gly | Ile | Pro | Phe | Ile | Ile | Asp | Asp | Asp | Val | Glu | Leu | Ala | Val | Arg |  |
| 65 |  |  |  | 70 |  |  |  | 75 |  |  |  | 80 |  |  |  |
| tgc | ggc | gcg | gac | ggg | gtg | cat | gtg | gga | cag | cat | gat | atg | gag | gca | ggc | 288 |
| Cys | Gly | Ala | Asp | Gly | Val | His | Val | Gly | Gln | His | Asp | Met | Glu | Ala | Gly |  |
|  |  |  | 85 |  |  |  | 90 |  |  |  | 95 |  |  |  |  |
| gcg | gtc | cgc | cgg | aaa | atc | gga | gac | ggc | atg | ctg | ctg | ggc | gta | tca | gtc | 336 |
| Ala | Val | Arg | Arg | Lys | Ile | Gly | Asp | Gly | Met | Leu | Leu | Gly | Val | Ser | Val |  |
|  |  |  | 100 |  |  |  | 105 |  |  |  | 110 |  |  |  |  |
| cag | act | gtg | gaa | cag | gca | gtg | gaa | gcc | gaa | aaa | aag | gga | gcg | gat | tac | 384 |
| Gln | Thr | Val | Glu | Gln | Ala | Val | Glu | Ala | Glu | Lys | Lys | Gly | Ala | Asp | Tyr |  |
|  |  | 115 |  |  |  | 120 |  |  |  | 125 |  |  |  |  |  |
| ctt | ggt | gtg | ggc | gct | gtg | ttt | tcc | act | tcc | acg | aaa | acg | gac | gca | cag | 432 |
| Leu | Gly | Val | Gly | Ala | Val | Phe | Ser | Thr | Ser | Thr | Lys | Thr | Asp | Ala | Gln |  |
| 130 |  |  |  | 135 |  |  |  | 140 |  |  |  |  |  |  |  |
| gag | gtt | tcc | ctg | gat | acc | ctc | cgg | gaa | atc | tgc | cgg | gcg | gtg | tcc | gta | 480 |
| Glu | Val | Ser | Leu | Asp | Thr | Leu | Arg | Glu | Ile | Cys | Arg | Ala | Val | Ser | Val |  |
| 145 |  |  |  | 150 |  |  |  | 155 |  |  |  | 160 |  |  |  |
| ccc | gtc | tgt | gca | atc | gga | ggg | ata | cac | aaa | gga | aat | atg | cat | ttg | ctg | 528 |
| Pro | Val | Cys | Ala | Ile | Gly | Gly | Ile | His | Lys | Gly | Asn | Met | His | Leu | Leu |  |
|  |  |  | 165 |  |  |  | 170 |  |  |  | 175 |  |  |  |  |
| cag | gat | acg | gga | atc | gat | ggg | gtg | gct | ttg | gtg | tcg | gcc | atc | ttt | tcc | 576 |
| Gln | Asp | Thr | Gly | Ile | Asp | Gly | Val | Ala | Leu | Val | Ser | Ala | Ile | Phe | Ser |  |
|  |  | 180 |  |  |  | 185 |  |  |  | 190 |  |  |  |  |  |
| agt | ccc | tgc | ata | cag | aag | gaa | tgc | agg | gag | ctg | cgg | gtc | ctg | gca | gag | 624 |
| Ser | Pro | Cys | Ile | Gln | Lys | Glu | Cys | Arg | Glu | Leu | Arg | Val | Leu | Ala | Glu |  |
|  |  | 195 |  |  |  | 200 |  |  |  | 205 |  |  |  |  |  |
| aga | ctg | aaa | agg | aaa | ggg | gct | att | ttt | gat | gcg | gac | gga | acc | ctg | ctg | 672 |
| Arg | Leu | Lys | Arg | Lys | Gly | Ala | Ile | Phe | Asp | Ala | Asp | Gly | Thr | Leu | Leu |  |
|  | 210 |  |  |  | 215 |  |  |  | 220 |  |  |  |  |  |  |
| gat | tcc | atg | tcc | gtt | tgg | gat | act | ctg | ggt | gaa | aaa | tat | ctg | cgg | aaa | 720 |
| Asp | Ser | Met | Ser | Val | Trp | Asp | Thr | Leu | Gly | Glu | Lys | Tyr | Leu | Arg | Lys |  |
| 225 |  |  |  | 230 |  |  |  | 235 |  |  |  | 240 |  |  |  |
| aag | ggt | att | gtt | ccg | gaa | aag | aac | atc | agg | gaa | aca | ata | aaa | aat | atg | 768 |
| Lys | Gly | Ile | Val | Pro | Glu | Lys | Asn | Ile | Arg | Glu | Thr | Ile | Lys | Asn | Met |  |
|  |  |  | 245 |  |  |  | 250 |  |  |  | 255 |  |  |  |  |
| agt | ctt | cct | cag | gct | gcg | gtc | tat | ttt | cag | act | gct | tat | ggg | att | gcg | 816 |
| Ser | Leu | Pro | Gln | Ala | Ala | Val | Tyr | Phe | Gln | Thr | Ala | Tyr | Gly | Ile | Ala |  |
|  |  | 260 |  |  |  | 265 |  |  |  | 270 |  |  |  |  |  |
| gat | gca | gaa | gac | aag | att | ata | gag | gat | att | aat | gga | ata | gcg | gcg | tcc | 864 |
| Asp | Ala | Glu | Asp | Lys | Ile | Ile | Glu | Asp | Ile | Asn | Gly | Ile | Ala | Ala | Ser |  |
|  | 275 |  |  |  | 280 |  |  |  | 285 |  |  |  |  |  |  |
| ttt | tac | atc | aat | gag | gtg | aag | ctg | aag | gaa | ggc | gtg | aaa | acg | gtt | ctg | 912 |
| Phe | Tyr | Ile | Asn | Glu | Val | Lys | Leu | Lys | Glu | Gly | Val | Lys | Thr | Val | Leu |  |
|  | 290 |  |  |  | 295 |  |  |  | 300 |  |  |  |  |  |  |
| gac | aag | ctg | aag | cag | aaa | aac | gta | aag | atg | tgt | gtg | gcg | acg | gct | acg | 960 |
| Asp | Lys | Leu | Lys | Gln | Lys | Asn | Val | Lys | Met | Cys | Val | Ala | Thr | Ala | Thr |  |
| 305 |  |  |  | 310 |  |  |  | 315 |  |  |  | 320 |  |  |  |
| gac | aaa | ggg | ctg | att | gaa | aag | gca | ctt | gag | aga | aac | gga | atc | aga | gat | 1008 |
| Asp | Lys | Gly | Leu | Ile | Glu | Lys | Ala | Leu | Glu | Arg | Asn | Gly | Ile | Arg | Asp |  |
|  |  | 325 |  |  |  | 330 |  |  |  | 335 |  |  |  |  |  |
| tat | ttt | gag | gct | gtc | ctc | acc | tgc | acg | gat | gtg | ggc | gcg | gga | aag | gat | 1056 |

```
Tyr Phe Glu Ala Val Leu Thr Cys Thr Asp Val Gly Ala Gly Lys Asp
                340                 345                 350 gag ccg gtt atc ttc cgt aag gcc ggg cag ctt ctc gga aca gca aaa      1104
Glu Pro Val Ile Phe Arg Lys Ala Gly Gln Leu Leu Gly Thr Ala Lys
            355                 360                 365 gag gat acc att gta att gaa gat gcc ttg tat gct gtt aag aca gcg      1152
Glu Asp Thr Ile Val Ile Glu Asp Ala Leu Tyr Ala Val Lys Thr Ala
370                 375                 380 aaa gag gac ggt ttc ctg gtg gcg gct gtt tat gat ccg tca gca gaa      1200
Lys Glu Asp Gly Phe Leu Val Ala Ala Val Tyr Asp Pro Ser Ala Glu
385                 390                 395                 400 aag gag gaa ccg gag atc cgg gag atc tct gac ttc tat ttc cgg tca      1248
Lys Glu Glu Pro Glu Ile Arg Glu Ile Ser Asp Phe Tyr Phe Arg Ser
                405                 410                 415 ttt aat gaa atg gag agt tat ctg aat gaa aaa agt tct tac gat agc      1296
Phe Asn Glu Met Glu Ser Tyr Leu Asn Glu Lys Ser Ser Tyr Asp Ser
            420                 425                 430 ggg ctc tga                                                          1305
Gly Leu <210> SEQ ID NO 42
<211> LENGTH: 434
<212> TYPE: PRT
<213> ORGANISM: Unknown
<220> FEATURE:
<223> OTHER INFORMATION: Description of Unknown:
      Lachnospiraceae bacterium sequence

<400> SEQUENCE: 42

Met Lys Cys Asp Arg Lys Thr Met Leu Leu Tyr Ala Val Thr Asp Arg
1               5                   10                  15

Ala Trp Thr Gly Glu Lys Thr Leu Leu Met Gln Val Glu Glu Ala Leu
            20                  25                  30

Ala Gly Gly Val Thr Cys Val Gln Leu Arg Glu Lys Asp Met Pro Lys
        35                  40                  45

Glu Gln Phe Leu Glu Glu Ala Glu Ser Ile Lys Arg Leu Cys His Lys
    50                  55                  60

Tyr Gly Ile Pro Phe Ile Ile Asp Asp Val Glu Leu Ala Val Arg
65                  70                  75                  80

Cys Gly Ala Asp Gly Val His Val Gly Gln His Asp Met Glu Ala Gly
                85                  90                  95

Ala Val Arg Arg Lys Ile Gly Asp Gly Met Leu Leu Gly Val Ser Val
            100                 105                 110

Gln Thr Val Glu Gln Ala Val Glu Ala Lys Lys Gly Ala Asp Tyr
        115                 120                 125

Leu Gly Val Gly Ala Val Phe Ser Thr Ser Lys Thr Asp Ala Gln
    130                 135                 140

Glu Val Ser Leu Asp Thr Leu Arg Glu Ile Cys Arg Ala Val Ser Val
145                 150                 155                 160

Pro Val Cys Ala Ile Gly Gly Ile His Lys Gly Asn Met His Leu Leu
                165                 170                 175

Gln Asp Thr Gly Ile Asp Gly Val Ala Leu Val Ser Ala Ile Phe Ser
            180                 185                 190

Ser Pro Cys Ile Gln Lys Glu Cys Arg Glu Leu Arg Val Leu Ala Glu
        195                 200                 205

Arg Leu Lys Arg Lys Gly Ala Ile Phe Asp Ala Asp Gly Thr Leu Leu
    210                 215                 220
```

-continued

```
Asp Ser Met Ser Val Trp Asp Thr Leu Gly Glu Lys Tyr Leu Arg Lys
225                 230                 235                 240

Lys Gly Ile Val Pro Glu Lys Asn Ile Arg Glu Thr Ile Lys Asn Met
            245                 250                 255

Ser Leu Pro Gln Ala Ala Val Tyr Phe Gln Thr Ala Tyr Gly Ile Ala
        260                 265                 270

Asp Ala Glu Asp Lys Ile Ile Glu Asp Ile Asn Gly Ile Ala Ala Ser
            275                 280                 285

Phe Tyr Ile Asn Glu Val Lys Leu Lys Glu Gly Val Lys Thr Val Leu
    290                 295                 300

Asp Lys Leu Lys Gln Lys Asn Val Lys Met Cys Val Ala Thr Ala Thr
305                 310                 315                 320

Asp Lys Gly Leu Ile Glu Lys Ala Leu Glu Arg Asn Gly Ile Arg Asp
            325                 330                 335

Tyr Phe Glu Ala Val Leu Thr Cys Thr Asp Val Gly Ala Gly Lys Asp
            340                 345                 350

Glu Pro Val Ile Phe Arg Lys Ala Gly Gln Leu Leu Gly Thr Ala Lys
        355                 360                 365

Glu Asp Thr Ile Val Ile Glu Asp Ala Leu Tyr Ala Val Lys Thr Ala
370                 375                 380

Lys Glu Asp Gly Phe Leu Val Ala Ala Val Tyr Asp Pro Ser Ala Glu
385                 390                 395                 400

Lys Glu Glu Pro Glu Ile Arg Glu Ile Ser Asp Phe Tyr Phe Arg Ser
            405                 410                 415

Phe Asn Glu Met Glu Ser Tyr Leu Asn Glu Lys Ser Ser Tyr Asp Ser
        420                 425                 430

Gly Leu

<210> SEQ ID NO 43
<211> LENGTH: 1305
<212> TYPE: DNA
<213> ORGANISM: Fusicatenibacter sp.
<220> FEATURE:
<221> NAME/KEY: CDS
<222> LOCATION: (1)..(1302)
<223> OTHER INFORMATION: Fusicatenibacter gene encoding TMP phosphatase
      [CUQ30753]

<400> SEQUENCE: 43 atg aaa tgt aac aga aag aca atg ctt ctt tat gcg gtg acc gac cgg      48
Met Lys Cys Asn Arg Lys Thr Met Leu Leu Tyr Ala Val Thr Asp Arg
1               5                   10                  15 gcc tgg aca gga gaa aag aca ctg ctt acg cag gtc gag gaa gcg ctg      96
Ala Trp Thr Gly Glu Lys Thr Leu Leu Thr Gln Val Glu Glu Ala Leu
            20                  25                  30 gca gga ggt gta acc tgt gtc cag ctt cgt gaa aag gat atg cca aag     144
Ala Gly Gly Val Thr Cys Val Gln Leu Arg Glu Lys Asp Met Pro Lys
        35                  40                  45 gag cag ttc ctg gaa gaa gcg gag agt ata aaa aga ctt tgc cat aaa     192
Glu Gln Phe Leu Glu Glu Ala Glu Ser Ile Lys Arg Leu Cys His Lys
    50                  55                  60 tat ggt gtc cct ttt ata att gac gat gat gtg gag ctg gcc gta cgc     240
Tyr Gly Val Pro Phe Ile Ile Asp Asp Asp Val Glu Leu Ala Val Arg
65                  70                  75                  80 tgc ggt gcg gac ggg gta cat gtg gga cag cat gat atg gag gca ggc     288
Cys Gly Ala Asp Gly Val His Val Gly Gln His Asp Met Glu Ala Gly
                85                  90                  95 gcg gtc cgc cgg aaa atc gga gac ggc atg ctg ctg ggc gta tca gtc     336
```

```
                Ala Val Arg Arg Lys Ile Gly Asp Gly Met Leu Leu Gly Val Ser Val
                                100                 105                 110 cag act gtg gaa cag gca gtg gaa gcc gag aaa aag gga gcg gat tac          384
Gln Thr Val Glu Gln Ala Val Glu Ala Glu Lys Lys Gly Ala Asp Tyr
            115                 120                 125 ctt ggt gtg ggc gct gtg ttt tcc act tcc acg aaa acg gac gca cag          432
Leu Gly Val Gly Ala Val Phe Ser Thr Ser Thr Lys Thr Asp Ala Gln
130                 135                 140 gag gtt tcc ctg gat acc ctc cgg gaa atc tgc cgg gcg gtg tcc gta          480
Glu Val Ser Leu Asp Thr Leu Arg Glu Ile Cys Arg Ala Val Ser Val
145                 150                 155                 160 ccc gtc tgt gca atc gga ggg ata cac aaa gga aat atg cat ttg ctg          528
Pro Val Cys Ala Ile Gly Gly Ile His Lys Gly Asn Met His Leu Leu
                165                 170                 175 cag gat acg gga atc gat ggg gtg gct ttg gtg tcg gcc atc ttt tcc          576
Gln Asp Thr Gly Ile Asp Gly Val Ala Leu Val Ser Ala Ile Phe Ser
            180                 185                 190 agt ccc tgc ata cag aag gaa tgc agg gag ctg cgg gcc ctg gca gag          624
Ser Pro Cys Ile Gln Lys Glu Cys Arg Glu Leu Arg Ala Leu Ala Glu
        195                 200                 205 agg ctg aaa agg aaa ggg gct att ttt gat gcg gac gga acc ctg ctg          672
Arg Leu Lys Arg Lys Gly Ala Ile Phe Asp Ala Asp Gly Thr Leu Leu
    210                 215                 220 gat tcc atg tct gtt tgg gat acc ctg ggt gaa aaa tat ctg cgg aaa          720
Asp Ser Met Ser Val Trp Asp Thr Leu Gly Glu Lys Tyr Leu Arg Lys
225                 230                 235                 240 aag ggt att gtt ccg gaa aag aac atc agg gaa aca ata aaa aat atg          768
Lys Gly Ile Val Pro Glu Lys Asn Ile Arg Glu Thr Ile Lys Asn Met
                245                 250                 255 agt ctt cct cag gcc gcg gtc tat ttt caa act gct tat ggg atc acg          816
Ser Leu Pro Gln Ala Ala Val Tyr Phe Gln Thr Ala Tyr Gly Ile Thr
            260                 265                 270 gat gca gaa gac aag att ata gag gat att aat gga ata gcg gcg tcc          864
Asp Ala Glu Asp Lys Ile Ile Glu Asp Ile Asn Gly Ile Ala Ala Ser
        275                 280                 285 ttt tac atc aat gag gtg aag ctg aag gaa ggc gtg aaa acg gtt ctg          912
Phe Tyr Ile Asn Glu Val Lys Leu Lys Glu Gly Val Lys Thr Val Leu
    290                 295                 300 gac aag ctg aag cag aaa aac gta aag atg tgt gtg gcg acg gct acg          960
Asp Lys Leu Lys Gln Lys Asn Val Lys Met Cys Val Ala Thr Ala Thr
305                 310                 315                 320 gac aag ggg ctg att gaa aag gca ctt gag aga aac gga atc aga gat         1008
Asp Lys Gly Leu Ile Glu Lys Ala Leu Glu Arg Asn Gly Ile Arg Asp
                325                 330                 335 tat ttt gag gct gtc ctc acc tgc acg gat gtg ggc gcg gga aag gat         1056
Tyr Phe Glu Ala Val Leu Thr Cys Thr Asp Val Gly Ala Gly Lys Asp
            340                 345                 350 gag ccg gtt atc ttc cgt aag gcc ggg cag ctt ctc gga acc gca aaa         1104
Glu Pro Val Ile Phe Arg Lys Ala Gly Gln Leu Leu Gly Thr Ala Lys
        355                 360                 365 gag gat acc att gta att gaa gat gcc ttg tat gct gtt aag aca gcg         1152
Glu Asp Thr Ile Val Ile Glu Asp Ala Leu Tyr Ala Val Lys Thr Ala
    370                 375                 380 aaa gag gac ggt ttc ctg gtg gcg gct gtt tat gat ccg tca gca gaa         1200
Lys Glu Asp Gly Phe Leu Val Ala Ala Val Tyr Asp Pro Ser Ala Glu
385                 390                 395                 400 aag gag gaa ccg gag atc cgg gag atc tct gac ttc tat ttc cgg tca         1248
Lys Glu Glu Pro Glu Ile Arg Glu Ile Ser Asp Phe Tyr Phe Arg Ser
                405                 410                 415
```

```
ttt aat gaa atg gag agt tat ctg aat gaa aaa agt tct tac gat agc    1296
Phe Asn Glu Met Glu Ser Tyr Leu Asn Glu Lys Ser Ser Tyr Asp Ser
            420                 425                 430 ggg ctc tga                                                         1305
Gly Leu <210> SEQ ID NO 44
<211> LENGTH: 434
<212> TYPE: PRT
<213> ORGANISM: Fusicatenibacter sp.

<400> SEQUENCE: 44

Met Lys Cys Asn Arg Lys Thr Met Leu Leu Tyr Ala Val Thr Asp Arg
1               5                   10                  15

Ala Trp Thr Gly Glu Lys Thr Leu Leu Thr Gln Val Glu Glu Ala Leu
            20                  25                  30

Ala Gly Gly Val Thr Cys Val Gln Leu Arg Glu Lys Asp Met Pro Lys
        35                  40                  45

Glu Gln Phe Leu Glu Glu Ala Glu Ser Ile Lys Arg Leu Cys His Lys
    50                  55                  60

Tyr Gly Val Pro Phe Ile Ile Asp Asp Val Glu Leu Ala Val Arg
65                  70                  75                  80

Cys Gly Ala Asp Gly Val His Val Gly Gln His Asp Met Glu Ala Gly
                85                  90                  95

Ala Val Arg Arg Lys Ile Gly Asp Gly Met Leu Leu Gly Val Ser Val
            100                 105                 110

Gln Thr Val Glu Gln Ala Val Glu Ala Glu Lys Lys Gly Ala Asp Tyr
        115                 120                 125

Leu Gly Val Gly Ala Val Phe Ser Thr Ser Thr Lys Thr Asp Ala Gln
    130                 135                 140

Glu Val Ser Leu Asp Thr Leu Arg Glu Ile Cys Arg Ala Val Ser Val
145                 150                 155                 160

Pro Val Cys Ala Ile Gly Gly Ile His Lys Gly Asn Met His Leu Leu
                165                 170                 175

Gln Asp Thr Gly Ile Asp Gly Val Ala Leu Val Ser Ala Ile Phe Ser
            180                 185                 190

Ser Pro Cys Ile Gln Lys Glu Cys Arg Glu Leu Arg Ala Leu Ala Glu
        195                 200                 205

Arg Leu Lys Arg Lys Gly Ala Ile Phe Asp Ala Asp Gly Thr Leu Leu
    210                 215                 220

Asp Ser Met Ser Val Trp Asp Thr Leu Gly Glu Lys Tyr Leu Arg Lys
225                 230                 235                 240

Lys Gly Ile Val Pro Glu Lys Asn Ile Arg Glu Thr Ile Lys Asn Met
                245                 250                 255

Ser Leu Pro Gln Ala Ala Val Tyr Phe Gln Thr Ala Tyr Gly Ile Thr
            260                 265                 270

Asp Ala Glu Asp Lys Ile Ile Glu Asp Ile Asn Gly Ile Ala Ala Ser
        275                 280                 285

Phe Tyr Ile Asn Glu Val Lys Leu Lys Glu Gly Val Lys Thr Val Leu
    290                 295                 300

Asp Lys Leu Lys Gln Lys Asn Val Lys Met Cys Val Ala Thr Ala Thr
305                 310                 315                 320

Asp Lys Gly Leu Ile Glu Lys Ala Leu Glu Arg Asn Gly Ile Arg Asp
                325                 330                 335

Tyr Phe Glu Ala Val Leu Thr Cys Thr Asp Val Gly Ala Gly Lys Asp
```

-continued

```
                    340                 345                 350
Glu Pro Val Ile Phe Arg Lys Ala Gly Gln Leu Leu Gly Thr Ala Lys
                355                 360                 365

Glu Asp Thr Ile Val Ile Glu Asp Ala Leu Tyr Ala Val Lys Thr Ala
    370                 375                 380

Lys Glu Asp Gly Phe Leu Val Ala Ala Val Tyr Asp Pro Ser Ala Glu
385                 390                 395                 400

Lys Glu Glu Pro Glu Ile Arg Glu Ile Ser Asp Phe Tyr Phe Arg Ser
                405                 410                 415

Phe Asn Glu Met Glu Ser Tyr Leu Asn Glu Lys Ser Ser Tyr Asp Ser
            420                 425                 430

Gly Leu

<210> SEQ ID NO 45
<211> LENGTH: 1296
<212> TYPE: DNA
<213> ORGANISM: Clostridium sp.
<220> FEATURE:
<221> NAME/KEY: CDS
<222> LOCATION: (1)..(1293)
<223> OTHER INFORMATION: Clostridium sp KLE1755 gene encoding TMP
      phosphatase [ERI68966]

<400> SEQUENCE: 45 atg aaa tgt gac aga agc atg ctg ctc ctc tat gcc gta acc gac cgt      48
Met Lys Cys Asp Arg Ser Met Leu Leu Leu Tyr Ala Val Thr Asp Arg
1               5                   10                  15 gcc tgg acg ggt aaa aaa aca ctg ctg cag cag gtg gag gaa gcc ctg      96
Ala Trp Thr Gly Lys Lys Thr Leu Leu Gln Gln Val Glu Glu Ala Leu
            20                  25                  30 gca ggc ggc gcc acc tgc atc cag ctt cgg gaa aag gag ctg ccg gag     144
Ala Gly Gly Ala Thr Cys Ile Gln Leu Arg Glu Lys Glu Leu Pro Glu
        35                  40                  45 gaa gaa ttc cgg cag gaa gcc ctg gct gtg aaa gaa ctt tgc cgc aga     192
Glu Glu Phe Arg Gln Glu Ala Leu Ala Val Lys Glu Leu Cys Arg Arg
    50                  55                  60 tac cat gtc cct ttc ctc att aac gac aac gta gag ctg gct gtc agc     240
Tyr His Val Pro Phe Leu Ile Asn Asp Asn Val Glu Leu Ala Val Ser
65                  70                  75                  80 tgc ggc gcg gac ggc gtc cat gtg ggc cag cac gac atg tct gcg gcg     288
Cys Gly Ala Asp Gly Val His Val Gly Gln His Asp Met Ser Ala Ala
                85                  90                  95 gat gtg cgc cgc aga atc ggc ccc ggc aaa ata ctg gga gta tcc gcg     336
Asp Val Arg Arg Arg Ile Gly Pro Gly Lys Ile Leu Gly Val Ser Ala
            100                 105                 110 cag acg gtg gag cag gcc cgc cag gcg gaa gaa gac ggc gca gat tat     384
Gln Thr Val Glu Gln Ala Arg Gln Ala Glu Glu Asp Gly Ala Asp Tyr
        115                 120                 125 ctg ggc gtg ggc gct gtt ttt tcc acc tcc acc aaa tcc gac gca gac     432
Leu Gly Val Gly Ala Val Phe Ser Thr Ser Thr Lys Ser Asp Ala Asp
    130                 135                 140 gcg gta tcc cat gag acc ctg caa aag atc tgc gcc gca gta tcc atc     480
Ala Val Ser His Glu Thr Leu Gln Lys Ile Cys Ala Ala Val Ser Ile
145                 150                 155                 160 ccc gtc tgc gcc ata ggc ggc atc cat aaa gaa aat ctg cat ttg ctc     528
Pro Val Cys Ala Ile Gly Gly Ile His Lys Glu Asn Leu His Leu Leu
                165                 170                 175 aaa ggc aca ggc atc gcc ggc gtg gcc ctt gtt tcc gcc atc ttc gca     576
Lys Gly Thr Gly Ile Ala Gly Val Ala Leu Val Ser Ala Ile Phe Ala
            180                 185                 190
```

```
agc ccg gat atc cgt aag tcc tgc gaa gac ctg aaa aaa ctg gcc ctg      624
Ser Pro Asp Ile Arg Lys Ser Cys Glu Asp Leu Lys Lys Leu Ala Leu
        195                 200                 205 cag ata aac gcg cag gac aca ctg gaa gca ctg ctg cat aca aac atc      672
Gln Ile Asn Ala Gln Asp Thr Leu Glu Ala Leu Leu His Thr Asn Ile
    210                 215                 220 cgc gga gcc atc ttt gac gcg gac ggc acc ctt tta gac tcc atg ggc      720
Arg Gly Ala Ile Phe Asp Ala Asp Gly Thr Leu Leu Asp Ser Met Gly
225                 230                 235                 240 atc tgg gat act ctg ggg gaa gat tac ctg cgt aca aaa ggg aaa atc      768
Ile Trp Asp Thr Leu Gly Glu Asp Tyr Leu Arg Thr Lys Gly Lys Ile
                245                 250                 255 ccc cgg gaa aac ctg cgt gaa acc ttc cgc gac atg agc ctt ctc cag      816
Pro Arg Glu Asn Leu Arg Glu Thr Phe Arg Asp Met Ser Leu Leu Gln
            260                 265                 270 gcc gcc tgc tat tac cgg gaa aat tac gcc ctt acg gaa agc cct gaa      864
Ala Ala Cys Tyr Tyr Arg Glu Asn Tyr Ala Leu Thr Glu Ser Pro Glu
        275                 280                 285 aaa ata gtg gaa gag ctt aac gcc atg atc gcc tcc ttc tat gaa aaa      912
Lys Ile Val Glu Glu Leu Asn Ala Met Ile Ala Ser Phe Tyr Glu Lys
    290                 295                 300 gaa gcc ccc ctg aag gaa gga gcc gcc gcc ttc ctg gaa gcg ctt tgc      960
Glu Ala Pro Leu Lys Glu Gly Ala Ala Ala Phe Leu Glu Ala Leu Cys
305                 310                 315                 320 caa aga aac ata aaa atg tgc att gca aca gcc acc gat cac agc ctt     1008
Gln Arg Asn Ile Lys Met Cys Ile Ala Thr Ala Thr Asp His Ser Leu
                325                 330                 335 atc cgg gcc gcc ctg aag cga tgc gga gtg ctg cat tac ttt act ttt     1056
Ile Arg Ala Ala Leu Lys Arg Cys Gly Val Leu His Tyr Phe Thr Phe
            340                 345                 350 ata ctt acc tgc gga caa gca gga gcg gga aaa gac acc ccc gcc att     1104
Ile Leu Thr Cys Gly Gln Ala Gly Ala Gly Lys Asp Thr Pro Ala Ile
        355                 360                 365 tat gaa gaa gcc ctg gcc ctg ctt gga acc gga aaa aaa gaa acc ttc     1152
Tyr Glu Glu Ala Leu Ala Leu Leu Gly Thr Gly Lys Lys Glu Thr Phe
    370                 375                 380 gtt ttt gaa gat gcc ctg tac gcc ctg aaa acg gcg aaa aca gcc ggc     1200
Val Phe Glu Asp Ala Leu Tyr Ala Leu Lys Thr Ala Lys Thr Ala Gly
385                 390                 395                 400 ttt cct aca gtc ggt gta aaa gac ccc tcc tcc gcc gga cag gaa ggg     1248
Phe Pro Thr Val Gly Val Lys Asp Pro Ser Ser Ala Gly Gln Glu Gly
                405                 410                 415 gag att ata aaa caa gcc gat tac tat ctt tat acc ttc acg aaa tga     1296
Glu Ile Ile Lys Gln Ala Asp Tyr Tyr Leu Tyr Thr Phe Thr Lys
            420                 425                 430

<210> SEQ ID NO 46
<211> LENGTH: 431
<212> TYPE: PRT
<213> ORGANISM: Clostridium sp.

<400> SEQUENCE: 46

Met Lys Cys Asp Arg Ser Met Leu Leu Leu Tyr Ala Val Thr Asp Arg
1               5                   10                  15

Ala Trp Thr Gly Lys Lys Thr Leu Leu Gln Gln Val Glu Glu Ala Leu
            20                  25                  30

Ala Gly Gly Ala Thr Cys Ile Gln Leu Arg Glu Lys Glu Leu Pro Glu
        35                  40                  45

Glu Glu Phe Arg Gln Glu Ala Leu Ala Val Lys Glu Leu Cys Arg Arg
```

```
        50                  55                  60
Tyr His Val Pro Phe Leu Ile Asn Asp Asn Val Glu Leu Ala Val Ser
 65                  70                  75                  80

Cys Gly Ala Asp Gly Val His Val Gly Gln His Asp Met Ser Ala Ala
                 85                  90                  95

Asp Val Arg Arg Ile Gly Pro Lys Ile Leu Gly Val Ser Ala
            100                 105                 110

Gln Thr Val Glu Gln Ala Arg Gln Ala Glu Asp Gly Ala Asp Tyr
            115                 120                 125

Leu Gly Val Gly Ala Val Phe Ser Thr Ser Thr Lys Ser Asp Ala Asp
            130                 135                 140

Ala Val Ser His Glu Thr Leu Gln Lys Ile Cys Ala Ala Val Ser Ile
145                 150                 155                 160

Pro Val Cys Ala Ile Gly Gly Ile His Lys Glu Asn Leu His Leu Leu
                165                 170                 175

Lys Gly Thr Gly Ile Ala Gly Val Ala Leu Val Ser Ala Ile Phe Ala
                180                 185                 190

Ser Pro Asp Ile Arg Lys Ser Cys Glu Asp Leu Lys Lys Leu Ala Leu
                195                 200                 205

Gln Ile Asn Ala Gln Asp Thr Leu Glu Ala Leu Leu His Thr Asn Ile
            210                 215                 220

Arg Gly Ala Ile Phe Asp Ala Asp Gly Thr Leu Leu Asp Ser Met Gly
225                 230                 235                 240

Ile Trp Asp Thr Leu Gly Glu Asp Tyr Leu Arg Thr Lys Gly Lys Ile
                245                 250                 255

Pro Arg Glu Asn Leu Arg Glu Thr Phe Arg Asp Met Ser Leu Leu Gln
                260                 265                 270

Ala Ala Cys Tyr Tyr Arg Glu Asn Tyr Ala Leu Thr Glu Ser Pro Glu
                275                 280                 285

Lys Ile Val Glu Glu Leu Asn Ala Met Ile Ala Ser Phe Tyr Glu Lys
            290                 295                 300

Glu Ala Pro Leu Lys Glu Gly Ala Ala Ala Phe Leu Glu Ala Leu Cys
305                 310                 315                 320

Gln Arg Asn Ile Lys Met Cys Ile Ala Thr Ala Thr Asp His Ser Leu
                325                 330                 335

Ile Arg Ala Ala Leu Lys Arg Cys Gly Val Leu His Tyr Phe Thr Phe
                340                 345                 350

Ile Leu Thr Cys Gly Gln Ala Gly Ala Gly Lys Asp Thr Pro Ala Ile
                355                 360                 365

Tyr Glu Glu Ala Leu Ala Leu Leu Gly Thr Gly Lys Lys Glu Thr Phe
            370                 375                 380

Val Phe Glu Asp Ala Leu Tyr Ala Leu Lys Thr Ala Lys Thr Ala Gly
385                 390                 395                 400

Phe Pro Thr Val Gly Val Lys Asp Pro Ser Ser Ala Gly Gln Glu Gly
                405                 410                 415

Glu Ile Ile Lys Gln Ala Asp Tyr Tyr Leu Tyr Thr Phe Thr Lys
            420                 425                 430

<210> SEQ ID NO 47
<211> LENGTH: 1452
<212> TYPE: DNA
<213> ORGANISM: Eubacterium hallii
<220> FEATURE:
<221> NAME/KEY: CDS
<222> LOCATION: (1)..(1449)
```

<223> OTHER INFORMATION: Eubacterium hallii gene encoding TMP phosphatase [EEG35494]

<400> SEQUENCE: 47

```
atg ata aaa gga gca atc ttt gat att gat gga act tta ctt gat tcc    48
Met Ile Lys Gly Ala Ile Phe Asp Ile Asp Gly Thr Leu Leu Asp Ser
1               5                   10                  15 atg ccc atc tgg gaa aat gca gga gcg aga tat ctt gct act ctt ggc    96
Met Pro Ile Trp Glu Asn Ala Gly Ala Arg Tyr Leu Ala Thr Leu Gly
                20                  25                  30 att aag gca aag cca gat tta aaa gaa cgg ctg gat gct tta tct ttg    144
Ile Lys Ala Lys Pro Asp Leu Lys Glu Arg Leu Asp Ala Leu Ser Leu
            35                  40                  45 cca gaa gga gcc atc tat atg caa aaa gag tat ggc ctt tcg gta tca    192
Pro Glu Gly Ala Ile Tyr Met Gln Lys Glu Tyr Gly Leu Ser Val Ser
        50                  55                  60 gca gaa gac att tta gaa gga gtc aat cag gtt gta aaa gat ttt tac    240
Ala Glu Asp Ile Leu Glu Gly Val Asn Gln Val Val Lys Asp Phe Tyr
65                  70                  75                  80 tat aaa gaa gcg gtc atg aag ccg gga gcc tat gcc tta gta aaa cgt    288
Tyr Lys Glu Ala Val Met Lys Pro Gly Ala Tyr Ala Leu Val Lys Arg
                85                  90                  95 ctg aaa gaa aat ggt gtg aag tta att ata gcc aca gcg aca gat aag    336
Leu Lys Glu Asn Gly Val Lys Leu Ile Ile Ala Thr Ala Thr Asp Lys
            100                 105                 110 gag atg gca aag gcg gcg ctt att cgt aac ggc ata tgg cag gac ttt    384
Glu Met Ala Lys Ala Ala Leu Ile Arg Asn Gly Ile Trp Gln Asp Phe
        115                 120                 125 acg gga atg att acc tgc gag gaa gcc gga gcc gga aag aca agc ccg    432
Thr Gly Met Ile Thr Cys Glu Glu Ala Gly Ala Gly Lys Thr Ser Pro
130                 135                 140 aag gta ttt gag ctt gca agg caa aag cta ggc act aaa aaa gag gaa    480
Lys Val Phe Glu Leu Ala Arg Gln Lys Leu Gly Thr Lys Lys Glu Glu
145                 150                 155                 160 aca tgg gta ttt gaa gat tct tta tat gcg gtg aaa act gct act gaa    528
Thr Trp Val Phe Glu Asp Ser Leu Tyr Ala Val Lys Thr Ala Thr Glu
                165                 170                 175 gct gga ttt cca gta tgc agt atc tac gat acc tac agt gtg gga aat    576
Ala Gly Phe Pro Val Cys Ser Ile Tyr Asp Thr Tyr Ser Val Gly Asn
            180                 185                 190 gcg aaa gaa atc cag aaa ctt tct aat att tat gtg aga gat ttt tcg    624
Ala Lys Glu Ile Gln Lys Leu Ser Asn Ile Tyr Val Arg Asp Phe Ser
        195                 200                 205 gag ata ggt gat tat tct ttt tca aat atg aaa aca gtt ctt aca att    672
Glu Ile Gly Asp Tyr Ser Phe Ser Asn Met Lys Thr Val Leu Thr Ile
    210                 215                 220 gca ggc agt gat tcg agc gga gga gca ggt att caa gcg gat atc aag    720
Ala Gly Ser Asp Ser Ser Gly Gly Ala Gly Ile Gln Ala Asp Ile Lys
225                 230                 235                 240 act tta act gtt cat aaa gta tat gcc atg act tgt atc acc gca ctt    768
Thr Leu Thr Val His Lys Val Tyr Ala Met Thr Cys Ile Thr Ala Leu
                245                 250                 255 acc gca caa aat aca gtc gga att acc ggg att atg cca gta cca gca    816
Thr Ala Gln Asn Thr Val Gly Ile Thr Gly Ile Met Pro Val Pro Ala
            260                 265                 270 gaa ttt ttt aaa aaa cag atg gaa agc att ttc aca gat ata aag cca    864
Glu Phe Phe Lys Lys Gln Met Glu Ser Ile Phe Thr Asp Ile Lys Pro
        275                 280                 285 gat gcg gtg aaa att gga atg att gct tca aag gaa cag gca gag att    912
Asp Ala Val Lys Ile Gly Met Ile Ala Ser Lys Glu Gln Ala Glu Ile
```

```
                290                 295                 300
atc gca gaa tac ctg gaa aaa tat tct atc aaa aat gta gtg gca gac      960
Ile Ala Glu Tyr Leu Glu Lys Tyr Ser Ile Lys Asn Val Val Ala Asp
305                 310                 315                 320 ccg gtg atg att tcg aca agc ggt acg gtt tta gta gaa gaa aca acg     1008
Pro Val Met Ile Ser Thr Ser Gly Thr Val Leu Val Glu Glu Thr Thr
                325                 330                 335 aga aag ata tta tat gag aaa tta tat cca aaa gtt tcc ctg cta acc     1056
Arg Lys Ile Leu Tyr Glu Lys Leu Tyr Pro Lys Val Ser Leu Leu Thr
            340                 345                 350 ccg aac att cca gaa acc gaa ttt tta tcc ggg ata aaa att acc gat     1104
Pro Asn Ile Pro Glu Thr Glu Phe Leu Ser Gly Ile Lys Ile Thr Asp
        355                 360                 365 aaa aaa aca agg gaa gaa gca gca aaa gtc att gca gac agg tgg aat     1152
Lys Lys Thr Arg Glu Glu Ala Ala Lys Val Ile Ala Asp Arg Trp Asn
370                 375                 380 tgt gcg gtc tta agt aag ggc ggt cac agc gaa gaa aat gcg gac gat     1200
Cys Ala Val Leu Ser Lys Gly Gly His Ser Glu Glu Asn Ala Asp Asp
385                 390                 395                 400 ttg ctt tat gag agt ttt ttg cag gaa gaa aaa aaa gaa aaa gcc gtt     1248
Leu Leu Tyr Glu Ser Phe Leu Gln Glu Glu Lys Lys Glu Lys Ala Val
                405                 410                 415 tgg ttt cca gaa gaa aga att gat aat cca aac aca cac gga acc ggc     1296
Trp Phe Pro Glu Glu Arg Ile Asp Asn Pro Asn Thr His Gly Thr Gly
            420                 425                 430 tgt aca ctt tca agt gcg gta gcg gca aat ctg gca aag gga ttt cct     1344
Cys Thr Leu Ser Ser Ala Val Ala Ala Asn Leu Ala Lys Gly Phe Pro
        435                 440                 445 gta gaa gaa tcc gta aaa aag gca aaa gta tac atc agc gga gca att     1392
Val Glu Glu Ser Val Lys Lys Ala Lys Val Tyr Ile Ser Gly Ala Ile
450                 455                 460 aga gca atg ctg aat ctt gga cag gga aat ggc ccg cta aat cat atg     1440
Arg Ala Met Leu Asn Leu Gly Gln Gly Asn Gly Pro Leu Asn His Met
465                 470                 475                 480 tgg gat ttg taa                                                      1452
Trp Asp Leu <210> SEQ ID NO 48
<211> LENGTH: 483
<212> TYPE: PRT
<213> ORGANISM: Eubacterium hallii

<400> SEQUENCE: 48

Met Ile Lys Gly Ala Ile Phe Asp Ile Asp Gly Thr Leu Leu Asp Ser
1               5                   10                  15

Met Pro Ile Trp Glu Asn Ala Gly Ala Arg Tyr Leu Ala Thr Leu Gly
                20                  25                  30

Ile Lys Ala Lys Pro Asp Leu Lys Glu Arg Leu Asp Ala Leu Ser Leu
            35                  40                  45

Pro Glu Gly Ala Ile Tyr Met Gln Lys Glu Tyr Gly Leu Ser Val Ser
        50                  55                  60

Ala Glu Asp Ile Leu Glu Gly Val Asn Gln Val Val Lys Asp Phe Tyr
65                  70                  75                  80

Tyr Lys Glu Ala Val Met Lys Pro Gly Ala Tyr Ala Leu Val Lys Arg
                85                  90                  95

Leu Lys Glu Asn Gly Val Lys Leu Ile Ile Ala Thr Ala Thr Asp Lys
            100                 105                 110

Glu Met Ala Lys Ala Ala Leu Ile Arg Asn Gly Ile Trp Gln Asp Phe
        115                 120                 125
```

```
Thr Gly Met Ile Thr Cys Glu Glu Ala Gly Ala Gly Lys Thr Ser Pro
            130                 135                 140
Lys Val Phe Glu Leu Ala Arg Gln Lys Leu Gly Thr Lys Lys Glu Glu
145                 150                 155                 160
Thr Trp Val Phe Glu Asp Ser Leu Tyr Ala Val Lys Thr Ala Thr Glu
                165                 170                 175
Ala Gly Phe Pro Val Cys Ser Ile Tyr Asp Thr Tyr Ser Val Gly Asn
            180                 185                 190
Ala Lys Glu Ile Gln Lys Leu Ser Asn Ile Tyr Val Arg Asp Phe Ser
        195                 200                 205
Glu Ile Gly Asp Tyr Ser Phe Ser Asn Met Lys Thr Val Leu Thr Ile
    210                 215                 220
Ala Gly Ser Asp Ser Ser Gly Ala Gly Ile Gln Ala Asp Ile Lys
225                 230                 235                 240
Thr Leu Thr Val His Lys Val Tyr Ala Met Thr Cys Ile Thr Ala Leu
                245                 250                 255
Thr Ala Gln Asn Thr Val Gly Ile Thr Gly Ile Met Pro Val Pro Ala
            260                 265                 270
Glu Phe Phe Lys Lys Gln Met Glu Ser Ile Phe Thr Asp Ile Lys Pro
        275                 280                 285
Asp Ala Val Lys Ile Gly Met Ile Ala Ser Lys Glu Gln Ala Glu Ile
    290                 295                 300
Ile Ala Glu Tyr Leu Glu Lys Tyr Ser Ile Lys Asn Val Val Ala Asp
305                 310                 315                 320
Pro Val Met Ile Ser Thr Ser Gly Thr Val Leu Val Glu Glu Thr Thr
                325                 330                 335
Arg Lys Ile Leu Tyr Glu Lys Leu Tyr Pro Lys Val Ser Leu Leu Thr
            340                 345                 350
Pro Asn Ile Pro Glu Thr Glu Phe Leu Ser Gly Ile Lys Ile Thr Asp
        355                 360                 365
Lys Lys Thr Arg Glu Glu Ala Ala Lys Val Ile Ala Asp Arg Trp Asn
    370                 375                 380
Cys Ala Val Leu Ser Lys Gly His Ser Glu Glu Asn Ala Asp Asp
385                 390                 395                 400
Leu Leu Tyr Glu Ser Phe Leu Gln Glu Lys Lys Glu Lys Ala Val
                405                 410                 415
Trp Phe Pro Glu Glu Arg Ile Asp Asn Pro Asn Thr His Gly Thr Gly
            420                 425                 430
Cys Thr Leu Ser Ser Ala Val Ala Asn Leu Ala Lys Gly Phe Pro
        435                 440                 445
Val Glu Glu Ser Val Lys Lys Ala Lys Val Tyr Ile Ser Gly Ala Ile
    450                 455                 460
Arg Ala Met Leu Asn Leu Gly Gln Gly Asn Gly Pro Leu Asn His Met
465                 470                 475                 480
Trp Asp Leu
```

<210> SEQ ID NO 49
<211> LENGTH: 1362
<212> TYPE: DNA
<213> ORGANISM: Eubacterium sp.
<220> FEATURE:
<221> NAME/KEY: CDS
<222> LOCATION: (1)..(1359)
<223> OTHER INFORMATION: Eubacterium sp. CAG:252 gene encoding TMP phosphatase [CDB67556]

<400> SEQUENCE: 49

```
atg aaa aat aaa ttt ttc aca cgc gag att tgt gtc tgc gtg cac ttg        48
Met Lys Asn Lys Phe Phe Thr Arg Glu Ile Cys Val Cys Val His Leu
1               5                   10                  15 aca caa act cgt tat gcg caa aaa acg tgc gca gaa atg agg aat agt        96
Thr Gln Thr Arg Tyr Ala Gln Lys Thr Cys Ala Glu Met Arg Asn Ser
            20                  25                  30 gtg aag gtt aaa gct gag gat atg cag cta tac gct gtt aca gat aca       144
Val Lys Val Lys Ala Glu Asp Met Gln Leu Tyr Ala Val Thr Asp Thr
        35                  40                  45 cag tgg ctt aat gga cgt gac ttt ctt gaa gta ata gaa agc gtt ctt       192
Gln Trp Leu Asn Gly Arg Asp Phe Leu Glu Val Ile Glu Ser Val Leu
    50                  55                  60 gca aat gga gct aca ttt tta cag tta agg gaa aaa aat gcc aca cat       240
Ala Asn Gly Ala Thr Phe Leu Gln Leu Arg Glu Lys Asn Ala Thr His
65                  70                  75                  80 gag gaa ata gtg gca aag gcg aag gca ata aag cca ata gct aag aag       288
Glu Glu Ile Val Ala Lys Ala Lys Ala Ile Lys Pro Ile Ala Lys Lys
                85                  90                  95 tac gga gtg cct ttt gtc ata gat gat gac ata tat gca gct aaa gag       336
Tyr Gly Val Pro Phe Val Ile Asp Asp Asp Ile Tyr Ala Ala Lys Glu
            100                 105                 110 gca gac gtg gat ggt gtc cac ata ggg cag aat gat gca agc tat gag       384
Ala Asp Val Asp Gly Val His Ile Gly Gln Asn Asp Ala Ser Tyr Glu
        115                 120                 125 aag gca aga gaa gtt ctt gga gaa ggc aag ata ata gga atg acg gtc       432
Lys Ala Arg Glu Val Leu Gly Glu Gly Lys Ile Ile Gly Met Thr Val
    130                 135                 140 aag aca agg cag cag gca gaa aat gcc ata aga ctt ggc gct gac tat       480
Lys Thr Arg Gln Gln Ala Glu Asn Ala Ile Arg Leu Gly Ala Asp Tyr
145                 150                 155                 160 gtt gga atg ggg gca gtg ttt cat aca agc act aaa aaa gat gca aag       528
Val Gly Met Gly Ala Val Phe His Thr Ser Thr Lys Lys Asp Ala Lys
                165                 170                 175 gat atg agc agg gaa aca ctt tta gag ctt gca ggg atg atg gag gat       576
Asp Met Ser Arg Glu Thr Leu Leu Glu Leu Ala Gly Met Met Glu Asp
            180                 185                 190 att ccg gtg gtc gcc att ggc ggc ata agc tat gat aac tgc gat tac       624
Ile Pro Val Val Ala Ile Gly Gly Ile Ser Tyr Asp Asn Cys Asp Tyr
        195                 200                 205 tta aag gac aca ggt gtt gat gga ata gca gtt gtt tca gcc ata ttt       672
Leu Lys Asp Thr Gly Val Asp Gly Ile Ala Val Val Ser Ala Ile Phe
    210                 215                 220 gca agt gat gac tgt gcg ctt gcc aca aga aag ctt ttt gta aag aca       720
Ala Ser Asp Asp Cys Ala Leu Ala Thr Arg Lys Leu Phe Val Lys Thr
225                 230                 235                 240 agg gaa ttg ttt gga aag aaa aga aac ata ata atg gat atg gat ggt       768
Arg Glu Leu Phe Gly Lys Lys Arg Asn Ile Ile Met Asp Met Asp Gly
                245                 250                 255 acg ctt gca gac tct atg cct ttc tgg aaa aac agc gca aga gag tat       816
Thr Leu Ala Asp Ser Met Pro Phe Trp Lys Asn Ser Ala Arg Glu Tyr
            260                 265                 270 gcg ata tta cgt gga gca gat att ccg gat aat ttc gat gag ata act       864
Ala Ile Leu Arg Gly Ala Asp Ile Pro Asp Asn Phe Asp Glu Ile Thr
        275                 280                 285 ggc gtt atg gac ctt aat gat tat gct gag tat gtt aaa aat gtt ctt       912
Gly Val Met Asp Leu Asn Asp Tyr Ala Glu Tyr Val Lys Asn Val Leu
    290                 295                 300
```

```
ggc ata gat act aat ctt gag cag ata aca gaa gcg gct gtc gag att      960
Gly Ile Asp Thr Asn Leu Glu Gln Ile Thr Glu Ala Ala Val Glu Ile
305                 310                 315                 320 atg aat aaa cat tac gaa aaa gat ata cct gca aag gac ggt atg aca     1008
Met Asn Lys His Tyr Glu Lys Asp Ile Pro Ala Lys Asp Gly Met Thr
                325                 330                 335 gag ctt gtc acg aga gaa tat aag gcc gga agc aga ctt gtt gtg ttt    1056
Glu Leu Val Thr Arg Glu Tyr Lys Ala Gly Ser Arg Leu Val Val Phe
            340                 345                 350 acg gct tca gat aga aga agt gtt gaa att ctt ctt tca cac ctt gga    1104
Thr Ala Ser Asp Arg Arg Ser Val Glu Ile Leu Leu Ser His Leu Gly
        355                 360                 365 ata aga gaa tgt ttt tat gat ata tat aca gtc tat gat gta gga ctt    1152
Ile Arg Glu Cys Phe Tyr Asp Ile Tyr Thr Val Tyr Asp Val Gly Leu
    370                 375                 380 aag aag agt gat aag aac agc tat ctt aag gtg gca gag ctt gca ggc    1200
Lys Lys Ser Asp Lys Asn Ser Tyr Leu Lys Val Ala Glu Leu Ala Gly
385                 390                 395                 400 atg aaa gat aca tca cag gta tgg gta tat gag gat ata tta aga ggt    1248
Met Lys Asp Thr Ser Gln Val Trp Val Tyr Glu Asp Ile Leu Arg Gly
                405                 410                 415 gta aag gca gcg aaa gag gcc gga ctt aat gtg tgt gca gtg tat gat    1296
Val Lys Ala Ala Lys Glu Ala Gly Leu Asn Val Cys Ala Val Tyr Asp
            420                 425                 430 gag gac tcc gca ggc gac tgg gag gac ata aaa gag ctt gcg gat aag    1344
Glu Asp Ser Ala Gly Asp Trp Glu Asp Ile Lys Glu Leu Ala Asp Lys
        435                 440                 445 acc ctt gaa ctt gtg taa                                            1362
Thr Leu Glu Leu Val
    450

<210> SEQ ID NO 50
<211> LENGTH: 453
<212> TYPE: PRT
<213> ORGANISM: Eubacterium sp.

<400> SEQUENCE: 50

Met Lys Asn Lys Phe Phe Thr Arg Glu Ile Cys Val Cys Val His Leu
1               5                   10                  15

Thr Gln Thr Arg Tyr Ala Gln Lys Thr Cys Ala Glu Met Arg Asn Ser
            20                  25                  30

Val Lys Val Lys Ala Glu Asp Met Gln Leu Tyr Ala Val Thr Asp Thr
        35                  40                  45

Gln Trp Leu Asn Gly Arg Asp Phe Leu Glu Val Ile Glu Ser Val Leu
    50                  55                  60

Ala Asn Gly Ala Thr Phe Leu Gln Leu Arg Glu Lys Asn Ala Thr His
65                  70                  75                  80

Glu Glu Ile Val Ala Lys Ala Lys Ala Ile Lys Pro Ile Ala Lys Lys
                85                  90                  95

Tyr Gly Val Pro Phe Val Ile Asp Asp Ile Tyr Ala Ala Lys Glu
            100                 105                 110

Ala Asp Val Asp Gly Val His Ile Gly Gln Asn Asp Ala Ser Tyr Glu
        115                 120                 125

Lys Ala Arg Glu Val Leu Gly Glu Gly Lys Ile Ile Gly Met Thr Val
    130                 135                 140

Lys Thr Arg Gln Gln Ala Glu Asn Ala Ile Arg Leu Gly Ala Asp Tyr
145                 150                 155                 160

Val Gly Met Gly Ala Val Phe His Thr Ser Thr Lys Lys Asp Ala Lys
```

```
                        165                 170                 175
Asp Met Ser Arg Glu Thr Leu Leu Glu Leu Ala Gly Met Met Glu Asp
            180                 185                 190

Ile Pro Val Val Ala Ile Gly Gly Ile Ser Tyr Asp Asn Cys Asp Tyr
            195                 200                 205

Leu Lys Asp Thr Gly Val Asp Gly Ile Ala Val Val Ser Ala Ile Phe
        210                 215                 220

Ala Ser Asp Asp Cys Ala Leu Ala Thr Arg Lys Leu Phe Val Lys Thr
225                 230                 235                 240

Arg Glu Leu Phe Gly Lys Lys Arg Asn Ile Ile Met Asp Met Asp Gly
                245                 250                 255

Thr Leu Ala Asp Ser Met Pro Phe Trp Lys Asn Ser Ala Arg Glu Tyr
            260                 265                 270

Ala Ile Leu Arg Gly Ala Asp Ile Pro Asp Asn Phe Asp Glu Ile Thr
            275                 280                 285

Gly Val Met Asp Leu Asn Asp Tyr Ala Glu Tyr Val Lys Asn Val Leu
        290                 295                 300

Gly Ile Asp Thr Asn Leu Glu Gln Ile Thr Glu Ala Ala Val Glu Ile
305                 310                 315                 320

Met Asn Lys His Tyr Glu Lys Asp Ile Pro Ala Lys Asp Gly Met Thr
                325                 330                 335

Glu Leu Val Thr Arg Glu Tyr Lys Ala Gly Ser Arg Leu Val Val Phe
            340                 345                 350

Thr Ala Ser Asp Arg Arg Ser Val Glu Ile Leu Leu Ser His Leu Gly
            355                 360                 365

Ile Arg Glu Cys Phe Tyr Asp Ile Tyr Thr Val Tyr Asp Val Gly Leu
        370                 375                 380

Lys Lys Ser Asp Lys Asn Ser Tyr Leu Lys Val Ala Glu Leu Ala Gly
385                 390                 395                 400

Met Lys Asp Thr Ser Gln Val Trp Val Tyr Glu Asp Ile Leu Arg Gly
                405                 410                 415

Val Lys Ala Ala Lys Glu Ala Gly Leu Asn Val Cys Ala Val Tyr Asp
            420                 425                 430

Glu Asp Ser Ala Gly Asp Trp Glu Asp Ile Lys Glu Leu Ala Asp Lys
            435                 440                 445

Thr Leu Glu Leu Val
        450

<210> SEQ ID NO 51
<211> LENGTH: 1260
<212> TYPE: DNA
<213> ORGANISM: Lachnospira pectinoschiza
<220> FEATURE:
<221> NAME/KEY: CDS
<222> LOCATION: (1)..(1257)
<223> OTHER INFORMATION: Lachnospiraceae pectinoschiza gene encoding TMP
      phosphatase [CUQ76318]

<400> SEQUENCE: 51 atg aaa gtt acc cgt gaa gat atg cag ctt tac gcc gtt aca gat acg      48
Met Lys Val Thr Arg Glu Asp Met Gln Leu Tyr Ala Val Thr Asp Thr
1               5                   10                  15 caa tgg ctt aat ggc agg gat ttc tat gaa gag att gag aaa gtc ctt      96
Gln Trp Leu Asn Gly Arg Asp Phe Tyr Glu Glu Ile Glu Lys Val Leu
            20                  25                  30 gcg gca gga gct aca ttt ttg cag tta aga gaa aag gat tcg aca cac     144
Ala Ala Gly Ala Thr Phe Leu Gln Leu Arg Glu Lys Asp Ser Thr His
```

```
                35                  40                  45
gag gag att gta aaa aaa gca ttg gca att aaa ccg ata gca aga aga    192
Glu Glu Ile Val Lys Lys Ala Leu Ala Ile Lys Pro Ile Ala Arg Arg
    50                  55                  60 tat ggt gtg cca ttt gtt ata gat gat gat ata tac gcg gcg tta gag    240
Tyr Gly Val Pro Phe Val Ile Asp Asp Asp Ile Tyr Ala Ala Leu Glu
65                  70                  75                  80 gca gat gtt gac gga gtt cat ata gga caa agt gat gca agc tac gaa    288
Ala Asp Val Asp Gly Val His Ile Gly Gln Ser Asp Ala Ser Tyr Glu
                85                  90                  95 aca gca aga gag ctt cta gga cct gac aag ata ata gga atg aca gta    336
Thr Ala Arg Glu Leu Leu Gly Pro Asp Lys Ile Ile Gly Met Thr Val
            100                 105                 110 aag aca cca gag cag gcg gca aat gcg gca aga ctt ggt gct gat tat    384
Lys Thr Pro Glu Gln Ala Ala Asn Ala Ala Arg Leu Gly Ala Asp Tyr
        115                 120                 125 gtt gga atg gga gct gta ttt cat aca agc acg aag aaa gat gcc aaa    432
Val Gly Met Gly Ala Val Phe His Thr Ser Thr Lys Lys Asp Ala Lys
    130                 135                 140 gat tta agc agg gat aat ctt ctt aag ctt aca gct atg ctt gat atg    480
Asp Leu Ser Arg Asp Asn Leu Leu Lys Leu Thr Ala Met Leu Asp Met
145                 150                 155                 160 ccg ata gtt gca att ggc ggc att aat tat gac aac tgt gat tat tta    528
Pro Ile Val Ala Ile Gly Gly Ile Asn Tyr Asp Asn Cys Asp Tyr Leu
                165                 170                 175 aaa gat aca ggc gtg gac gga att gct gtt gta tcg gcg ata ttt gca    576
Lys Asp Thr Gly Val Asp Gly Ile Ala Val Val Ser Ala Ile Phe Ala
            180                 185                 190 agt gat gac tgc gcg gag gcg aca cga aag ctt tat aag aag aca aga    624
Ser Asp Asp Cys Ala Glu Ala Thr Arg Lys Leu Tyr Lys Lys Thr Arg
        195                 200                 205 aag ctg ttt aat tat aat aag aac ata ata ttt gat atg gac gga aca    672
Lys Leu Phe Asn Tyr Asn Lys Asn Ile Ile Phe Asp Met Asp Gly Thr
    210                 215                 220 ctt gtt gac tct atg ccg ttc tgg aag aat agt gca agg gaa tat gcc    720
Leu Val Asp Ser Met Pro Phe Trp Lys Asn Ser Ala Arg Glu Tyr Ala
225                 230                 235                 240 att tta aga ggt gct aag ctt cca aag aat ttt gat gag ata aca gga    768
Ile Leu Arg Gly Ala Lys Leu Pro Lys Asn Phe Asp Glu Ile Thr Gly
                245                 250                 255 gtt atg gac ctt tcg gaa tat gcg gct tat ctg caa aat gtt ctt ggg    816
Val Met Asp Leu Ser Glu Tyr Ala Ala Tyr Leu Gln Asn Val Leu Gly
            260                 265                 270 att gat aca tcg cta gaa cag ata aca gag gca gca gtt gat att atg    864
Ile Asp Thr Ser Leu Glu Gln Ile Thr Glu Ala Ala Val Asp Ile Met
        275                 280                 285 aat aag cat tat gca agt gat att cct gca aag aag gga atg ata aag    912
Asn Lys His Tyr Ala Ser Asp Ile Pro Ala Lys Lys Gly Met Ile Lys
    290                 295                 300 ctt ata aga aga gaa tat gag gct gga agc aag ctt gta ata ttc agt    960
Leu Ile Arg Arg Glu Tyr Glu Ala Gly Ser Lys Leu Val Ile Phe Ser
305                 310                 315                 320 gct tcc gat act tcc agt gtg gaa att ctt ctt aaa agg tta gaa ata   1008
Ala Ser Asp Thr Ser Ser Val Glu Ile Leu Leu Lys Arg Leu Glu Ile
                325                 330                 335 tat gaa tgt ttt gag gga ata tac aca gta tat gat gtc ggc ata gga   1056
Tyr Glu Cys Phe Glu Gly Ile Tyr Thr Val Tyr Asp Val Gly Ile Gly
            340                 345                 350 aag agt gat aag gaa agc tat aaa aag gtt gcc agg tca gca gga atg   1104
```

```
                                                      Lys Ser Asp Lys Glu Ser Tyr Lys Val Ala Arg Ser Ala Gly Met
                                                                  355                 360                 365 gat ata tct gat acg tgg gtg tat gag gat att cta aga ggc gtt cgg              1152
Asp Ile Ser Asp Thr Trp Val Tyr Glu Asp Ile Leu Arg Gly Val Arg
            370                 375                 380 gcg gca cat aat gct gga ttg aaa gtg tgt gcg gta tat gat aaa gac              1200
Ala Ala His Asn Ala Gly Leu Lys Val Cys Ala Val Tyr Asp Lys Asp
385                 390                 395                 400 tcg gca gat gac tgg gat gag ata tgc agt att gca gat aaa tgt ata              1248
Ser Ala Asp Asp Trp Asp Glu Ile Cys Ser Ile Ala Asp Lys Cys Ile
                405                 410                 415 ata acc gga taa                                                              1260
Ile Thr Gly <210> SEQ ID NO 52
<211> LENGTH: 419
<212> TYPE: PRT
<213> ORGANISM: Lachnospira pectinoschiza

<400> SEQUENCE: 52

Met Lys Val Thr Arg Glu Asp Met Gln Leu Tyr Ala Val Thr Asp Thr
1               5                   10                  15

Gln Trp Leu Asn Gly Arg Asp Phe Tyr Glu Ile Glu Lys Val Leu
            20                  25                  30

Ala Ala Gly Ala Thr Phe Leu Gln Leu Arg Glu Lys Asp Ser Thr His
            35                  40                  45

Glu Glu Ile Val Lys Lys Ala Leu Ala Ile Lys Pro Ile Ala Arg Arg
        50                  55                  60

Tyr Gly Val Pro Phe Val Ile Asp Asp Ile Tyr Ala Ala Leu Glu
65              70                  75                  80

Ala Asp Val Asp Gly Val His Ile Gly Gln Ser Asp Ala Ser Tyr Glu
                85                  90                  95

Thr Ala Arg Glu Leu Leu Gly Pro Asp Lys Ile Ile Gly Met Thr Val
            100                 105                 110

Lys Thr Pro Glu Gln Ala Ala Asn Ala Ala Arg Leu Gly Ala Asp Tyr
        115                 120                 125

Val Gly Met Gly Ala Val Phe His Thr Ser Thr Lys Lys Asp Ala Lys
130                 135                 140

Asp Leu Ser Arg Asp Asn Leu Leu Lys Leu Thr Ala Met Leu Asp Met
145                 150                 155                 160

Pro Ile Val Ala Ile Gly Gly Ile Asn Tyr Asp Asn Cys Asp Tyr Leu
                165                 170                 175

Lys Asp Thr Gly Val Asp Gly Ile Ala Val Val Ser Ala Ile Phe Ala
            180                 185                 190

Ser Asp Asp Cys Ala Glu Ala Thr Arg Lys Leu Tyr Lys Lys Thr Arg
        195                 200                 205

Lys Leu Phe Asn Tyr Asn Lys Asn Ile Ile Phe Asp Met Asp Gly Thr
    210                 215                 220

Leu Val Asp Ser Met Pro Phe Trp Lys Asn Ser Ala Arg Glu Tyr Ala
225                 230                 235                 240

Ile Leu Arg Gly Ala Lys Leu Pro Lys Asn Phe Asp Glu Ile Thr Gly
                245                 250                 255

Val Met Asp Leu Ser Glu Tyr Ala Ala Tyr Leu Gln Asn Val Leu Gly
            260                 265                 270

Ile Asp Thr Ser Leu Glu Gln Ile Thr Glu Ala Ala Val Asp Ile Met
        275                 280                 285
```

```
Asn Lys His Tyr Ala Ser Asp Ile Pro Ala Lys Lys Gly Met Ile Lys
            290                 295                 300

Leu Ile Arg Arg Glu Tyr Glu Ala Gly Ser Lys Leu Val Ile Phe Ser
305                 310                 315                 320

Ala Ser Asp Thr Ser Ser Val Glu Ile Leu Leu Lys Arg Leu Glu Ile
                325                 330                 335

Tyr Glu Cys Phe Glu Gly Ile Tyr Thr Val Tyr Asp Val Gly Ile Gly
                340                 345                 350

Lys Ser Asp Lys Glu Ser Tyr Lys Lys Val Ala Arg Ser Ala Gly Met
            355                 360                 365

Asp Ile Ser Asp Thr Trp Val Tyr Glu Asp Ile Leu Arg Gly Val Arg
    370                 375                 380

Ala Ala His Asn Ala Gly Leu Lys Val Cys Ala Val Tyr Asp Lys Asp
385                 390                 395                 400

Ser Ala Asp Asp Trp Asp Glu Ile Cys Ser Ile Ala Asp Lys Cys Ile
                405                 410                 415

Ile Thr Gly

<210> SEQ ID NO 53
<211> LENGTH: 1296
<212> TYPE: DNA
<213> ORGANISM: Unknown
<220> FEATURE:
<223> OTHER INFORMATION: Description of Unknown:
      Peptostreptococcaceae bacterium sequence
<220> FEATURE:
<221> NAME/KEY: CDS
<222> LOCATION: (1)..(1293)
<223> OTHER INFORMATION: Peptostreptococcaceae bacterium OBRC8 gene
      encoding TMP phosphatase[WP_009530263]

<400> SEQUENCE: 53
```

| | | | | | | | | | | | | | | | | |
|---|---|---|---|---|---|---|---|---|---|---|---|---|---|---|---|---|
| atg | aaa | aat | att | gac | tat | aca | atg | tat | tac | gtc | acc | gat | gaa | gac | ctt | 48 |
| Met | Lys | Asn | Ile | Asp | Tyr | Thr | Met | Tyr | Tyr | Val | Thr | Asp | Glu | Asp | Leu | |
| 1 | | | | 5 | | | | | 10 | | | | | 15 | | |
| ttg | agc | agt | aat | cat | acc | ttg | gaa | aca | tct | gta | caa | gat | gcc | att | tta | 96 |
| Leu | Ser | Ser | Asn | His | Thr | Leu | Glu | Thr | Ser | Val | Gln | Asp | Ala | Ile | Leu | |
| | | 20 | | | | | 25 | | | | | 30 | | | | |
| ggt | ggc | tgt | aca | atg | ata | cag | ctt | cga | gaa | aaa | cat | tca | tcc | act | ctc | 144 |
| Gly | Gly | Cys | Thr | Met | Ile | Gln | Leu | Arg | Glu | Lys | His | Ser | Ser | Thr | Leu | |
| | 35 | | | | | 40 | | | | | 45 | | | | | |
| gat | ttt | tat | aac | aaa | gcc | ata | aaa | att | aaa | gcc | att | tgc | gac | aag | tac | 192 |
| Asp | Phe | Tyr | Asn | Lys | Ala | Ile | Lys | Ile | Lys | Ala | Ile | Cys | Asp | Lys | Tyr | |
| 50 | | | | | 55 | | | | | 60 | | | | | | |
| aac | ata | cct | ctt | ata | ata | aat | gac | aga | ata | gat | gta | gct | ctt | gca | ata | 240 |
| Asn | Ile | Pro | Leu | Ile | Ile | Asn | Asp | Arg | Ile | Asp | Val | Ala | Leu | Ala | Ile | |
| 65 | | | | | 70 | | | | | 75 | | | | | 80 | |
| aac | gca | gac | gga | gta | cat | ctc | gga | caa | gac | gat | atg | cct | ctt | gat | att | 288 |
| Asn | Ala | Asp | Gly | Val | His | Leu | Gly | Gln | Asp | Asp | Met | Pro | Leu | Asp | Ile | |
| | | | | 85 | | | | | 90 | | | | | 95 | | |
| gca | aga | aaa | att | atg | gga | gat | ggc | aaa | att | ata | gga | ata | tca | act | gca | 336 |
| Ala | Arg | Lys | Ile | Met | Gly | Asp | Gly | Lys | Ile | Ile | Gly | Ile | Ser | Thr | Ala | |
| | | | 100 | | | | | 105 | | | | | 110 | | | |
| act | tta | gat | gaa | gct | cta | atc | gct | caa | caa | ggc | ggt | gca | gat | tat | gta | 384 |
| Thr | Leu | Asp | Glu | Ala | Leu | Ile | Ala | Gln | Gln | Gly | Gly | Ala | Asp | Tyr | Val | |
| | | | 115 | | | | | 120 | | | | | 125 | | | |
| gga | gta | ggt | gct | atg | tac | agc | aca | aac | aca | aaa | acc | gat | gcc | aat | ttg | 432 |
| Gly | Val | Gly | Ala | Met | Tyr | Ser | Thr | Asn | Thr | Lys | Thr | Asp | Ala | Asn | Leu | |
| | | 130 | | | | | 135 | | | | | 140 | | | | |

| | | | | | | | | | | | | | | | | |
|---|---|---|---|---|---|---|---|---|---|---|---|---|---|---|---|---|
| aca | act | ata | aac | gag | ctt | aca | aaa | ata | aaa | aac | aat | cta | aaa | ata | cct | 480 |
| Thr | Thr | Ile | Asn | Glu | Leu | Thr | Lys | Ile | Lys | Asn | Asn | Leu | Lys | Ile | Pro | |
| 145 | | | | 150 | | | | | 155 | | | | | 160 | | |
| gta | gtt | gca | atc | ggc | ggt | ata | aac | ctt | gac | aca | ata | cct | gct | cta | aaa | 528 |
| Val | Val | Ala | Ile | Gly | Gly | Ile | Asn | Leu | Asp | Thr | Ile | Pro | Ala | Leu | Lys | |
| | | | | 165 | | | | | 170 | | | | | 175 | | |
| cct | gca | caa | ata | gac | gga | gtt | gca | ata | gta | tcc | gct | ata | tct | atg | cag | 576 |
| Pro | Ala | Gln | Ile | Asp | Gly | Val | Ala | Ile | Val | Ser | Ala | Ile | Ser | Met | Gln | |
| | | | 180 | | | | | 185 | | | | | 190 | | | |
| gaa | gat | acc | gta | tct | gca | aca | aga | aaa | tta | aaa | aat | act | ttt | ttg | aaa | 624 |
| Glu | Asp | Thr | Val | Ser | Ala | Thr | Arg | Lys | Leu | Lys | Asn | Thr | Phe | Leu | Lys | |
| | | 195 | | | | | 200 | | | | | 205 | | | | |
| caa | tat | caa | act | aaa | ggc | gta | ata | ttc | gat | att | gac | ggt | act | ctg | ctt | 672 |
| Gln | Tyr | Gln | Thr | Lys | Gly | Val | Ile | Phe | Asp | Ile | Asp | Gly | Thr | Leu | Leu | |
| | 210 | | | | | 215 | | | | | 220 | | | | | |
| gaa | act | atg | aac | ata | tgg | gac | aat | gta | ctt | cta | aac | ctt | atg | aat | aca | 720 |
| Glu | Thr | Met | Asn | Ile | Trp | Asp | Asn | Val | Leu | Leu | Asn | Leu | Met | Asn | Thr | |
| 225 | | | | 230 | | | | | 235 | | | | | 240 | | |
| ctt | aat | atc | agc | tat | acc | gaa | gat | gaa | ata | caa | aaa | ata | tgg | aat | atg | 768 |
| Leu | Asn | Ile | Ser | Tyr | Thr | Glu | Asp | Glu | Ile | Gln | Lys | Ile | Trp | Asn | Met | |
| | | | | 245 | | | | | 250 | | | | | 255 | | |
| ggt | ttt | gca | gag | ctt | gca | cag | ttc | agc | ata | aaa | aaa | ttc | aag | ctt | gat | 816 |
| Gly | Phe | Ala | Glu | Leu | Ala | Gln | Phe | Ser | Ile | Lys | Lys | Phe | Lys | Leu | Asp | |
| | | | 260 | | | | | 265 | | | | | 270 | | | |
| atg | agt | gta | aaa | gaa | ttt | tgg | caa | ctt | ata | aaa | aaa | tta | tca | gtc | gaa | 864 |
| Met | Ser | Val | Lys | Glu | Phe | Trp | Gln | Leu | Ile | Lys | Lys | Leu | Ser | Val | Glu | |
| | | 275 | | | | | 280 | | | | | 285 | | | | |
| gag | tat | aaa | aat | agc | aaa | ata | cac | tta | aaa | aaa | ggt | gca | aaa | aaa | ctg | 912 |
| Glu | Tyr | Lys | Asn | Ser | Lys | Ile | His | Leu | Lys | Lys | Gly | Ala | Lys | Lys | Leu | |
| | 290 | | | | | 295 | | | | | 300 | | | | | |
| ctt | gag | tat | ctc | aaa | gaa | aaa | ggt | gta | aaa | tta | gcc | ata | gca | act | gcc | 960 |
| Leu | Glu | Tyr | Leu | Lys | Glu | Lys | Gly | Val | Lys | Leu | Ala | Ile | Ala | Thr | Ala | |
| 305 | | | | 310 | | | | | 315 | | | | | 320 | | |
| ctt | tgc | aaa | gaa | cag | tat | gaa | ata | gtg | ctt | aca | aag | aca | ggt | atc | ata | 1008 |
| Leu | Cys | Lys | Glu | Gln | Tyr | Glu | Ile | Val | Leu | Thr | Lys | Thr | Gly | Ile | Ile | |
| | | | | 325 | | | | | 330 | | | | | 335 | | |
| gac | tat | ttt | gac | ata | ata | gca | tca | agc | gta | gat | tta | aaa | atg | gaa | aaa | 1056 |
| Asp | Tyr | Phe | Asp | Ile | Ile | Ala | Ser | Ser | Val | Asp | Leu | Lys | Met | Glu | Lys | |
| | | | 340 | | | | | 345 | | | | | 350 | | | |
| tca | gac | aga | caa | ata | ttt | gac | tat | ata | gca | aaa | aat | cta | caa | gtt | cca | 1104 |
| Ser | Asp | Arg | Gln | Ile | Phe | Asp | Tyr | Ile | Ala | Lys | Asn | Leu | Gln | Val | Pro | |
| | | 355 | | | | | 360 | | | | | 365 | | | | |
| aac | aaa | aat | ctt | att | ttc | ttt | gaa | gac | gac | ata | aac | tcg | tca | aca | ggt | 1152 |
| Asn | Lys | Asn | Leu | Ile | Phe | Phe | Glu | Asp | Asp | Ile | Asn | Ser | Ser | Thr | Gly | |
| | 370 | | | | | 375 | | | | | 380 | | | | | |
| gcc | aag | ttg | gca | gga | cta | aaa | ctg | tgc | att | gta | tca | aac | aag | aaa | tat | 1200 |
| Ala | Lys | Leu | Ala | Gly | Leu | Lys | Leu | Cys | Ile | Val | Ser | Asn | Lys | Lys | Tyr | |
| 385 | | | | 390 | | | | | 395 | | | | | 400 | | |
| aac | ggt | aac | agc | aaa | ttt | gac | gct | ctc | ata | gat | tat | aaa | ata | gat | gat | 1248 |
| Asn | Gly | Asn | Ser | Lys | Phe | Asp | Ala | Leu | Ile | Asp | Tyr | Lys | Ile | Asp | Asp | |
| | | | | 405 | | | | | 410 | | | | | 415 | | |
| ttt | gaa | aat | aaa | ttg | ata | tat | gat | gaa | ata | ata | gtg | gag | aaa | aat | tag | 1296 |
| Phe | Glu | Asn | Lys | Leu | Ile | Tyr | Asp | Glu | Ile | Ile | Val | Glu | Lys | Asn | | |
| | | | 420 | | | | | 425 | | | | | 430 | | | |

<210> SEQ ID NO 54
<211> LENGTH: 431
<212> TYPE: PRT
<213> ORGANISM: Unknown
<220> FEATURE:
<223> OTHER INFORMATION: Description of Unknown:

Peptostreptococcaceae bacterium sequence

<400> SEQUENCE: 54

```
Met Lys Asn Ile Asp Tyr Thr Met Tyr Tyr Val Thr Asp Glu Asp Leu
1               5                   10                  15
Leu Ser Ser Asn His Thr Leu Glu Thr Ser Val Gln Asp Ala Ile Leu
            20                  25                  30
Gly Gly Cys Thr Met Ile Gln Leu Arg Glu Lys His Ser Ser Thr Leu
        35                  40                  45
Asp Phe Tyr Asn Lys Ala Ile Lys Ile Lys Ala Ile Cys Asp Lys Tyr
    50                  55                  60
Asn Ile Pro Leu Ile Ile Asn Asp Arg Ile Asp Val Ala Leu Ala Ile
65                  70                  75                  80
Asn Ala Asp Gly Val His Leu Gly Gln Asp Asp Met Pro Leu Asp Ile
                85                  90                  95
Ala Arg Lys Ile Met Gly Asp Gly Lys Ile Ile Gly Ile Ser Thr Ala
            100                 105                 110
Thr Leu Asp Glu Ala Leu Ile Ala Gln Gln Gly Gly Ala Asp Tyr Val
        115                 120                 125
Gly Val Gly Ala Met Tyr Ser Thr Asn Thr Lys Thr Asp Ala Asn Leu
    130                 135                 140
Thr Thr Ile Asn Glu Leu Thr Lys Ile Lys Asn Asn Leu Lys Ile Pro
145                 150                 155                 160
Val Val Ala Ile Gly Gly Ile Asn Leu Asp Thr Ile Pro Ala Leu Lys
                165                 170                 175
Pro Ala Gln Ile Asp Gly Val Ala Ile Val Ser Ala Ile Ser Met Gln
            180                 185                 190
Glu Asp Thr Val Ser Ala Thr Arg Lys Leu Lys Asn Thr Phe Leu Lys
        195                 200                 205
Gln Tyr Gln Thr Lys Gly Val Ile Phe Asp Ile Asp Gly Thr Leu Leu
    210                 215                 220
Glu Thr Met Asn Ile Trp Asp Asn Val Leu Leu Asn Leu Met Asn Thr
225                 230                 235                 240
Leu Asn Ile Ser Tyr Thr Glu Asp Glu Ile Gln Lys Ile Trp Asn Met
                245                 250                 255
Gly Phe Ala Glu Leu Ala Gln Phe Ser Ile Lys Lys Phe Lys Leu Asp
            260                 265                 270
Met Ser Val Lys Glu Phe Trp Gln Leu Ile Lys Lys Leu Ser Val Glu
        275                 280                 285
Glu Tyr Lys Asn Ser Lys Ile His Leu Lys Lys Gly Ala Lys Lys Leu
    290                 295                 300
Leu Glu Tyr Leu Lys Glu Lys Gly Val Lys Leu Ala Ile Ala Thr Ala
305                 310                 315                 320
Leu Cys Lys Glu Gln Tyr Glu Ile Val Leu Thr Lys Thr Gly Ile Ile
                325                 330                 335
Asp Tyr Phe Asp Ile Ile Ala Ser Ser Val Asp Leu Lys Met Glu Lys
            340                 345                 350
Ser Asp Arg Gln Ile Phe Asp Tyr Ile Ala Lys Asn Leu Gln Val Pro
        355                 360                 365
Asn Lys Asn Leu Ile Phe Phe Glu Asp Asp Ile Asn Ser Ser Thr Gly
    370                 375                 380
Ala Lys Leu Ala Gly Leu Lys Leu Cys Ile Val Ser Asn Lys Lys Tyr
385                 390                 395                 400
```

```
Asn Gly Asn Ser Lys Phe Asp Ala Leu Ile Asp Tyr Lys Ile Asp Asp
                405                 410                 415

Phe Glu Asn Lys Leu Ile Tyr Asp Glu Ile Ile Val Glu Lys Asn
        420                 425                 430

<210> SEQ ID NO 55
<211> LENGTH: 1296
<212> TYPE: DNA
<213> ORGANISM: Unknown
<220> FEATURE:
<223> OTHER INFORMATION: Description of Unknown:
      Peptostreptococcaceae bacterium sequence
<220> FEATURE:
<221> NAME/KEY: CDS
<222> LOCATION: (1)..(1293)
<223> OTHER INFORMATION: Peptostreptococcaceae bacterium CM2 gene
      encoding TMP phosphatase[WP_009527854]

<400> SEQUENCE: 55
```

| | | | | | | | | | | | | | | | | |
|---|---|---|---|---|---|---|---|---|---|---|---|---|---|---|---|---|
| atg | aaa | aat | att | gac | tat | aca | atg | tat | tac | gtc | acc | gat | gaa | gac | ctt | 48 |
| Met | Lys | Asn | Ile | Asp | Tyr | Thr | Met | Tyr | Tyr | Val | Thr | Asp | Glu | Asp | Leu | |
| 1 | | | | 5 | | | | | 10 | | | | | 15 | | |
| ttg | agc | agt | aat | cac | acc | ttg | gaa | aca | tct | gtg | caa | gat | gcc | att | tta | 96 |
| Leu | Ser | Ser | Asn | His | Thr | Leu | Glu | Thr | Ser | Val | Gln | Asp | Ala | Ile | Leu | |
| | | | 20 | | | | | 25 | | | | | 30 | | | |
| ggt | ggc | tgt | aca | atg | ata | cag | ctt | cga | gaa | aaa | cat | tca | tcc | act | ctc | 144 |
| Gly | Gly | Cys | Thr | Met | Ile | Gln | Leu | Arg | Glu | Lys | His | Ser | Ser | Thr | Leu | |
| | 35 | | | | | 40 | | | | | 45 | | | | | |
| gat | ttt | tat | aac | aaa | gcc | gta | aaa | att | aaa | gct | att | tgc | gac | aag | tac | 192 |
| Asp | Phe | Tyr | Asn | Lys | Ala | Val | Lys | Ile | Lys | Ala | Ile | Cys | Asp | Lys | Tyr | |
| 50 | | | | | 55 | | | | | 60 | | | | | | |
| aac | ata | cct | ctt | ata | ata | aat | gac | aga | ata | gac | gta | gct | ctt | gca | ata | 240 |
| Asn | Ile | Pro | Leu | Ile | Ile | Asn | Asp | Arg | Ile | Asp | Val | Ala | Leu | Ala | Ile | |
| 65 | | | | | 70 | | | | | 75 | | | | | 80 | |
| aat | gca | gac | gga | gta | cat | ctc | gga | caa | gac | gat | atg | cct | ctt | gat | att | 288 |
| Asn | Ala | Asp | Gly | Val | His | Leu | Gly | Gln | Asp | Asp | Met | Pro | Leu | Asp | Ile | |
| | | | 85 | | | | | 90 | | | | | 95 | | | |
| gca | aga | aaa | att | atg | gga | gat | ggc | aaa | att | ata | gga | ata | tca | acc | tca | 336 |
| Ala | Arg | Lys | Ile | Met | Gly | Asp | Gly | Lys | Ile | Ile | Gly | Ile | Ser | Thr | Ser | |
| | | 100 | | | | | 105 | | | | | 110 | | | | |
| act | tta | gat | gaa | gct | cta | atc | gct | caa | caa | ggc | ggt | gca | gat | tat | gta | 384 |
| Thr | Leu | Asp | Glu | Ala | Leu | Ile | Ala | Gln | Gln | Gly | Gly | Ala | Asp | Tyr | Val | |
| | | 115 | | | | | 120 | | | | | 125 | | | | |
| ggt | gta | ggt | gct | atg | tac | agc | aca | aac | aca | aaa | act | gat | gcc | aat | ttg | 432 |
| Gly | Val | Gly | Ala | Met | Tyr | Ser | Thr | Asn | Thr | Lys | Thr | Asp | Ala | Asn | Leu | |
| 130 | | | | | 135 | | | | | 140 | | | | | | |
| aca | act | ata | gac | gag | ctt | aca | aaa | ata | aaa | aac | aat | tta | aaa | ata | cct | 480 |
| Thr | Thr | Ile | Asp | Glu | Leu | Thr | Lys | Ile | Lys | Asn | Asn | Leu | Lys | Ile | Pro | |
| 145 | | | | | 150 | | | | | 155 | | | | | 160 | |
| gtt | gtt | gca | atc | ggc | ggt | ata | aac | ctt | gac | act | ata | ccc | gct | cta | aaa | 528 |
| Val | Val | Ala | Ile | Gly | Gly | Ile | Asn | Leu | Asp | Thr | Ile | Pro | Ala | Leu | Lys | |
| | | | 165 | | | | | 170 | | | | | 175 | | | |
| cct | gcg | caa | ata | gac | gga | gtt | gca | ata | gta | tcc | gct | ata | tct | atg | cag | 576 |
| Pro | Ala | Gln | Ile | Asp | Gly | Val | Ala | Ile | Val | Ser | Ala | Ile | Ser | Met | Gln | |
| | | | 180 | | | | | 185 | | | | | 190 | | | |
| gaa | gat | acc | gta | tct | gca | aca | aga | aaa | tta | aaa | aat | act | ttt | ttg | aaa | 624 |
| Glu | Asp | Thr | Val | Ser | Ala | Thr | Arg | Lys | Leu | Lys | Asn | Thr | Phe | Leu | Lys | |
| | | | 195 | | | | | 200 | | | | | 205 | | | |
| caa | tat | caa | act | aaa | ggc | gta | ata | ttc | gat | att | gac | ggt | act | ctg | ctt | 672 |
| Gln | Tyr | Gln | Thr | Lys | Gly | Val | Ile | Phe | Asp | Ile | Asp | Gly | Thr | Leu | Leu | |
| | | | 210 | | | | | 215 | | | | | 220 | | | |
| gaa | act | atg | aac | ata | tgg | gac | aat | gta | ctt | cta | aat | ctt | atg | aat | acg | 720 |

| | | | | | | | | | | | | | | |
|---|---|---|---|---|---|---|---|---|---|---|---|---|---|---|
| Glu | Thr | Met | Asn | Ile | Trp | Asp | Asn | Val | Leu | Leu | Asn | Leu | Met | Asn | Thr |
| 225 | | | | 230 | | | | | 235 | | | | 240 | | |

| | | | | | | | | | | | | | | | |
|---|---|---|---|---|---|---|---|---|---|---|---|---|---|---|---|
| ctt | aat | atc | cgc | tat | acc | gaa | gat | gaa | ata | caa | aag | ata | tgg | aat | atg | 768 |
| Leu | Asn | Ile | Arg | Tyr | Thr | Glu | Asp | Glu | Ile | Gln | Lys | Ile | Trp | Asn | Met |
| | | | 245 | | | | | 250 | | | | | 255 | | |

| | | | | | | | | | | | | | | | |
|---|---|---|---|---|---|---|---|---|---|---|---|---|---|---|---|
| ggt | ttt | gca | gag | ctt | gca | cag | ttc | agc | ata | aaa | aaa | ttc | aag | ctt | gat | 816 |
| Gly | Phe | Ala | Glu | Leu | Ala | Gln | Phe | Ser | Ile | Lys | Lys | Phe | Lys | Leu | Asp |
| | | | 260 | | | | | 265 | | | | | 270 | | |

| | | | | | | | | | | | | | | | |
|---|---|---|---|---|---|---|---|---|---|---|---|---|---|---|---|
| atg | agt | gta | aaa | gaa | ttt | tgg | caa | ctt | ata | aaa | aaa | tta | tca | gtc | gaa | 864 |
| Met | Ser | Val | Lys | Glu | Phe | Trp | Gln | Leu | Ile | Lys | Lys | Leu | Ser | Val | Glu |
| | | 275 | | | | | 280 | | | | | 285 | | | |

| | | | | | | | | | | | | | | | |
|---|---|---|---|---|---|---|---|---|---|---|---|---|---|---|---|
| gag | tat | aaa | aat | agc | aaa | ata | cac | tta | aaa | aaa | ggt | gca | aaa | aaa | ctg | 912 |
| Glu | Tyr | Lys | Asn | Ser | Lys | Ile | His | Leu | Lys | Lys | Gly | Ala | Lys | Lys | Leu |
| | | 290 | | | | | 295 | | | | | 300 | | | |

| | | | | | | | | | | | | | | | |
|---|---|---|---|---|---|---|---|---|---|---|---|---|---|---|---|
| ctt | gag | tat | ctc | aaa | gaa | aaa | ggt | gta | aaa | tta | gcc | ata | gca | act | gcc | 960 |
| Leu | Glu | Tyr | Leu | Lys | Glu | Lys | Gly | Val | Lys | Leu | Ala | Ile | Ala | Thr | Ala |
| 305 | | | | 310 | | | | | 315 | | | | | 320 | |

| | | | | | | | | | | | | | | | |
|---|---|---|---|---|---|---|---|---|---|---|---|---|---|---|---|
| ctt | tgc | aaa | gaa | cag | tat | gaa | ata | gtg | ctt | aca | aag | aca | ggt | atc | ata | 1008 |
| Leu | Cys | Lys | Glu | Gln | Tyr | Glu | Ile | Val | Leu | Thr | Lys | Thr | Gly | Ile | Ile |
| | | | 325 | | | | | 330 | | | | | 335 | | |

| | | | | | | | | | | | | | | | |
|---|---|---|---|---|---|---|---|---|---|---|---|---|---|---|---|
| gac | tat | ttt | gac | ata | ata | gca | tca | agc | gta | gat | tta | aaa | atg | gaa | aaa | 1056 |
| Asp | Tyr | Phe | Asp | Ile | Ile | Ala | Ser | Ser | Val | Asp | Leu | Lys | Met | Glu | Lys |
| | | | 340 | | | | | 345 | | | | | 350 | | |

| | | | | | | | | | | | | | | | |
|---|---|---|---|---|---|---|---|---|---|---|---|---|---|---|---|
| tca | gat | aga | caa | ata | ttt | gac | tat | ata | gca | aaa | aat | cta | caa | gtt | cca | 1104 |
| Ser | Asp | Arg | Gln | Ile | Phe | Asp | Tyr | Ile | Ala | Lys | Asn | Leu | Gln | Val | Pro |
| | | 355 | | | | | 360 | | | | | 365 | | | |

| | | | | | | | | | | | | | | | |
|---|---|---|---|---|---|---|---|---|---|---|---|---|---|---|---|
| aac | aaa | aat | ttt | att | ttc | ttt | gaa | gac | gac | ata | aac | tcg | tca | aca | ggt | 1152 |
| Asn | Lys | Asn | Phe | Ile | Phe | Phe | Glu | Asp | Asp | Ile | Asn | Ser | Ser | Thr | Gly |
| | 370 | | | | | 375 | | | | | 380 | | | | |

| | | | | | | | | | | | | | | | |
|---|---|---|---|---|---|---|---|---|---|---|---|---|---|---|---|
| gca | aaa | cgt | gca | gga | gta | aaa | ctg | tgc | att | gta | tca | aac | aag | aaa | tat | 1200 |
| Ala | Lys | Arg | Ala | Gly | Val | Lys | Leu | Cys | Ile | Val | Ser | Asn | Lys | Lys | Tyr |
| 385 | | | | 390 | | | | | 395 | | | | | 400 | |

| | | | | | | | | | | | | | | | |
|---|---|---|---|---|---|---|---|---|---|---|---|---|---|---|---|
| aat | ggt | aac | agc | aaa | ttt | gac | gct | ctc | ata | gat | tat | aaa | ata | gat | gat | 1248 |
| Asn | Gly | Asn | Ser | Lys | Phe | Asp | Ala | Leu | Ile | Asp | Tyr | Lys | Ile | Asp | Asp |
| | | | 405 | | | | | 410 | | | | | 415 | | |

| | | | | | | | | | | | | | | |
|---|---|---|---|---|---|---|---|---|---|---|---|---|---|---|
| ttt | gaa | aat | aaa | ttg | ata | tat | gat | gaa | ata | ata | gtg | gag | aaa | aat | tag | 1296 |
| Phe | Glu | Asn | Lys | Leu | Ile | Tyr | Asp | Glu | Ile | Ile | Val | Glu | Lys | Asn | |
| | | | 420 | | | | | 425 | | | | | 430 | | |

<210> SEQ ID NO 56
<211> LENGTH: 431
<212> TYPE: PRT
<213> ORGANISM: Unknown
<220> FEATURE:
<223> OTHER INFORMATION: Description of Unknown:
      Peptostreptococcaceae bacterium sequence

<400> SEQUENCE: 56

| | | | | | | | | | | | |
|---|---|---|---|---|---|---|---|---|---|---|---|
| Met | Lys | Asn | Ile | Asp | Tyr | Thr | Met | Tyr | Tyr | Val | Thr | Asp | Glu | Asp | Leu |
| 1 | | | | 5 | | | | | 10 | | | | | 15 | |

| | | | | | | | | | | | |
|---|---|---|---|---|---|---|---|---|---|---|---|
| Leu | Ser | Ser | Asn | His | Thr | Leu | Glu | Thr | Ser | Val | Gln | Asp | Ala | Ile | Leu |
| | | | 20 | | | | | 25 | | | | | 30 | | |

| | | | | | | | | | | | |
|---|---|---|---|---|---|---|---|---|---|---|---|
| Gly | Gly | Cys | Thr | Met | Ile | Gln | Leu | Arg | Glu | Lys | His | Ser | Ser | Thr | Leu |
| | | 35 | | | | | 40 | | | | | 45 | | | |

| | | | | | | | | | | | |
|---|---|---|---|---|---|---|---|---|---|---|---|
| Asp | Phe | Tyr | Asn | Lys | Ala | Val | Lys | Ile | Lys | Ala | Ile | Cys | Asp | Lys | Tyr |
| | 50 | | | | | 55 | | | | | 60 | | | | |

| | | | | | | | | | | | |
|---|---|---|---|---|---|---|---|---|---|---|---|
| Asn | Ile | Pro | Leu | Ile | Ile | Asn | Asp | Arg | Ile | Asp | Val | Ala | Leu | Ala | Ile |
| 65 | | | | 70 | | | | | 75 | | | | | 80 | |

| | | | | | | | | | | | |
|---|---|---|---|---|---|---|---|---|---|---|---|
| Asn | Ala | Asp | Gly | Val | His | Leu | Gly | Gln | Asp | Asp | Met | Pro | Leu | Asp | Ile |
| | | | 85 | | | | | 90 | | | | | 95 | | |

```
Ala Arg Lys Ile Met Gly Asp Gly Lys Ile Gly Ile Ser Thr Ser
            100                 105                 110

Thr Leu Asp Glu Ala Leu Ile Ala Gln Gln Gly Gly Ala Asp Tyr Val
        115                 120                 125

Gly Val Gly Ala Met Tyr Ser Thr Asn Thr Lys Thr Asp Ala Asn Leu
    130                 135                 140

Thr Thr Ile Asp Glu Leu Thr Lys Ile Lys Asn Asn Leu Lys Ile Pro
145                 150                 155                 160

Val Val Ala Ile Gly Gly Ile Asn Leu Asp Thr Ile Pro Ala Leu Lys
                165                 170                 175

Pro Ala Gln Ile Asp Gly Val Ala Ile Val Ser Ala Ile Ser Met Gln
            180                 185                 190

Glu Asp Thr Val Ser Ala Thr Arg Lys Leu Lys Asn Thr Phe Leu Lys
        195                 200                 205

Gln Tyr Gln Thr Lys Gly Val Ile Phe Asp Ile Asp Gly Thr Leu Leu
    210                 215                 220

Glu Thr Met Asn Ile Trp Asp Asn Val Leu Leu Asn Leu Met Asn Thr
225                 230                 235                 240

Leu Asn Ile Arg Tyr Thr Glu Asp Glu Ile Gln Lys Ile Trp Asn Met
                245                 250                 255

Gly Phe Ala Glu Leu Ala Gln Phe Ser Ile Lys Lys Phe Lys Leu Asp
            260                 265                 270

Met Ser Val Lys Glu Phe Trp Gln Leu Ile Lys Lys Leu Ser Val Glu
        275                 280                 285

Glu Tyr Lys Asn Ser Lys Ile His Leu Lys Lys Gly Ala Lys Lys Leu
    290                 295                 300

Leu Glu Tyr Leu Lys Glu Lys Gly Val Lys Leu Ala Ile Ala Thr Ala
305                 310                 315                 320

Leu Cys Lys Glu Gln Tyr Glu Ile Val Leu Thr Lys Thr Gly Ile Ile
                325                 330                 335

Asp Tyr Phe Asp Ile Ile Ala Ser Ser Val Asp Leu Lys Met Glu Lys
            340                 345                 350

Ser Asp Arg Gln Ile Phe Asp Tyr Ile Ala Lys Asn Leu Gln Val Pro
        355                 360                 365

Asn Lys Asn Phe Ile Phe Phe Glu Asp Asp Ile Asn Ser Ser Thr Gly
    370                 375                 380

Ala Lys Arg Ala Gly Val Lys Leu Cys Ile Val Ser Asn Lys Lys Tyr
385                 390                 395                 400

Asn Gly Asn Ser Lys Phe Asp Ala Leu Ile Asp Tyr Lys Ile Asp Asp
                405                 410                 415

Phe Glu Asn Lys Leu Ile Tyr Asp Glu Ile Ile Val Glu Lys Asn
            420                 425                 430

<210> SEQ ID NO 57
<211> LENGTH: 1365
<212> TYPE: DNA
<213> ORGANISM: Atopobium sp.
<220> FEATURE:
<221> NAME/KEY: CDS
<222> LOCATION: (1)..(1362)
<223> OTHER INFORMATION: Atopobium sp. ICM42b gene encoding TMP
      phosphatase [WP_035427744]

<400> SEQUENCE: 57 atg cag gtg acc ggt gca att ttt gat tgc gat gga act ctt gtt gat    48
Met Gln Val Thr Gly Ala Ile Phe Asp Cys Asp Gly Thr Leu Val Asp
```

```
          1               5                  10                 15
     tca atg cgc gtt tgg cat aac gtt ttt ggc gct gtt ctt cct aaa tat     96
     Ser Met Arg Val Trp His Asn Val Phe Gly Ala Val Leu Pro Lys Tyr
                     20                  25                  30 ggc aag act att gat tcg gat att ttt gac cgc gta gag gct gtt tcc    144
     Gly Lys Thr Ile Asp Ser Asp Ile Phe Asp Arg Val Glu Ala Val Ser
                 35                  40                  45 ctc att ggt gga tgt cag att tgc gtt gat gaa ctg gat ttg cct att    192
     Leu Ile Gly Gly Cys Gln Ile Cys Val Asp Glu Leu Asp Leu Pro Ile
     50                  55                  60 aca gcg gaa gct ttg tat gaa gag ttc tgc gcg tac gta att gat cag    240
     Thr Ala Glu Ala Leu Tyr Glu Glu Phe Cys Ala Tyr Val Ile Asp Gln
     65                  70                  75                  80 tac caa cat cat gtt tca atc att ccc ggt gca aag gag ttc tta cag    288
     Tyr Gln His His Val Ser Ile Ile Pro Gly Ala Lys Glu Phe Leu Gln
                         85                  90                  95 gag ctc tac gat gca ggt att cct atg gcc gtt gct tcg tca act ccc    336
     Glu Leu Tyr Asp Ala Gly Ile Pro Met Ala Val Ala Ser Ser Thr Pro
                     100                 105                 110 gtg cga gaa gtt cgt gca gct ctg gca gct caa ggt att gag cac ctc    384
     Val Arg Glu Val Arg Ala Ala Leu Ala Ala Gln Gly Ile Glu His Leu
                 115                 120                 125 ttc aaa aca gtg gtc tca aca gaa gat gtg ggg gga gtg gac aag gtt    432
     Phe Lys Thr Val Val Ser Thr Glu Asp Val Gly Gly Val Asp Lys Val
             130                 135                 140 gag cct gat gtt tat ctt gag gct ctt cgc cgt ctt ggc acc gat aag    480
     Glu Pro Asp Val Tyr Leu Glu Ala Leu Arg Arg Leu Gly Thr Asp Lys
     145                 150                 155                 160 gca act acc tgg gtc ttc gag gat gcc ccg ttt ggc gca cag aca gca    528
     Ala Thr Thr Trp Val Phe Glu Asp Ala Pro Phe Gly Ala Gln Thr Ala
                         165                 170                 175 caa aat gcg ggc ttt cct gtg gta gcg ctc tac aat gat cat gac ggc    576
     Gln Asn Ala Gly Phe Pro Val Val Ala Leu Tyr Asn Asp His Asp Gly
                     180                 185                 190 cgc gac ccc gtc ttt atg cgc gag cac tct aac atc ttt gcc cac acc    624
     Arg Asp Pro Val Phe Met Arg Glu His Ser Asn Ile Phe Ala His Thr
                 195                 200                 205 tac ggc gag ctg tcg ctt ctg cgc ctt cag gac tac gag cgc cct ctg    672
     Tyr Gly Glu Leu Ser Leu Leu Arg Leu Gln Asp Tyr Glu Arg Pro Leu
             210                 215                 220 acc gca gcg cct tct ggc gag aaa ccc ctt gag gtc ctt gtt gtg ggc    720
     Thr Ala Ala Pro Ser Gly Glu Lys Pro Leu Glu Val Leu Val Val Gly
     225                 230                 235                 240 gga tcc cca gag gcg gtt tca cac acg acg ctg tct acc tgc gcc caa    768
     Gly Ser Pro Glu Ala Val Ser His Thr Thr Leu Ser Thr Cys Ala Gln
                         245                 250                 255 agc gct gac tac ctg ata gcg gtt gac cat ggt gca gat gca tgt cac    816
     Ser Ala Asp Tyr Leu Ile Ala Val Asp His Gly Ala Asp Ala Cys His
                     260                 265                 270 gct gcc ggc gtg att cca cag ctt gcg ctt gga gac ttt gac tcg gct    864
     Ala Ala Gly Val Ile Pro Gln Leu Ala Leu Gly Asp Phe Asp Ser Ala
                 275                 280                 285 aca cca gaa act ctg gct tgg ctc aaa gag cag cag gta cct tgc atg    912
     Thr Pro Glu Thr Leu Ala Trp Leu Lys Glu Gln Gln Val Pro Cys Met
             290                 295                 300 aag ttt aat gcg gac aag tac gat acc gac ctg gct ctt gct tta aag    960
     Lys Phe Asn Ala Asp Lys Tyr Asp Thr Asp Leu Ala Leu Ala Leu Lys
     305                 310                 315                 320 tcc gcc gag tac gag gct att cgt aga gat agc aag ctc tct ctt acg   1008
```

```
                Ser Ala Glu Tyr Glu Ala Ile Arg Arg Asp Ser Lys Leu Ser Leu Thr
                                325                 330                 335 gtt gtc tcc aca tct ggc gga cac ctt gat cac cag ctt gta gtg ctt        1056
Val Val Ser Thr Ser Gly Gly His Leu Asp His Gln Leu Val Val Leu
            340                 345                 350 ggt ctt ctc gcc acg tgg gca aag acg ggc aag gca agt gtt cga gtt        1104
Gly Leu Leu Ala Thr Trp Ala Lys Thr Gly Lys Ala Ser Val Arg Val
            355                 360                 365 att gaa aat gac ttt gag atg cgc ttt tta act gca ggc cag gtt gat        1152
Ile Glu Asn Asp Phe Glu Met Arg Phe Leu Thr Ala Gly Gln Val Asp
        370                 375                 380 tct tgg cag ctg agc gca act gat gta ggt aaa aag atg tcc ctt gtg        1200
Ser Trp Gln Leu Ser Ala Thr Asp Val Gly Lys Lys Met Ser Leu Val
385                 390                 395                 400 gct ttg tca gag gag tgc gag gtt tct gag gcc ggc atg aag tgg aat        1248
Ala Leu Ser Glu Glu Cys Glu Val Ser Glu Ala Gly Met Lys Trp Asn
                405                 410                 415 ctt gat cac cag aag ttc acc ttg ctg gga gac gac ggt att tca aat        1296
Leu Asp His Gln Lys Phe Thr Leu Leu Gly Asp Asp Gly Ile Ser Asn
            420                 425                 430 atc gtc gaa tca gac aat tcc tgg gta agg tgc gag aag ggc tgt ctt        1344
Ile Val Glu Ser Asp Asn Ser Trp Val Arg Cys Glu Lys Gly Cys Leu
        435                 440                 445 ttg gtg cag ctt tgg aac taa                                            1365
Leu Val Gln Leu Trp Asn
    450

<210> SEQ ID NO 58
<211> LENGTH: 454
<212> TYPE: PRT
<213> ORGANISM: Atopobium sp.

<400> SEQUENCE: 58

Met Gln Val Thr Gly Ala Ile Phe Asp Cys Asp Gly Thr Leu Val Asp
1               5                   10                  15

Ser Met Arg Val Trp His Asn Val Phe Gly Ala Val Leu Pro Lys Tyr
            20                  25                  30

Gly Lys Thr Ile Asp Ser Asp Ile Phe Asp Arg Val Glu Ala Val Ser
        35                  40                  45

Leu Ile Gly Gly Cys Gln Ile Cys Val Asp Glu Leu Asp Leu Pro Ile
    50                  55                  60

Thr Ala Glu Ala Leu Tyr Glu Glu Phe Cys Ala Tyr Val Ile Asp Gln
65                  70                  75                  80

Tyr Gln His His Val Ser Ile Ile Pro Gly Ala Lys Glu Phe Leu Gln
                85                  90                  95

Glu Leu Tyr Asp Ala Gly Ile Pro Met Ala Val Ala Ser Ser Thr Pro
            100                 105                 110

Val Arg Glu Val Arg Ala Ala Leu Ala Ala Gln Gly Ile Glu His Leu
        115                 120                 125

Phe Lys Thr Val Val Ser Thr Glu Asp Val Gly Val Asp Lys Val
    130                 135                 140

Glu Pro Asp Val Tyr Leu Glu Ala Leu Arg Arg Leu Gly Thr Asp Lys
145                 150                 155                 160

Ala Thr Thr Trp Val Phe Glu Asp Ala Pro Phe Gly Ala Gln Thr Ala
                165                 170                 175

Gln Asn Ala Gly Phe Pro Val Val Ala Leu Tyr Asn Asp His Asp Gly
            180                 185                 190
```

```
Arg Asp Pro Val Phe Met Arg Glu His Ser Asn Ile Phe Ala His Thr
            195                 200                 205

Tyr Gly Glu Leu Ser Leu Leu Arg Leu Gln Asp Tyr Glu Arg Pro Leu
    210                 215                 220

Thr Ala Ala Pro Ser Gly Glu Lys Pro Leu Glu Val Leu Val Gly
225                 230                 235                 240

Gly Ser Pro Glu Ala Val Ser His Thr Thr Leu Ser Thr Cys Ala Gln
                245                 250                 255

Ser Ala Asp Tyr Leu Ile Ala Val Asp His Gly Ala Asp Ala Cys His
            260                 265                 270

Ala Ala Gly Val Ile Pro Gln Leu Ala Leu Gly Asp Phe Asp Ser Ala
        275                 280                 285

Thr Pro Glu Thr Leu Ala Trp Leu Lys Glu Gln Gln Val Pro Cys Met
290                 295                 300

Lys Phe Asn Ala Asp Lys Tyr Asp Thr Asp Leu Ala Leu Ala Leu Lys
305                 310                 315                 320

Ser Ala Glu Tyr Glu Ala Ile Arg Arg Asp Ser Lys Leu Ser Leu Thr
                325                 330                 335

Val Val Ser Thr Ser Gly Gly His Leu Asp His Gln Leu Val Val Leu
            340                 345                 350

Gly Leu Leu Ala Thr Trp Ala Lys Thr Gly Lys Ala Ser Val Arg Val
        355                 360                 365

Ile Glu Asn Asp Phe Glu Met Arg Phe Leu Thr Ala Gly Gln Val Asp
    370                 375                 380

Ser Trp Gln Leu Ser Ala Thr Asp Val Gly Lys Lys Met Ser Leu Val
385                 390                 395                 400

Ala Leu Ser Glu Glu Cys Glu Val Ser Glu Ala Gly Met Lys Trp Asn
                405                 410                 415

Leu Asp His Gln Lys Phe Thr Leu Leu Gly Asp Gly Ile Ser Asn
            420                 425                 430

Ile Val Glu Ser Asp Asn Ser Trp Val Arg Cys Glu Lys Gly Cys Leu
        435                 440                 445

Leu Val Gln Leu Trp Asn
    450

<210> SEQ ID NO 59
<211> LENGTH: 1365
<212> TYPE: DNA
<213> ORGANISM: Atopobium parvulum
<220> FEATURE:
<221> NAME/KEY: CDS
<222> LOCATION: (1)..(1362)
<223> OTHER INFORMATION: Atopobium parvulum gene encoding TMP
      phosphatase [WP_035433109]

<400> SEQUENCE: 59 atg cag gtg acc ggt gca att ttt gat tgc gat gga act ctt gtt gat      48
Met Gln Val Thr Gly Ala Ile Phe Asp Cys Asp Gly Thr Leu Val Asp
1               5                   10                  15 tca atg cac gtt tgg cac aac gtt ttt ggc gct gtt ctt cct aaa tac      96
Ser Met His Val Trp His Asn Val Phe Gly Ala Val Leu Pro Lys Tyr
            20                  25                  30 ggc aag act att gat tcg gat att ttt gac cgc gta gag gct gtt tcc     144
Gly Lys Thr Ile Asp Ser Asp Ile Phe Asp Arg Val Glu Ala Val Ser
        35                  40                  45 ctc att ggt gga tgt cag att tgc gtt gat gag ctg gat ttg cct att     192
Leu Ile Gly Gly Cys Gln Ile Cys Val Asp Glu Leu Asp Leu Pro Ile
    50                  55                  60
```

```
aca gcg gaa gct tta tat gaa gag ttc tgc gcg tac gta act gat cag    240
Thr Ala Glu Ala Leu Tyr Glu Glu Phe Cys Ala Tyr Val Thr Asp Gln
 65                  70                  75                  80 tac cga cat cat gtt tca atc att ccc ggt gca aag gag ttc tta cag    288
Tyr Arg His His Val Ser Ile Ile Pro Gly Ala Lys Glu Phe Leu Gln
                     85                  90                  95 gaa ctc cac gac gca ggc att cct atg gcc gtt gct tcg tca act ccc    336
Glu Leu His Asp Ala Gly Ile Pro Met Ala Val Ala Ser Ser Thr Pro
                100                 105                 110 gtg cga gaa gtt cgt gca gct ctg gca gct caa ggt att gag cac ctc    384
Val Arg Glu Val Arg Ala Ala Leu Ala Ala Gln Gly Ile Glu His Leu
                115                 120                 125 ttt aaa aca gtg gtc tca acg gaa gat gtg ggg gga gtg gac aag gtt    432
Phe Lys Thr Val Val Ser Thr Glu Asp Val Gly Gly Val Asp Lys Val
130                 135                 140 gag cca gat gtt tac ctt gag gct ctt cgc cgt ctt ggc act gat aag    480
Glu Pro Asp Val Tyr Leu Glu Ala Leu Arg Arg Leu Gly Thr Asp Lys
145                 150                 155                 160 gca act acc tgg gtc ttc gag gat gct ccg ttt ggc gca cag aca gca    528
Ala Thr Thr Trp Val Phe Glu Asp Ala Pro Phe Gly Ala Gln Thr Ala
                165                 170                 175 caa aat gca ggc ttt cct gtg gct gta ctc tac aac gac cac gat ggc    576
Gln Asn Ala Gly Phe Pro Val Ala Val Leu Tyr Asn Asp His Asp Gly
                180                 185                 190 cgc gac ccc gtc ttt atg cgc gag cac tct aac atc ttt gcc cac acc    624
Arg Asp Pro Val Phe Met Arg Glu His Ser Asn Ile Phe Ala His Thr
                195                 200                 205 tac ggc gag ctg tcg ctt ctg cgc ctt cag gac tac gag cgc cct ctg    672
Tyr Gly Glu Leu Ser Leu Leu Arg Leu Gln Asp Tyr Glu Arg Pro Leu
                210                 215                 220 acc gca gcg cct tct ggc gag aaa ccc ctt gag gtc ctt gtt gtg ggc    720
Thr Ala Ala Pro Ser Gly Glu Lys Pro Leu Glu Val Leu Val Val Gly
225                 230                 235                 240 gga tcc cca gag gcg gtt tcg cac acg acg ctg tct acc tgc gcc caa    768
Gly Ser Pro Glu Ala Val Ser His Thr Thr Leu Ser Thr Cys Ala Gln
                245                 250                 255 agc gct gac tac ctg ata gcg gtt gac cat ggc gca gat gtc tgt cac    816
Ser Ala Asp Tyr Leu Ile Ala Val Asp His Gly Ala Asp Val Cys His
                260                 265                 270 gct gcc ggc gtg att cca caa ctt gcg ctt gga gac ttt gac tcc gct    864
Ala Ala Gly Val Ile Pro Gln Leu Ala Leu Gly Asp Phe Asp Ser Ala
                275                 280                 285 aca cca gaa act ctg gct tgg ctc aaa gag cag cag gta cct tgc atg    912
Thr Pro Glu Thr Leu Ala Trp Leu Lys Glu Gln Gln Val Pro Cys Met
                290                 295                 300 aag ttt aat gcg gac aag tac gat acc gac ctg gcg cta gca ttg aaa    960
Lys Phe Asn Ala Asp Lys Tyr Asp Thr Asp Leu Ala Leu Ala Leu Lys
305                 310                 315                 320 tca gct gaa tat gag gca att cgt aga gat agc aag ctc tct ctg acg   1008
Ser Ala Glu Tyr Glu Ala Ile Arg Arg Asp Ser Lys Leu Ser Leu Thr
                325                 330                 335 gtt gtc tcc aca tct ggc ggc cac ctt gat cac cag ctt gta gtg ctt   1056
Val Val Ser Thr Ser Gly Gly His Leu Asp His Gln Leu Val Val Leu
                340                 345                 350 ggt ctt ctc gcc acg tgg gca aag acg ggc aag gca agc gtt cga gtt   1104
Gly Leu Leu Ala Thr Trp Ala Lys Thr Gly Lys Ala Ser Val Arg Val
                355                 360                 365 att gag aat gac ttt gag atg cgc ttt tta gtt gct ggc cag gtg gat   1152
Ile Glu Asn Asp Phe Glu Met Arg Phe Leu Val Ala Gly Gln Val Asp
```

```
                370                 375                 380
tct tgg cag ctg aac act atc aat gta ggt aaa aag att tct ctt gta     1200
Ser Trp Gln Leu Asn Thr Ile Asn Val Gly Lys Lys Ile Ser Leu Val
385                 390                 395                 400 gct ttg tca gag gag tgc gag gtt tct gag gcc ggc atg aag tgg aat     1248
Ala Leu Ser Glu Glu Cys Glu Val Ser Glu Ala Gly Met Lys Trp Asn
                405                 410                 415 ctt gat cac cag aag ttc acc ttg ctg gga gac gac ggt att tca aac     1296
Leu Asp His Gln Lys Phe Thr Leu Leu Gly Asp Asp Gly Ile Ser Asn
            420                 425                 430 ata gtt gaa tca gac aat tcc tgg gta agg tgc gag aag ggc tgt ctt     1344
Ile Val Glu Ser Asp Asn Ser Trp Val Arg Cys Glu Lys Gly Cys Leu
        435                 440                 445 ttg gtg cag ctt tgg aac taa                                         1365
Leu Val Gln Leu Trp Asn
    450
```

<210> SEQ ID NO 60
<211> LENGTH: 454
<212> TYPE: PRT
<213> ORGANISM: Atopobium parvulum

<400> SEQUENCE: 60

```
Met Gln Val Thr Gly Ala Ile Phe Asp Cys Asp Gly Thr Leu Val Asp
1               5                   10                  15

Ser Met His Val Trp His Asn Val Phe Gly Ala Val Leu Pro Lys Tyr
            20                  25                  30

Gly Lys Thr Ile Asp Ser Asp Ile Phe Asp Arg Val Glu Ala Val Ser
        35                  40                  45

Leu Ile Gly Gly Cys Gln Ile Cys Val Asp Glu Leu Asp Leu Pro Ile
    50                  55                  60

Thr Ala Glu Ala Leu Tyr Glu Glu Phe Cys Ala Tyr Val Thr Asp Gln
65                  70                  75                  80

Tyr Arg His His Val Ser Ile Ile Pro Gly Ala Lys Glu Phe Leu Gln
                85                  90                  95

Glu Leu His Asp Ala Gly Ile Pro Met Ala Val Ala Ser Ser Thr Pro
            100                 105                 110

Val Arg Glu Val Arg Ala Ala Leu Ala Ala Gln Gly Ile Glu His Leu
        115                 120                 125

Phe Lys Thr Val Val Ser Thr Glu Asp Val Gly Gly Val Asp Lys Val
    130                 135                 140

Glu Pro Asp Val Tyr Leu Glu Ala Leu Arg Arg Leu Gly Thr Asp Lys
145                 150                 155                 160

Ala Thr Thr Trp Val Phe Glu Asp Ala Pro Phe Gly Ala Gln Thr Ala
                165                 170                 175

Gln Asn Ala Gly Phe Pro Val Ala Val Leu Tyr Asn Asp His Asp Gly
            180                 185                 190

Arg Asp Pro Val Phe Met Arg Glu His Ser Asn Ile Phe Ala His Thr
        195                 200                 205

Tyr Gly Glu Leu Ser Leu Leu Arg Leu Gln Asp Tyr Glu Arg Pro Leu
    210                 215                 220

Thr Ala Ala Pro Ser Gly Glu Lys Pro Leu Glu Val Leu Val Val Gly
225                 230                 235                 240

Gly Ser Pro Glu Ala Val Ser His Thr Thr Leu Ser Thr Cys Ala Gln
                245                 250                 255

Ser Ala Asp Tyr Leu Ile Ala Val Asp His Gly Ala Asp Val Cys His
```

```
                    260                 265                 270
Ala Ala Gly Val Ile Pro Gln Leu Ala Leu Gly Asp Phe Asp Ser Ala
            275                 280                 285

Thr Pro Glu Thr Leu Ala Trp Leu Lys Glu Gln Gln Val Pro Cys Met
        290                 295                 300

Lys Phe Asn Ala Asp Lys Tyr Asp Thr Asp Leu Ala Leu Ala Leu Lys
305                 310                 315                 320

Ser Ala Glu Tyr Glu Ala Ile Arg Arg Asp Ser Lys Leu Ser Leu Thr
                325                 330                 335

Val Val Ser Thr Ser Gly Gly His Leu Asp His Gln Leu Val Val Leu
            340                 345                 350

Gly Leu Leu Ala Thr Trp Ala Lys Thr Gly Lys Ala Ser Val Arg Val
        355                 360                 365

Ile Glu Asn Asp Phe Glu Met Arg Phe Leu Val Ala Gly Gln Val Asp
370                 375                 380

Ser Trp Gln Leu Asn Thr Ile Asn Val Gly Lys Lys Ile Ser Leu Val
385                 390                 395                 400

Ala Leu Ser Glu Glu Cys Glu Val Ser Glu Ala Gly Met Lys Trp Asn
                405                 410                 415

Leu Asp His Gln Lys Phe Thr Leu Leu Gly Asp Asp Gly Ile Ser Asn
            420                 425                 430

Ile Val Glu Ser Asp Asn Ser Trp Val Arg Cys Glu Lys Gly Cys Leu
        435                 440                 445

Leu Val Gln Leu Trp Asn
    450
```

<210> SEQ ID NO 61
<211> LENGTH: 1383
<212> TYPE: DNA
<213> ORGANISM: Atopobium rimae
<220> FEATURE:
<221> NAME/KEY: CDS
<222> LOCATION: (1)..(1380)
<223> OTHER INFORMATION: Atopobium rimae gene encoding TMP phosphatase
      [WP_003148415]

<400> SEQUENCE: 61

```
atg cag ata acg ggt gca atc ttt gat ctt gat ggg aca ctg gtt gac    48
Met Gln Ile Thr Gly Ala Ile Phe Asp Leu Asp Gly Thr Leu Val Asp
1               5                  10                  15 tcc atg tgg atg tgg aga aga tcg ttc gga gat gtt tta gaa gac ctg    96
Ser Met Trp Met Trp Arg Arg Ser Phe Gly Asp Val Leu Glu Asp Leu
                20                  25                  30 cat atc aat atg act ccg gat ttt ttt aaa agg gtc gag gcc att tcg   144
His Ile Asn Met Thr Pro Asp Phe Phe Lys Arg Val Glu Ala Ile Ser
            35                  40                  45 ctt tac gat ggt tgc gta gcg tgt att gag gaa ttt aat ctt cct tta   192
Leu Tyr Asp Gly Cys Val Ala Cys Ile Glu Glu Phe Asn Leu Pro Leu
        50                  55                  60 tcc gca gaa gag ctg tat gaa aag ttc ctt ttg tat gta caa acg gta   240
Ser Ala Glu Glu Leu Tyr Glu Lys Phe Leu Leu Tyr Val Gln Thr Val
65                  70                  75                  80 tat tcg cac gat att aaa agc att gcg ggg gct acc gac ttt ctc cag   288
Tyr Ser His Asp Ile Lys Ser Ile Ala Gly Ala Thr Asp Phe Leu Gln
                85                  90                  95 gaa ctt ttt gac gca gga ata cct ctt gcc att gct tct tct acg cca   336
Glu Leu Phe Asp Ala Gly Ile Pro Leu Ala Ile Ala Ser Ser Thr Pro
            100                 105                 110
```

|   |   |
|---|---|
| tct cgt gcc ata cat gtt gct ctt gaa gcc caa ggt atg gag aag ttt<br>Ser Arg Ala Ile His Val Ala Leu Glu Ala Gln Gly Met Glu Lys Phe<br>115                        120                      125 | 384 |
| ttt aaa gcg gtt gtg tgt acc gaa gac gtc ggg ggt gtc gat aaa gca<br>Phe Lys Ala Val Val Cys Thr Glu Asp Val Gly Gly Val Asp Lys Ala<br>130                        135                      140 | 432 |
| aaa ccc gat gtc tat ctt gag gct ctc aga cgc ctg ggc acc gat aaa<br>Lys Pro Asp Val Tyr Leu Glu Ala Leu Arg Arg Leu Gly Thr Asp Lys<br>145                      150                      155                      160 | 480 |
| gca cac acg tgg gtc ttt gag gac gct gag ttt ggt gta cat acg gca<br>Ala His Thr Trp Val Phe Glu Asp Ala Glu Phe Gly Val His Thr Ala<br>                      165                      170                      175 | 528 |
| caa acc gag ggc ttt ccc gtt gtt gcg ctg ttc aat ggc aaa gac ggc<br>Gln Thr Glu Gly Phe Pro Val Val Ala Leu Phe Asn Gly Lys Asp Gly<br>                      180                      185                      190 | 576 |
| cgt gat ctt gag tat atg aag gcg cac tct gat ctt ctc gca cat gat<br>Arg Asp Leu Glu Tyr Met Lys Ala His Ser Asp Leu Leu Ala His Asp<br>195                      200                      205 | 624 |
| tat cga gaa ctc tct ctt gcc cgc att tac gat tat gaa cgg gtg acg<br>Tyr Arg Glu Leu Ser Leu Ala Arg Ile Tyr Asp Tyr Glu Arg Val Thr<br>210                      215                      220 | 672 |
| aat cag cca cat ctg ggc gcc tca tcg gct cag aag gtc ttt tcg gtt<br>Asn Gln Pro His Leu Gly Ala Ser Ser Ala Gln Lys Val Phe Ser Val<br>225                      230                      235                      240 | 720 |
| ctc gtt gtt gat gga tct ccc acg cca agt tca gcc gcg ctg gtt tca<br>Leu Val Val Asp Gly Ser Pro Thr Pro Ser Ser Ala Ala Leu Val Ser<br>                      245                      250                      255 | 768 |
| gaa ctt tca tca tgc tcg gat tat gtc gtt gct gca gat cgc ggg gca<br>Glu Leu Ser Ser Cys Ser Asp Tyr Val Val Ala Ala Asp Arg Gly Ala<br>                      260                      265                      270 | 816 |
| tat atc tgc aag gag gcc ggt gtc gtt cct gat att gcg tgc gga gac<br>Tyr Ile Cys Lys Glu Ala Gly Val Val Pro Asp Ile Ala Cys Gly Asp<br>275                      280                      285 | 864 |
| ttt gat tcc gtg gga gaa gag aca ctc tct tgg atc cat gca caa aag<br>Phe Asp Ser Val Gly Glu Glu Thr Leu Ser Trp Ile His Ala Gln Lys<br>290                      295                      300 | 912 |
| gtg cac acg att gct tat cct caa gat aag tac gag acc gat ttg tct<br>Val His Thr Ile Ala Tyr Pro Gln Asp Lys Tyr Glu Thr Asp Leu Ser<br>305                      310                      315                      320 | 960 |
| ctt gca ctc aat gcc gct tgc cat gaa gca acc cgt caa gca ctt ccg<br>Leu Ala Leu Asn Ala Ala Cys His Glu Ala Thr Arg Gln Ala Leu Pro<br>                      325                      330                      335 | 1008 |
| ctg tca ctg aca ctt acc tgc gct tcc ggc ggc agg ctt gat cat gag<br>Leu Ser Leu Thr Leu Thr Cys Ala Ser Gly Gly Arg Leu Asp His Glu<br>                      340                      345                      350 | 1056 |
| ctt ggt gta gtg ggg ctt ctg gct cga tta agc act gcc tca tgg agg<br>Leu Gly Val Val Gly Leu Leu Ala Arg Leu Ser Thr Ala Ser Trp Arg<br>355                      360                      365 | 1104 |
| gtg cgg att gtt gag gat gcc ttt gaa gca agg att ctt tcg gca gat<br>Val Arg Ile Val Glu Asp Ala Phe Glu Ala Arg Ile Leu Ser Ala Asp<br>370                      375                      380 | 1152 |
| acg tat gcg gcg tgg agg ctc tca gaa aaa gat cga gga aag aca ctg<br>Thr Tyr Ala Ala Trp Arg Leu Ser Glu Lys Asp Arg Gly Lys Thr Leu<br>385                      390                      395                      400 | 1200 |
| tcg gtg ctt ccg ctt cag gaa gaa acg gtg att acc gag atc ggt atg<br>Ser Val Leu Pro Leu Gln Glu Glu Thr Val Ile Thr Glu Ile Gly Met<br>                      405                      410                      415 | 1248 |
| caa tgg gac ctt gcc tca cga act ttg ctg ctc ctg tct gat gaa gga<br>Gln Trp Asp Leu Ala Ser Arg Thr Leu Leu Leu Leu Ser Asp Glu Gly<br>                      420                      425                      430 | 1296 |

```
att tcc aat gtg gta caa acg gat gtg gca caa ata cat tgc gag aag    1344
Ile Ser Asn Val Val Gln Thr Asp Val Ala Gln Ile His Cys Glu Lys
        435                 440                 445 ggc aag gcg ctc gtg gtg ctt ctc gca aat gaa tcg tga                1383
Gly Lys Ala Leu Val Val Leu Leu Ala Asn Glu Ser
    450                 455                 460
```

<210> SEQ ID NO 62
<211> LENGTH: 460
<212> TYPE: PRT
<213> ORGANISM: Atopobium rimae

<400> SEQUENCE: 62

```
Met Gln Ile Thr Gly Ala Ile Phe Asp Leu Asp Gly Thr Leu Val Asp
1               5                   10                  15

Ser Met Trp Met Trp Arg Arg Ser Phe Gly Asp Val Leu Glu Asp Leu
                20                  25                  30

His Ile Asn Met Thr Pro Asp Phe Phe Lys Arg Val Glu Ala Ile Ser
            35                  40                  45

Leu Tyr Asp Gly Cys Val Ala Cys Ile Glu Glu Phe Asn Leu Pro Leu
        50                  55                  60

Ser Ala Glu Glu Leu Tyr Glu Lys Phe Leu Leu Tyr Val Gln Thr Val
65                  70                  75                  80

Tyr Ser His Asp Ile Lys Ser Ile Ala Gly Ala Thr Asp Phe Leu Gln
                85                  90                  95

Glu Leu Phe Asp Ala Gly Ile Pro Leu Ala Ile Ala Ser Ser Thr Pro
            100                 105                 110

Ser Arg Ala Ile His Val Ala Leu Glu Ala Gln Gly Met Glu Lys Phe
        115                 120                 125

Phe Lys Ala Val Val Cys Thr Glu Asp Val Gly Val Asp Lys Ala
130                 135                 140

Lys Pro Asp Val Tyr Leu Glu Ala Leu Arg Arg Leu Gly Thr Asp Lys
145                 150                 155                 160

Ala His Thr Trp Val Phe Glu Asp Ala Glu Phe Gly Val His Thr Ala
                165                 170                 175

Gln Thr Glu Gly Phe Pro Val Val Ala Leu Phe Asn Gly Lys Asp Gly
            180                 185                 190

Arg Asp Leu Glu Tyr Met Lys Ala His Ser Asp Leu Leu Ala His Asp
        195                 200                 205

Tyr Arg Glu Leu Ser Leu Ala Arg Ile Tyr Asp Tyr Glu Arg Val Thr
    210                 215                 220

Asn Gln Pro His Leu Gly Ala Ser Ala Gln Lys Val Phe Ser Val
225                 230                 235                 240

Leu Val Val Asp Gly Ser Pro Thr Pro Ser Ser Ala Ala Leu Val Ser
                245                 250                 255

Glu Leu Ser Ser Cys Ser Asp Tyr Val Val Ala Ala Asp Arg Gly Ala
            260                 265                 270

Tyr Ile Cys Lys Glu Ala Gly Val Pro Asp Ile Ala Cys Gly Asp
        275                 280                 285

Phe Asp Ser Val Gly Glu Glu Thr Leu Ser Trp Ile His Ala Gln Lys
    290                 295                 300

Val His Thr Ile Ala Tyr Pro Gln Asp Lys Tyr Glu Thr Asp Leu Ser
305                 310                 315                 320

Leu Ala Leu Asn Ala Ala Cys His Glu Ala Thr Arg Gln Ala Leu Pro
                325                 330                 335
```

```
Leu Ser Leu Thr Leu Thr Cys Ala Ser Gly Gly Arg Leu Asp His Glu
            340                 345                 350

Leu Gly Val Val Gly Leu Leu Ala Arg Leu Ser Thr Ala Ser Trp Arg
            355                 360                 365

Val Arg Ile Val Glu Asp Ala Phe Glu Ala Arg Ile Leu Ser Ala Asp
    370                 375                 380

Thr Tyr Ala Ala Trp Arg Leu Ser Glu Lys Asp Arg Gly Lys Thr Leu
385                 390                 395                 400

Ser Val Leu Pro Leu Gln Glu Thr Val Ile Thr Glu Ile Gly Met
                405                 410                 415

Gln Trp Asp Leu Ala Ser Arg Thr Leu Leu Leu Ser Asp Glu Gly
            420                 425                 430

Ile Ser Asn Val Val Gln Thr Asp Val Ala Gln Ile His Cys Glu Lys
            435                 440                 445

Gly Lys Ala Leu Val Val Leu Leu Ala Asn Glu Ser
450                 455                 460

<210> SEQ ID NO 63
<211> LENGTH: 1380
<212> TYPE: DNA
<213> ORGANISM: Olsenella uli
<220> FEATURE:
<221> NAME/KEY: CDS
<222> LOCATION: (1)..(1377)
<223> OTHER INFORMATION: Olsenella uli gene encoding TMP phosphatase
      [WP_013251930]

<400> SEQUENCE: 63 atg ccc atc aag gcc gcc atc ttc gac tgt gac gga acg ctg gtc gac      48
Met Pro Ile Lys Ala Ala Ile Phe Asp Cys Asp Gly Thr Leu Val Asp
1               5                  10                  15 tcc atg ccc ctg tgg cat gac gtg acg gtc gaa ctg ctg cgc cgc cac      96
Ser Met Pro Leu Trp His Asp Val Thr Val Glu Leu Leu Arg Arg His
                20                  25                  30 cat gtc gcc gac gcc gag gag gcg ttc gtc cgc acc gag tcg ctt ccc     144
His Val Ala Asp Ala Glu Glu Ala Phe Val Arg Thr Glu Ser Leu Pro
            35                  40                  45 atg gtc gag atg tgc cat gcc ttc cac gac gag tgg ggc gtt gag gcc     192
Met Val Glu Met Cys His Ala Phe His Asp Glu Trp Gly Val Glu Ala
        50                  55                  60 gag ggc gag gag ctg gtg cgc gag ctg gtc gat atg gtc cgc gag ggg     240
Glu Gly Glu Glu Leu Val Arg Glu Leu Val Asp Met Val Arg Glu Gly
65                  70                  75                  80 tat cgc agc cgg gtt agc ctg ctg ccg ggc tgc cgg gcg ttt ctg gac     288
Tyr Arg Ser Arg Val Ser Leu Leu Pro Gly Cys Arg Ala Phe Leu Asp
                85                  90                  95 gag ctg gcg tct gcg ggc gtc cgc atg gtc gtc gcg tcg tcg acg gct     336
Glu Leu Ala Ser Ala Gly Val Arg Met Val Val Ala Ser Ser Thr Ala
            100                 105                 110 ccg gag gag ctc tcc gtc gcg cta tcg gcg cag ggg gtc gac ggc tac     384
Pro Glu Glu Leu Ser Val Ala Leu Ser Ala Gln Gly Val Asp Gly Tyr
        115                 120                 125 ttc gag cgg gtc ttc tcc acg gga ggc ccc ata cgc agc aag gac tac     432
Phe Glu Arg Val Phe Ser Thr Gly Gly Pro Ile Arg Ser Lys Asp Tyr
    130                 135                 140 ccg gac atc tgg gag ctg gtc ctg gac tac ctg ggc acc gac ccg gct     480
Pro Asp Ile Trp Glu Leu Val Leu Asp Tyr Leu Gly Thr Asp Pro Ala
145                 150                 155                 160 gac acc tgg gtc ttc gag gac gcc ccg ttt ggg atg cgg acg gcc cga     528
```

|  |  |  |  |  |  |  |  |  |  |  |  |  |
|---|---|---|---|---|---|---|---|---|---|---|---|---|
| Asp | Thr | Trp | Val | Phe | Glu | Asp | Ala | Pro | Phe | Gly | Met | Arg | Thr | Ala | Arg |
|  |  |  |  | 165 |  |  |  |  | 170 |  |  |  | 175 |  |  |

| tcg | gtc | ggc | gcc | aac | acc | gtc | tgc | ctg | ttc | agc | cca | cac | ggg | gac | cgc | 576 |
|---|---|---|---|---|---|---|---|---|---|---|---|---|---|---|---|---|
| Ser | Val | Gly | Ala | Asn | Thr | Val | Cys | Leu | Phe | Ser | Pro | His | Gly | Asp | Arg |  |
|  |  |  | 180 |  |  |  |  | 185 |  |  |  |  | 190 |  |  |  |

| gac | ctt | gcg | gcc | tgc | gag | cgc | tac | gct | gac | ata | ctg | gtc | cac | agc | tac | 624 |
|---|---|---|---|---|---|---|---|---|---|---|---|---|---|---|---|---|
| Asp | Leu | Ala | Ala | Cys | Glu | Arg | Tyr | Ala | Asp | Ile | Leu | Val | His | Ser | Tyr |  |
|  |  | 195 |  |  |  |  | 200 |  |  |  |  | 205 |  |  |  |  |

| cac | gag | cta | tcg | ctc | gcc | ctg | ctg | gac | gac | tac | gcc | cgt | ccg | ccg | caa | 672 |
|---|---|---|---|---|---|---|---|---|---|---|---|---|---|---|---|---|
| His | Glu | Leu | Ser | Leu | Ala | Leu | Leu | Asp | Asp | Tyr | Ala | Arg | Pro | Pro | Gln |  |
| 210 |  |  |  |  | 215 |  |  |  |  | 220 |  |  |  |  |  |  |

| gcg | tcc | ccc | tcg | gcc | cac | cct | cgc | ctc | gcg | ccg | ctt | cgc | gtc | ctc | gtc | 720 |
|---|---|---|---|---|---|---|---|---|---|---|---|---|---|---|---|---|
| Ala | Ser | Pro | Ser | Ala | His | Pro | Arg | Leu | Ala | Pro | Leu | Arg | Val | Leu | Val |  |
| 225 |  |  |  |  | 230 |  |  |  |  | 235 |  |  |  |  | 240 |  |

| gtg | ggc | gcc | tcg | ccc | gag | cgc | ccg | tct | tcg | gcg | ctg | ctc | cgc | tcc | ctg | 768 |
|---|---|---|---|---|---|---|---|---|---|---|---|---|---|---|---|---|
| Val | Gly | Ala | Ser | Pro | Glu | Arg | Pro | Ser | Ser | Ala | Leu | Leu | Arg | Ser | Leu |  |
|  |  |  |  | 245 |  |  |  |  | 250 |  |  |  |  | 255 |  |  |

| gcc | gcc | agt | acc | gac | tac | gtc | atc | gcc | gcc | gac | gcc | ggg | gcc | gac | gcg | 816 |
|---|---|---|---|---|---|---|---|---|---|---|---|---|---|---|---|---|
| Ala | Ala | Ser | Thr | Asp | Tyr | Val | Ile | Ala | Ala | Asp | Ala | Gly | Ala | Asp | Ala |  |
|  |  |  | 260 |  |  |  |  | 265 |  |  |  |  | 270 |  |  |  |

| ctg | cgc | tcc | tgt | ggc | atc | gcc | ccc | gac | gtc | ttc | tgc | ggc | gac | gcc | gac | 864 |
|---|---|---|---|---|---|---|---|---|---|---|---|---|---|---|---|---|
| Leu | Arg | Ser | Cys | Gly | Ile | Ala | Pro | Asp | Val | Phe | Cys | Gly | Asp | Ala | Asp |  |
|  |  | 275 |  |  |  |  | 280 |  |  |  |  | 285 |  |  |  |  |

| tcg | gca | acg | ggc | gaa | tcg | gct | gcg | tgg | gcc | cgc | tcg | gtc | gcc | cgt | gcg | 912 |
|---|---|---|---|---|---|---|---|---|---|---|---|---|---|---|---|---|
| Ser | Ala | Thr | Gly | Glu | Ser | Ala | Ala | Trp | Ala | Arg | Ser | Val | Ala | Arg | Ala |  |
| 290 |  |  |  |  | 295 |  |  |  |  | 300 |  |  |  |  |  |  |

| gac | ata | gag | ttt | ccc | tcc | gag | aag | tac | gcg | acc | gac | ctc | gcc | ctc | gcc | 960 |
|---|---|---|---|---|---|---|---|---|---|---|---|---|---|---|---|---|
| Asp | Ile | Glu | Phe | Pro | Ser | Glu | Lys | Tyr | Ala | Thr | Asp | Leu | Ala | Leu | Ala |  |
| 305 |  |  |  |  | 310 |  |  |  |  | 315 |  |  |  |  | 320 |  |

| atc | tcc | tgc | gcc | cgc | cat | gag | gcc | gct | cga | cgc | aac | gcg | cgg | ctg | gag | 1008 |
|---|---|---|---|---|---|---|---|---|---|---|---|---|---|---|---|---|
| Ile | Ser | Cys | Ala | Arg | His | Glu | Ala | Ala | Arg | Arg | Asn | Ala | Arg | Leu | Glu |  |
|  |  |  |  | 325 |  |  |  |  | 330 |  |  |  |  | 335 |  |  |

| ctc | acg | ctg | acc | ggc | gtc | acg | ggc | ggc | agg | ccc | gac | cac | gcc | ctt | gcc | 1056 |
|---|---|---|---|---|---|---|---|---|---|---|---|---|---|---|---|---|
| Leu | Thr | Leu | Thr | Gly | Val | Thr | Gly | Gly | Arg | Pro | Asp | His | Ala | Leu | Ala |  |
|  |  |  | 340 |  |  |  |  | 345 |  |  |  |  | 350 |  |  |  |

| gtc | gtg | ggt | cag | ctc | gcg | cgg | aac | gct | gac | gcc | tcg | ccg | cgc | atc | gtg | 1104 |
|---|---|---|---|---|---|---|---|---|---|---|---|---|---|---|---|---|
| Val | Val | Gly | Gln | Leu | Ala | Arg | Asn | Ala | Asp | Ala | Ser | Pro | Arg | Ile | Val |  |
|  |  | 355 |  |  |  |  | 360 |  |  |  |  | 365 |  |  |  |  |

| gag | gac | ggc | ttc | gag | tgc | cga | ctg | ctc | agc | ccc | tct | ggc | act | gcg | tgc | 1152 |
|---|---|---|---|---|---|---|---|---|---|---|---|---|---|---|---|---|
| Glu | Asp | Gly | Phe | Glu | Cys | Arg | Leu | Leu | Ser | Pro | Ser | Gly | Thr | Ala | Cys |  |
| 370 |  |  |  |  | 375 |  |  |  |  | 380 |  |  |  |  |  |  |

| tgg | gag | ctg | ggt | ggg | gcc | cac | gtg | cca | gcc | gcc | ggg | gtc | gag | ggg | acg | 1200 |
|---|---|---|---|---|---|---|---|---|---|---|---|---|---|---|---|---|
| Trp | Glu | Leu | Gly | Gly | Ala | His | Val | Pro | Ala | Ala | Gly | Val | Glu | Gly | Thr |  |
| 385 |  |  |  |  | 390 |  |  |  |  | 395 |  |  |  |  | 400 |  |

| ctc | ttc | tcg | gcc | att | ccc | gtg | gca | gag | ggg | acc | atg | ctc | tcc | gag | cgg | 1248 |
|---|---|---|---|---|---|---|---|---|---|---|---|---|---|---|---|---|
| Leu | Phe | Ser | Ala | Ile | Pro | Val | Ala | Glu | Gly | Thr | Met | Leu | Ser | Glu | Arg |  |
|  |  |  |  | 405 |  |  |  |  | 410 |  |  |  |  | 415 |  |  |

| ggc | ttc | aag | tgg | gag | ctg | gat | cat | cgt | gag | ctg | ccc | ctt | ctg | ggg | gat | 1296 |
|---|---|---|---|---|---|---|---|---|---|---|---|---|---|---|---|---|
| Gly | Phe | Lys | Trp | Glu | Leu | Asp | His | Arg | Glu | Leu | Pro | Leu | Leu | Gly | Asp |  |
|  |  |  | 420 |  |  |  |  | 425 |  |  |  |  | 430 |  |  |  |

| gag | gga | atc | tcg | aac | gtg | gtc | acg | tcc | gcg | acg | gcc | agc | gtc | gag | tgc | 1344 |
|---|---|---|---|---|---|---|---|---|---|---|---|---|---|---|---|---|
| Glu | Gly | Ile | Ser | Asn | Val | Val | Thr | Ser | Ala | Thr | Ala | Ser | Val | Glu | Cys |  |
|  |  |  | 435 |  |  |  |  | 440 |  |  |  |  | 445 |  |  |  |

| cat | gcc | ggc | gca | gtt | gcg | gcg | ttc | ctg | ttg | gca | tag |  |  |  |  | 1380 |
|---|---|---|---|---|---|---|---|---|---|---|---|---|---|---|---|---|
| His | Ala | Gly | Ala | Val | Ala | Ala | Phe | Leu | Leu | Ala |  |  |  |  |  |  |
|  |  | 450 |  |  |  |  | 455 |  |  |  |  |  |  |  |  |  |

<210> SEQ ID NO 64
<211> LENGTH: 459
<212> TYPE: PRT

<213> ORGANISM: Olsenella uli

<400> SEQUENCE: 64

```
Met Pro Ile Lys Ala Ala Ile Phe Asp Cys Asp Gly Thr Leu Val Asp
1               5                   10                  15

Ser Met Pro Leu Trp His Asp Val Thr Val Glu Leu Leu Arg Arg His
            20                  25                  30

His Val Ala Asp Ala Glu Glu Ala Phe Val Arg Thr Glu Ser Leu Pro
        35                  40                  45

Met Val Glu Met Cys His Ala Phe His Asp Glu Trp Gly Val Glu Ala
50                  55                  60

Glu Gly Glu Glu Leu Val Arg Glu Leu Val Asp Met Val Arg Glu Gly
65                  70                  75                  80

Tyr Arg Ser Arg Val Ser Leu Leu Pro Gly Cys Arg Ala Phe Leu Asp
                85                  90                  95

Glu Leu Ala Ser Ala Gly Val Arg Met Val Val Ala Ser Ser Thr Ala
            100                 105                 110

Pro Glu Glu Leu Ser Val Ala Leu Ser Ala Gln Gly Val Asp Gly Tyr
        115                 120                 125

Phe Glu Arg Val Phe Ser Thr Gly Gly Pro Ile Arg Ser Lys Asp Tyr
130                 135                 140

Pro Asp Ile Trp Glu Leu Val Leu Asp Tyr Leu Gly Thr Asp Pro Ala
145                 150                 155                 160

Asp Thr Trp Val Phe Glu Asp Ala Pro Phe Gly Met Arg Thr Ala Arg
                165                 170                 175

Ser Val Gly Ala Asn Thr Val Cys Leu Phe Ser Pro His Gly Asp Arg
            180                 185                 190

Asp Leu Ala Ala Cys Glu Arg Tyr Ala Asp Ile Leu Val His Ser Tyr
        195                 200                 205

His Glu Leu Ser Leu Ala Leu Leu Asp Asp Tyr Ala Arg Pro Pro Gln
210                 215                 220

Ala Ser Pro Ser Ala His Pro Arg Leu Ala Pro Leu Arg Val Leu Val
225                 230                 235                 240

Val Gly Ala Ser Pro Glu Arg Pro Ser Ser Ala Leu Leu Arg Ser Leu
                245                 250                 255

Ala Ala Ser Thr Asp Tyr Val Ile Ala Ala Asp Ala Gly Ala Asp Ala
            260                 265                 270

Leu Arg Ser Cys Gly Ile Ala Pro Asp Val Phe Cys Gly Asp Ala Asp
        275                 280                 285

Ser Ala Thr Gly Glu Ser Ala Trp Ala Arg Ser Val Ala Arg Ala
290                 295                 300

Asp Ile Glu Phe Pro Ser Glu Lys Tyr Ala Thr Asp Leu Ala Leu Ala
305                 310                 315                 320

Ile Ser Cys Ala Arg His Glu Ala Ala Arg Asn Ala Arg Leu Glu
                325                 330                 335

Leu Thr Leu Thr Gly Val Thr Gly Gly Arg Pro Asp His Ala Leu Ala
            340                 345                 350

Val Val Gly Gln Leu Ala Arg Asn Ala Asp Ala Ser Pro Arg Ile Val
        355                 360                 365

Glu Asp Gly Phe Glu Cys Arg Leu Leu Ser Pro Ser Gly Thr Ala Cys
370                 375                 380

Trp Glu Leu Gly Gly Ala His Val Pro Ala Ala Gly Val Glu Gly Thr
385                 390                 395                 400
```

```
Leu Phe Ser Ala Ile Pro Val Ala Glu Gly Thr Met Leu Ser Glu Arg
            405                 410                 415

Gly Phe Lys Trp Glu Leu Asp His Arg Glu Leu Pro Leu Leu Gly Asp
        420                 425                 430

Glu Gly Ile Ser Asn Val Val Thr Ser Ala Thr Ala Ser Val Glu Cys
            435                 440                 445

His Ala Gly Ala Val Ala Ala Phe Leu Leu Ala
    450                 455

<210> SEQ ID NO 65
<211> LENGTH: 762
<212> TYPE: DNA
<213> ORGANISM: Atopobium minutum
<220> FEATURE:
<221> NAME/KEY: CDS
<222> LOCATION: (1)..(759)
<223> OTHER INFORMATION: Atopobium minutum gene encoding TMP phosphatase
      [KRN55115]

<400> SEQUENCE: 65
```

| | | | | | | | | | | | | | | | | |
|---|---|---|---|---|---|---|---|---|---|---|---|---|---|---|---|---|
| atg | tgg | gct | aaa | acc | tct | cga | cat | tgt | acg | caa | aaa | ggc | ttt | acc | atg | 48 |
| Met | Trp | Ala | Lys | Thr | Ser | Arg | His | Cys | Thr | Gln | Lys | Gly | Phe | Thr | Met | |
| 1 | | | | 5 | | | | | 10 | | | | | 15 | | |

```
aac cct gca cgc att tta ttt gat gga gga act tgt atg gca ata agc      96
Asn Pro Ala Arg Ile Leu Phe Asp Gly Gly Thr Cys Met Ala Ile Ser
            20                  25                  30 ggc gca atc ttt gac tgt gac ggc acg ctg gtt gat tct atg tat atg    144
Gly Ala Ile Phe Asp Cys Asp Gly Thr Leu Val Asp Ser Met Tyr Met
        35                  40                  45 tgg tgg gac gcc ttt ccc cgc ctg ctt gcc agc cat ggc ttt gct atg    192
Trp Trp Asp Ala Phe Pro Arg Leu Leu Ala Ser His Gly Phe Ala Met
    50                  55                  60 acg cct cag atc gag aaa atc ttg cat gag tgt gag gcg gtc agc ttg    240
Thr Pro Gln Ile Glu Lys Ile Leu His Glu Cys Glu Ala Val Ser Leu
65                  70                  75                  80 gat gaa gag atc cat acg ctg cgc aac gct ctt gct att ccc gct tct    288
Asp Glu Glu Ile His Thr Leu Arg Asn Ala Leu Ala Ile Pro Ala Ser
                85                  90                  95 gcc gag cag cta gca caa gaa tta tcc cag aat att agc aat gcg tat    336
Ala Glu Gln Leu Ala Gln Glu Leu Ser Gln Asn Ile Ser Asn Ala Tyr
            100                 105                 110 gcc tca gag atc aaa gca tgg cct gcc gtt aag ccg ttc ttg gat cag    384
Ala Ser Glu Ile Lys Ala Trp Pro Ala Val Lys Pro Phe Leu Asp Gln
        115                 120                 125 ctc aaa gac gca ggt atc ccc atg atc att tgt act tct acc gga gcc    432
Leu Lys Asp Ala Gly Ile Pro Met Ile Ile Cys Thr Ser Thr Gly Ala
    130                 135                 140 aaa gaa gtt ggt ctg tgc atg gat cat ctt ggt ttg tcc aag ttt ttt    480
Lys Glu Val Gly Leu Cys Met Asp His Leu Gly Leu Ser Lys Phe Phe
145                 150                 155                 160 gta gat att gtc agc gcg gaa gaa aac aat ttc acc aaa act gag cca    528
Val Asp Ile Val Ser Ala Glu Glu Asn Asn Phe Thr Lys Thr Glu Pro
                165                 170                 175 gat atc tat tac tat gcg cta aaa aag ctt ggt acc act aaa gag aca    576
Asp Ile Tyr Tyr Tyr Ala Leu Lys Lys Leu Gly Thr Thr Lys Glu Thr
            180                 185                 190 acc tgg gta ttt gag gat gct ccg ttt ggc ctt act acc tct gag cgt    624
Thr Trp Val Phe Glu Asp Ala Pro Phe Gly Leu Thr Thr Ser Glu Arg
        195                 200                 205 gca gga ttt cct aat gtg tgc gtc ttt aat gcg cac gat aag cgc gat    672
Ala Gly Phe Pro Asn Val Cys Val Phe Asn Ala His Asp Lys Arg Asp
```

```
gag gac ttt ttg cgt ctt cat gct acg ttg ttt acg cac ata tat gag    720
Glu Asp Phe Leu Arg Leu His Ala Thr Leu Phe Thr His Ile Tyr Glu
225                 230                 235                 240 gat att tcc ctt gcg gat ttg cag tcg tac ccc acc aag taa             762
Asp Ile Ser Leu Ala Asp Leu Gln Ser Tyr Pro Thr Lys
                245                 250
```

<210> SEQ ID NO 66
<211> LENGTH: 253
<212> TYPE: PRT
<213> ORGANISM: Atopobium minutum

<400> SEQUENCE: 66

```
Met Trp Ala Lys Thr Ser Arg His Cys Thr Gln Lys Gly Phe Thr Met
1               5                   10                  15

Asn Pro Ala Arg Ile Leu Phe Asp Gly Gly Thr Cys Met Ala Ile Ser
            20                  25                  30

Gly Ala Ile Phe Asp Cys Asp Gly Thr Leu Val Asp Ser Met Tyr Met
        35                  40                  45

Trp Trp Asp Ala Phe Pro Arg Leu Leu Ala Ser His Gly Phe Ala Met
    50                  55                  60

Thr Pro Gln Ile Glu Lys Ile Leu His Glu Cys Glu Ala Val Ser Leu
65                  70                  75                  80

Asp Glu Glu Ile His Thr Leu Arg Asn Ala Leu Ala Ile Pro Ala Ser
                85                  90                  95

Ala Glu Gln Leu Ala Gln Glu Leu Ser Gln Asn Ile Ser Asn Ala Tyr
            100                 105                 110

Ala Ser Glu Ile Lys Ala Trp Pro Ala Val Lys Pro Phe Leu Asp Gln
        115                 120                 125

Leu Lys Asp Ala Gly Ile Pro Met Ile Ile Cys Thr Ser Thr Gly Ala
    130                 135                 140

Lys Glu Val Gly Leu Cys Met Asp His Leu Gly Leu Ser Lys Phe Phe
145                 150                 155                 160

Val Asp Ile Val Ser Ala Glu Glu Asn Asn Phe Thr Lys Thr Glu Pro
                165                 170                 175

Asp Ile Tyr Tyr Tyr Ala Leu Lys Lys Leu Gly Thr Lys Glu Thr
            180                 185                 190

Thr Trp Val Phe Glu Asp Ala Pro Phe Gly Leu Thr Thr Ser Glu Arg
        195                 200                 205

Ala Gly Phe Pro Asn Val Cys Val Phe Asn Ala His Asp Lys Arg Asp
    210                 215                 220

Glu Asp Phe Leu Arg Leu His Ala Thr Leu Phe Thr His Ile Tyr Glu
225                 230                 235                 240

Asp Ile Ser Leu Ala Asp Leu Gln Ser Tyr Pro Thr Lys
                245                 250
```

<210> SEQ ID NO 67
<211> LENGTH: 648
<212> TYPE: DNA
<213> ORGANISM: Syntrophomonas wolfei
<220> FEATURE:
<221> NAME/KEY: CDS
<222> LOCATION: (1)..(645)
<223> OTHER INFORMATION: Syntrophomonas wolfei gene encoding TMP phosphatase [WP_011640074]

<400> SEQUENCE: 67

| | | | | | | | | | | | | | | | | |
|---|---|---|---|---|---|---|---|---|---|---|---|---|---|---|---|---|
| atg | gga | gag | aaa | tta | ata | att | ttt | atg | gat | ttc | gat | ggc | act | att | tct | 48 |
| Met | Gly | Glu | Lys | Leu | Ile | Ile | Phe | Met | Asp | Phe | Asp | Gly | Thr | Ile | Ser | |
| 1 | | | | 5 | | | | | 10 | | | | | 15 | | |
| cgg | gag | gat | gtc | tgc | aat | aag | atg | gca | gcc | agg | tat | gcc | ggc | agg | gac | 96 |
| Arg | Glu | Asp | Val | Cys | Asn | Lys | Met | Ala | Ala | Arg | Tyr | Ala | Gly | Arg | Asp | |
| | | | 20 | | | | | 25 | | | | | 30 | | | |
| tgg | gag | gaa | ata | aac | cgc | ctc | tgg | gaa | gag | gga | ggt | att | act | act | gga | 144 |
| Trp | Glu | Glu | Ile | Asn | Arg | Leu | Trp | Glu | Glu | Gly | Gly | Ile | Thr | Thr | Gly | |
| | 35 | | | | | 40 | | | | | 45 | | | | | |
| gag | tgc | gcc | agt | cgt | att | ctt | tca | tca | atg | gag | gta | ggg | gcg | gct | gaa | 192 |
| Glu | Cys | Ala | Ser | Arg | Ile | Leu | Ser | Ser | Met | Glu | Val | Gly | Ala | Ala | Glu | |
| | 50 | | | | | 55 | | | | | 60 | | | | | |
| ttg | gag | gcc | ttt | ttt | cag | gct | cag | gaa | gta | gac | ccc | ggc | ttt | tcc | cct | 240 |
| Leu | Glu | Ala | Phe | Phe | Gln | Ala | Gln | Glu | Val | Asp | Pro | Gly | Phe | Ser | Pro | |
| 65 | | | | | 70 | | | | | 75 | | | | | 80 | |
| ttc | ctg | gac | tgg | gta | caa | aaa | aat | cag | cac | ctc | ccc | att | ata | ttg | agc | 288 |
| Phe | Leu | Asp | Trp | Val | Gln | Lys | Asn | Gln | His | Leu | Pro | Ile | Ile | Leu | Ser | |
| | | | | 85 | | | | | 90 | | | | | 95 | | |
| gat | ggt | tat | gac | cgc | tat | ata | aaa | agc | ata | tta | cgg | ggc | cag | ggc | tgg | 336 |
| Asp | Gly | Tyr | Asp | Arg | Tyr | Ile | Lys | Ser | Ile | Leu | Arg | Gly | Gln | Gly | Trp | |
| | | | 100 | | | | | 105 | | | | | 110 | | | |
| gaa | atc | gag | ttt | tat | gcc | aat | aaa | tta | tac | tgg | gat | gac | gcc | tgg | cgg | 384 |
| Glu | Ile | Glu | Phe | Tyr | Ala | Asn | Lys | Leu | Tyr | Trp | Asp | Asp | Ala | Trp | Arg | |
| | | 115 | | | | | 120 | | | | | 125 | | | | |
| atg | gaa | tcg | ccc | tac | ctg | gat | gaa | gaa | tgc | ttt | aaa | tgt | ggg | gta | tgc | 432 |
| Met | Glu | Ser | Pro | Tyr | Leu | Asp | Glu | Glu | Cys | Phe | Lys | Cys | Gly | Val | Cys | |
| | 130 | | | | | 135 | | | | | 140 | | | | | |
| aag | agc | aag | ata | atc | cag | gaa | aga | agt | tta | ccc | ggc | tat | ctc | aca | gta | 480 |
| Lys | Ser | Lys | Ile | Ile | Gln | Glu | Arg | Ser | Leu | Pro | Gly | Tyr | Leu | Thr | Val | |
| 145 | | | | | 150 | | | | | 155 | | | | | 160 | |
| tat | atc | gga | gat | ggc | tac | tcc | gat | ttc | tgc | ccg | gcg | gcc | tct | tgt | gat | 528 |
| Tyr | Ile | Gly | Asp | Gly | Tyr | Ser | Asp | Phe | Cys | Pro | Ala | Ala | Ser | Cys | Asp | |
| | | | | 165 | | | | | 170 | | | | | 175 | | |
| att | gtt | ttt | gcc | aaa | aat | gaa | ctg | gcc | ggc | tac | tgc | cag | aaa | gag | ggt | 576 |
| Ile | Val | Phe | Ala | Lys | Asn | Glu | Leu | Ala | Gly | Tyr | Cys | Gln | Lys | Glu | Gly | |
| | | | 180 | | | | | 185 | | | | | 190 | | | |
| tta | act | tac | tac | ccc | tac | cgg | gat | ttt | cac | gat | att | ctc | cag | caa | ctg | 624 |
| Leu | Thr | Tyr | Tyr | Pro | Tyr | Arg | Asp | Phe | His | Asp | Ile | Leu | Gln | Gln | Leu | |
| | | 195 | | | | | 200 | | | | | 205 | | | | |
| ccg | agg | att | gtt | agc | agg | atg | tag | | | | | | | | | 648 |
| Pro | Arg | Ile | Val | Ser | Arg | Met | | | | | | | | | | |
| | 210 | | | | 215 | | | | | | | | | | | |

<210> SEQ ID NO 68
<211> LENGTH: 215
<212> TYPE: PRT
<213> ORGANISM: Syntrophomonas wolfei

<400> SEQUENCE: 68

Met Gly Glu Lys Leu Ile Ile Phe Met Asp Phe Asp Gly Thr Ile Ser
1               5                   10                  15

Arg Glu Asp Val Cys Asn Lys Met Ala Ala Arg Tyr Ala Gly Arg Asp
            20                  25                  30

Trp Glu Glu Ile Asn Arg Leu Trp Glu Glu Gly Gly Ile Thr Thr Gly
        35                  40                  45

Glu Cys Ala Ser Arg Ile Leu Ser Ser Met Glu Val Gly Ala Ala Glu
    50                  55                  60

Leu Glu Ala Phe Phe Gln Ala Gln Glu Val Asp Pro Gly Phe Ser Pro
65                  70                  75                  80

```
                Phe Leu Asp Trp Val Gln Lys Asn Gln His Leu Pro Ile Ile Leu Ser
                                 85                  90                  95

Asp Gly Tyr Asp Arg Tyr Ile Lys Ser Ile Leu Arg Gly Gln Gly Trp
                            100                 105                 110

Glu Ile Glu Phe Tyr Ala Asn Lys Leu Tyr Trp Asp Asp Ala Trp Arg
                            115                 120                 125

Met Glu Ser Pro Tyr Leu Asp Glu Glu Cys Phe Lys Cys Gly Val Cys
                130                 135                 140

Lys Ser Lys Ile Ile Gln Glu Arg Ser Leu Pro Gly Tyr Leu Thr Val
                145                 150                 155                 160

Tyr Ile Gly Asp Gly Tyr Ser Asp Phe Cys Pro Ala Ala Ser Cys Asp
                                165                 170                 175

Ile Val Phe Ala Lys Asn Glu Leu Ala Gly Tyr Cys Gln Lys Glu Gly
                            180                 185                 190

Leu Thr Tyr Tyr Pro Tyr Arg Asp Phe His Asp Ile Leu Gln Gln Leu
                            195                 200                 205

Pro Arg Ile Val Ser Arg Met
                210                 215

<210> SEQ ID NO 69
<211> LENGTH: 666
<212> TYPE: DNA
<213> ORGANISM: Desulfitobacterium hafniense
<220> FEATURE:
<221> NAME/KEY: CDS
<222> LOCATION: (1)..(663)
<223> OTHER INFORMATION: Desulfitobacterium hafniense gene encoding TMP
      phosphatase [WP_018212876]

<400> SEQUENCE: 69 atg gag gaa ttg aac agt att ttc ttc gtg gat ttt gac ggc acc atc        48
Met Glu Glu Leu Asn Ser Ile Phe Phe Val Asp Phe Asp Gly Thr Ile
1               5                   10                  15 gtc act cag gat atg tgt gca gtc ctc gtt gaa acc ttg gcc ggg gaa        96
Val Thr Gln Asp Met Cys Ala Val Leu Val Glu Thr Leu Ala Gly Glu
            20                  25                  30 gga tgg cgg gag att aat gaa ctt tgg gaa aga aaa gag ctt tcc acc       144
Gly Trp Arg Glu Ile Asn Glu Leu Trp Glu Arg Lys Glu Leu Ser Thr
        35                  40                  45 ctg gag tgc gcc cgc cgg acc ttt aaa ctc ttt aac agc aat gac ccg       192
Leu Glu Cys Ala Arg Arg Thr Phe Lys Leu Phe Asn Ser Asn Asp Pro
    50                  55                  60 gaa gtt ttt cgc cag ctt atc ggg cag gcg gtg ttc gat ccc gga ttt       240
Glu Val Phe Arg Gln Leu Ile Gly Gln Ala Val Phe Asp Pro Gly Phe
65                  70                  75                  80 tta gat ttt gcc gct ttt tgt gaa cag aga gga ttt ccc ctc atc att       288
Leu Asp Phe Ala Ala Phe Cys Glu Gln Arg Gly Phe Pro Leu Ile Ile
                85                  90                  95 ctc agc gac gga tat gat ttc tat att gag tac ctc ttg caa aga gag       336
Leu Ser Asp Gly Tyr Asp Phe Tyr Ile Glu Tyr Leu Leu Gln Arg Glu
            100                 105                 110 gga ttg aac ctg cca tac tat gcc aac aaa ttg ctg ttt gct ccc caa       384
Gly Leu Asn Leu Pro Tyr Tyr Ala Asn Lys Leu Leu Phe Ala Pro Gln
        115                 120                 125 ctt gac gta gaa acc ccc tac agc tcc ggc gaa tgt gat cta tgc ggg       432
Leu Asp Val Glu Thr Pro Tyr Ser Ser Gly Glu Cys Asp Leu Cys Gly
    130                 135                 140 gtc tgc aaa ctg cag ctg atg gaa aaa ttg ctt aaa ccc ggt tgc cga       480
Val Cys Lys Leu Gln Leu Met Glu Lys Leu Leu Lys Pro Gly Cys Arg
145                 150                 155                 160
```

```
tcc gtc tat atc gga gat ggg act tcc gat ttt tgc ccg gcg gaa agg      528
Ser Val Tyr Ile Gly Asp Gly Thr Ser Asp Phe Cys Pro Ala Glu Arg
            165                 170                 175 gcg gat aag gtc ttt gcc agg agc agg ctt tat cag cat tgc cag gag      576
Ala Asp Lys Val Phe Ala Arg Ser Arg Leu Tyr Gln His Cys Gln Glu
        180                 185                 190 gtg ggc aaa gaa gcc cag cta ttc caa tcg ttt cag gat att ctt cag      624
Val Gly Lys Glu Ala Gln Leu Phe Gln Ser Phe Gln Asp Ile Leu Gln
    195                 200                 205 aca gtt gaa cat tgg gga agg gaa gag gag gaa ggg act tga              666
Thr Val Glu His Trp Gly Arg Glu Glu Glu Glu Gly Thr
210                 215                 220
```

<210> SEQ ID NO 70
<211> LENGTH: 221
<212> TYPE: PRT
<213> ORGANISM: Desulfitobacterium hafniense

<400> SEQUENCE: 70

```
Met Glu Glu Leu Asn Ser Ile Phe Phe Val Asp Phe Asp Gly Thr Ile
1               5                   10                  15

Val Thr Gln Asp Met Cys Ala Val Leu Val Glu Thr Leu Ala Gly Glu
            20                  25                  30

Gly Trp Arg Glu Ile Asn Glu Leu Trp Glu Arg Lys Glu Leu Ser Thr
        35                  40                  45

Leu Glu Cys Ala Arg Arg Thr Phe Lys Leu Phe Asn Ser Asn Asp Pro
    50                  55                  60

Glu Val Phe Arg Gln Leu Ile Gly Gln Ala Val Phe Asp Pro Gly Phe
65                  70                  75                  80

Leu Asp Phe Ala Ala Phe Cys Glu Gln Arg Gly Phe Pro Leu Ile Ile
                85                  90                  95

Leu Ser Asp Gly Tyr Asp Phe Tyr Ile Glu Tyr Leu Leu Gln Arg Glu
            100                 105                 110

Gly Leu Asn Leu Pro Tyr Tyr Ala Asn Lys Leu Leu Phe Ala Pro Gln
        115                 120                 125

Leu Asp Val Glu Thr Pro Tyr Ser Ser Gly Glu Cys Asp Leu Cys Gly
    130                 135                 140

Val Cys Lys Leu Gln Leu Met Glu Lys Leu Leu Lys Pro Gly Cys Arg
145                 150                 155                 160

Ser Val Tyr Ile Gly Asp Gly Thr Ser Asp Phe Cys Pro Ala Glu Arg
                165                 170                 175

Ala Asp Lys Val Phe Ala Arg Ser Arg Leu Tyr Gln His Cys Gln Glu
            180                 185                 190

Val Gly Lys Glu Ala Gln Leu Phe Gln Ser Phe Gln Asp Ile Leu Gln
        195                 200                 205

Thr Val Glu His Trp Gly Arg Glu Glu Glu Glu Gly Thr
    210                 215                 220
```

<210> SEQ ID NO 71
<211> LENGTH: 642
<212> TYPE: DNA
<213> ORGANISM: Pelotomaculum thermopropionicum
<220> FEATURE:
<221> NAME/KEY: CDS
<222> LOCATION: (1)..(639)
<223> OTHER INFORMATION: Pelotomaculum thermopropionicum gene encoding
      TMP phosphatase [WP_012032097]

<400> SEQUENCE: 71

```
atg gaa aaa gtt ttt ttt gtt gat ttt gac ggg acg gta acc aaa aag     48
Met Glu Lys Val Phe Phe Val Asp Phe Asp Gly Thr Val Thr Lys Lys
1               5                   10                  15 gat acc tgc gtg gcc atg atc gag gcc ttt gcc ggc ggc aac tgg aga     96
Asp Thr Cys Val Ala Met Ile Glu Ala Phe Ala Gly Gly Asn Trp Arg
                20                  25                  30 gag att aac gag gcg tgg gaa aga aaa gaa att tcc acg gaa gaa tgt    144
Glu Ile Asn Glu Ala Trp Glu Arg Lys Glu Ile Ser Thr Glu Glu Cys
        35                  40                  45 gca aac atg atc ttc agg ctt ttc cgc gcc ggc att gaa gac atc agg    192
Ala Asn Met Ile Phe Arg Leu Phe Arg Ala Gly Ile Glu Asp Ile Arg
    50                  55                  60 aag ctt ttg gac ggt atc gag ata gac ggc cat ttt aaa gat ttt ctt    240
Lys Leu Leu Asp Gly Ile Glu Ile Asp Gly His Phe Lys Asp Phe Leu
65                  70                  75                  80 tct ttt tgc cgg gaa aga ggc tat aaa ata tac atc ctc agc gac ggt    288
Ser Phe Cys Arg Glu Arg Gly Tyr Lys Ile Tyr Ile Leu Ser Asp Gly
                85                  90                  95 tac gac ttt tgc att gag acg gtg ttt aaa aaa cac gga ata gag ctg    336
Tyr Asp Phe Cys Ile Glu Thr Val Phe Lys Lys His Gly Ile Glu Leu
            100                 105                 110 ccg tac tat gcc aac aaa atg gtt tac ggc aat ggt ttt aaa ata gaa    384
Pro Tyr Tyr Ala Asn Lys Met Val Tyr Gly Asn Gly Phe Lys Ile Glu
        115                 120                 125 tgc ttc agg ccc aac ccg gcc tgc ggt att tgc ggg acc tgc aag acc    432
Cys Phe Arg Pro Asn Pro Ala Cys Gly Ile Cys Gly Thr Cys Lys Thr
    130                 135                 140 aag ctg att gag gag ctt aaa ggg gac ggc agc cag gtt att tac att    480
Lys Leu Ile Glu Glu Leu Lys Gly Asp Gly Ser Gln Val Ile Tyr Ile
145                 150                 155                 160 ggc gac gga tat tcg gac aca tgc ccg gcc atg aaa gcc gat gtg gtt    528
Gly Asp Gly Tyr Ser Asp Thr Cys Pro Ala Met Lys Ala Asp Val Val
                165                 170                 175 ttt gcc aag gga gta ttg tac agg cat tgc cgg gaa aac ggc aaa aag    576
Phe Ala Lys Gly Val Leu Tyr Arg His Cys Arg Glu Asn Gly Lys Lys
            180                 185                 190 gct att tat tat aat aac ttt ggt gat att att aat tat ttt ttc caa    624
Ala Ile Tyr Tyr Asn Asn Phe Gly Asp Ile Ile Asn Tyr Phe Phe Gln
        195                 200                 205 ata aaa aaa agt ttg taa                                            642
Ile Lys Lys Ser Leu
        210
```

<210> SEQ ID NO 72
<211> LENGTH: 213
<212> TYPE: PRT
<213> ORGANISM: Pelotomaculum thermopropionicum

<400> SEQUENCE: 72

```
Met Glu Lys Val Phe Phe Val Asp Phe Asp Gly Thr Val Thr Lys Lys
1               5                   10                  15

Asp Thr Cys Val Ala Met Ile Glu Ala Phe Ala Gly Gly Asn Trp Arg
                20                  25                  30

Glu Ile Asn Glu Ala Trp Glu Arg Lys Glu Ile Ser Thr Glu Glu Cys
        35                  40                  45

Ala Asn Met Ile Phe Arg Leu Phe Arg Ala Gly Ile Glu Asp Ile Arg
    50                  55                  60

Lys Leu Leu Asp Gly Ile Glu Ile Asp Gly His Phe Lys Asp Phe Leu
65                  70                  75                  80
```

Ser Phe Cys Arg Glu Arg Gly Tyr Lys Ile Tyr Ile Leu Ser Asp Gly
            85                  90                  95

Tyr Asp Phe Cys Ile Glu Thr Val Phe Lys Lys His Gly Ile Glu Leu
            100                 105                 110

Pro Tyr Tyr Ala Asn Lys Met Val Tyr Gly Asn Gly Phe Lys Ile Glu
            115                 120                 125

Cys Phe Arg Pro Asn Pro Ala Cys Gly Ile Cys Gly Thr Cys Lys Thr
130                 135                 140

Lys Leu Ile Glu Glu Leu Lys Gly Asp Gly Ser Gln Val Ile Tyr Ile
145                 150                 155                 160

Gly Asp Gly Tyr Ser Asp Thr Cys Pro Ala Met Lys Ala Asp Val Val
                165                 170                 175

Phe Ala Lys Gly Val Leu Tyr Arg His Cys Arg Glu Asn Gly Lys Lys
            180                 185                 190

Ala Ile Tyr Tyr Asn Asn Phe Gly Asp Ile Ile Asn Tyr Phe Phe Gln
            195                 200                 205

Ile Lys Lys Ser Leu
    210

<210> SEQ ID NO 73
<211> LENGTH: 651
<212> TYPE: DNA
<213> ORGANISM: Desulfotomaculum ruminis
<220> FEATURE:
<221> NAME/KEY: CDS
<222> LOCATION: (1)..(648)
<223> OTHER INFORMATION: Desulfotomaculum ruminis gene encoding TMP
      phosphatase [WP_013840216]

<400> SEQUENCE: 73 atg gaa acc att ctt ttt ctg gat ttt gac ggc acc att acc gag cag      48
Met Glu Thr Ile Leu Phe Leu Asp Phe Asp Gly Thr Ile Thr Glu Gln
1               5                   10                  15 gat acc tgc gat atg ctg atg gag cgc tac ggc aat gcg gaa tgt ctg      96
Asp Thr Cys Asp Met Leu Met Glu Arg Tyr Gly Asn Ala Glu Cys Leu
            20                  25                  30 gaa ttg aac cgg cgc tgg gaa cgc aag gaa att tcc acc atg gaa tgt     144
Glu Leu Asn Arg Arg Trp Glu Arg Lys Glu Ile Ser Thr Met Glu Cys
        35                  40                  45 gcc cgg cag tcc ttc cgg caa atg cag gta act ccc gag gtt cta aag     192
Ala Arg Gln Ser Phe Arg Gln Met Gln Val Thr Pro Glu Val Leu Lys
50                  55                  60 cgg ttg gtg cag gag gtg aag gta gac cct cat ttg aaa gaa ttg ctc     240
Arg Leu Val Gln Glu Val Lys Val Asp Pro His Leu Lys Glu Leu Leu
65                  70                  75                  80 cgt ttc tgt gag cag gag aat tac ccc gcc tat att ttg agc gat ggg     288
Arg Phe Cys Glu Gln Glu Asn Tyr Pro Ala Tyr Ile Leu Ser Asp Gly
            85                  90                  95 tat gaa ccc atc att cag ggg gta ctg cag cgg gaa gga ata aaa ata     336
Tyr Glu Pro Ile Ile Gln Gly Val Leu Gln Arg Glu Gly Ile Lys Ile
            100                 105                 110 tct tgt ttt tgc aac ggg ttg tcc ttt gac ggc cag tac cgg gtc atg     384
Ser Cys Phe Cys Asn Gly Leu Ser Phe Asp Gly Gln Tyr Arg Val Met
            115                 120                 125 gcg cct cac tat aat ccc cgg tgc ggc cgg tgc gga acc tgt aaa caa     432
Ala Pro His Tyr Asn Pro Arg Cys Gly Arg Cys Gly Thr Cys Lys Gln
130                 135                 140 aag ctg gtg gaa cgc ctg ggt cag ccg ggc gcc cgg aag att ttt gtg     480
Lys Leu Val Glu Arg Leu Gly Gln Pro Gly Ala Arg Lys Ile Phe Val
145                 150                 155                 160

```
                              -continued
145                 150                 155                 160
gga gac ggt tat tcg gat ttc tgt gcc gca gag tcc tgc agt aag gtc      528
Gly Asp Gly Tyr Ser Asp Phe Cys Ala Ala Glu Ser Cys Ser Lys Val
                165                 170                 175 ttt gct aaa aaa aat tta ttg aag tat tgc ctg gaa aac cag att ccg      576
Phe Ala Lys Lys Asn Leu Leu Lys Tyr Cys Leu Glu Asn Gln Ile Pro
        180                 185                 190 gcc cac ccc tat gaa acc ctg gga gag gtt tta cag tgg ctg aga gga      624
Ala His Pro Tyr Glu Thr Leu Gly Glu Val Leu Gln Trp Leu Arg Gly
        195                 200                 205 gag gct gaa cat gga cat ccg gtt taa                                  651
Glu Ala Glu His Gly His Pro Val
        210                 215

<210> SEQ ID NO 74
<211> LENGTH: 216
<212> TYPE: PRT
<213> ORGANISM: Desulfotomaculum ruminis

<400> SEQUENCE: 74

Met Glu Thr Ile Leu Phe Leu Asp Phe Asp Gly Thr Ile Thr Glu Gln
1               5                   10                  15

Asp Thr Cys Asp Met Leu Met Glu Arg Tyr Gly Asn Ala Glu Cys Leu
            20                  25                  30

Glu Leu Asn Arg Arg Trp Glu Arg Lys Glu Ile Ser Thr Met Glu Cys
        35                  40                  45

Ala Arg Gln Ser Phe Arg Gln Met Gln Val Thr Pro Glu Val Leu Lys
    50                  55                  60

Arg Leu Val Gln Glu Val Lys Val Asp Pro His Leu Lys Glu Leu Leu
65                  70                  75                  80

Arg Phe Cys Glu Gln Glu Asn Tyr Pro Ala Tyr Ile Leu Ser Asp Gly
                85                  90                  95

Tyr Glu Pro Ile Ile Gln Gly Val Leu Gln Arg Glu Gly Ile Lys Ile
            100                 105                 110

Ser Cys Phe Cys Asn Gly Leu Ser Phe Asp Gly Gln Tyr Arg Val Met
        115                 120                 125

Ala Pro His Tyr Asn Pro Arg Cys Gly Arg Cys Gly Thr Cys Lys Gln
    130                 135                 140

Lys Leu Val Glu Arg Leu Gly Gln Pro Gly Ala Arg Lys Ile Phe Val
145                 150                 155                 160

Gly Asp Gly Tyr Ser Asp Phe Cys Ala Ala Glu Ser Cys Ser Lys Val
                165                 170                 175

Phe Ala Lys Lys Asn Leu Leu Lys Tyr Cys Leu Glu Asn Gln Ile Pro
            180                 185                 190

Ala His Pro Tyr Glu Thr Leu Gly Glu Val Leu Gln Trp Leu Arg Gly
        195                 200                 205

Glu Ala Glu His Gly His Pro Val
    210                 215

<210> SEQ ID NO 75
<211> LENGTH: 1896
<212> TYPE: DNA
<213> ORGANISM: Escherichia coli
<220> FEATURE:
<221> NAME/KEY: CDS
<222> LOCATION: (1)..(1893)
<223> OTHER INFORMATION: ThiC gene from E. coli encoding HMP-P synthase

<400> SEQUENCE: 75
```

```
atg tct gca aca aaa ctg acc cgc cgc gaa caa cgc gcc cgg gcc caa        48
Met Ser Ala Thr Lys Leu Thr Arg Arg Glu Gln Arg Ala Arg Ala Gln
1               5                   10                  15 cat ttt atc gac acc ctg gaa ggc acc gcc ttt ccc aac tca aaa cgc        96
His Phe Ile Asp Thr Leu Glu Gly Thr Ala Phe Pro Asn Ser Lys Arg
                20                  25                  30 att tat atc act ggc aca cac ccc ggc gtg cgc gtg ccg atg cgt gag       144
Ile Tyr Ile Thr Gly Thr His Pro Gly Val Arg Val Pro Met Arg Glu
            35                  40                  45 atc cag ctt agc ccg acg cta att ggc ggt agc aaa gaa cag ccg cag       192
Ile Gln Leu Ser Pro Thr Leu Ile Gly Gly Ser Lys Glu Gln Pro Gln
        50                  55                  60 tac gaa gaa aac gaa gcg att ccg gtc tac gac acc tcc ggc ccg tat       240
Tyr Glu Glu Asn Glu Ala Ile Pro Val Tyr Asp Thr Ser Gly Pro Tyr
65                  70                  75                  80 ggt gat ccg cag att gcc att aac gtg cag caa ggg ctg gca aaa cta       288
Gly Asp Pro Gln Ile Ala Ile Asn Val Gln Gln Gly Leu Ala Lys Leu
                85                  90                  95 cgc cag ccg tgg atc gat gcg cgc ggc gat acc gaa gaa ctt acc gtg       336
Arg Gln Pro Trp Ile Asp Ala Arg Gly Asp Thr Glu Glu Leu Thr Val
                100                 105                 110 cgc agt tcc gat tac act aaa gcg cgg ctg gca gat gat ggc ctc gac       384
Arg Ser Ser Asp Tyr Thr Lys Ala Arg Leu Ala Asp Asp Gly Leu Asp
            115                 120                 125 gaa ctg cgt ttt agc ggc gta cta aca cca aaa cgc gcc aaa gca gga       432
Glu Leu Arg Phe Ser Gly Val Leu Thr Pro Lys Arg Ala Lys Ala Gly
        130                 135                 140 cgc cgt gtc acc caa ctg cac tac gcc cgc cag ggc atc atc acg ccg       480
Arg Arg Val Thr Gln Leu His Tyr Ala Arg Gln Gly Ile Ile Thr Pro
145                 150                 155                 160 gaa atg gaa ttc atc gcc atc cgc gag aat atg ggc cgc gag cgc atc       528
Glu Met Glu Phe Ile Ala Ile Arg Glu Asn Met Gly Arg Glu Arg Ile
                165                 170                 175 cgt agc gag gtt tta cgc cac cag cat ccg gga atg agc ttt ggc gca       576
Arg Ser Glu Val Leu Arg His Gln His Pro Gly Met Ser Phe Gly Ala
                180                 185                 190 cat ctg ccg gaa aat atc act gcg gaa ttt gtc cgt gat gaa gtt gct       624
His Leu Pro Glu Asn Ile Thr Ala Glu Phe Val Arg Asp Glu Val Ala
            195                 200                 205 gcc gga cgt gcg att atc ccg gcc aac att aat cat ccg gaa tcg gag       672
Ala Gly Arg Ala Ile Ile Pro Ala Asn Ile Asn His Pro Glu Ser Glu
        210                 215                 220 ccg atg att att ggt cgc aat ttc ctg gta aaa gtt aac gcc aat atc       720
Pro Met Ile Ile Gly Arg Asn Phe Leu Val Lys Val Asn Ala Asn Ile
225                 230                 235                 240 ggc aac tcg gcg gtc acc tct tcc atc gaa gaa gaa gtg gaa aag ctg       768
Gly Asn Ser Ala Val Thr Ser Ser Ile Glu Glu Glu Val Glu Lys Leu
                245                 250                 255 gta tgg tcc acg cgc tgg gga gcg gat acg gtg atg gat ctc tcc acc       816
Val Trp Ser Thr Arg Trp Gly Ala Asp Thr Val Met Asp Leu Ser Thr
                260                 265                 270 ggt cgc tat att cac gaa acc cgc gag tgg att ttg cgt aac agc ccg       864
Gly Arg Tyr Ile His Glu Thr Arg Glu Trp Ile Leu Arg Asn Ser Pro
            275                 280                 285 gtg ccg atc ggt aca gtg ccg atc tac cag gcg ctg gag aag gtt aac       912
Val Pro Ile Gly Thr Val Pro Ile Tyr Gln Ala Leu Glu Lys Val Asn
        290                 295                 300 ggg atc gcc gaa gat ctt acc tgg gaa gcg ttc cgc gac acg ctg ctg       960
Gly Ile Ala Glu Asp Leu Thr Trp Glu Ala Phe Arg Asp Thr Leu Leu
```

```
                305                 310                 315                 320
gaa cag gcc gag caa ggt gtg gat tac ttc act atc cat gcg ggc gta          1008
Glu Gln Ala Glu Gln Gly Val Asp Tyr Phe Thr Ile His Ala Gly Val
                    325                 330                 335 ctg ctg cgc tat gtg ccg atg acc gcg aaa cgc ctg acc ggt atc gtc          1056
Leu Leu Arg Tyr Val Pro Met Thr Ala Lys Arg Leu Thr Gly Ile Val
            340                 345                 350 tct cgc ggc ggt tcg att atg gcg aaa tgg tgc ctc tcc cat cat cag          1104
Ser Arg Gly Gly Ser Ile Met Ala Lys Trp Cys Leu Ser His His Gln
        355                 360                 365 gaa aat ttc ctc tat caa cac ttc cgc gaa att tgt gaa atc tgt gcc          1152
Glu Asn Phe Leu Tyr Gln His Phe Arg Glu Ile Cys Glu Ile Cys Ala
    370                 375                 380 gct tat gac gtt tcg ctg tcg ctg ggc gac ggt ctg cgc ccc ggt tct          1200
Ala Tyr Asp Val Ser Leu Ser Leu Gly Asp Gly Leu Arg Pro Gly Ser
385                 390                 395                 400 att cag gac gcc aac gat gaa gcg cag ttt gcc gag ctg cat acg ctg          1248
Ile Gln Asp Ala Asn Asp Glu Ala Gln Phe Ala Glu Leu His Thr Leu
                405                 410                 415 ggc gaa ctg acc aaa att gcc tgg gaa tat gac gtg cag gtg atg att          1296
Gly Glu Leu Thr Lys Ile Ala Trp Glu Tyr Asp Val Gln Val Met Ile
            420                 425                 430 gaa ggc cca ggc cac gtg ccg atg cag atg atc cgc cgc aat atg acc          1344
Glu Gly Pro Gly His Val Pro Met Gln Met Ile Arg Arg Asn Met Thr
        435                 440                 445 gag gag tta gag cac tgc cac gaa gcg ccg ttt tac act ctg ggg ccg          1392
Glu Glu Leu Glu His Cys His Glu Ala Pro Phe Tyr Thr Leu Gly Pro
    450                 455                 460 cta act acc gat att gcg ccg ggc tat gac cac ttc acg tcg ggg att          1440
Leu Thr Thr Asp Ile Ala Pro Gly Tyr Asp His Phe Thr Ser Gly Ile
465                 470                 475                 480 ggt gcg gcg atg att ggc tgg ttt ggc tgc gcg atg ctc tgt tac gta          1488
Gly Ala Ala Met Ile Gly Trp Phe Gly Cys Ala Met Leu Cys Tyr Val
                485                 490                 495 acg cca aaa gag cat ctg ggt ctg ccc aat aaa gaa gat gtt aag cag          1536
Thr Pro Lys Glu His Leu Gly Leu Pro Asn Lys Glu Asp Val Lys Gln
            500                 505                 510 ggg ctt atc acc tat aag att gct gcc cac gcc gct gac ctg gcg aaa          1584
Gly Leu Ile Thr Tyr Lys Ile Ala Ala His Ala Ala Asp Leu Ala Lys
        515                 520                 525 ggg cat ccg ggc gcg caa att cgc gat aac gcc atg tcg aaa gcc cgc          1632
Gly His Pro Gly Ala Gln Ile Arg Asp Asn Ala Met Ser Lys Ala Arg
    530                 535                 540 ttc gaa ttt cgc tgg gaa gac cag ttt aat ctg gcc ctc gac ccg ttt          1680
Phe Glu Phe Arg Trp Glu Asp Gln Phe Asn Leu Ala Leu Asp Pro Phe
545                 550                 555                 560 acc gcc cgc gct tat cac gat gaa acc ctg ccg caa gag tca ggt aaa          1728
Thr Ala Arg Ala Tyr His Asp Glu Thr Leu Pro Gln Glu Ser Gly Lys
                565                 570                 575 gtc gcc cat ttt tgc tcc atg tgt ggg ccg aaa ttc tgc tcg atg aaa          1776
Val Ala His Phe Cys Ser Met Cys Gly Pro Lys Phe Cys Ser Met Lys
            580                 585                 590 atc agc cag gaa gtg cgt gat tac gcc gcc acg caa act att gaa atg          1824
Ile Ser Gln Glu Val Arg Asp Tyr Ala Ala Thr Gln Thr Ile Glu Met
        595                 600                 605 gga atg gcg gat atg tcg gag aac ttc cgt gcc aga ggc gga gaa atc          1872
Gly Met Ala Asp Met Ser Glu Asn Phe Arg Ala Arg Gly Gly Glu Ile
    610                 615                 620 tac ctg cgt aag gag gaa gcg tga                                          1896
```

Tyr Leu Arg Lys Glu Glu Ala
625                 630

<210> SEQ ID NO 76
<211> LENGTH: 631
<212> TYPE: PRT
<213> ORGANISM: Escherichia coli

<400> SEQUENCE: 76

Met Ser Ala Thr Lys Leu Thr Arg Arg Glu Gln Arg Ala Arg Ala Gln
1               5                   10                  15

His Phe Ile Asp Thr Leu Glu Gly Thr Ala Phe Pro Asn Ser Lys Arg
            20                  25                  30

Ile Tyr Ile Thr Gly Thr His Pro Gly Val Arg Val Pro Met Arg Glu
        35                  40                  45

Ile Gln Leu Ser Pro Thr Leu Ile Gly Gly Ser Lys Glu Gln Pro Gln
    50                  55                  60

Tyr Glu Glu Asn Glu Ala Ile Pro Val Tyr Asp Thr Ser Gly Pro Tyr
65                  70                  75                  80

Gly Asp Pro Gln Ile Ala Ile Asn Val Gln Gln Gly Leu Ala Lys Leu
                85                  90                  95

Arg Gln Pro Trp Ile Asp Ala Arg Gly Asp Thr Glu Glu Leu Thr Val
            100                 105                 110

Arg Ser Ser Asp Tyr Thr Lys Ala Arg Leu Ala Asp Asp Gly Leu Asp
        115                 120                 125

Glu Leu Arg Phe Ser Gly Val Leu Thr Pro Lys Arg Ala Lys Ala Gly
    130                 135                 140

Arg Arg Val Thr Gln Leu His Tyr Ala Arg Gln Gly Ile Ile Thr Pro
145                 150                 155                 160

Glu Met Glu Phe Ile Ala Ile Arg Glu Asn Met Gly Arg Glu Arg Ile
                165                 170                 175

Arg Ser Glu Val Leu Arg His Gln His Pro Gly Met Ser Phe Gly Ala
            180                 185                 190

His Leu Pro Glu Asn Ile Thr Ala Glu Phe Val Arg Asp Glu Val Ala
        195                 200                 205

Ala Gly Arg Ala Ile Ile Pro Ala Asn Ile Asn His Pro Glu Ser Glu
    210                 215                 220

Pro Met Ile Ile Gly Arg Asn Phe Leu Val Lys Val Asn Ala Asn Ile
225                 230                 235                 240

Gly Asn Ser Ala Val Thr Ser Ser Ile Glu Glu Glu Val Glu Lys Leu
                245                 250                 255

Val Trp Ser Thr Arg Trp Gly Ala Asp Thr Val Met Asp Leu Ser Thr
            260                 265                 270

Gly Arg Tyr Ile His Glu Thr Arg Glu Trp Ile Leu Arg Asn Ser Pro
        275                 280                 285

Val Pro Ile Gly Thr Val Pro Ile Tyr Gln Ala Leu Glu Lys Val Asn
    290                 295                 300

Gly Ile Ala Glu Asp Leu Thr Trp Glu Ala Phe Arg Asp Thr Leu Leu
305                 310                 315                 320

Glu Gln Ala Glu Gln Gly Val Asp Tyr Phe Thr Ile His Ala Gly Val
                325                 330                 335

Leu Leu Arg Tyr Val Pro Met Thr Ala Lys Arg Leu Thr Gly Ile Val
            340                 345                 350

Ser Arg Gly Gly Ser Ile Met Ala Lys Trp Cys Leu Ser His His Gln
        355                 360                 365

```
Glu Asn Phe Leu Tyr Gln His Phe Arg Glu Ile Cys Glu Ile Cys Ala
        370                 375                 380

Ala Tyr Asp Val Ser Leu Ser Leu Gly Asp Gly Leu Arg Pro Gly Ser
385                 390                 395                 400

Ile Gln Asp Ala Asn Asp Glu Ala Gln Phe Ala Glu Leu His Thr Leu
            405                 410                 415

Gly Glu Leu Thr Lys Ile Ala Trp Glu Tyr Asp Val Gln Val Met Ile
        420                 425                 430

Glu Gly Pro Gly His Val Pro Met Gln Met Ile Arg Arg Asn Met Thr
        435                 440                 445

Glu Glu Leu Glu His Cys His Glu Ala Pro Phe Tyr Thr Leu Gly Pro
    450                 455                 460

Leu Thr Thr Asp Ile Ala Pro Gly Tyr Asp His Phe Thr Ser Gly Ile
465                 470                 475                 480

Gly Ala Ala Met Ile Gly Trp Phe Gly Cys Ala Met Leu Cys Tyr Val
            485                 490                 495

Thr Pro Lys Glu His Leu Gly Leu Pro Asn Lys Glu Asp Val Lys Gln
        500                 505                 510

Gly Leu Ile Thr Tyr Lys Ile Ala Ala His Ala Ala Asp Leu Ala Lys
        515                 520                 525

Gly His Pro Gly Ala Gln Ile Arg Asp Asn Ala Met Ser Lys Ala Arg
    530                 535                 540

Phe Glu Phe Arg Trp Glu Asp Gln Phe Asn Leu Ala Leu Asp Pro Phe
545                 550                 555                 560

Thr Ala Arg Ala Tyr His Asp Glu Thr Leu Pro Gln Glu Ser Gly Lys
            565                 570                 575

Val Ala His Phe Cys Ser Met Cys Gly Pro Lys Phe Cys Ser Met Lys
        580                 585                 590

Ile Ser Gln Glu Val Arg Asp Tyr Ala Ala Thr Gln Thr Ile Glu Met
        595                 600                 605

Gly Met Ala Asp Met Ser Glu Asn Phe Arg Ala Arg Gly Gly Glu Ile
    610                 615                 620

Tyr Leu Arg Lys Glu Glu Ala
625                 630

<210> SEQ ID NO 77
<211> LENGTH: 1371
<212> TYPE: DNA
<213> ORGANISM: Synechococcus elongatus
<220> FEATURE:
<221> NAME/KEY: CDS
<222> LOCATION: (1)..(1368)
<223> OTHER INFORMATION: ThiC gene from Synechococcus_elongatus_PCC_
      7942:_[NC_007604] encoding a HMP-P synthase

<400> SEQUENCE: 77 atg cgc agc gac tgg atc gca ccc cgc cga ggc caa gcc aac gtc act      48
Met Arg Ser Asp Trp Ile Ala Pro Arg Arg Gly Gln Ala Asn Val Thr
1               5                   10                  15 caa atg cac tac gcc cgc caa ggc gtg atc acc gaa gaa atg gac ttc      96
Gln Met His Tyr Ala Arg Gln Gly Val Ile Thr Glu Glu Met Asp Phe
            20                  25                  30 gtg gcg cgg cgc gaa aat ctg cca gcc gat cta att cgg gat gaa gtg     144
Val Ala Arg Arg Glu Asn Leu Pro Ala Asp Leu Ile Arg Asp Glu Val
        35                  40                  45 gca cgg ggt cgg atg att atc ccc gcc aac atc aac cac acc aat ttg     192
Ala Arg Gly Arg Met Ile Ile Pro Ala Asn Ile Asn His Thr Asn Leu
```

|  |  |  |  |  |  |  |  |  |  |  |  |  |  |  |  |  |
|---|---|---|---|---|---|---|---|---|---|---|---|---|---|---|---|---|
|  |  |  | 50 |  |  |  |  | 55 |  |  |  |  | 60 |  |  |  |

```
gag ccg atg gcg atc ggc att gcc tcc aag tgc aag gtc aac gcc aac      240
Glu Pro Met Ala Ile Gly Ile Ala Ser Lys Cys Lys Val Asn Ala Asn
 65          70                  75                  80 atc ggt gct tcg cct aac gcc tcc aac atc gat gaa gaa gtc gag aag      288
Ile Gly Ala Ser Pro Asn Ala Ser Asn Ile Asp Glu Glu Val Glu Lys
                 85                  90                  95 ctg aag ctc gcg gtc aaa tac ggt gcc gat acc gtc atg gac ctc tcg      336
Leu Lys Leu Ala Val Lys Tyr Gly Ala Asp Thr Val Met Asp Leu Ser
            100                 105                 110 acc ggc ggc ggc aac ctc gat gag att cgc acc gcg atc atc aat gct      384
Thr Gly Gly Gly Asn Leu Asp Glu Ile Arg Thr Ala Ile Ile Asn Ala
        115                 120                 125 tcg ccg gta ccg atc ggc acc gtg ccg gtc tac caa gcc ctg gaa tcc      432
Ser Pro Val Pro Ile Gly Thr Val Pro Val Tyr Gln Ala Leu Glu Ser
    130                 135                 140 gtt cac ggg cgc atc gaa aaa ctc agc gcc gac gac ttc ttg cat gtg      480
Val His Gly Arg Ile Glu Lys Leu Ser Ala Asp Asp Phe Leu His Val
145                 150                 155                 160 atc gaa aag cac tgc gaa cag ggc gtc gac tac caa acc atc cac gcc      528
Ile Glu Lys His Cys Glu Gln Gly Val Asp Tyr Gln Thr Ile His Ala
                165                 170                 175 ggt ctg ctg att gaa cac ctg ccc aag gtc aag agc cgg atc acc ggg      576
Gly Leu Leu Ile Glu His Leu Pro Lys Val Lys Ser Arg Ile Thr Gly
            180                 185                 190 att gtt tcg cgg ggc ggc ggc atc att gcc cag tgg atg ctc tac cac      624
Ile Val Ser Arg Gly Gly Gly Ile Ile Ala Gln Trp Met Leu Tyr His
        195                 200                 205 cac aag caa aac ccg ctc tat acc cac ttt cgc gac atc atc gaa atc      672
His Lys Gln Asn Pro Leu Tyr Thr His Phe Arg Asp Ile Ile Glu Ile
    210                 215                 220 ttc aag cgc tac gac tgt agc ttc agc ttg ggt gac tcg ctc cgg ccg      720
Phe Lys Arg Tyr Asp Cys Ser Phe Ser Leu Gly Asp Ser Leu Arg Pro
225                 230                 235                 240 ggt tgc ctg cac gat gct agc gac gat gcc cag ctc agc gag ctg aag      768
Gly Cys Leu His Asp Ala Ser Asp Asp Ala Gln Leu Ser Glu Leu Lys
                245                 250                 255 act ctc ggt caa ctg acg cgg gtt gct tgg gaa cac gac gtg caa gtc      816
Thr Leu Gly Gln Leu Thr Arg Val Ala Trp Glu His Asp Val Gln Val
            260                 265                 270 atg gtc gaa ggg cca ggc cac gtt ccc atg gac cag atc gag ttc aac      864
Met Val Glu Gly Pro Gly His Val Pro Met Asp Gln Ile Glu Phe Asn
        275                 280                 285 gtc cgc aag caa atg gaa gag tgc tca gaa gct ccc ttc tac gtc ttg      912
Val Arg Lys Gln Met Glu Glu Cys Ser Glu Ala Pro Phe Tyr Val Leu
    290                 295                 300 ggt ccc ctc gtg acc gac att gca ccg ggc tat gac cac atc acc agc      960
Gly Pro Leu Val Thr Asp Ile Ala Pro Gly Tyr Asp His Ile Thr Ser
305                 310                 315                 320 gcg atc ggg gca gca atg gcg ggc tgg tat ggc acg gca atg ctc tgc     1008
Ala Ile Gly Ala Ala Met Ala Gly Trp Tyr Gly Thr Ala Met Leu Cys
                325                 330                 335 tac gtc acg ccc aaa gag cac ttg ggt ctg ccc aat gcg gaa gat gtg     1056
Tyr Val Thr Pro Lys Glu His Leu Gly Leu Pro Asn Ala Glu Asp Val
            340                 345                 350 cgc aat ggt ttg atc gcc tac aaa att gcg gct cat gca gca gat atc     1104
Arg Asn Gly Leu Ile Ala Tyr Lys Ile Ala Ala His Ala Ala Asp Ile
        355                 360                 365 gct cgc cac cgt ccg ggt gct cgc gat cgc gat gat gaa ctg agt cgg     1152
Ala Arg His Arg Pro Gly Ala Arg Asp Arg Asp Asp Glu Leu Ser Arg
```

```
Ala Arg His Arg Pro Gly Ala Arg Asp Arg Asp Asp Glu Leu Ser Arg
        370                 375                 380 gca cgc tac gcc ttc gac tgg aac aag caa ttt gac ttg agc ctc gat    1200
Ala Arg Tyr Ala Phe Asp Trp Asn Lys Gln Phe Asp Leu Ser Leu Asp
385                 390                 395                 400 cca gag cgg gcg cgg gaa tac cac gac gaa act ctg cca gca gat atc    1248
Pro Glu Arg Ala Arg Glu Tyr His Asp Glu Thr Leu Pro Ala Asp Ile
                405                 410                 415 tac aaa acg gca gaa ttc tgt tcg atg tgt gga ccg aag cac tgt ccg    1296
Tyr Lys Thr Ala Glu Phe Cys Ser Met Cys Gly Pro Lys His Cys Pro
            420                 425                 430 atg caa acc aag atc acc gag gaa gat cta acc gag ttg gaa aaa ttc    1344
Met Gln Thr Lys Ile Thr Glu Glu Asp Leu Thr Glu Leu Glu Lys Phe
        435                 440                 445 ctc gag aaa gat agc gct ctg gcg tag                                1371
Leu Glu Lys Asp Ser Ala Leu Ala
    450                 455

<210> SEQ ID NO 78
<211> LENGTH: 456
<212> TYPE: PRT
<213> ORGANISM: Synechococcus elongatus

<400> SEQUENCE: 78

Met Arg Ser Asp Trp Ile Ala Pro Arg Gly Gln Ala Asn Val Thr
1               5                   10                  15

Gln Met His Tyr Ala Arg Gln Gly Val Ile Thr Glu Glu Met Asp Phe
            20                  25                  30

Val Ala Arg Arg Glu Asn Leu Pro Ala Asp Leu Ile Arg Asp Glu Val
        35                  40                  45

Ala Arg Gly Arg Met Ile Ile Pro Ala Asn Ile Asn His Thr Asn Leu
    50                  55                  60

Glu Pro Met Ala Ile Gly Ile Ala Ser Lys Cys Lys Val Asn Ala Asn
65                  70                  75                  80

Ile Gly Ala Ser Pro Asn Ala Ser Asn Ile Asp Glu Glu Val Glu Lys
                85                  90                  95

Leu Lys Leu Ala Val Lys Tyr Gly Ala Asp Thr Val Met Asp Leu Ser
            100                 105                 110

Thr Gly Gly Gly Asn Leu Asp Glu Ile Arg Thr Ala Ile Ile Asn Ala
        115                 120                 125

Ser Pro Val Pro Ile Gly Thr Val Pro Val Tyr Gln Ala Leu Glu Ser
    130                 135                 140

Val His Gly Arg Ile Glu Lys Leu Ser Ala Asp Asp Phe Leu His Val
145                 150                 155                 160

Ile Glu Lys His Cys Glu Gln Gly Val Asp Tyr Gln Thr Ile His Ala
                165                 170                 175

Gly Leu Leu Ile Glu His Leu Pro Lys Val Lys Ser Arg Ile Thr Gly
            180                 185                 190

Ile Val Ser Arg Gly Gly Gly Ile Ala Gln Trp Met Leu Tyr His
        195                 200                 205

His Lys Gln Asn Pro Leu Tyr Thr His Phe Arg Asp Ile Ile Glu Ile
    210                 215                 220

Phe Lys Arg Tyr Asp Cys Ser Phe Ser Leu Gly Asp Ser Leu Arg Pro
225                 230                 235                 240

Gly Cys Leu His Asp Ala Ser Asp Asp Ala Gln Leu Ser Glu Leu Lys
                245                 250                 255
```

```
Thr Leu Gly Gln Leu Thr Arg Val Ala Trp Glu His Asp Gln Val
            260                 265                 270

Met Val Glu Gly Pro Gly His Val Pro Met Asp Gln Ile Glu Phe Asn
        275                 280                 285

Val Arg Lys Gln Met Glu Glu Cys Ser Glu Ala Pro Phe Tyr Val Leu
    290                 295                 300

Gly Pro Leu Val Thr Asp Ile Ala Pro Gly Tyr Asp His Ile Thr Ser
305                 310                 315                 320

Ala Ile Gly Ala Ala Met Ala Gly Trp Tyr Gly Thr Ala Met Leu Cys
                325                 330                 335

Tyr Val Thr Pro Lys Glu His Leu Gly Leu Pro Asn Ala Glu Asp Val
            340                 345                 350

Arg Asn Gly Leu Ile Ala Tyr Lys Ile Ala Ala His Ala Ala Asp Ile
        355                 360                 365

Ala Arg His Arg Pro Gly Ala Arg Asp Arg Asp Asp Glu Leu Ser Arg
    370                 375                 380

Ala Arg Tyr Ala Phe Asp Trp Asn Lys Gln Phe Asp Leu Ser Leu Asp
385                 390                 395                 400

Pro Glu Arg Ala Arg Glu Tyr His Asp Glu Thr Leu Pro Ala Asp Ile
                405                 410                 415

Tyr Lys Thr Ala Glu Phe Cys Ser Met Cys Gly Pro Lys His Cys Pro
            420                 425                 430

Met Gln Thr Lys Ile Thr Glu Glu Asp Leu Thr Glu Leu Glu Lys Phe
        435                 440                 445

Leu Glu Lys Asp Ser Ala Leu Ala
    450                 455

<210> SEQ ID NO 79
<211> LENGTH: 1764
<212> TYPE: DNA
<213> ORGANISM: Corynebacterium glutamicum
<220> FEATURE:
<221> NAME/KEY: CDS
<222> LOCATION: (1)..(1761)
<223> OTHER INFORMATION: ThiC gene from Corynebacterium glutamicum
      encoding an HMP-P synthase

<400> SEQUENCE: 79 atg acg cct acc caa aat gag atc cac ccg aaa cat agc tac tcc ccc        48
Met Thr Pro Thr Gln Asn Glu Ile His Pro Lys His Ser Tyr Ser Pro
1               5                   10                  15 atc cgc aag gac ggt ctc gag gtc ccg gag acc gaa atc cgc ctc gat       96
Ile Arg Lys Asp Gly Leu Glu Val Pro Glu Thr Glu Ile Arg Leu Asp
            20                  25                  30 gac tcg cca agc ggc ccc aac gaa ccc ttc cgc atc tac cgc acc cgt      144
Asp Ser Pro Ser Gly Pro Asn Glu Pro Phe Arg Ile Tyr Arg Thr Arg
        35                  40                  45 ggc cca gaa acc aac ccc aag cag gga ctt ccg cgg ctg cgc gag tca      192
Gly Pro Glu Thr Asn Pro Lys Gln Gly Leu Pro Arg Leu Arg Glu Ser
    50                  55                  60 tgg atc acc gcc cgc ggc gac gtt gcc acc tat cag ggg cgc gag cgt      240
Trp Ile Thr Ala Arg Gly Asp Val Ala Thr Tyr Gln Gly Arg Glu Arg
65                  70                  75                  80 ttg ctt atc gac gac ggc cgc tcg gca atg cgt cga ggt caa gct tcg      288
Leu Leu Ile Asp Asp Gly Arg Ser Ala Met Arg Arg Gly Gln Ala Ser
            85                  90                  95 gct gag tgg aaa ggc caa aaa cca gct cct ttg aag gcg cta cct ggc      336
Ala Glu Trp Lys Gly Gln Lys Pro Ala Pro Leu Lys Ala Leu Pro Gly
            100                 105                 110
```

```
aaa aga gtc acc caa atg gcc tat gca cgt gct ggc gtg att act cgt    384
Lys Arg Val Thr Gln Met Ala Tyr Ala Arg Ala Gly Val Ile Thr Arg
        115                 120                 125 gaa atg gag ttt gta gcg ctg cgc gaa cac gtt gat gcg gag ttt gtg    432
Glu Met Glu Phe Val Ala Leu Arg Glu His Val Asp Ala Glu Phe Val
130                 135                 140 cgc tct gag gtg gcg cgc ggt cgg gcc att att ccc aac aac gtc aac    480
Arg Ser Glu Val Ala Arg Gly Arg Ala Ile Ile Pro Asn Asn Val Asn
145                 150                 155                 160 cac ccc gaa tct gaa ccg atg att att ggt cgc aaa ttt ttg acc aaa    528
His Pro Glu Ser Glu Pro Met Ile Ile Gly Arg Lys Phe Leu Thr Lys
                165                 170                 175 atc aac gcc aat att ggc aat tct gcg gtc acc tct tca atc gag gaa    576
Ile Asn Ala Asn Ile Gly Asn Ser Ala Val Thr Ser Ser Ile Glu Glu
            180                 185                 190 gag gtg tcc aag ctg cag tgg gcc acg cgc tgg ggt gcc gat acc gtg    624
Glu Val Ser Lys Leu Gln Trp Ala Thr Arg Trp Gly Ala Asp Thr Val
        195                 200                 205 atg gat cta tcc acc ggc gat gat att cac acc acc cgc gaa tgg att    672
Met Asp Leu Ser Thr Gly Asp Asp Ile His Thr Thr Arg Glu Trp Ile
210                 215                 220 atc cgc aac tcc ccc gtt cct atc ggc acc gtc ccg atc tac caa gcg    720
Ile Arg Asn Ser Pro Val Pro Ile Gly Thr Val Pro Ile Tyr Gln Ala
225                 230                 235                 240 ctg gaa aaa gta aat ggc gtg gcc gca gac ctt aac tgg gaa gta ttc    768
Leu Glu Lys Val Asn Gly Val Ala Ala Asp Leu Asn Trp Glu Val Phe
                245                 250                 255 cgc gat acc atc att gag cag tgt gaa caa ggc gtg gac tat atg acc    816
Arg Asp Thr Ile Ile Glu Gln Cys Glu Gln Gly Val Asp Tyr Met Thr
            260                 265                 270 atc cac gcc ggc gtc ctg ctg gct tat atc cca ctg act acc cgt cgt    864
Ile His Ala Gly Val Leu Leu Ala Tyr Ile Pro Leu Thr Thr Arg Arg
        275                 280                 285 gtc acc ggc att gtc tcc cgc ggc gga tcc att atg gcc ggt tgg tgt    912
Val Thr Gly Ile Val Ser Arg Gly Gly Ser Ile Met Ala Gly Trp Cys
290                 295                 300 ctg gcg cat cac cgc gaa tca ttc ctc tac gag cat ttc gac gag ctg    960
Leu Ala His His Arg Glu Ser Phe Leu Tyr Glu His Phe Asp Glu Leu
305                 310                 315                 320 tgc gaa atc ttt gca caa tat gac gtc gca ttc tcc ctc ggt gat ggc   1008
Cys Glu Ile Phe Ala Gln Tyr Asp Val Ala Phe Ser Leu Gly Asp Gly
                325                 330                 335 cta cgc ccc gga tcg ctt gcc gat gcc aac gac gcc gcg caa ttc gcc   1056
Leu Arg Pro Gly Ser Leu Ala Asp Ala Asn Asp Ala Ala Gln Phe Ala
            340                 345                 350 gag ctg aaa acc att ggt gag ctc acc caa cgc gcc tgg gaa tac gat   1104
Glu Leu Lys Thr Ile Gly Glu Leu Thr Gln Arg Ala Trp Glu Tyr Asp
        355                 360                 365 gta caa gta atg gtc gaa gga cct gga cac gtg cca cta aac atg atc   1152
Val Gln Val Met Val Glu Gly Pro Gly His Val Pro Leu Asn Met Ile
370                 375                 380 cag gaa aac aac gag ctg gaa caa aag tgg gca gcg gac gca cct ttt   1200
Gln Glu Asn Asn Glu Leu Glu Gln Lys Trp Ala Ala Asp Ala Pro Phe
385                 390                 395                 400 tac act ctt gga cca cta gtt acc gac atc gct cca ggt tat gac cac   1248
Tyr Thr Leu Gly Pro Leu Val Thr Asp Ile Ala Pro Gly Tyr Asp His
                405                 410                 415 atc act tct gcc att ggt gca gct cac atc gcc atg ggt ggc acc gcc   1296
Ile Thr Ser Ala Ile Gly Ala Ala His Ile Ala Met Gly Gly Thr Ala
```

```
                420             425             430
atg ctg tgt tat gtc acc ccg aaa gaa cac ctt ggc ctg ccc aac cgt       1344
Met Leu Cys Tyr Val Thr Pro Lys Glu His Leu Gly Leu Pro Asn Arg
        435             440             445 gac gac gtc aaa acc ggc gta atc acc tac aag ctc gct gcc cac gca       1392
Asp Asp Val Lys Thr Gly Val Ile Thr Tyr Lys Leu Ala Ala His Ala
450             455             460 gca gat gtg gcc aag ggt cat ccc ggc gcg cgt gcc tgg gac gac gcc       1440
Ala Asp Val Ala Lys Gly His Pro Gly Ala Arg Ala Trp Asp Asp Ala
465             470             475             480 atg agt aaa gcg cgt ttt gaa ttc cgt tgg aat gat cag ttt gcg ctc       1488
Met Ser Lys Ala Arg Phe Glu Phe Arg Trp Asn Asp Gln Phe Ala Leu
                485             490             495 tcc ctc gac ccc gac act gca atc gct tat cac gac gaa acc ctg ccg       1536
Ser Leu Asp Pro Asp Thr Ala Ile Ala Tyr His Asp Glu Thr Leu Pro
        500             505             510 gca gag cct gcg aaa acc gca cac ttc tgt tca atg tgt ggc ccg aag       1584
Ala Glu Pro Ala Lys Thr Ala His Phe Cys Ser Met Cys Gly Pro Lys
    515             520             525 ttc tgc tcc atg cga att agc cag gac att cgc gat atg ttt ggc gat       1632
Phe Cys Ser Met Arg Ile Ser Gln Asp Ile Arg Asp Met Phe Gly Asp
530             535             540 caa atc gcg gaa ttg ggg atg cct ggg gtt ggg gat tct tct agt gct       1680
Gln Ile Ala Glu Leu Gly Met Pro Gly Val Gly Asp Ser Ser Ser Ala
545             550             555             560 gtt gct tct agt ggg gca cgg gag ggg atg gct gag aaa tcc cgg gaa       1728
Val Ala Ser Ser Gly Ala Arg Glu Gly Met Ala Glu Lys Ser Arg Glu
                565             570             575 ttt att gct ggt ggt gcg gag gtt tat cgg cgt tag                       1764
Phe Ile Ala Gly Gly Ala Glu Val Tyr Arg Arg
        580             585

<210> SEQ ID NO 80
<211> LENGTH: 587
<212> TYPE: PRT
<213> ORGANISM: Corynebacterium glutamicum

<400> SEQUENCE: 80

Met Thr Pro Thr Gln Asn Glu Ile His Pro Lys His Ser Tyr Ser Pro
1               5                   10                  15

Ile Arg Lys Asp Gly Leu Glu Val Pro Glu Thr Glu Ile Arg Leu Asp
            20                  25                  30

Asp Ser Pro Ser Gly Pro Asn Glu Pro Phe Arg Ile Tyr Arg Thr Arg
        35                  40                  45

Gly Pro Glu Thr Asn Pro Lys Gln Gly Leu Pro Arg Leu Arg Glu Ser
    50                  55                  60

Trp Ile Thr Ala Arg Gly Asp Val Ala Thr Tyr Gln Gly Arg Glu Arg
65                  70                  75                  80

Leu Leu Ile Asp Asp Gly Arg Ser Ala Met Arg Arg Gly Gln Ala Ser
                85                  90                  95

Ala Glu Trp Lys Gly Gln Lys Pro Ala Pro Leu Lys Ala Leu Pro Gly
            100                 105                 110

Lys Arg Val Thr Gln Met Ala Tyr Ala Arg Ala Gly Val Ile Thr Arg
        115                 120                 125

Glu Met Glu Phe Val Ala Leu Arg Glu His Val Asp Ala Glu Phe Val
    130                 135                 140

Arg Ser Glu Val Ala Arg Gly Arg Ala Ile Ile Pro Asn Asn Val Asn
145                 150                 155                 160
```

His Pro Glu Ser Glu Pro Met Ile Ile Gly Arg Lys Phe Leu Thr Lys
                    165                 170                 175

Ile Asn Ala Asn Ile Gly Asn Ser Ala Val Thr Ser Ser Ile Glu Glu
            180                 185                 190

Glu Val Ser Lys Leu Gln Trp Ala Thr Arg Trp Gly Ala Asp Thr Val
        195                 200                 205

Met Asp Leu Ser Thr Gly Asp Asp Ile His Thr Thr Arg Glu Trp Ile
210                 215                 220

Ile Arg Asn Ser Pro Val Pro Ile Gly Thr Val Pro Ile Tyr Gln Ala
225                 230                 235                 240

Leu Glu Lys Val Asn Gly Val Ala Ala Asp Leu Asn Trp Glu Val Phe
                245                 250                 255

Arg Asp Thr Ile Ile Glu Gln Cys Glu Gln Gly Val Asp Tyr Met Thr
                260                 265                 270

Ile His Ala Gly Val Leu Leu Ala Tyr Ile Pro Leu Thr Thr Arg Arg
        275                 280                 285

Val Thr Gly Ile Val Ser Arg Gly Gly Ser Ile Met Ala Gly Trp Cys
        290                 295                 300

Leu Ala His His Arg Glu Ser Phe Leu Tyr Glu His Phe Asp Glu Leu
305                 310                 315                 320

Cys Glu Ile Phe Ala Gln Tyr Asp Val Ala Phe Ser Leu Gly Asp Gly
                325                 330                 335

Leu Arg Pro Gly Ser Leu Ala Asp Ala Asn Asp Ala Ala Gln Phe Ala
                340                 345                 350

Glu Leu Lys Thr Ile Gly Glu Leu Thr Gln Arg Ala Trp Glu Tyr Asp
        355                 360                 365

Val Gln Val Met Val Glu Gly Pro Gly His Val Pro Leu Asn Met Ile
        370                 375                 380

Gln Glu Asn Asn Glu Leu Glu Gln Lys Trp Ala Ala Asp Ala Pro Phe
385                 390                 395                 400

Tyr Thr Leu Gly Pro Leu Val Thr Asp Ile Ala Pro Gly Tyr Asp His
                405                 410                 415

Ile Thr Ser Ala Ile Gly Ala Ala His Ile Ala Met Gly Gly Thr Ala
            420                 425                 430

Met Leu Cys Tyr Val Thr Pro Lys Glu His Leu Gly Leu Pro Asn Arg
        435                 440                 445

Asp Asp Val Lys Thr Gly Val Ile Thr Tyr Lys Leu Ala Ala His Ala
450                 455                 460

Ala Asp Val Ala Lys Gly His Pro Gly Ala Arg Ala Trp Asp Asp Ala
465                 470                 475                 480

Met Ser Lys Ala Arg Phe Glu Phe Arg Trp Asn Asp Gln Phe Ala Leu
                485                 490                 495

Ser Leu Asp Pro Asp Thr Ala Ile Ala Tyr His Asp Glu Thr Leu Pro
                500                 505                 510

Ala Glu Pro Ala Lys Thr Ala His Phe Cys Ser Met Cys Gly Pro Lys
        515                 520                 525

Phe Cys Ser Met Arg Ile Ser Gln Asp Ile Arg Asp Met Phe Gly Asp
        530                 535                 540

Gln Ile Ala Glu Leu Gly Met Pro Gly Val Gly Asp Ser Ser Ser Ala
545                 550                 555                 560

Val Ala Ser Ser Gly Ala Arg Glu Gly Met Ala Glu Lys Ser Arg Glu
                565                 570                 575

```
Phe Ile Ala Gly Gly Ala Glu Val Tyr Arg Arg
            580                 585

<210> SEQ ID NO 81
<211> LENGTH: 1869
<212> TYPE: DNA
<213> ORGANISM: Candidatus Baumannia cicadellinicola
<220> FEATURE:
<221> NAME/KEY: CDS
<222> LOCATION: (1)..(1866)
<223> OTHER INFORMATION: ThiC gene from Candidatus Baumannia
      cicadellinicola [WP_011520252] encoding HMP-P synthase

<400> SEQUENCE: 81 atg tca aga tca tca ata cct gct tca cgc cga gtg agc cgt gca aaa       48
Met Ser Arg Ser Ser Ile Pro Ala Ser Arg Arg Val Ser Arg Ala Lys
1               5                   10                  15 gca cag gct ttt atg gat agc tta aca ggt agt agc tat ttt cct aac       96
Ala Gln Ala Phe Met Asp Ser Leu Thr Gly Ser Ser Tyr Phe Pro Asn
            20                  25                  30 tca aga agg ata tat tta caa ggt aaa aca cct tca gta cat gta cca      144
Ser Arg Arg Ile Tyr Leu Gln Gly Lys Thr Pro Ser Val His Val Pro
        35                  40                  45 atg cgt gaa att aag cta cat cct aca ttg atc ggt aaa aac ggt gaa      192
Met Arg Glu Ile Lys Leu His Pro Thr Leu Ile Gly Lys Asn Gly Glu
    50                  55                  60 cat tat gag gat aat caa cct ata cca gtt tat gat act tca ggt cct      240
His Tyr Glu Asp Asn Gln Pro Ile Pro Val Tyr Asp Thr Ser Gly Pro
65                  70                  75                  80 tac ggt gat cct act ata gca att aac gta cgt aca ggt ctt aac cgg      288
Tyr Gly Asp Pro Thr Ile Ala Ile Asn Val Arg Thr Gly Leu Asn Arg
                85                  90                  95 tta cgc gag ata tgg att ctt gca cga caa gat agt gag cca ata agt      336
Leu Arg Glu Ile Trp Ile Leu Ala Arg Gln Asp Ser Glu Pro Ile Ser
            100                 105                 110 aat aat aat aac gat cgt cag agt tca gat aaa cag tta agt ttt act      384
Asn Asn Asn Asn Asp Arg Gln Ser Ser Asp Lys Gln Leu Ser Phe Thr
        115                 120                 125 act aac tat aat cca cgc cga gct agc tat gga cgc tgt att aca caa      432
Thr Asn Tyr Asn Pro Arg Arg Ala Ser Tyr Gly Arg Cys Ile Thr Gln
    130                 135                 140 tta cat tac gca cgt gcc ggt atc ata acg cca gaa atg gag ttt ata      480
Leu His Tyr Ala Arg Ala Gly Ile Ile Thr Pro Glu Met Glu Phe Ile
145                 150                 155                 160 gct tta cgt gaa aat atg ggc cga gaa cgt att agt agc aac gtg cta      528
Ala Leu Arg Glu Asn Met Gly Arg Glu Arg Ile Ser Ser Asn Val Leu
                165                 170                 175 cat cag cag cat tta ggt tct aac ttt ggt gct aaa aaa gct gat cat      576
His Gln Gln His Leu Gly Ser Asn Phe Gly Ala Lys Lys Ala Asp His
            180                 185                 190 att aca gca gaa ttt gtc cgg cag gaa gta gca gca gga cgt gct att      624
Ile Thr Ala Glu Phe Val Arg Gln Glu Val Ala Ala Gly Arg Ala Ile
        195                 200                 205 ata cct agt aat att aat cat cca gaa tct gag cca atg atc att ggc      672
Ile Pro Ser Asn Ile Asn His Pro Glu Ser Glu Pro Met Ile Ile Gly
    210                 215                 220 cgt aat ttt ctc gta aaa gta aat gca aat att ggt aac tca gca gta      720
Arg Asn Phe Leu Val Lys Val Asn Ala Asn Ile Gly Asn Ser Ala Val
225                 230                 235                 240 aca tct tct att gag gaa gaa gtc gaa aag tta gta tgg gct act cgt      768
Thr Ser Ser Ile Glu Glu Glu Val Glu Lys Leu Val Trp Ala Thr Arg
                245                 250                 255
```

```
tgg gga gct gat aca gtc atg gac tta tct act ggt agt tat att cac     816
Trp Gly Ala Asp Thr Val Met Asp Leu Ser Thr Gly Ser Tyr Ile His
        260                 265                 270 gaa act aga gaa tgg ata tta cgt aat agc cca gta cct ata ggt act     864
Glu Thr Arg Glu Trp Ile Leu Arg Asn Ser Pro Val Pro Ile Gly Thr
    275                 280                 285 gta cct atc tat caa gcg tta gaa aaa gta aat gga gtc ata gaa aat     912
Val Pro Ile Tyr Gln Ala Leu Glu Lys Val Asn Gly Val Ile Glu Asn
290                 295                 300 ctt aat tgg gat att ttc tac gag aca tta tta gaa caa gct aac caa     960
Leu Asn Trp Asp Ile Phe Tyr Glu Thr Leu Leu Glu Gln Ala Asn Gln
305                 310                 315                 320 gga gta gat tat ttt acg att cat gct ggc gta tta aaa cgt tat gtt    1008
Gly Val Asp Tyr Phe Thr Ile His Ala Gly Val Leu Lys Arg Tyr Val
                325                 330                 335 cta cta aca gct agt agg tta act ggt atc gta tcg cgt ggt ggc tct    1056
Leu Leu Thr Ala Ser Arg Leu Thr Gly Ile Val Ser Arg Gly Gly Ser
            340                 345                 350 att atg gct caa tgg agt tta gta cat aat cag gaa aac ttc ctt tat    1104
Ile Met Ala Gln Trp Ser Leu Val His Asn Gln Glu Asn Phe Leu Tyr
        355                 360                 365 gag cat ttt agt gaa att tgc aag ctt tgt gct gct tat gat att gct    1152
Glu His Phe Ser Glu Ile Cys Lys Leu Cys Ala Ala Tyr Asp Ile Ala
    370                 375                 380 cta tct ctt gga gat ggt cta aga ccc ggt tcc gta caa gat gct aat    1200
Leu Ser Leu Gly Asp Gly Leu Arg Pro Gly Ser Val Gln Asp Ala Asn
385                 390                 395                 400 gat gaa gca caa ttt tct gag tta cat aca cta ggc gaa tta act aaa    1248
Asp Glu Ala Gln Phe Ser Glu Leu His Thr Leu Gly Glu Leu Thr Lys
                405                 410                 415 att gcc tgg gaa tat gat gtg caa gta atg atc gaa gga cct ggt cat    1296
Ile Ala Trp Glu Tyr Asp Val Gln Val Met Ile Glu Gly Pro Gly His
            420                 425                 430 att cca cta cat atg att gag cgt aat atg act gat caa ctt aaa tat    1344
Ile Pro Leu His Met Ile Glu Arg Asn Met Thr Asp Gln Leu Lys Tyr
        435                 440                 445 tgc cac gaa gca cca ttc tac act ctc gga cca ctc aca aca gat att    1392
Cys His Glu Ala Pro Phe Tyr Thr Leu Gly Pro Leu Thr Thr Asp Ile
    450                 455                 460 gct cct ggt tat gac cac ttt act tca ggt att ggt gcc gca cta ata    1440
Ala Pro Gly Tyr Asp His Phe Thr Ser Gly Ile Gly Ala Ala Leu Ile
465                 470                 475                 480 ggc tgg ttt gga tgt gct atg ctg tgc tat gta act cct aaa gag cat    1488
Gly Trp Phe Gly Cys Ala Met Leu Cys Tyr Val Thr Pro Lys Glu His
                485                 490                 495 cta ggt tta cct aat aag gaa gac gta aaa cag ggt tta att gcc tat    1536
Leu Gly Leu Pro Asn Lys Glu Asp Val Lys Gln Gly Leu Ile Ala Tyr
            500                 505                 510 aaa att gcc gca cat gct gca gat cta gct aaa gga cat cct ggt gct    1584
Lys Ile Ala Ala His Ala Ala Asp Leu Ala Lys Gly His Pro Gly Ala
        515                 520                 525 caa ata cgt gat aat gct atg tca aaa gct cgt ttc gaa ttt cgc tgg    1632
Gln Ile Arg Asp Asn Ala Met Ser Lys Ala Arg Phe Glu Phe Arg Trp
    530                 535                 540 gaa gat caa ttt aac tta gct tta gat cct ttt acg gcg cgt atg tat    1680
Glu Asp Gln Phe Asn Leu Ala Leu Asp Pro Phe Thr Ala Arg Met Tyr
545                 550                 555                 560 cac gat gaa act ata ccg caa aca gca gga aaa tta gca aat ttt tgc    1728
His Asp Glu Thr Ile Pro Gln Thr Ala Gly Lys Leu Ala Asn Phe Cys
```

```
                565                 570                 575
tcg atg tgt ggt cct aag ttt tgt tct atg aag cta tca aaa aaa ata    1776
Ser Met Cys Gly Pro Lys Phe Cys Ser Met Lys Leu Ser Lys Lys Ile
            580                 585                 590 cgt aat tac act aat atg aaa aat ata aaa act att agt aat agt ttc    1824
Arg Asn Tyr Thr Asn Met Lys Asn Ile Lys Thr Ile Ser Asn Ser Phe
            595                 600                 605 atg aat aaa tta gat aat agc ggt att aaa aat gct gac cga taa        1869
Met Asn Lys Leu Asp Asn Ser Gly Ile Lys Asn Ala Asp Arg
            610                 615                 620

<210> SEQ ID NO 82
<211> LENGTH: 622
<212> TYPE: PRT
<213> ORGANISM: Candidatus Baumannia cicadellinicola

<400> SEQUENCE: 82

Met Ser Arg Ser Ser Ile Pro Ala Ser Arg Arg Val Ser Arg Ala Lys
1               5                   10                  15

Ala Gln Ala Phe Met Asp Ser Leu Thr Gly Ser Ser Tyr Phe Pro Asn
            20                  25                  30

Ser Arg Arg Ile Tyr Leu Gln Gly Lys Thr Pro Ser Val His Val Pro
        35                  40                  45

Met Arg Glu Ile Lys Leu His Pro Thr Leu Ile Gly Lys Asn Gly Glu
    50                  55                  60

His Tyr Glu Asp Asn Gln Pro Ile Pro Val Tyr Asp Thr Ser Gly Pro
65              70                  75                  80

Tyr Gly Asp Pro Thr Ile Ala Ile Asn Val Arg Thr Gly Leu Asn Arg
                85                  90                  95

Leu Arg Glu Ile Trp Ile Leu Ala Arg Gln Asp Ser Glu Pro Ile Ser
            100                 105                 110

Asn Asn Asn Asn Asp Arg Gln Ser Ser Asp Lys Gln Leu Ser Phe Thr
        115                 120                 125

Thr Asn Tyr Asn Pro Arg Arg Ala Ser Tyr Gly Arg Cys Ile Thr Gln
    130                 135                 140

Leu His Tyr Ala Arg Ala Gly Ile Ile Thr Pro Glu Met Glu Phe Ile
145                 150                 155                 160

Ala Leu Arg Glu Asn Met Gly Arg Glu Arg Ile Ser Ser Asn Val Leu
                165                 170                 175

His Gln Gln His Leu Gly Ser Asn Phe Gly Ala Lys Lys Ala Asp His
            180                 185                 190

Ile Thr Ala Glu Phe Val Arg Gln Glu Val Ala Ala Gly Arg Ala Ile
        195                 200                 205

Ile Pro Ser Asn Ile Asn His Pro Glu Ser Glu Pro Met Ile Ile Gly
    210                 215                 220

Arg Asn Phe Leu Val Lys Val Asn Ala Asn Ile Gly Asn Ser Ala Val
225                 230                 235                 240

Thr Ser Ser Ile Glu Glu Glu Val Glu Lys Leu Val Trp Ala Thr Arg
                245                 250                 255

Trp Gly Ala Asp Thr Val Met Asp Leu Ser Thr Gly Ser Tyr Ile His
            260                 265                 270

Glu Thr Arg Glu Trp Ile Leu Arg Asn Ser Pro Val Pro Ile Gly Thr
        275                 280                 285

Val Pro Ile Tyr Gln Ala Leu Glu Lys Val Asn Gly Val Ile Glu Asn
    290                 295                 300
```

```
Leu Asn Trp Asp Ile Phe Tyr Glu Thr Leu Leu Glu Gln Ala Asn Gln
305                 310                 315                 320

Gly Val Asp Tyr Phe Thr Ile His Ala Gly Val Leu Lys Arg Tyr Val
            325                 330                 335

Leu Leu Thr Ala Ser Arg Leu Thr Gly Ile Val Ser Arg Gly Gly Ser
        340                 345                 350

Ile Met Ala Gln Trp Ser Leu Val His Asn Gln Glu Asn Phe Leu Tyr
    355                 360                 365

Glu His Phe Ser Glu Ile Cys Lys Leu Cys Ala Ala Tyr Asp Ile Ala
370                 375                 380

Leu Ser Leu Gly Asp Gly Leu Arg Pro Gly Ser Val Gln Asp Ala Asn
385                 390                 395                 400

Asp Glu Ala Gln Phe Ser Glu Leu His Thr Leu Gly Glu Leu Thr Lys
                405                 410                 415

Ile Ala Trp Glu Tyr Asp Val Gln Val Met Ile Glu Gly Pro Gly His
            420                 425                 430

Ile Pro Leu His Met Ile Glu Arg Asn Met Thr Asp Gln Leu Lys Tyr
        435                 440                 445

Cys His Glu Ala Pro Phe Tyr Thr Leu Gly Pro Leu Thr Thr Asp Ile
450                 455                 460

Ala Pro Gly Tyr Asp His Phe Thr Ser Gly Ile Gly Ala Ala Leu Ile
465                 470                 475                 480

Gly Trp Phe Gly Cys Ala Met Leu Cys Tyr Val Thr Pro Lys Glu His
                485                 490                 495

Leu Gly Leu Pro Asn Lys Glu Asp Val Lys Gln Gly Leu Ile Ala Tyr
            500                 505                 510

Lys Ile Ala Ala His Ala Ala Asp Leu Ala Lys Gly His Pro Gly Ala
        515                 520                 525

Gln Ile Arg Asp Asn Ala Met Ser Lys Ala Arg Phe Glu Phe Arg Trp
    530                 535                 540

Glu Asp Gln Phe Asn Leu Ala Leu Asp Pro Phe Thr Ala Arg Met Tyr
545                 550                 555                 560

His Asp Glu Thr Ile Pro Gln Thr Ala Gly Lys Leu Ala Asn Phe Cys
                565                 570                 575

Ser Met Cys Gly Pro Lys Phe Cys Ser Met Lys Leu Ser Lys Lys Ile
            580                 585                 590

Arg Asn Tyr Thr Asn Met Lys Asn Ile Lys Thr Ile Ser Asn Ser Phe
        595                 600                 605

Met Asn Lys Leu Asp Asn Ser Gly Ile Lys Asn Ala Asp Arg
    610                 615                 620

<210> SEQ ID NO 83
<211> LENGTH: 636
<212> TYPE: DNA
<213> ORGANISM: Escherichia coli
<220> FEATURE:
<221> NAME/KEY: CDS
<222> LOCATION: (1)..(633)
<223> OTHER INFORMATION: ThiE gene from E. coli encoding thiamine
      phosphate synthase

<400> SEQUENCE: 83 atg tat cag cct gat ttt cct cct gta cct ttt cgt tca gga ctg tac    48
Met Tyr Gln Pro Asp Phe Pro Pro Val Pro Phe Arg Ser Gly Leu Tyr
1               5                   10                  15 ccg gtg gtg gac agc gta cag tgg atc gaa cgt ctg ttg gat gca ggc    96
Pro Val Val Asp Ser Val Gln Trp Ile Glu Arg Leu Leu Asp Ala Gly
```

```
                  20                  25                  30
gta cgt act ctc cag cta cgc atc aaa gat cgg cgc gat gaa gag gtg    144
Val Arg Thr Leu Gln Leu Arg Ile Lys Asp Arg Arg Asp Glu Glu Val
         35                  40                  45 gaa gcc gat gtc gtg gcg gca att gcg ctg ggc cgc cgc tat aac gcg    192
Glu Ala Asp Val Val Ala Ala Ile Ala Leu Gly Arg Arg Tyr Asn Ala
 50                  55                  60 cga ttg ttt atc aac gat tac tgg cgg ctg gcg atc aag cat cag gcg    240
Arg Leu Phe Ile Asn Asp Tyr Trp Arg Leu Ala Ile Lys His Gln Ala
 65                  70                  75                  80 tat ggc gtc cat ttg ggg cag gaa gat ttg caa gcc acc gat ctc aat    288
Tyr Gly Val His Leu Gly Gln Glu Asp Leu Gln Ala Thr Asp Leu Asn
                 85                  90                  95 gcc atc cgc gcg gca ggc ctg cgg ctg ggc gtt tcg aca cat gac gat    336
Ala Ile Arg Ala Ala Gly Leu Arg Leu Gly Val Ser Thr His Asp Asp
            100                 105                 110 atg gaa atc gac gtc gcg ctg gca gca cgc ccc tct tat atc gcg ctg    384
Met Glu Ile Asp Val Ala Leu Ala Ala Arg Pro Ser Tyr Ile Ala Leu
        115                 120                 125 gga cat gtg ttc ccg acg caa acc aaa cag atg cct tct gca ccg cag    432
Gly His Val Phe Pro Thr Gln Thr Lys Gln Met Pro Ser Ala Pro Gln
    130                 135                 140 ggg ctg gaa cag ctg gca cgg cat gtt gag cga ctg gcg gat tat ccc    480
Gly Leu Glu Gln Leu Ala Arg His Val Glu Arg Leu Ala Asp Tyr Pro
145                 150                 155                 160 acc gtg gcg att ggc ggt atc agt ctg gca cgc gcg cct gcg gtg ata    528
Thr Val Ala Ile Gly Gly Ile Ser Leu Ala Arg Ala Pro Ala Val Ile
                165                 170                 175 gca acg ggt gtc ggc agt atc gcc gtc gtc agc gcc att act caa gcc    576
Ala Thr Gly Val Gly Ser Ile Ala Val Val Ser Ala Ile Thr Gln Ala
            180                 185                 190 gca gac tgg cgt ttg gca acg gca cag ttg ctg gaa att gca gga gtt    624
Ala Asp Trp Arg Leu Ala Thr Ala Gln Leu Leu Glu Ile Ala Gly Val
        195                 200                 205 ggc gat gaa tga                                                    636
Gly Asp Glu
    210
```

<210> SEQ ID NO 84
<211> LENGTH: 211
<212> TYPE: PRT
<213> ORGANISM: Escherichia coli

<400> SEQUENCE: 84

```
Met Tyr Gln Pro Asp Phe Pro Pro Val Pro Phe Arg Ser Gly Leu Tyr
 1               5                  10                  15

Pro Val Val Asp Ser Val Gln Trp Ile Glu Arg Leu Leu Asp Ala Gly
                20                  25                  30

Val Arg Thr Leu Gln Leu Arg Ile Lys Asp Arg Arg Asp Glu Glu Val
            35                  40                  45

Glu Ala Asp Val Val Ala Ala Ile Ala Leu Gly Arg Arg Tyr Asn Ala
        50                  55                  60

Arg Leu Phe Ile Asn Asp Tyr Trp Arg Leu Ala Ile Lys His Gln Ala
 65                  70                  75                  80

Tyr Gly Val His Leu Gly Gln Glu Asp Leu Gln Ala Thr Asp Leu Asn
                 85                  90                  95

Ala Ile Arg Ala Ala Gly Leu Arg Leu Gly Val Ser Thr His Asp Asp
            100                 105                 110
```

```
Met Glu Ile Asp Val Ala Leu Ala Ala Arg Pro Ser Tyr Ile Ala Leu
            115                 120                 125
Gly His Val Phe Pro Thr Gln Thr Lys Gln Met Pro Ser Ala Pro Gln
        130                 135                 140
Gly Leu Glu Gln Leu Ala Arg His Val Glu Arg Leu Ala Asp Tyr Pro
145                 150                 155                 160
Thr Val Ala Ile Gly Gly Ile Ser Leu Ala Arg Ala Pro Ala Val Ile
                165                 170                 175
Ala Thr Gly Val Gly Ser Ile Ala Val Ser Ala Ile Thr Gln Ala
            180                 185                 190
Ala Asp Trp Arg Leu Ala Thr Ala Gln Leu Leu Glu Ile Ala Gly Val
        195                 200                 205
Gly Asp Glu
    210

<210> SEQ ID NO 85
<211> LENGTH: 756
<212> TYPE: DNA
<213> ORGANISM: Escherichia coli
<220> FEATURE:
<221> NAME/KEY: CDS
<222> LOCATION: (1)..(753)
<223> OTHER INFORMATION: ThiF gene from E. coli encoding a ThiS
      adenylyltransferase

<400> SEQUENCE: 85 atg aat gac cgt gac ttt atg cgt tat agc cgc caa atc ctg ctc gac         48
Met Asn Asp Arg Asp Phe Met Arg Tyr Ser Arg Gln Ile Leu Leu Asp
1               5                   10                  15 gat atc gct ctg gac ggg cag caa aaa ctg ctc gac agc cag gtg ctg         96
Asp Ile Ala Leu Asp Gly Gln Gln Lys Leu Leu Asp Ser Gln Val Leu
                20                  25                  30 att atc ggt ctg gcg ggg ctg ggt aca cct gct gcg ctg tac ctg gcg        144
Ile Ile Gly Leu Gly Gly Leu Gly Thr Pro Ala Ala Leu Tyr Leu Ala
            35                  40                  45 ggc gct ggc gtc ggg acg ctg gta ctg gca gat gac gac gat gtg cat        192
Gly Ala Gly Val Gly Thr Leu Val Leu Ala Asp Asp Asp Asp Val His
        50                  55                  60 tta agc aat ctg caa cga caa atc ctc ttt acc act gaa gat atc gat        240
Leu Ser Asn Leu Gln Arg Gln Ile Leu Phe Thr Thr Glu Asp Ile Asp
65                  70                  75                  80 cgc ccg aaa tcg cag gtc agc caa cag cga ctg aca cag ttg aat ccc        288
Arg Pro Lys Ser Gln Val Ser Gln Gln Arg Leu Thr Gln Leu Asn Pro
                85                  90                  95 gac att caa ctg aca gca tta caa caa cgg tta acg ggt gag gcg tta        336
Asp Ile Gln Leu Thr Ala Leu Gln Gln Arg Leu Thr Gly Glu Ala Leu
            100                 105                 110 aaa gat gcg gtt gca cgg gcc gat gtg gtg ctc gac tgt acc gac aat        384
Lys Asp Ala Val Ala Arg Ala Asp Val Val Leu Asp Cys Thr Asp Asn
        115                 120                 125 atg gcg act cgc cag gag att aat gcc gcc tgc gtg gca ctc aac acg        432
Met Ala Thr Arg Gln Glu Ile Asn Ala Ala Cys Val Ala Leu Asn Thr
    130                 135                 140 ccg ctt atc acc gcc agc gcg gtc gga ttt ggc ggt cag ttg atg gta        480
Pro Leu Ile Thr Ala Ser Ala Val Gly Phe Gly Gly Gln Leu Met Val
145                 150                 155                 160 ctg acg ccg ccc tgg gag cag ggg tgt tac cgc tgc ctg tgg cca gat        528
Leu Thr Pro Pro Trp Glu Gln Gly Cys Tyr Arg Cys Leu Trp Pro Asp
                165                 170                 175 aac cag gag cca gaa cgc aac tgc cgc acg gcg ggc gtg gtt ggc ccg        576
Asn Gln Glu Pro Glu Arg Asn Cys Arg Thr Ala Gly Val Val Gly Pro
```

```
                Asn Gln Glu Pro Glu Arg Asn Cys Arg Thr Ala Gly Val Val Gly Pro
                                180                 185                 190 gtg gtc ggg gtt atg ggc act ttg cag gca ctg gaa gcc att aag tta              624
Val Val Gly Val Met Gly Thr Leu Gln Ala Leu Glu Ala Ile Lys Leu
        195                 200                 205 tta agc ggt ata gag aca cct gcg gga gaa ctc cga ctg ttc gac ggt              672
Leu Ser Gly Ile Glu Thr Pro Ala Gly Glu Leu Arg Leu Phe Asp Gly
210                 215                 220 aaa tcg agc cag tgg cgc agc ctg gcg ttg cgc cgc gcc agt ggt tgc              720
Lys Ser Ser Gln Trp Arg Ser Leu Ala Leu Arg Arg Ala Ser Gly Cys
225                 230                 235                 240 ccg gta tgc gga gga agc aat gca gat cct gtt taa                              756
Pro Val Cys Gly Gly Ser Asn Ala Asp Pro Val
                245                 250

<210> SEQ ID NO 86
<211> LENGTH: 251
<212> TYPE: PRT
<213> ORGANISM: Escherichia coli

<400> SEQUENCE: 86

Met Asn Asp Arg Asp Phe Met Arg Tyr Ser Arg Gln Ile Leu Leu Asp
1               5                   10                  15

Asp Ile Ala Leu Asp Gly Gln Gln Lys Leu Leu Asp Ser Gln Val Leu
            20                  25                  30

Ile Ile Gly Leu Gly Gly Leu Gly Thr Pro Ala Ala Leu Tyr Leu Ala
        35                  40                  45

Gly Ala Gly Val Gly Thr Leu Val Leu Ala Asp Asp Asp Val His
    50                  55                  60

Leu Ser Asn Leu Gln Arg Gln Ile Leu Phe Thr Thr Glu Asp Ile Asp
65                  70                  75                  80

Arg Pro Lys Ser Gln Val Ser Gln Gln Arg Leu Thr Gln Leu Asn Pro
                85                  90                  95

Asp Ile Gln Leu Thr Ala Leu Gln Arg Leu Thr Gly Glu Ala Leu
            100                 105                 110

Lys Asp Ala Val Ala Arg Ala Asp Val Val Leu Asp Cys Thr Asp Asn
        115                 120                 125

Met Ala Thr Arg Gln Glu Ile Asn Ala Ala Cys Val Ala Leu Asn Thr
    130                 135                 140

Pro Leu Ile Thr Ala Ser Ala Val Gly Phe Gly Gly Gln Leu Met Val
145                 150                 155                 160

Leu Thr Pro Pro Trp Glu Gln Gly Cys Tyr Arg Cys Leu Trp Pro Asp
                165                 170                 175

Asn Gln Glu Pro Glu Arg Asn Cys Arg Thr Ala Gly Val Val Gly Pro
            180                 185                 190

Val Val Gly Val Met Gly Thr Leu Gln Ala Leu Glu Ala Ile Lys Leu
        195                 200                 205

Leu Ser Gly Ile Glu Thr Pro Ala Gly Glu Leu Arg Leu Phe Asp Gly
    210                 215                 220

Lys Ser Ser Gln Trp Arg Ser Leu Ala Leu Arg Arg Ala Ser Gly Cys
225                 230                 235                 240

Pro Val Cys Gly Gly Ser Asn Ala Asp Pro Val
                245                 250

<210> SEQ ID NO 87
<211> LENGTH: 201
<212> TYPE: DNA
```

```
<213> ORGANISM: Escherichia coli
<220> FEATURE:
<221> NAME/KEY: CDS
<222> LOCATION: (1)..(198)
<223> OTHER INFORMATION: ThiS gene from E. coli encoding Sulfur-carrier
      protein

<400> SEQUENCE: 87 atg cag atc ctg ttt aac gat caa gcg atg cag tgc gcc gcc ggg caa      48
Met Gln Ile Leu Phe Asn Asp Gln Ala Met Gln Cys Ala Ala Gly Gln
1               5                   10                  15 act gtt cac gaa cta ctg gag caa ctc gac caa cga caa gcg ggc gcg      96
Thr Val His Glu Leu Leu Glu Gln Leu Asp Gln Arg Gln Ala Gly Ala
                20                  25                  30 gct ctg gcg att aat cag caa atc gtc ccg cgt gag cag tgg gcg caa     144
Ala Leu Ala Ile Asn Gln Gln Ile Val Pro Arg Glu Gln Trp Ala Gln
            35                  40                  45 cat atc gtg cag gat ggc gac cag atc ctg ctt ttt cag gtt att gca     192
His Ile Val Gln Asp Gly Asp Gln Ile Leu Leu Phe Gln Val Ile Ala
        50                  55                  60 ggg ggt tga                                                         201
Gly Gly
65

<210> SEQ ID NO 88
<211> LENGTH: 66
<212> TYPE: PRT
<213> ORGANISM: Escherichia coli

<400> SEQUENCE: 88

Met Gln Ile Leu Phe Asn Asp Gln Ala Met Gln Cys Ala Ala Gly Gln
1               5                   10                  15

Thr Val His Glu Leu Leu Glu Gln Leu Asp Gln Arg Gln Ala Gly Ala
                20                  25                  30

Ala Leu Ala Ile Asn Gln Gln Ile Val Pro Arg Glu Gln Trp Ala Gln
            35                  40                  45

His Ile Val Gln Asp Gly Asp Gln Ile Leu Leu Phe Gln Val Ile Ala
        50                  55                  60

Gly Gly
65

<210> SEQ ID NO 89
<211> LENGTH: 771
<212> TYPE: DNA
<213> ORGANISM: Escherichia coli
<220> FEATURE:
<221> NAME/KEY: CDS
<222> LOCATION: (1)..(768)
<223> OTHER INFORMATION: ThiG gene from E. coli encoding Thiazole
      synthase

<400> SEQUENCE: 89 atg tta cgt att gcg gac aaa acg ttt gat tca cat ctg ttt acc ggc      48
Met Leu Arg Ile Ala Asp Lys Thr Phe Asp Ser His Leu Phe Thr Gly
1               5                   10                  15 aca ggg aaa ttc gct tct tca caa ctg atg gtg gag gcg atc cgc gct      96
Thr Gly Lys Phe Ala Ser Ser Gln Leu Met Val Glu Ala Ile Arg Ala
                20                  25                  30 tcc ggc agc cag ctg gtg aca ctg gcg atg aaa cgt gtc gac ttg cgc     144
Ser Gly Ser Gln Leu Val Thr Leu Ala Met Lys Arg Val Asp Leu Arg
            35                  40                  45 cag cac aac gac gct atc ctc gaa ccg ctt atc gcg gcg ggt gtg acc     192
Gln His Asn Asp Ala Ile Leu Glu Pro Leu Ile Ala Ala Gly Val Thr
```

```
                    50                   55                   60
ctg ctg cca aat aca tcc ggg gcg aaa aca gcg gaa gaa gcc att ttc      240
Leu Leu Pro Asn Thr Ser Gly Ala Lys Thr Ala Glu Glu Ala Ile Phe
 65                  70                   75                   80 gcc gcc cat ctg gct cgt gaa gcg tta ggc aca aac tgg tta aaa tta      288
Ala Ala His Leu Ala Arg Glu Ala Leu Gly Thr Asn Trp Leu Lys Leu
                 85                   90                   95 gag att cac cct gac gcc cgc tgg ctg ttg ccc gat ccc atc gaa acc      336
Glu Ile His Pro Asp Ala Arg Trp Leu Leu Pro Asp Pro Ile Glu Thr
                    100                  105                  110 ctg aaa gcc gcc gaa acg ctg gta caa cag gga ttt gtc gtg ctg cct      384
Leu Lys Ala Ala Glu Thr Leu Val Gln Gln Gly Phe Val Val Leu Pro
            115                  120                  125 tac tgc ggg gcc gat ccg gta ttg tgt aaa cgt ctg gaa gaa gtc ggc      432
Tyr Cys Gly Ala Asp Pro Val Leu Cys Lys Arg Leu Glu Glu Val Gly
        130                  135                  140 tgt gca gcg gtg atg ccg ctc ggc gcg ccg att ggc tcg aat cag gga      480
Cys Ala Ala Val Met Pro Leu Gly Ala Pro Ile Gly Ser Asn Gln Gly
145                  150                  155                  160 ctg gaa acc cgc gcc atg ctg gag att att atc cag cag gcc aca gtg      528
Leu Glu Thr Arg Ala Met Leu Glu Ile Ile Ile Gln Gln Ala Thr Val
                 165                  170                  175 ccg gtg gtt gtc gat gct ggc atc ggc gtt ccc agc cat gcc gcg cag      576
Pro Val Val Val Asp Ala Gly Ile Gly Val Pro Ser His Ala Ala Gln
                    180                  185                  190 gcg ctg gaa atg ggg gcc gac gcg gtg tta gtg aat acg gcg att gcc      624
Ala Leu Glu Met Gly Ala Asp Ala Val Leu Val Asn Thr Ala Ile Ala
            195                  200                  205 gtc gcg gac gat ccc gtc aac atg gcg aag gca ttt cgt ctg gcg gta      672
Val Ala Asp Asp Pro Val Asn Met Ala Lys Ala Phe Arg Leu Ala Val
        210                  215                  220 gaa gca ggc cta ctg gca cgt cag tcc gga ccg ggc agc cgc agt tat      720
Glu Ala Gly Leu Leu Ala Arg Gln Ser Gly Pro Gly Ser Arg Ser Tyr
225                  230                  235                  240 ttt gct cat gcc acc agc ccg ctg acc gga ttt ctg gag gca tcg gca      768
Phe Ala His Ala Thr Ser Pro Leu Thr Gly Phe Leu Glu Ala Ser Ala
                 245                  250                  255 tga                                                                   771
```

<210> SEQ ID NO 90
<211> LENGTH: 256
<212> TYPE: PRT
<213> ORGANISM: Escherichia coli

<400> SEQUENCE: 90

```
Met Leu Arg Ile Ala Asp Lys Thr Phe Asp Ser His Leu Phe Thr Gly
 1               5                  10                  15

Thr Gly Lys Phe Ala Ser Ser Gln Leu Met Val Glu Ala Ile Arg Ala
                20                  25                  30

Ser Gly Ser Gln Leu Val Thr Leu Ala Met Lys Arg Val Asp Leu Arg
            35                  40                  45

Gln His Asn Asp Ala Ile Leu Glu Pro Leu Ile Ala Ala Gly Val Thr
        50                  55                  60

Leu Leu Pro Asn Thr Ser Gly Ala Lys Thr Ala Glu Glu Ala Ile Phe
65                  70                  75                  80

Ala Ala His Leu Ala Arg Glu Ala Leu Gly Thr Asn Trp Leu Lys Leu
                85                  90                  95

Glu Ile His Pro Asp Ala Arg Trp Leu Leu Pro Asp Pro Ile Glu Thr
```

```
                       100                 105                 110
Leu Lys Ala Ala Glu Thr Leu Val Gln Gln Gly Phe Val Val Leu Pro
            115                 120                 125

Tyr Cys Gly Ala Asp Pro Val Leu Cys Lys Arg Leu Glu Glu Val Gly
            130                 135                 140

Cys Ala Ala Val Met Pro Leu Gly Ala Pro Ile Gly Ser Asn Gln Gly
145                 150                 155                 160

Leu Glu Thr Arg Ala Met Leu Glu Ile Ile Gln Gln Ala Thr Val
                165                 170                 175

Pro Val Val Val Asp Ala Gly Ile Gly Val Pro Ser His Ala Ala Gln
                180                 185                 190

Ala Leu Glu Met Gly Ala Asp Ala Val Leu Val Asn Thr Ala Ile Ala
            195                 200                 205

Val Ala Asp Asp Pro Val Asn Met Ala Lys Ala Phe Arg Leu Ala Val
            210                 215                 220

Glu Ala Gly Leu Leu Ala Arg Gln Ser Gly Pro Gly Ser Arg Ser Tyr
225                 230                 235                 240

Phe Ala His Ala Thr Ser Pro Leu Thr Gly Phe Leu Glu Ala Ser Ala
                245                 250                 255

<210> SEQ ID NO 91
<211> LENGTH: 1134
<212> TYPE: DNA
<213> ORGANISM: Escherichia coli
<220> FEATURE:
<221> NAME/KEY: CDS
<222> LOCATION: (1)..(1131)
<223> OTHER INFORMATION: ThiH gene from E. coli encoding 2-iminoacetate
      synthase

<400> SEQUENCE: 91 atg aaa acc ttc agc gat cgc tgg cga caa ctg gac tgg gac gac atc        48
Met Lys Thr Phe Ser Asp Arg Trp Arg Gln Leu Asp Trp Asp Asp Ile
1               5                   10                  15 cgc ctg cgt atc aac ggc aaa acg gct gct gac gta gag cgg gcg cta        96
Arg Leu Arg Ile Asn Gly Lys Thr Ala Ala Asp Val Glu Arg Ala Leu
                20                  25                  30 aat gcc tcg caa ctc acc cgc gac gac atg atg gcg ctg tta tcg cct       144
Asn Ala Ser Gln Leu Thr Arg Asp Asp Met Met Ala Leu Leu Ser Pro
            35                  40                  45 gcc gcc agt ggc tat ctg gaa caa ctg gcc caa cgg gcg cag cgt ctg       192
Ala Ala Ser Gly Tyr Leu Glu Gln Leu Ala Gln Arg Ala Gln Arg Leu
        50                  55                  60 acc cgt cag cga ttt ggc aac aca gtt agt ttc tac gtc ccg ctt tat       240
Thr Arg Gln Arg Phe Gly Asn Thr Val Ser Phe Tyr Val Pro Leu Tyr
65                  70                  75                  80 ctt tcc aat ctt tgc gct aac gac tgc acg tac tgt gga ttt tcc atg       288
Leu Ser Asn Leu Cys Ala Asn Asp Cys Thr Tyr Cys Gly Phe Ser Met
                85                  90                  95 agt aat cgc atc aag cgc aaa acg ctg gat gaa gcg gat att gcc agg       336
Ser Asn Arg Ile Lys Arg Lys Thr Leu Asp Glu Ala Asp Ile Ala Arg
            100                 105                 110 gaa agt gcc gct ata cgg gag atg ggc ttt gaa cat ctg ctg tta gtc       384
Glu Ser Ala Ala Ile Arg Glu Met Gly Phe Glu His Leu Leu Leu Val
        115                 120                 125 act ggt gaa cat cag gcg aaa gtg ggg atg gat tac ttt cgt cgt cat       432
Thr Gly Glu His Gln Ala Lys Val Gly Met Asp Tyr Phe Arg Arg His
    130                 135                 140 ctc cct gcc ctt cgt gaa cag ttc tct tca cta cag atg gaa gtg caa       480
```

```
Leu Pro Ala Leu Arg Glu Gln Phe Ser Ser Leu Gln Met Glu Val Gln
145                 150                 155                 160 ccg ctg gcg gag acg gaa tac gcc gag tta aag caa ctt ggt ctg gat      528
Pro Leu Ala Glu Thr Glu Tyr Ala Glu Leu Lys Gln Leu Gly Leu Asp
                165                 170                 175 ggc gtg atg gtt tat cag gag aca tat cac gag gcg act tat gcc cgc      576
Gly Val Met Val Tyr Gln Glu Thr Tyr His Glu Ala Thr Tyr Ala Arg
            180                 185                 190 cat cat ctg aaa ggc aaa aaa cag gac ttc ttc tgg cgg ctg gaa acg      624
His His Leu Lys Gly Lys Lys Gln Asp Phe Phe Trp Arg Leu Glu Thr
                195                 200                 205 ccg gat cgg ctg ggg cgt gcg ggg att gat aag ata ggc ctc ggc gcg      672
Pro Asp Arg Leu Gly Arg Ala Gly Ile Asp Lys Ile Gly Leu Gly Ala
210                 215                 220 cta att ggc ctt tcc gac aac tgg cgc gtt gac agc tat atg gtt gcc      720
Leu Ile Gly Leu Ser Asp Asn Trp Arg Val Asp Ser Tyr Met Val Ala
225                 230                 235                 240 gaa cat ttg cta tgg ctg caa cag cat tac tgg caa agc cgt tac tct      768
Glu His Leu Leu Trp Leu Gln Gln His Tyr Trp Gln Ser Arg Tyr Ser
                245                 250                 255 gtc tcc ttt ccg cgc ctg cgc ccg tgt act ggc ggc att gag cct gcg      816
Val Ser Phe Pro Arg Leu Arg Pro Cys Thr Gly Gly Ile Glu Pro Ala
            260                 265                 270 tcg att atg gat gaa cgc cag tta gtg caa acc atc tgc gcc ttc cga      864
Ser Ile Met Asp Glu Arg Gln Leu Val Gln Thr Ile Cys Ala Phe Arg
        275                 280                 285 ctg ctt gca ccg gag att gaa ctg tca ctc tcc acg cgg gaa tca ccg      912
Leu Leu Ala Pro Glu Ile Glu Leu Ser Leu Ser Thr Arg Glu Ser Pro
290                 295                 300 tgg ttt cgc gat cgc gtt att ccg ctg gcg atc aat aac gtc agc gcc      960
Trp Phe Arg Asp Arg Val Ile Pro Leu Ala Ile Asn Asn Val Ser Ala
305                 310                 315                 320 ttc tcg aaa acg cag cca ggt ggc tat gcc gat aat cac ccc gag ttg     1008
Phe Ser Lys Thr Gln Pro Gly Gly Tyr Ala Asp Asn His Pro Glu Leu
                325                 330                 335 gaa cag ttc tca ccg cac gac gat cgc aga ccg gaa gcg gtt gct gcc     1056
Glu Gln Phe Ser Pro His Asp Asp Arg Arg Pro Glu Ala Val Ala Ala
            340                 345                 350 gcg tta acc gct cag ggt ttg cag ccg gta tgg aaa gac tgg gac agc     1104
Ala Leu Thr Ala Gln Gly Leu Gln Pro Val Trp Lys Asp Trp Asp Ser
        355                 360                 365 tat ctg gga cgc gcc tcg caa aga cta tga                             1134
Tyr Leu Gly Arg Ala Ser Gln Arg Leu
    370                 375

<210> SEQ ID NO 92
<211> LENGTH: 377
<212> TYPE: PRT
<213> ORGANISM: Escherichia coli

<400> SEQUENCE: 92

Met Lys Thr Phe Ser Asp Arg Trp Arg Gln Leu Asp Trp Asp Asp Ile
1                   5                   10                  15

Arg Leu Arg Ile Asn Gly Lys Thr Ala Ala Asp Val Glu Arg Ala Leu
                20                  25                  30

Asn Ala Ser Gln Leu Thr Arg Asp Asp Met Met Ala Leu Leu Ser Pro
            35                  40                  45

Ala Ala Ser Gly Tyr Leu Glu Gln Leu Ala Gln Arg Ala Gln Arg Leu
        50                  55                  60
```

```
Thr Arg Gln Arg Phe Gly Asn Thr Val Ser Phe Tyr Val Pro Leu Tyr
 65                  70                  75                  80

Leu Ser Asn Leu Cys Ala Asn Asp Cys Thr Tyr Cys Gly Phe Ser Met
                 85                  90                  95

Ser Asn Arg Ile Lys Arg Lys Thr Leu Asp Glu Ala Asp Ile Ala Arg
            100                 105                 110

Glu Ser Ala Ala Ile Arg Glu Met Gly Phe Glu His Leu Leu Leu Val
        115                 120                 125

Thr Gly Glu His Gln Ala Lys Val Gly Met Asp Tyr Phe Arg Arg His
130                 135                 140

Leu Pro Ala Leu Arg Glu Gln Phe Ser Ser Leu Gln Met Glu Val Gln
145                 150                 155                 160

Pro Leu Ala Glu Thr Glu Tyr Ala Glu Leu Lys Gln Leu Gly Leu Asp
                165                 170                 175

Gly Val Met Val Tyr Gln Glu Thr Tyr His Glu Ala Thr Tyr Ala Arg
            180                 185                 190

His His Leu Lys Gly Lys Lys Gln Asp Phe Phe Trp Arg Leu Glu Thr
        195                 200                 205

Pro Asp Arg Leu Gly Arg Ala Gly Ile Asp Lys Ile Gly Leu Gly Ala
210                 215                 220

Leu Ile Gly Leu Ser Asp Asn Trp Arg Val Asp Ser Tyr Met Val Ala
225                 230                 235                 240

Glu His Leu Leu Trp Leu Gln His Tyr Trp Gln Ser Arg Tyr Ser
                245                 250                 255

Val Ser Phe Pro Arg Leu Arg Pro Cys Thr Gly Gly Ile Glu Pro Ala
            260                 265                 270

Ser Ile Met Asp Glu Arg Gln Leu Val Gln Thr Ile Cys Ala Phe Arg
        275                 280                 285

Leu Leu Ala Pro Glu Ile Glu Leu Ser Leu Ser Thr Arg Glu Ser Pro
290                 295                 300

Trp Phe Arg Asp Arg Val Ile Pro Leu Ala Ile Asn Asn Val Ser Ala
305                 310                 315                 320

Phe Ser Lys Thr Gln Pro Gly Gly Tyr Ala Asp Asn His Pro Glu Leu
                325                 330                 335

Glu Gln Phe Ser Pro His Asp Asp Arg Arg Pro Glu Ala Val Ala Ala
            340                 345                 350

Ala Leu Thr Ala Gln Gly Leu Gln Pro Val Trp Lys Asp Trp Asp Ser
        355                 360                 365

Tyr Leu Gly Arg Ala Ser Gln Arg Leu
370                 375

<210> SEQ ID NO 93
<211> LENGTH: 1110
<212> TYPE: DNA
<213> ORGANISM: Escherichia coli
<220> FEATURE:
<221> NAME/KEY: CDS
<222> LOCATION: (1)..(1107)
<223> OTHER INFORMATION: ThiO gene from E. coli encoding Glycine oxidase

<400> SEQUENCE: 93 atg aaa agg cat tat gaa gca gtg gtg att gga ggc gga att atc ggt    48
Met Lys Arg His Tyr Glu Ala Val Val Ile Gly Gly Gly Ile Ile Gly
  1               5                  10                  15 tcc gca att gct tat tat ttg gca aag gaa aac aaa aac acc gca ttg    96
Ser Ala Ile Ala Tyr Tyr Leu Ala Lys Glu Asn Lys Asn Thr Ala Leu
             20                  25                  30
```

```
ttt gaa agc gga aca atg ggc gga aga acg aca agt gcc gct gcc gga       144
Phe Glu Ser Gly Thr Met Gly Gly Arg Thr Thr Ser Ala Ala Ala Gly
         35                  40                  45 atg ctg ggc gcc cat gcc gaa tgc gag gaa cgt gac gcg ttt ttt gat       192
Met Leu Gly Ala His Ala Glu Cys Glu Glu Arg Asp Ala Phe Phe Asp
 50                  55                  60 ttc gct atg cac agt cag cgt ctg tac aaa ggt ctt gga gaa gag ctt       240
Phe Ala Met His Ser Gln Arg Leu Tyr Lys Gly Leu Gly Glu Glu Leu
65                  70                  75                  80 tat gca tta tcc ggt gtg gat atc agg cag cat aac ggc ggt atg ttt       288
Tyr Ala Leu Ser Gly Val Asp Ile Arg Gln His Asn Gly Gly Met Phe
                 85                  90                  95 aag ctt gca ttt tct gaa gaa gat gtg ctg cag ctg aga cag atg gac       336
Lys Leu Ala Phe Ser Glu Glu Asp Val Leu Gln Leu Arg Gln Met Asp
            100                 105                 110 gat ttg gac tct gtc agc tgg tat tca aaa gaa gag gtg tta gaa aaa       384
Asp Leu Asp Ser Val Ser Trp Tyr Ser Lys Glu Glu Val Leu Glu Lys
        115                 120                 125 gag ccg tat gcg tct ggt gac atc ttt ggt gca tct ttt att cag gat       432
Glu Pro Tyr Ala Ser Gly Asp Ile Phe Gly Ala Ser Phe Ile Gln Asp
130                 135                 140 gat gtg cat gtg gag cct tat ttt gtt tgc aag gca tat gtg aaa gca       480
Asp Val His Val Glu Pro Tyr Phe Val Cys Lys Ala Tyr Val Lys Ala
145                 150                 155                 160 gca aaa atg ctt ggg gcg gag att ttt gag cat acg ccc gtc ctg cat       528
Ala Lys Met Leu Gly Ala Glu Ile Phe Glu His Thr Pro Val Leu His
                165                 170                 175 gtc gaa cgt gac ggt gaa gcc ctg ttc atc aag acc cct agc gga gac       576
Val Glu Arg Asp Gly Glu Ala Leu Phe Ile Lys Thr Pro Ser Gly Asp
            180                 185                 190 gta tgg gct aat cat gtt gtc gtt gcc agc ggg gtg tgg agc gga atg       624
Val Trp Ala Asn His Val Val Val Ala Ser Gly Val Trp Ser Gly Met
        195                 200                 205 ttt ttt aaa cag ctt gga ctg aac aat gct ttt ctc cct gta aaa ggg       672
Phe Phe Lys Gln Leu Gly Leu Asn Asn Ala Phe Leu Pro Val Lys Gly
210                 215                 220 gag tgc ctg tcc gtt tgg aat gat gat atc ccg ctg aca aaa acg ctt       720
Glu Cys Leu Ser Val Trp Asn Asp Asp Ile Pro Leu Thr Lys Thr Leu
225                 230                 235                 240 tac cat gat cac tgc tat atc gta ccg aga aaa agc gga aga ctg gtt       768
Tyr His Asp His Cys Tyr Ile Val Pro Arg Lys Ser Gly Arg Leu Val
                245                 250                 255 gtc ggc gcg aca atg aag ccg ggg gac tgg agt gaa aca ccg gat ctt       816
Val Gly Ala Thr Met Lys Pro Gly Asp Trp Ser Glu Thr Pro Asp Leu
            260                 265                 270 ggc gga ttg gaa tct gtt atg aaa aaa gca aaa acg atg ctg ccg gct       864
Gly Gly Leu Glu Ser Val Met Lys Lys Ala Lys Thr Met Leu Pro Ala
        275                 280                 285 ata cag aat atg aag gtg gat cgt ttt tgg gcg gga ctc cgt ccg gga       912
Ile Gln Asn Met Lys Val Asp Arg Phe Trp Ala Gly Leu Arg Pro Gly
290                 295                 300 aca aag gat gga aaa ccg tac atc ggc aga cat cct gag gac agc cgt       960
Thr Lys Asp Gly Lys Pro Tyr Ile Gly Arg His Pro Glu Asp Ser Arg
305                 310                 315                 320 att tta ttt gcg gct ggc cat ttc aga aac ggg atc ctg ctt gct ccc      1008
Ile Leu Phe Ala Ala Gly His Phe Arg Asn Gly Ile Leu Leu Ala Pro
                325                 330                 335 gca acg ggc gct ttg atc agt gat ctc atc atg aat aaa gag gtc aac      1056
Ala Thr Gly Ala Leu Ile Ser Asp Leu Ile Met Asn Lys Glu Val Asn
```

```
              340             345             350
caa gac tgg ctg cac gca ttc cga att gat cgc aag gag gcg gtt cag         1104
Gln Asp Trp Leu His Ala Phe Arg Ile Asp Arg Lys Glu Ala Val Gln
        355                 360                 365 ata tga                                                                  1110
Ile <210> SEQ ID NO 94
<211> LENGTH: 369
<212> TYPE: PRT
<213> ORGANISM: Escherichia coli

<400> SEQUENCE: 94

Met Lys Arg His Tyr Glu Ala Val Val Ile Gly Gly Ile Ile Gly
1               5                   10                  15

Ser Ala Ile Ala Tyr Tyr Leu Ala Lys Glu Asn Lys Asn Thr Ala Leu
                20                  25                  30

Phe Glu Ser Gly Thr Met Gly Gly Arg Thr Thr Ser Ala Ala Ala Gly
            35                  40                  45

Met Leu Gly Ala His Ala Glu Cys Glu Glu Arg Asp Ala Phe Phe Asp
        50                  55                  60

Phe Ala Met His Ser Gln Arg Leu Tyr Lys Gly Leu Gly Glu Glu Leu
65                  70                  75                  80

Tyr Ala Leu Ser Gly Val Asp Ile Arg Gln His Asn Gly Gly Met Phe
                85                  90                  95

Lys Leu Ala Phe Ser Glu Glu Asp Val Leu Gln Leu Arg Gln Met Asp
            100                 105                 110

Asp Leu Asp Ser Val Ser Trp Tyr Ser Lys Glu Glu Val Leu Glu Lys
        115                 120                 125

Glu Pro Tyr Ala Ser Gly Asp Ile Phe Gly Ala Ser Phe Ile Gln Asp
    130                 135                 140

Asp Val His Val Glu Pro Tyr Phe Val Cys Lys Ala Tyr Val Lys Ala
145                 150                 155                 160

Ala Lys Met Leu Gly Ala Glu Ile Phe Glu His Thr Pro Val Leu His
                165                 170                 175

Val Glu Arg Asp Gly Glu Ala Leu Phe Ile Lys Thr Pro Ser Gly Asp
            180                 185                 190

Val Trp Ala Asn His Val Val Ala Ser Gly Val Trp Ser Gly Met
        195                 200                 205

Phe Phe Lys Gln Leu Gly Leu Asn Asn Ala Phe Leu Pro Val Lys Gly
    210                 215                 220

Glu Cys Leu Ser Val Trp Asn Asp Asp Ile Pro Leu Thr Lys Thr Leu
225                 230                 235                 240

Tyr His Asp His Cys Tyr Ile Val Pro Arg Lys Ser Gly Arg Leu Val
                245                 250                 255

Val Gly Ala Thr Met Lys Pro Gly Asp Trp Ser Glu Thr Pro Asp Leu
            260                 265                 270

Gly Gly Leu Glu Ser Val Met Lys Lys Ala Lys Thr Met Leu Pro Ala
        275                 280                 285

Ile Gln Asn Met Lys Val Asp Arg Phe Trp Ala Gly Leu Arg Pro Gly
    290                 295                 300

Thr Lys Asp Gly Lys Pro Tyr Ile Gly Arg His Pro Glu Asp Ser Arg
305                 310                 315                 320

Ile Leu Phe Ala Ala Gly His Phe Arg Asn Gly Ile Leu Leu Ala Pro
                325                 330                 335
```

```
                Ala Thr Gly Ala Leu Ile Ser Asp Leu Ile Met Asn Lys Glu Val Asn
                                340                 345                 350

Gln Asp Trp Leu His Ala Phe Arg Ile Asp Arg Lys Glu Ala Val Gln
                            355                 360                 365

Ile

<210> SEQ ID NO 95
<211> LENGTH: 1098
<212> TYPE: DNA
<213> ORGANISM: Pseudomonas putida
<220> FEATURE:
<221> NAME/KEY: CDS
<222> LOCATION: (1)..(1095)
<223> OTHER INFORMATION: ThiO gene from Pseudomonas putida encoding a
      Glycine oxidase

<400> SEQUENCE: 95 atg agc aag caa gta gtg gtg gtc ggt ggc ggg gtc att ggc ctg ctg        48
Met Ser Lys Gln Val Val Val Val Gly Gly Gly Val Ile Gly Leu Leu
1               5                   10                  15 acg gca ttc aac ctg gcg gcg agc gtc gac cag gtg gtg gta tgc gac        96
Thr Ala Phe Asn Leu Ala Ala Ser Val Asp Gln Val Val Val Cys Asp
                20                  25                  30 cag ggc gaa gta ggg cgc gag tcc tcc tgg gct ggg ggc ggt atc gtc       144
Gln Gly Glu Val Gly Arg Glu Ser Ser Trp Ala Gly Gly Gly Ile Val
            35                  40                  45 tcg ccc ctg tat cct tgg cgc tac agc ccg gca gtg acc gcc ctg gcg       192
Ser Pro Leu Tyr Pro Trp Arg Tyr Ser Pro Ala Val Thr Ala Leu Ala
        50                  55                  60 cat tgg tcg cag gac ttt tac cca cag ttg ggc gag cgc ttg ttc gcc       240
His Trp Ser Gln Asp Phe Tyr Pro Gln Leu Gly Glu Arg Leu Phe Ala
65                  70                  75                  80 agc acg ggc ctg gat cct gag gtg cat acc acc ggg ctt tac tgg ctc       288
Ser Thr Gly Leu Asp Pro Glu Val His Thr Thr Gly Leu Tyr Trp Leu
                85                  90                  95 gac ctg gat gac caa gcc cag gcc ttg gcg tgg gca ggc cgt cag cag       336
Asp Leu Asp Asp Gln Ala Gln Ala Leu Ala Trp Ala Gly Arg Gln Gln
            100                 105                 110 cgt ccg ctg agc gcc gtg gat att tca gcg gtg tac gac gca gtc cct       384
Arg Pro Leu Ser Ala Val Asp Ile Ser Ala Val Tyr Asp Ala Val Pro
        115                 120                 125 gtg ctg ggg cca ggc ttt gag cga gcc ctc tac atg gaa ggc gtg gcc       432
Val Leu Gly Pro Gly Phe Glu Arg Ala Leu Tyr Met Glu Gly Val Ala
    130                 135                 140 aat gtg cgc aac ccg cgc ctg gtc aaa tcg ctg aag gcg gcg ttg ctg       480
Asn Val Arg Asn Pro Arg Leu Val Lys Ser Leu Lys Ala Ala Leu Leu
145                 150                 155                 160 gca ttg ccc aat gtg agc gtg cgc gag cac tgc cag atc acg ggg ttc       528
Ala Leu Pro Asn Val Ser Val Arg Glu His Cys Gln Ile Thr Gly Phe
                165                 170                 175 gtg cag cag ggc gct cgt atc att ggg gtg agc acc gct gaa ggc gag       576
Val Gln Gln Gly Ala Arg Ile Ile Gly Val Ser Thr Ala Glu Gly Glu
            180                 185                 190 ctg gcc gcc gac gaa gtc gta ctg agc gcc ggt gcc tgg agc ggc gaa       624
Leu Ala Ala Asp Glu Val Val Leu Ser Ala Gly Ala Trp Ser Gly Glu
        195                 200                 205 ctg ctg cgc cac ttg ggc ctt gag ctt cca gtc gag ccg gta aaa ggg       672
Leu Leu Arg His Leu Gly Leu Glu Leu Pro Val Glu Pro Val Lys Gly
    210                 215                 220 cag atg atc ctg ttc aaa tgc gct gaa gat ttt ctg cca agc atg gtg       720
Gln Met Ile Leu Phe Lys Cys Ala Glu Asp Phe Leu Pro Ser Met Val
```

```
                Gln Met Ile Leu Phe Lys Cys Ala Glu Asp Phe Leu Pro Ser Met Val
                225                 230                 235                 240 ctt gcc aaa ggt cgt tat gca att ccg cgt cgg gat ggt cac att ctg        768
Leu Ala Lys Gly Arg Tyr Ala Ile Pro Arg Arg Asp Gly His Ile Leu
                245                 250                 255 gtg ggc agc acg ctg gag cat gcc ggc tac gac aag aca ccc acc gat        816
Val Gly Ser Thr Leu Glu His Ala Gly Tyr Asp Lys Thr Pro Thr Asp
            260                 265                 270 gag gcg ttg gcc agc ctc aag gca tcg gcg gtg gat ctg ctc ccc ggc        864
Glu Ala Leu Ala Ser Leu Lys Ala Ser Ala Val Asp Leu Leu Pro Gly
        275                 280                 285 ctg gaa ggc gcg cac gtg gtt gcc cac tgg gcc ggg ctg cgg cca ggt        912
Leu Glu Gly Ala His Val Val Ala His Trp Ala Gly Leu Arg Pro Gly
    290                 295                 300 tcg cca gaa ggc gtt ccg ttt atc ggg ccg gta ccc ggc ttc gat ggg        960
Ser Pro Glu Gly Val Pro Phe Ile Gly Pro Val Pro Gly Phe Asp Gly
305                 310                 315                 320 tta tgg ctg aac tgc ggc cat tac cga aac ggg ctg gtg ctg gcg ccc       1008
Leu Trp Leu Asn Cys Gly His Tyr Arg Asn Gly Leu Val Leu Ala Pro
                325                 330                 335 gct tcg tgc caa ctg ctg gcc gat ttg ctc aat ggc gcc gag ccc atc       1056
Ala Ser Cys Gln Leu Leu Ala Asp Leu Leu Asn Gly Ala Glu Pro Ile
            340                 345                 350 atc gac ccg tca ccc tac gcc ccg tct ggg cgc ctt ggc taa              1098
Ile Asp Pro Ser Pro Tyr Ala Pro Ser Gly Arg Leu Gly
        355                 360                 365

<210> SEQ ID NO 96
<211> LENGTH: 365
<212> TYPE: PRT
<213> ORGANISM: Pseudomonas putida

<400> SEQUENCE: 96

Met Ser Lys Gln Val Val Val Gly Gly Val Ile Gly Leu Leu
1               5                   10                  15

Thr Ala Phe Asn Leu Ala Ala Ser Val Asp Gln Val Val Cys Asp
                20                  25                  30

Gln Gly Glu Val Gly Arg Glu Ser Trp Ala Gly Gly Ile Val
            35                  40                  45

Ser Pro Leu Tyr Pro Trp Arg Tyr Ser Pro Ala Val Thr Ala Leu Ala
    50                  55                  60

His Trp Ser Gln Asp Phe Tyr Pro Gln Leu Gly Glu Arg Leu Phe Ala
65                  70                  75                  80

Ser Thr Gly Leu Asp Pro Glu Val His Thr Thr Gly Leu Tyr Trp Leu
                85                  90                  95

Asp Leu Asp Asp Gln Ala Gln Ala Leu Ala Trp Ala Gly Arg Gln Gln
            100                 105                 110

Arg Pro Leu Ser Ala Val Asp Ile Ser Ala Val Tyr Asp Ala Val Pro
        115                 120                 125

Val Leu Gly Pro Gly Phe Glu Arg Ala Leu Tyr Met Glu Gly Val Ala
    130                 135                 140

Asn Val Arg Asn Pro Arg Leu Val Lys Ser Leu Lys Ala Ala Leu Leu
145                 150                 155                 160

Ala Leu Pro Asn Val Ser Val Arg Glu His Cys Gln Ile Thr Gly Phe
                165                 170                 175

Val Gln Gln Gly Ala Arg Ile Ile Gly Val Ser Thr Ala Glu Gly Glu
            180                 185                 190
```

```
Leu Ala Ala Asp Glu Val Val Leu Ser Ala Gly Ala Trp Ser Gly Glu
            195                 200                 205

Leu Leu Arg His Leu Gly Leu Glu Leu Pro Val Glu Pro Val Lys Gly
        210                 215                 220

Gln Met Ile Leu Phe Lys Cys Ala Glu Asp Phe Leu Pro Ser Met Val
225                 230                 235                 240

Leu Ala Lys Gly Arg Tyr Ala Ile Pro Arg Arg Asp Gly His Ile Leu
                245                 250                 255

Val Gly Ser Thr Leu Glu His Ala Gly Tyr Asp Lys Thr Pro Thr Asp
            260                 265                 270

Glu Ala Leu Ala Ser Leu Lys Ala Ser Ala Val Asp Leu Leu Pro Gly
        275                 280                 285

Leu Glu Gly Ala His Val Val Ala His Trp Ala Gly Leu Arg Pro Gly
    290                 295                 300

Ser Pro Glu Gly Val Pro Phe Ile Gly Pro Val Pro Gly Phe Asp Gly
305                 310                 315                 320

Leu Trp Leu Asn Cys Gly His Tyr Arg Asn Gly Leu Val Leu Ala Pro
                325                 330                 335

Ala Ser Cys Gln Leu Leu Ala Asp Leu Leu Asn Gly Ala Glu Pro Ile
            340                 345                 350

Ile Asp Pro Ser Pro Tyr Ala Pro Ser Gly Arg Leu Gly
        355                 360                 365

<210> SEQ ID NO 97
<211> LENGTH: 1140
<212> TYPE: DNA
<213> ORGANISM: Synechococcus elongatus
<220> FEATURE:
<221> NAME/KEY: CDS
<222> LOCATION: (1)..(1137)
<223> OTHER INFORMATION: ThiO gene from Synechococcus elongatus encoding
      a Glycine oxidase

<400> SEQUENCE: 97 atg gcg ttc gag gta gcc gtc ttt ggg ggc ggc gtc att ggc ttg gcg      48
Met Ala Phe Glu Val Ala Val Phe Gly Gly Gly Val Ile Gly Leu Ala
1               5                   10                  15 atc gcg cta gaa ctg cga tcg cga ggc gcg atg gtg cag gtc tac agt      96
Ile Ala Leu Glu Leu Arg Ser Arg Gly Ala Met Val Gln Val Tyr Ser
            20                  25                  30 caa aac act cag gcg gcg gca ggt cgt gtg gca gca ggg atg ttg gcg     144
Gln Asn Thr Gln Ala Ala Ala Gly Arg Val Ala Ala Gly Met Leu Ala
        35                  40                  45 ccc cag tcg gaa ggc atc gaa gtc ggg ccc atg ctg gat ctg ggg ctg     192
Pro Gln Ser Glu Gly Ile Glu Val Gly Pro Met Leu Asp Leu Gly Leu
    50                  55                  60 cgc agc cga tcg ctc tac gcc cgc tgg acc cag caa ctc gaa caa ctc     240
Arg Ser Arg Ser Leu Tyr Ala Arg Trp Thr Gln Gln Leu Glu Gln Leu
65                  70                  75                  80 agc ggt caa gac agt ggc tac tgg ccc tgc ggc att ttg gtg ccc ctg     288
Ser Gly Gln Asp Ser Gly Tyr Trp Pro Cys Gly Ile Leu Val Pro Leu
                85                  90                  95 agt gag gcc aaa aat cgc gat cgc tat cct cat cca gca gaa tct ccg     336
Ser Glu Ala Lys Asn Arg Asp Arg Tyr Pro His Pro Ala Glu Ser Pro
            100                 105                 110 ggg caa tgg ctc tcg gca gcg gac tta cga gac ttt cag ccc gca cta     384
Gly Gln Trp Leu Ser Ala Ala Asp Leu Arg Asp Phe Gln Pro Ala Leu
        115                 120                 125 tgc tct gac cta atc ggt ggc tgg tgg ttt tcc caa gaa ggg caa gtt     432
```

```
                Cys Ser Asp Leu Ile Gly Gly Trp Trp Phe Ser Gln Glu Gly Gln Val
                    130                 135                 140 gat agt cgc cgt gcc ctg tat cca gcg ctg cga gcc gcc gcg atc gcc        480
Asp Ser Arg Arg Ala Leu Tyr Pro Ala Leu Arg Ala Ala Ala Ile Ala
145                 150                 155                 160 agt ggc gtc acg atc cat gaa agc gtg gcg ctg cgg gag tta tct gta        528
Ser Gly Val Thr Ile His Glu Ser Val Ala Leu Arg Glu Leu Ser Val
                165                 170                 175 aca ggc gat cgc ctg caa tcc gcg atg acc gat cgc ggg cca gtt caa        576
Thr Gly Asp Arg Leu Gln Ser Ala Met Thr Asp Arg Gly Pro Val Gln
            180                 185                 190 gct gac gcc tac gtt ctg gca acc ggc gct tgg tcc ggc gac tgg cta        624
Ala Asp Ala Tyr Val Leu Ala Thr Gly Ala Trp Ser Gly Asp Trp Leu
        195                 200                 205 caa ctg ccg gtc tat ccc gtt aaa ggc caa atg ttc tcg ctg caa gct        672
Gln Leu Pro Val Tyr Pro Val Lys Gly Gln Met Phe Ser Leu Gln Ala
    210                 215                 220 gac ccg cgt ttg ctg aac cac gtt ttg ttt ggt gag cgg gtg tat att        720
Asp Pro Arg Leu Leu Asn His Val Leu Phe Gly Glu Arg Val Tyr Ile
225                 230                 235                 240 gtg ccg cgc cga gat ggt ctg att gtg gtc ggt gcc acc atg gaa gcg        768
Val Pro Arg Arg Asp Gly Leu Ile Val Val Gly Ala Thr Met Glu Ala
                245                 250                 255 acg gcg gga ttc agg act ggc aac acc gct ggc ccc tta cag agc ttg        816
Thr Ala Gly Phe Arg Thr Gly Asn Thr Ala Gly Pro Leu Gln Ser Leu
            260                 265                 270 atg gcc gag gcg atc gcc ctc gtt ccg gct ctg gcg gac tgt cca ctg        864
Met Ala Glu Ala Ile Ala Leu Val Pro Ala Leu Ala Asp Cys Pro Leu
        275                 280                 285 gtt gaa act tgg tgg gga tac cgt ccc gcg aca cca gat gaa tgg ccg        912
Val Glu Thr Trp Trp Gly Tyr Arg Pro Ala Thr Pro Asp Glu Trp Pro
    290                 295                 300 atc ctg ggg caa ggc ccc gct gag aac tta ttc ttg gcg acc ggc cac        960
Ile Leu Gly Gln Gly Pro Ala Glu Asn Leu Phe Leu Ala Thr Gly His
305                 310                 315                 320 tac cgc aac ggt atg ctg ctc gcc cca att acc gct cag cta ctc gct       1008
Tyr Arg Asn Gly Met Leu Leu Ala Pro Ile Thr Ala Gln Leu Leu Ala
                325                 330                 335 gac caa att ctc gac cac tgc acg gat caa ctg ctt cat gcc ttc cgt       1056
Asp Gln Ile Leu Asp His Cys Thr Asp Gln Leu Leu His Ala Phe Arg
            340                 345                 350 tac gac cgc ttc tcc agc cat gac tcc agc acc cat caa ccc tta ccc       1104
Tyr Asp Arg Phe Ser Ser His Asp Ser Ser Thr His Gln Pro Leu Pro
        355                 360                 365 gct ctt gca ggc ttg tca gcg tca acg ggt cag tga                       1140
Ala Leu Ala Gly Leu Ser Ala Ser Thr Gly Gln
    370                 375

<210> SEQ ID NO 98
<211> LENGTH: 379
<212> TYPE: PRT
<213> ORGANISM: Synechococcus elongatus

<400> SEQUENCE: 98

Met Ala Phe Glu Val Ala Val Phe Gly Gly Gly Val Ile Gly Leu Ala
1               5                   10                  15

Ile Ala Leu Glu Leu Arg Ser Arg Gly Ala Met Val Gln Val Tyr Ser
            20                  25                  30

Gln Asn Thr Gln Ala Ala Ala Gly Arg Val Ala Ala Gly Met Leu Ala
        35                  40                  45
```

Pro Gln Ser Glu Gly Ile Glu Val Gly Pro Met Leu Asp Leu Gly Leu
 50                  55                  60

Arg Ser Arg Ser Leu Tyr Ala Arg Trp Thr Gln Gln Leu Glu Gln Leu
 65                  70                  75                  80

Ser Gly Gln Asp Ser Gly Tyr Trp Pro Cys Gly Ile Leu Val Pro Leu
                 85                  90                  95

Ser Glu Ala Lys Asn Arg Asp Arg Tyr Pro His Pro Ala Glu Ser Pro
                100                 105                 110

Gly Gln Trp Leu Ser Ala Ala Asp Leu Arg Asp Phe Gln Pro Ala Leu
                115                 120                 125

Cys Ser Asp Leu Ile Gly Gly Trp Trp Phe Ser Gln Glu Gly Gln Val
                130                 135                 140

Asp Ser Arg Arg Ala Leu Tyr Pro Ala Leu Arg Ala Ala Ile Ala
145                 150                 155                 160

Ser Gly Val Thr Ile His Glu Ser Val Ala Leu Arg Glu Leu Ser Val
                165                 170                 175

Thr Gly Asp Arg Leu Gln Ser Ala Met Thr Asp Arg Gly Pro Val Gln
                180                 185                 190

Ala Asp Ala Tyr Val Leu Ala Thr Gly Ala Trp Ser Gly Asp Trp Leu
                195                 200                 205

Gln Leu Pro Val Tyr Pro Val Lys Gly Gln Met Phe Ser Leu Gln Ala
                210                 215                 220

Asp Pro Arg Leu Leu Asn His Val Leu Phe Gly Glu Arg Val Tyr Ile
225                 230                 235                 240

Val Pro Arg Arg Asp Gly Leu Ile Val Val Gly Ala Thr Met Glu Ala
                245                 250                 255

Thr Ala Gly Phe Arg Thr Gly Asn Thr Ala Gly Pro Leu Gln Ser Leu
                260                 265                 270

Met Ala Glu Ala Ile Ala Leu Val Pro Ala Leu Ala Asp Cys Pro Leu
                275                 280                 285

Val Glu Thr Trp Trp Gly Tyr Arg Pro Ala Thr Pro Asp Glu Trp Pro
                290                 295                 300

Ile Leu Gly Gln Gly Pro Ala Glu Asn Leu Phe Leu Ala Thr Gly His
305                 310                 315                 320

Tyr Arg Asn Gly Met Leu Leu Ala Pro Ile Thr Ala Gln Leu Leu Ala
                325                 330                 335

Asp Gln Ile Leu Asp His Cys Thr Asp Gln Leu Leu His Ala Phe Arg
                340                 345                 350

Tyr Asp Arg Phe Ser Ser His Asp Ser Ser Thr His Gln Pro Leu Pro
                355                 360                 365

Ala Leu Ala Gly Leu Ser Ala Ser Thr Gly Gln
                370                 375

<210> SEQ ID NO 99
<211> LENGTH: 801
<212> TYPE: DNA
<213> ORGANISM: Escherichia coli
<220> FEATURE:
<221> NAME/KEY: CDS
<222> LOCATION: (1)..(798)
<223> OTHER INFORMATION: ThiD gene from E. coli encoding
      phosphohydroxymethylpyrimidine kinase

<400> SEQUENCE: 99 atg aaa cga att aac gct ctg acg att gcc ggt act gat ccg agt ggt    48
Met Lys Arg Ile Asn Ala Leu Thr Ile Ala Gly Thr Asp Pro Ser Gly

```
              1               5                  10                 15
   ggt gcg ggg att cag gcc gat ctt aaa acc ttc tcg gca ctt ggc gct     96
   Gly Ala Gly Ile Gln Ala Asp Leu Lys Thr Phe Ser Ala Leu Gly Ala
                   20                  25                  30 tat ggt tgc tca gtt att act gca ctg gtg gcg caa aat acc cgt ggc    144
   Tyr Gly Cys Ser Val Ile Thr Ala Leu Val Ala Gln Asn Thr Arg Gly
               35                  40                  45 gta cag tcg gtg tat cgc att gag cct gat ttt gtc gcc gcc cag ctc    192
   Val Gln Ser Val Tyr Arg Ile Glu Pro Asp Phe Val Ala Ala Gln Leu
       50                  55                  60 gat tcg gtg ttc agc gat gtg cga atc gat acc act aaa atc ggt atg    240
   Asp Ser Val Phe Ser Asp Val Arg Ile Asp Thr Thr Lys Ile Gly Met
   65                  70                  75                  80 ctg gcg gaa acc gat att gtt gaa gcg gtg gca gaa cgg ttg caa cgt    288
   Leu Ala Glu Thr Asp Ile Val Glu Ala Val Ala Glu Arg Leu Gln Arg
                   85                  90                  95 tat cag atc caa aac gtg gta ctc gac acc gtt atg ctg gca aaa agc    336
   Tyr Gln Ile Gln Asn Val Val Leu Asp Thr Val Met Leu Ala Lys Ser
               100                 105                 110 ggc gac ccg ctg ctt tca cct tcg gcg gtt gct acg ctg cgc agt cga    384
   Gly Asp Pro Leu Leu Ser Pro Ser Ala Val Ala Thr Leu Arg Ser Arg
       115                 120                 125 tta ttg cca cag gtt tca tta ata acg cca aac ttg ccc gaa gct gcc    432
   Leu Leu Pro Gln Val Ser Leu Ile Thr Pro Asn Leu Pro Glu Ala Ala
   130                 135                 140 gcc ttg ctc gac gcg cca cac gcg cgc acc gaa cag gaa atg ctg gaa    480
   Ala Leu Leu Asp Ala Pro His Ala Arg Thr Glu Gln Glu Met Leu Glu
   145                 150                 155                 160 caa ggg cga tcg ctg ttg gcg atg ggc tgt ggc gca gtg cta atg aaa    528
   Gln Gly Arg Ser Leu Leu Ala Met Gly Cys Gly Ala Val Leu Met Lys
                   165                 170                 175 ggt ggt cat ctg gat gat gag caa agc ccg gac tgg ctg ttt acc cgc    576
   Gly Gly His Leu Asp Asp Glu Gln Ser Pro Asp Trp Leu Phe Thr Arg
               180                 185                 190 gag ggt gaa caa cgg ttt acc gca ccg cgc att atg acc aaa aac acc    624
   Glu Gly Glu Gln Arg Phe Thr Ala Pro Arg Ile Met Thr Lys Asn Thr
       195                 200                 205 cac ggc act ggt tgt aca ctc tct gcg gcg ttg gct gca cta cgc ccg    672
   His Gly Thr Gly Cys Thr Leu Ser Ala Ala Leu Ala Ala Leu Arg Pro
   210                 215                 220 cgc cat aca aac tgg gct gac acc gta cag gag gca aaa agc tgg ctt    720
   Arg His Thr Asn Trp Ala Asp Thr Val Gln Glu Ala Lys Ser Trp Leu
   225                 230                 235                 240 tca tcg gcg tta gcc cag gcc gac acg ctg gaa gtt ggt cac ggt att    768
   Ser Ser Ala Leu Ala Gln Ala Asp Thr Leu Glu Val Gly His Gly Ile
                   245                 250                 255 ggt ccg gtt cac cac ttc cac gcc tgg tgg tga                        801
   Gly Pro Val His His Phe His Ala Trp Trp
               260                 265

<210> SEQ ID NO 100
<211> LENGTH: 266
<212> TYPE: PRT
<213> ORGANISM: Escherichia coli

<400> SEQUENCE: 100

Met Lys Arg Ile Asn Ala Leu Thr Ile Ala Gly Thr Asp Pro Ser Gly
1               5                   10                  15

Gly Ala Gly Ile Gln Ala Asp Leu Lys Thr Phe Ser Ala Leu Gly Ala
                20                  25                  30
```

```
Tyr Gly Cys Ser Val Ile Thr Ala Leu Val Ala Gln Asn Thr Arg Gly
        35                  40                  45

Val Gln Ser Val Tyr Arg Ile Glu Pro Asp Phe Val Ala Ala Gln Leu
 50                  55                  60

Asp Ser Val Phe Ser Asp Val Arg Ile Asp Thr Thr Lys Ile Gly Met
 65                  70                  75                  80

Leu Ala Glu Thr Asp Ile Val Glu Ala Val Ala Glu Arg Leu Gln Arg
                 85                  90                  95

Tyr Gln Ile Gln Asn Val Val Leu Asp Thr Val Met Leu Ala Lys Ser
            100                 105                 110

Gly Asp Pro Leu Leu Ser Pro Ser Ala Val Ala Thr Leu Arg Ser Arg
        115                 120                 125

Leu Leu Pro Gln Val Ser Leu Ile Thr Pro Asn Leu Pro Glu Ala Ala
130                 135                 140

Ala Leu Leu Asp Ala Pro His Ala Arg Thr Glu Gln Glu Met Leu Glu
145                 150                 155                 160

Gln Gly Arg Ser Leu Leu Ala Met Gly Cys Gly Ala Val Leu Met Lys
                165                 170                 175

Gly Gly His Leu Asp Asp Glu Gln Ser Pro Asp Trp Leu Phe Thr Arg
            180                 185                 190

Glu Gly Glu Gln Arg Phe Thr Ala Pro Arg Ile Met Thr Lys Asn Thr
        195                 200                 205

His Gly Thr Gly Cys Thr Leu Ser Ala Ala Leu Ala Ala Leu Arg Pro
210                 215                 220

Arg His Thr Asn Trp Ala Asp Thr Val Gln Glu Ala Lys Ser Trp Leu
225                 230                 235                 240

Ser Ser Ala Leu Ala Gln Ala Asp Thr Leu Glu Val Gly His Gly Ile
                245                 250                 255

Gly Pro Val His His Phe His Ala Trp Trp
            260                 265

<210> SEQ ID NO 101
<211> LENGTH: 984
<212> TYPE: DNA
<213> ORGANISM: Escherichia coli
<220> FEATURE:
<221> NAME/KEY: CDS
<222> LOCATION: (1)..(981)
<223> OTHER INFORMATION: ThiB gene from E. coli encoding a thiamine ABC
      transporter periplasmic binding protein

<400> SEQUENCE: 101 atg tta aaa aaa tgt ctg ccc ctg ctg ttg ctg tgc aca gcg ccc gtt        48
Met Leu Lys Lys Cys Leu Pro Leu Leu Leu Leu Cys Thr Ala Pro Val
 1               5                  10                  15 ttc gct aaa ccc gtt ctg act gtt tat acc tac gat tcc ttc gcc gcc        96
Phe Ala Lys Pro Val Leu Thr Val Tyr Thr Tyr Asp Ser Phe Ala Ala
                20                  25                  30 gac tgg ggg cct ggt ccg gtg gtt aaa aaa gcc ttt gaa gcc gac tgt       144
Asp Trp Gly Pro Gly Pro Val Val Lys Lys Ala Phe Glu Ala Asp Cys
        35                  40                  45 aat tgc gaa ctg aaa ctg gtg gcg ctg gaa gat ggc gtt tcg ctt ctc       192
Asn Cys Glu Leu Lys Leu Val Ala Leu Glu Asp Gly Val Ser Leu Leu
 50                  55                  60 aac cgt cta cgg atg gaa ggc aaa aac agt aaa gcc gat gtg gtg ctg       240
Asn Arg Leu Arg Met Glu Gly Lys Asn Ser Lys Ala Asp Val Val Leu
 65                  70                  75                  80
```

```
ggg ctg gat aac aac ctg tta gac gcc gcc agt aaa acc gga ctg ttt       288
Gly Leu Asp Asn Asn Leu Leu Asp Ala Ala Ser Lys Thr Gly Leu Phe
                85                  90                  95 gcc aaa agc ggt gtg gca gcg gat gcc gtt aac gtt ccc ggc ggc tgg       336
Ala Lys Ser Gly Val Ala Ala Asp Ala Val Asn Val Pro Gly Gly Trp
        100                 105                 110 aat aat gac act ttc gta ccg ttt gat tat ggc tac ttc gcc ttc gtt       384
Asn Asn Asp Thr Phe Val Pro Phe Asp Tyr Gly Tyr Phe Ala Phe Val
    115                 120                 125 tat gac aag aac aaa ctg aaa aac ccg cca caa agc ctg aaa gaa ctg       432
Tyr Asp Lys Asn Lys Leu Lys Asn Pro Pro Gln Ser Leu Lys Glu Leu
130                 135                 140 gtt gag agc gat caa aac tgg cgg gtg att tat cag gat ccg cgc acc       480
Val Glu Ser Asp Gln Asn Trp Arg Val Ile Tyr Gln Asp Pro Arg Thr
145                 150                 155                 160 agt aca ccg ggg ctg ggt ctg ttg cta tgg atg caa aaa gtc tat ggc       528
Ser Thr Pro Gly Leu Gly Leu Leu Leu Trp Met Gln Lys Val Tyr Gly
                165                 170                 175 gat gac gcc cca caa gcc tgg cag aaa ctg gcg aag aaa acg gtc acg       576
Asp Asp Ala Pro Gln Ala Trp Gln Lys Leu Ala Lys Lys Thr Val Thr
        180                 185                 190 gtc acc aaa ggc tgg agc gaa gcc tac ggc ctg ttt tta aaa ggt gaa       624
Val Thr Lys Gly Trp Ser Glu Ala Tyr Gly Leu Phe Leu Lys Gly Glu
    195                 200                 205 agc gat ctg gta ctg agt tac acc acc tct ccg gct tat cac att ctc       672
Ser Asp Leu Val Leu Ser Tyr Thr Thr Ser Pro Ala Tyr His Ile Leu
210                 215                 220 gaa gag aag aaa gat aac tac gcc gcc gcg aac ttc agc gaa ggt cac       720
Glu Glu Lys Lys Asp Asn Tyr Ala Ala Ala Asn Phe Ser Glu Gly His
225                 230                 235                 240 tat ctg caa gtg gaa gtc gcc gcc cgc acc gct gcc agc aag cag ccg       768
Tyr Leu Gln Val Glu Val Ala Ala Arg Thr Ala Ala Ser Lys Gln Pro
                245                 250                 255 gag ctg gcg caa aaa ttc ctc cag ttt atg gtt tct ccg gct ttc cag       816
Glu Leu Ala Gln Lys Phe Leu Gln Phe Met Val Ser Pro Ala Phe Gln
        260                 265                 270 aat gcg atc cca acc ggc aac tgg atg tat ccg gtg gca aac gtc acg       864
Asn Ala Ile Pro Thr Gly Asn Trp Met Tyr Pro Val Ala Asn Val Thr
    275                 280                 285 ctg cct gcc ggt ttt gaa aaa ttg acc aaa ccc gca acc acg ttg gag       912
Leu Pro Ala Gly Phe Glu Lys Leu Thr Lys Pro Ala Thr Thr Leu Glu
290                 295                 300 ttc acg cca gcc gaa gtg gcg gca caa cgt cag gca tgg att agc gaa       960
Phe Thr Pro Ala Glu Val Ala Ala Gln Arg Gln Ala Trp Ile Ser Glu
305                 310                 315                 320 tgg caa cgc gcc gtc agc cgt taa                                       984
Trp Gln Arg Ala Val Ser Arg
                325

<210> SEQ ID NO 102
<211> LENGTH: 327
<212> TYPE: PRT
<213> ORGANISM: Escherichia coli

<400> SEQUENCE: 102

Met Leu Lys Lys Cys Leu Pro Leu Leu Leu Cys Thr Ala Pro Val
1               5                   10                  15

Phe Ala Lys Pro Val Leu Thr Val Tyr Thr Tyr Asp Ser Phe Ala Ala
            20                  25                  30

Asp Trp Gly Pro Gly Pro Val Val Lys Lys Ala Phe Glu Ala Asp Cys
```

```
                35                  40                  45
Asn Cys Glu Leu Lys Leu Val Ala Leu Glu Asp Gly Val Ser Leu Leu
 50                  55                  60

Asn Arg Leu Arg Met Glu Gly Lys Asn Ser Lys Ala Asp Val Val Leu
 65                  70                  75                  80

Gly Leu Asp Asn Asn Leu Leu Asp Ala Ala Ser Lys Thr Gly Leu Phe
                 85                  90                  95

Ala Lys Ser Gly Val Ala Ala Asp Ala Val Asn Val Pro Gly Gly Trp
            100                 105                 110

Asn Asn Asp Thr Phe Val Pro Phe Asp Tyr Gly Tyr Phe Ala Phe Val
        115                 120                 125

Tyr Asp Lys Asn Lys Leu Lys Asn Pro Pro Gln Ser Leu Lys Glu Leu
130                 135                 140

Val Glu Ser Asp Gln Asn Trp Arg Val Ile Tyr Gln Asp Pro Arg Thr
145                 150                 155                 160

Ser Thr Pro Gly Leu Gly Leu Leu Leu Trp Met Gln Lys Val Tyr Gly
                165                 170                 175

Asp Asp Ala Pro Gln Ala Trp Gln Lys Leu Ala Lys Lys Thr Val Thr
            180                 185                 190

Val Thr Lys Gly Trp Ser Glu Ala Tyr Gly Leu Phe Leu Lys Gly Glu
        195                 200                 205

Ser Asp Leu Val Leu Ser Tyr Thr Thr Ser Pro Ala Tyr His Ile Leu
210                 215                 220

Glu Glu Lys Lys Asp Asn Tyr Ala Ala Ala Asn Phe Ser Glu Gly His
225                 230                 235                 240

Tyr Leu Gln Val Glu Val Ala Ala Arg Thr Ala Ala Ser Lys Gln Pro
                245                 250                 255

Glu Leu Ala Gln Lys Phe Leu Gln Phe Met Val Ser Pro Ala Phe Gln
            260                 265                 270

Asn Ala Ile Pro Thr Gly Asn Trp Met Tyr Pro Val Ala Asn Val Thr
        275                 280                 285

Leu Pro Ala Gly Phe Glu Lys Leu Thr Lys Pro Ala Thr Thr Leu Glu
290                 295                 300

Phe Thr Pro Ala Glu Val Ala Ala Gln Arg Gln Ala Trp Ile Ser Glu
305                 310                 315                 320

Trp Gln Arg Ala Val Ser Arg
                325

<210> SEQ ID NO 103
<211> LENGTH: 1611
<212> TYPE: DNA
<213> ORGANISM: Escherichia coli
<220> FEATURE:
<221> NAME/KEY: CDS
<222> LOCATION: (1)..(1608)
<223> OTHER INFORMATION: ThiP gene from E. coli encoding a thiamine ABC
      transporter permease

<400> SEQUENCE: 103 atg gca acg cgc cgt cag ccg tta att ccc ggc tgg tta att cca ggt      48
Met Ala Thr Arg Arg Gln Pro Leu Ile Pro Gly Trp Leu Ile Pro Gly
 1               5                  10                  15 gta agc gcc acc acg ctg gtg gta gcg gtt gcg ctg gcg gcg ttt ctc      96
Val Ser Ala Thr Thr Leu Val Val Ala Val Ala Leu Ala Ala Phe Leu
             20                  25                  30 gcc ctg tgg tgg aac gcg ccg cag gat gac tgg gtg gca gtc tgg cag     144
Ala Leu Trp Trp Asn Ala Pro Gln Asp Asp Trp Val Ala Val Trp Gln
         35                  40                  45
```

```
              35                  40                  45
gac agc tat ctg tgg cat gtg gtg cgc ttc tcc ttc tgg cag gcg ttt      192
Asp Ser Tyr Leu Trp His Val Val Arg Phe Ser Phe Trp Gln Ala Phe
 50                  55                  60 ctc tcg gca ctg ctc tct gtc ata ccc gcg ata ttc ctc gcc cgc gcg      240
Leu Ser Ala Leu Leu Ser Val Ile Pro Ala Ile Phe Leu Ala Arg Ala
 65                  70                  75                  80 ctc tat cgc agg cgc ttt ccg ggt cgg ctg gcg ctg ttg cgt ctg tgt      288
Leu Tyr Arg Arg Arg Phe Pro Gly Arg Leu Ala Leu Leu Arg Leu Cys
                 85                  90                  95 gca atg acc ttg atc ctc ccg gtg ttg gtc gct gtt ttc ggc att ctt      336
Ala Met Thr Leu Ile Leu Pro Val Leu Val Ala Val Phe Gly Ile Leu
            100                 105                 110 agc gtc tat ggt cgc cag ggc tgg ctg gca aca ctc tgc caa tcg ctc      384
Ser Val Tyr Gly Arg Gln Gly Trp Leu Ala Thr Leu Cys Gln Ser Leu
        115                 120                 125 ggt ctg gag tgg acc ttt tcg ccc tac ggc ctg caa ggt att ttg ctg      432
Gly Leu Glu Trp Thr Phe Ser Pro Tyr Gly Leu Gln Gly Ile Leu Leu
    130                 135                 140 gcc cat gtg ttt ttt aat ctg ccg atg gcg agc cgc tta tta ctc cag      480
Ala His Val Phe Phe Asn Leu Pro Met Ala Ser Arg Leu Leu Leu Gln
145                 150                 155                 160 gca ctg gaa aac atc ccc ggc gaa cag cgt caa ctt gcc gcc cag ctt      528
Ala Leu Glu Asn Ile Pro Gly Glu Gln Arg Gln Leu Ala Ala Gln Leu
                165                 170                 175 ggg atg cgt agc tgg cat ttt ttc cgc ttc gtc gaa tgg ccg tgg tta      576
Gly Met Arg Ser Trp His Phe Phe Arg Phe Val Glu Trp Pro Trp Leu
            180                 185                 190 cgg cga caa atc ccg ccg gtt gct gcg ctt atc ttt atg ctc tgt ttc      624
Arg Arg Gln Ile Pro Pro Val Ala Ala Leu Ile Phe Met Leu Cys Phe
        195                 200                 205 gcc agc ttc gcc acc gtg cta tcg ctg ggg ggc ggt ccg cag gcg acc      672
Ala Ser Phe Ala Thr Val Leu Ser Leu Gly Gly Gly Pro Gln Ala Thr
    210                 215                 220 act atc gag ctg gca atc tat cag gcg ctg agt tac gac tac gat cct      720
Thr Ile Glu Leu Ala Ile Tyr Gln Ala Leu Ser Tyr Asp Tyr Asp Pro
225                 230                 235                 240 gcc cgc gcg gca atg ctg gcg ctg ctc cag atg gtg tgc tgc ctc ggg      768
Ala Arg Ala Ala Met Leu Ala Leu Leu Gln Met Val Cys Cys Leu Gly
                245                 250                 255 ctg gtg ctg ttg agt cag cga ttg agt aag gcc att gcg ccc ggc acc      816
Leu Val Leu Leu Ser Gln Arg Leu Ser Lys Ala Ile Ala Pro Gly Thr
            260                 265                 270 acg ctg ctg caa ggc tgg cgc gac ccg gac gat cgt ctg cat agc cgc      864
Thr Leu Leu Gln Gly Trp Arg Asp Pro Asp Asp Arg Leu His Ser Arg
        275                 280                 285 att tgc gac acg gtg tta att gtg ctg gcg ctg ctg ttg ctg cca          912
Ile Cys Asp Thr Val Leu Ile Val Leu Ala Leu Leu Leu Leu Pro
    290                 295                 300 ccg tta ctg gcg gtg atc gtc gat ggg gta aat cgc cag ttg ccg gaa      960
Pro Leu Leu Ala Val Ile Val Asp Gly Val Asn Arg Gln Leu Pro Glu
305                 310                 315                 320 gtg ctg gca caa ccg gtg ctg tgg cag gcg ctg tgg acc tcg ttg cgt     1008
Val Leu Ala Gln Pro Val Leu Trp Gln Ala Leu Trp Thr Ser Leu Arg
                325                 330                 335 att gcg ctg gcg gca ggt gta ttg tgc gta gtg ctg acc atg atg ctg     1056
Ile Ala Leu Ala Ala Gly Val Leu Cys Val Val Leu Thr Met Met Leu
            340                 345                 350 cta tgg agc agt cgc gaa ctg cgg gcg cgg cag aaa atg ctg gcg ggt     1104
```

```
Leu Trp Ser Ser Arg Glu Leu Arg Ala Arg Gln Lys Met Leu Ala Gly
            355                 360                 365 cag gtg ctg gag atg agc ggc atg ttg atc ctc gcc atg ccg ggg att      1152
Gln Val Leu Glu Met Ser Gly Met Leu Ile Leu Ala Met Pro Gly Ile
        370                 375                 380 gtg ctg gct acc ggc ttc ttt tta ctg ctc aac aac act atc ggc ctg      1200
Val Leu Ala Thr Gly Phe Phe Leu Leu Leu Asn Asn Thr Ile Gly Leu
385                 390                 395                 400 cca caa tct gct gac ggc att gtg att ttc acc aat gcg tta atg gcg      1248
Pro Gln Ser Ala Asp Gly Ile Val Ile Phe Thr Asn Ala Leu Met Ala
                405                 410                 415 atc cct tat gcg ctg aaa gtg ctg gaa aac ccg atg cgc gat atc acc      1296
Ile Pro Tyr Ala Leu Lys Val Leu Glu Asn Pro Met Arg Asp Ile Thr
            420                 425                 430 gcc cgc tac agc atg tta tgt cag tcg ctg ggg att gaa ggc tgg tca      1344
Ala Arg Tyr Ser Met Leu Cys Gln Ser Leu Gly Ile Glu Gly Trp Ser
        435                 440                 445 cgc tta aaa gtg gtg gag ctg cgc gcc ctg aaa cgt cca ctg gcg cag      1392
Arg Leu Lys Val Val Glu Leu Arg Ala Leu Lys Arg Pro Leu Ala Gln
450                 455                 460 gcg ctg gcc ttt gca tgc gtg ctg tcg att ggt gat ttt ggc gtg gtg      1440
Ala Leu Ala Phe Ala Cys Val Leu Ser Ile Gly Asp Phe Gly Val Val
465                 470                 475                 480 gcg ttg ttc ggt aac gat gat ttc cgc acc ctg ccg ttt tat ctc tac      1488
Ala Leu Phe Gly Asn Asp Asp Phe Arg Thr Leu Pro Phe Tyr Leu Tyr
                485                 490                 495 cag caa att ggc tcc tat cgc agc cag gac ggt gcg gtc acc gcg tta      1536
Gln Gln Ile Gly Ser Tyr Arg Ser Gln Asp Gly Ala Val Thr Ala Leu
            500                 505                 510 att ctg ctg ctc tgt ttt ctg ctg ttt acc gtg att gaa aaa cta          1584
Ile Leu Leu Leu Cys Phe Leu Leu Phe Thr Val Ile Glu Lys Leu
        515                 520                 525 ccg ggg cga aat gtt aaa act gac tga                                  1611
Pro Gly Arg Asn Val Lys Thr Asp
    530                 535

<210> SEQ ID NO 104
<211> LENGTH: 536
<212> TYPE: PRT
<213> ORGANISM: Escherichia coli

<400> SEQUENCE: 104

Met Ala Thr Arg Arg Gln Pro Leu Ile Pro Gly Trp Leu Ile Pro Gly
1               5                   10                  15

Val Ser Ala Thr Thr Leu Val Val Ala Val Ala Leu Ala Ala Phe Leu
            20                  25                  30

Ala Leu Trp Trp Asn Ala Pro Gln Asp Asp Trp Val Ala Val Trp Gln
        35                  40                  45

Asp Ser Tyr Leu Trp His Val Val Arg Phe Ser Phe Trp Gln Ala Phe
    50                  55                  60

Leu Ser Ala Leu Leu Ser Val Ile Pro Ala Ile Phe Leu Ala Arg Ala
65                  70                  75                  80

Leu Tyr Arg Arg Arg Phe Pro Gly Arg Leu Ala Leu Leu Arg Leu Cys
                85                  90                  95

Ala Met Thr Leu Ile Leu Pro Val Leu Val Ala Val Phe Gly Ile Leu
            100                 105                 110

Ser Val Tyr Gly Arg Gln Gly Trp Leu Ala Thr Leu Cys Gln Ser Leu
        115                 120                 125
```

```
Gly Leu Glu Trp Thr Phe Ser Pro Tyr Gly Leu Gln Gly Ile Leu Leu
    130                 135                 140

Ala His Val Phe Phe Asn Leu Pro Met Ala Ser Arg Leu Leu Leu Gln
145                 150                 155                 160

Ala Leu Glu Asn Ile Pro Gly Glu Gln Arg Gln Leu Ala Ala Gln Leu
                165                 170                 175

Gly Met Arg Ser Trp His Phe Phe Arg Phe Val Glu Trp Pro Trp Leu
            180                 185                 190

Arg Arg Gln Ile Pro Pro Val Ala Ala Leu Ile Phe Met Leu Cys Phe
        195                 200                 205

Ala Ser Phe Ala Thr Val Leu Ser Leu Gly Gly Pro Gln Ala Thr
210                 215                 220

Thr Ile Glu Leu Ala Ile Tyr Gln Ala Leu Ser Tyr Asp Tyr Asp Pro
225                 230                 235                 240

Ala Arg Ala Ala Met Leu Ala Leu Leu Gln Met Val Cys Cys Leu Gly
                245                 250                 255

Leu Val Leu Leu Ser Gln Arg Leu Ser Lys Ala Ile Ala Pro Gly Thr
                260                 265                 270

Thr Leu Leu Gln Gly Trp Arg Asp Pro Asp Asp Arg Leu His Ser Arg
            275                 280                 285

Ile Cys Asp Thr Val Leu Ile Val Leu Ala Leu Leu Leu Leu Leu Pro
        290                 295                 300

Pro Leu Leu Ala Val Ile Val Asp Gly Val Asn Arg Gln Leu Pro Glu
305                 310                 315                 320

Val Leu Ala Gln Pro Val Leu Trp Gln Ala Leu Trp Thr Ser Leu Arg
                325                 330                 335

Ile Ala Leu Ala Ala Gly Val Leu Cys Val Val Leu Thr Met Met Leu
                340                 345                 350

Leu Trp Ser Ser Arg Glu Leu Arg Ala Arg Gln Lys Met Leu Ala Gly
            355                 360                 365

Gln Val Leu Glu Met Ser Gly Met Leu Ile Leu Ala Met Pro Gly Ile
    370                 375                 380

Val Leu Ala Thr Gly Phe Phe Leu Leu Leu Asn Asn Thr Ile Gly Leu
385                 390                 395                 400

Pro Gln Ser Ala Asp Gly Ile Val Ile Phe Thr Asn Ala Leu Met Ala
                405                 410                 415

Ile Pro Tyr Ala Leu Lys Val Leu Glu Asn Pro Met Arg Asp Ile Thr
                420                 425                 430

Ala Arg Tyr Ser Met Leu Cys Gln Ser Leu Gly Ile Glu Gly Trp Ser
            435                 440                 445

Arg Leu Lys Val Val Glu Leu Arg Ala Leu Lys Arg Pro Leu Ala Gln
        450                 455                 460

Ala Leu Ala Phe Ala Cys Val Leu Ser Ile Gly Asp Phe Gly Val Val
465                 470                 475                 480

Ala Leu Phe Gly Asn Asp Asp Phe Arg Thr Leu Pro Phe Tyr Leu Tyr
                485                 490                 495

Gln Gln Ile Gly Ser Tyr Arg Ser Gln Asp Gly Ala Val Thr Ala Leu
            500                 505                 510

Ile Leu Leu Leu Leu Cys Phe Leu Phe Thr Val Ile Glu Lys Leu
        515                 520                 525

Pro Gly Arg Asn Val Lys Thr Asp
530                 535
```

```
<210> SEQ ID NO 105
<211> LENGTH: 699
<212> TYPE: DNA
<213> ORGANISM: Escherichia coli
<220> FEATURE:
<221> NAME/KEY: CDS
<222> LOCATION: (1)..(696)
<223> OTHER INFORMATION: ThiQ gene from E. coli encoding a thiamine ABC
      transporter ATPase

<400> SEQUENCE: 105 atg tta aaa ctg act gat atc acc tgg ctt tac cac cat ttg ccg atg      48
Met Leu Lys Leu Thr Asp Ile Thr Trp Leu Tyr His His Leu Pro Met
 1               5                  10                  15 cgt ttt agc tta acg gtg gaa cgc ggc gag cag gtg gcg atc ctc ggg      96
Arg Phe Ser Leu Thr Val Glu Arg Gly Glu Gln Val Ala Ile Leu Gly
            20                  25                  30 cca agc ggc gcg ggt aaa agt acc ctg ctg aat ttg atc gcc ggt ttt     144
Pro Ser Gly Ala Gly Lys Ser Thr Leu Leu Asn Leu Ile Ala Gly Phe
        35                  40                  45 ctg acg cca gcc agc ggt tcg ctg act atc gat ggc gta gat cac aca     192
Leu Thr Pro Ala Ser Gly Ser Leu Thr Ile Asp Gly Val Asp His Thr
    50                  55                  60 act atg ccg ccg tca cgc cgt ccg gtg tcg atg ctg ttt cag gag aac     240
Thr Met Pro Pro Ser Arg Arg Pro Val Ser Met Leu Phe Gln Glu Asn
65                  70                  75                  80 aac ctg ttc agc cac ctg acg gtc gca cag aac atc ggg ctg ggg cta     288
Asn Leu Phe Ser His Leu Thr Val Ala Gln Asn Ile Gly Leu Gly Leu
                85                  90                  95 aat ccg gga ttg aaa ctg aac gcg gta cag cag ggg aaa atg cac gct     336
Asn Pro Gly Leu Lys Leu Asn Ala Val Gln Gln Gly Lys Met His Ala
            100                 105                 110 atc gcc cgc cag atg ggg att gat aat tta atg gcg cgg tta ccg ggc     384
Ile Ala Arg Gln Met Gly Ile Asp Asn Leu Met Ala Arg Leu Pro Gly
        115                 120                 125 gag ctt tcc ggc ggt cag cga cag cga gtg gcg tta gcg cgt tgt ctg     432
Glu Leu Ser Gly Gly Gln Arg Gln Arg Val Ala Leu Ala Arg Cys Leu
    130                 135                 140 gta cgc gaa cag ccg att tta ttg ctc gat gaa ccg ttc tct gcg ctc     480
Val Arg Glu Gln Pro Ile Leu Leu Leu Asp Glu Pro Phe Ser Ala Leu
145                 150                 155                 160 gat ccg gcg tta cgt cag gag atg ttg acg ctg gtg agc acg agc tgc     528
Asp Pro Ala Leu Arg Gln Glu Met Leu Thr Leu Val Ser Thr Ser Cys
                165                 170                 175 cag cag caa aaa atg acg cta ttg atg gtg tcg cac agc gtg gaa gat     576
Gln Gln Gln Lys Met Thr Leu Leu Met Val Ser His Ser Val Glu Asp
            180                 185                 190 gcg gcg cgg atc gcc acg cgc tcg gta gta gtc gcc gac ggg cgc atc     624
Ala Ala Arg Ile Ala Thr Arg Ser Val Val Val Ala Asp Gly Arg Ile
        195                 200                 205 gcc tgg cag ggt atg acc aat gag ttg ttg agc ggt aag gca agt gct     672
Ala Trp Gln Gly Met Thr Asn Glu Leu Leu Ser Gly Lys Ala Ser Ala
    210                 215                 220 tcg gca cta ttg ggg att acg ggt tag                                 699
Ser Ala Leu Leu Gly Ile Thr Gly
225                 230

<210> SEQ ID NO 106
<211> LENGTH: 232
<212> TYPE: PRT
<213> ORGANISM: Escherichia coli

<400> SEQUENCE: 106
```

```
Met Leu Lys Leu Thr Asp Ile Thr Trp Leu Tyr His His Leu Pro Met
1               5                   10                  15

Arg Phe Ser Leu Thr Val Glu Arg Gly Glu Gln Val Ala Ile Leu Gly
            20                  25                  30

Pro Ser Gly Ala Gly Lys Ser Thr Leu Leu Asn Leu Ile Ala Gly Phe
        35                  40                  45

Leu Thr Pro Ala Ser Gly Ser Leu Thr Ile Asp Gly Val Asp His Thr
    50                  55                  60

Thr Met Pro Pro Ser Arg Arg Pro Val Ser Met Leu Phe Gln Glu Asn
65                  70                  75                  80

Asn Leu Phe Ser His Leu Thr Val Ala Gln Asn Ile Gly Leu Gly Leu
            85                  90                  95

Asn Pro Gly Leu Lys Leu Asn Ala Val Gln Gln Gly Lys Met His Ala
            100                 105                 110

Ile Ala Arg Gln Met Gly Ile Asp Asn Leu Met Ala Arg Leu Pro Gly
            115                 120                 125

Glu Leu Ser Gly Gly Gln Arg Gln Arg Val Ala Leu Ala Arg Cys Leu
    130                 135                 140

Val Arg Glu Gln Pro Ile Leu Leu Leu Asp Glu Pro Phe Ser Ala Leu
145                 150                 155                 160

Asp Pro Ala Leu Arg Gln Glu Met Leu Thr Leu Val Ser Thr Ser Cys
                165                 170                 175

Gln Gln Gln Lys Met Thr Leu Leu Met Val Ser His Ser Val Glu Asp
            180                 185                 190

Ala Ala Arg Ile Ala Thr Arg Ser Val Val Ala Asp Gly Arg Ile
            195                 200                 205

Ala Trp Gln Gly Met Thr Asn Glu Leu Leu Ser Gly Lys Ala Ser Ala
210                 215                 220

Ser Ala Leu Leu Gly Ile Thr Gly
225                 230
```

<210> SEQ ID NO 107
<211> LENGTH: 789
<212> TYPE: DNA
<213> ORGANISM: Escherichia coli
<220> FEATURE:
<221> NAME/KEY: CDS
<222> LOCATION: (1)..(786)
<223> OTHER INFORMATION: ThiM gene from E. coli encoding a
      Hydroxyethylthiazole kinase

<400> SEQUENCE: 107

```
atg caa gtc gac ctg ctg ggt tca gcg caa tct gcg cac gcg tta cac    48
Met Gln Val Asp Leu Leu Gly Ser Ala Gln Ser Ala His Ala Leu His
1               5                   10                  15 ctt ttt cac caa cat tcc cct ctt gtg cac tgc atg acc aat gat gtg    96
Leu Phe His Gln His Ser Pro Leu Val His Cys Met Thr Asn Asp Val
            20                  25                  30 gtg caa acc ttt acc gcc aat acc ttg ctg gcg ctc ggt gca tcg cca   144
Val Gln Thr Phe Thr Ala Asn Thr Leu Leu Ala Leu Gly Ala Ser Pro
        35                  40                  45 gcg atg gtt atc gaa acc gaa gag gcc agt cag ttt gcg gct atc gcc   192
Ala Met Val Ile Glu Thr Glu Glu Ala Ser Gln Phe Ala Ala Ile Ala
    50                  55                  60 agt gcc ttg ttg att aac gtt ggc aca ctg acg cag cca cgc gct cag   240
Ser Ala Leu Leu Ile Asn Val Gly Thr Leu Thr Gln Pro Arg Ala Gln
65                  70                  75                  80
```

| | | |
|---|---|---|
| gcg atg cgt gct gcc gtt gag caa gca aaa agc tct caa aca ccc tgg<br>Ala Met Arg Ala Ala Val Glu Gln Ala Lys Ser Ser Gln Thr Pro Trp<br>                        85                        90                    95 | 288 |
| acg ctt gat cca gta gcg gtg ggt gcg ctc gat tat cgc cgc cat ttt<br>Thr Leu Asp Pro Val Ala Val Gly Ala Leu Asp Tyr Arg Arg His Phe<br>                      100                   105                  110 | 336 |
| tgt cat gaa ctt tta tct ttt aaa ccg gca gcg ata cgt ggt aat gct<br>Cys His Glu Leu Leu Ser Phe Lys Pro Ala Ala Ile Arg Gly Asn Ala<br>         115                   120                   125 | 384 |
| tcg gaa atc atg gca tta gct ggc att gct aat ggc gga cgg gga gtg<br>Ser Glu Ile Met Ala Leu Ala Gly Ile Ala Asn Gly Gly Arg Gly Val<br>130                   135                   140 | 432 |
| gat acc act gac gcc gca gct aac gcg ata ccc gct gca caa aca ctg<br>Asp Thr Thr Asp Ala Ala Ala Asn Ala Ile Pro Ala Ala Gln Thr Leu<br>145                   150                   155                160 | 480 |
| gca cgg gaa act ggc gca atc gtc gtg gtc act ggc gag atg gat tat<br>Ala Arg Glu Thr Gly Ala Ile Val Val Val Thr Gly Glu Met Asp Tyr<br>                      165                   170                 175 | 528 |
| gtt acc gat gga cat cgt atc att ggt att cac ggt ggt gat ccg tta<br>Val Thr Asp Gly His Arg Ile Ile Gly Ile His Gly Gly Asp Pro Leu<br>               180                   185                   190 | 576 |
| atg acc aaa gtg gta gga act ggc tgt gca tta tcg gcg gtt gtc gct<br>Met Thr Lys Val Val Gly Thr Gly Cys Ala Leu Ser Ala Val Val Ala<br>195                   200                   205 | 624 |
| gcc tgc tgt gcg tta cca ggc gat acg ctg gaa aat gtc gca tct gcc<br>Ala Cys Cys Ala Leu Pro Gly Asp Thr Leu Glu Asn Val Ala Ser Ala<br>210                   215                   220 | 672 |
| tgt cac tgg atg aaa caa gcc gga gaa cgc gca gtc gcc aga agc gag<br>Cys His Trp Met Lys Gln Ala Gly Glu Arg Ala Val Ala Arg Ser Glu<br>225                   230                   235                240 | 720 |
| ggg cca ggc agt ttt gtt cca cat ttc ctt gat gcg ctc tgg caa ttg<br>Gly Pro Gly Ser Phe Val Pro His Phe Leu Asp Ala Leu Trp Gln Leu<br>                      245                   250                 255 | 768 |
| acg cag gag gtg cag gca tga<br>Thr Gln Glu Val Gln Ala<br>               260 | 789 |

<210> SEQ ID NO 108
<211> LENGTH: 262
<212> TYPE: PRT
<213> ORGANISM: Escherichia coli

<400> SEQUENCE: 108

Met Gln Val Asp Leu Leu Gly Ser Ala Gln Ser Ala His Ala Leu His
1               5                   10                  15

Leu Phe His Gln His Ser Pro Leu Val His Cys Met Thr Asn Asp Val
                20                  25                  30

Val Gln Thr Phe Thr Ala Asn Thr Leu Leu Ala Leu Gly Ala Ser Pro
            35                  40                  45

Ala Met Val Ile Glu Thr Glu Ala Ser Gln Phe Ala Ala Ile Ala
        50                  55                  60

Ser Ala Leu Leu Ile Asn Val Gly Thr Leu Thr Gln Pro Arg Ala Gln
65                  70                  75                  80

Ala Met Arg Ala Ala Val Glu Gln Ala Lys Ser Ser Gln Thr Pro Trp
                85                  90                  95

Thr Leu Asp Pro Val Ala Val Gly Ala Leu Asp Tyr Arg Arg His Phe
            100                 105                 110

Cys His Glu Leu Leu Ser Phe Lys Pro Ala Ala Ile Arg Gly Asn Ala
        115                 120                 125

```
Ser Glu Ile Met Ala Leu Ala Gly Ile Ala Asn Gly Arg Gly Val
    130                 135                 140

Asp Thr Thr Asp Ala Ala Asn Ala Ile Pro Ala Ala Gln Thr Leu
145                 150                 155                 160

Ala Arg Glu Thr Gly Ala Ile Val Val Thr Gly Glu Met Asp Tyr
                165                 170                 175

Val Thr Asp Gly His Arg Ile Ile Gly Ile His Gly Asp Pro Leu
                180                 185                 190

Met Thr Lys Val Val Gly Thr Gly Cys Ala Leu Ser Ala Val Ala
                195                 200                 205

Ala Cys Cys Ala Leu Pro Gly Asp Thr Leu Glu Asn Val Ala Ser Ala
    210                 215                 220

Cys His Trp Met Lys Gln Ala Gly Glu Arg Ala Val Ala Arg Ser Glu
225                 230                 235                 240

Gly Pro Gly Ser Phe Val Pro His Phe Leu Asp Ala Leu Trp Gln Leu
                245                 250                 255

Thr Gln Glu Val Gln Ala
            260
```

```
<210> SEQ ID NO 109
<211> LENGTH: 978
<212> TYPE: DNA
<213> ORGANISM: Escherichia coli
<220> FEATURE:
<221> NAME/KEY: CDS
<222> LOCATION: (1)..(975)
<223> OTHER INFORMATION: ThiL gene from E. coli encoding thiamine-
      phosphate kinase (Note: mutation at nucleotides 133-135 (GGT to
      GAC) encodes a G133D substitution)

<400> SEQUENCE: 109 atg gca tgt ggc gag ttc tcc ctg att gcc cgt tat ttt gac cgt gta      48
Met Ala Cys Gly Glu Phe Ser Leu Ile Ala Arg Tyr Phe Asp Arg Val
1               5                   10                  15 aga agt tct cgt ctt gat gtc gaa ctg ggc atc ggc gac gat tgc gca      96
Arg Ser Ser Arg Leu Asp Val Glu Leu Gly Ile Gly Asp Asp Cys Ala
            20                  25                  30 ctt ctc aat atc ccc gag aaa cag acc ctg gcg atc agc act gat acg     144
Leu Leu Asn Ile Pro Glu Lys Gln Thr Leu Ala Ile Ser Thr Asp Thr
        35                  40                  45 ctg gtg gcg ggt aac cat ttc ctc cct gat atc gat cct gct gat ctg     192
Leu Val Ala Gly Asn His Phe Leu Pro Asp Ile Asp Pro Ala Asp Leu
    50                  55                  60 gct tat aaa gca ctg gcg gtg aac cta agc gat ctg gca gcg atg ggg     240
Ala Tyr Lys Ala Leu Ala Val Asn Leu Ser Asp Leu Ala Ala Met Gly
65                  70                  75                  80 gcc gat ccg gcc tgg ctg acg ctg gca tta acc tta ccg gac gta gac     288
Ala Asp Pro Ala Trp Leu Thr Leu Ala Leu Thr Leu Pro Asp Val Asp
                85                  90                  95 gaa gcg tgg ctt gag tcc ttc agc gac agt ttg ttt gat ctt ctc aat     336
Glu Ala Trp Leu Glu Ser Phe Ser Asp Ser Leu Phe Asp Leu Leu Asn
            100                 105                 110 tat tac gat atg caa ctc att ggc ggc gat acc acg cgt ggg cca tta     384
Tyr Tyr Asp Met Gln Leu Ile Gly Gly Asp Thr Thr Arg Gly Pro Leu
        115                 120                 125 tca atg acg ttg ggt atc cac ggc ttt gtt ccg atg gga cga gcc tta     432
Ser Met Thr Leu Gly Ile His Gly Phe Val Pro Met Gly Arg Ala Leu
    130                 135                 140 acg cgc tct ggg gcg aaa ccg ggt gac tgg atc tat gtg acc ggt aca     480
Thr Arg Ser Gly Ala Lys Pro Gly Asp Trp Ile Tyr Val Thr Gly Thr
```

```
Thr Arg Ser Gly Ala Lys Pro Gly Asp Trp Ile Tyr Val Thr Gly Thr
145                 150                 155                 160 ccg ggc gat agc gcc gcc ggg ctg gcg att ttg caa aac cgt ttg cag      528
Pro Gly Asp Ser Ala Ala Gly Leu Ala Ile Leu Gln Asn Arg Leu Gln
                165                 170                 175 gtt gcc gat gct aaa gat gcg gac tac ttg atc aaa cgt cat ctc cgt      576
Val Ala Asp Ala Lys Asp Ala Asp Tyr Leu Ile Lys Arg His Leu Arg
            180                 185                 190 cca tcg ccg cgt att tta cag ggg cag gca ctg cgc gat ctg gca aat      624
Pro Ser Pro Arg Ile Leu Gln Gly Gln Ala Leu Arg Asp Leu Ala Asn
        195                 200                 205 tca gcc atc gat ctc tct gac ggt ttg att tcc gat ctc ggg cat atc      672
Ser Ala Ile Asp Leu Ser Asp Gly Leu Ile Ser Asp Leu Gly His Ile
    210                 215                 220 gtg aaa gcc agc gac tgc ggc gca cgt att gac ctg gca ttg ctg ccg      720
Val Lys Ala Ser Asp Cys Gly Ala Arg Ile Asp Leu Ala Leu Leu Pro
225                 230                 235                 240 ttt tct gat gcg ctt tct cgc cat gtt gaa ccg gaa cag gcg ctg cgc      768
Phe Ser Asp Ala Leu Ser Arg His Val Glu Pro Glu Gln Ala Leu Arg
                245                 250                 255 tgg gcg ctc tct ggc ggt gaa gat tac gag ttg tgt ttc act gtg ccg      816
Trp Ala Leu Ser Gly Gly Glu Asp Tyr Glu Leu Cys Phe Thr Val Pro
            260                 265                 270 gaa ctg aac cgt ggc gcg ctg gat gtg gct ctc gga cac ctg ggc gta      864
Glu Leu Asn Arg Gly Ala Leu Asp Val Ala Leu Gly His Leu Gly Val
        275                 280                 285 ccg ttt acc tgt atc ggg caa atg acc gcc gat atc gaa ggg ctt tgt      912
Pro Phe Thr Cys Ile Gly Gln Met Thr Ala Asp Ile Glu Gly Leu Cys
    290                 295                 300 ttt att cgt gac ggc gaa cct gtt aca tta gac tgg aaa gga tat gac      960
Phe Ile Arg Asp Gly Glu Pro Val Thr Leu Asp Trp Lys Gly Tyr Asp
305                 310                 315                 320 cat ttt gcc acg cca taa                                              978
His Phe Ala Thr Pro
                325

<210> SEQ ID NO 110
<211> LENGTH: 325
<212> TYPE: PRT
<213> ORGANISM: Escherichia coli

<400> SEQUENCE: 110

Met Ala Cys Gly Glu Phe Ser Leu Ile Ala Arg Tyr Phe Asp Arg Val
1               5                   10                  15

Arg Ser Ser Arg Leu Asp Val Glu Leu Gly Ile Gly Asp Asp Cys Ala
            20                  25                  30

Leu Leu Asn Ile Pro Glu Lys Gln Thr Leu Ala Ile Ser Thr Asp Thr
        35                  40                  45

Leu Val Ala Gly Asn His Phe Leu Pro Asp Ile Asp Pro Ala Asp Leu
    50                  55                  60

Ala Tyr Lys Ala Leu Ala Val Asn Leu Ser Asp Leu Ala Ala Met Gly
65                  70                  75                  80

Ala Asp Pro Ala Trp Leu Thr Leu Ala Leu Thr Leu Pro Asp Val Asp
                85                  90                  95

Glu Ala Trp Leu Glu Ser Phe Ser Asp Ser Leu Phe Asp Leu Leu Asn
            100                 105                 110

Tyr Tyr Asp Met Gln Leu Ile Gly Gly Asp Thr Thr Arg Gly Pro Leu
        115                 120                 125
```

```
Ser Met Thr Leu Gly Ile His Gly Phe Val Pro Met Gly Arg Ala Leu
    130                 135                 140
Thr Arg Ser Gly Ala Lys Pro Gly Asp Trp Ile Tyr Val Thr Gly Thr
145                 150                 155                 160
Pro Gly Asp Ser Ala Ala Gly Leu Ala Ile Leu Gln Asn Arg Leu Gln
                165                 170                 175
Val Ala Asp Ala Lys Asp Ala Asp Tyr Leu Ile Lys Arg His Leu Arg
            180                 185                 190
Pro Ser Pro Arg Ile Leu Gln Gly Gln Ala Leu Arg Asp Leu Ala Asn
        195                 200                 205
Ser Ala Ile Asp Leu Ser Asp Gly Leu Ile Ser Asp Leu Gly His Ile
    210                 215                 220
Val Lys Ala Ser Asp Cys Gly Ala Arg Ile Asp Leu Ala Leu Leu Pro
225                 230                 235                 240
Phe Ser Asp Ala Leu Ser Arg His Val Glu Pro Glu Gln Ala Leu Arg
                245                 250                 255
Trp Ala Leu Ser Gly Gly Glu Asp Tyr Glu Leu Cys Phe Thr Val Pro
            260                 265                 270
Glu Leu Asn Arg Gly Ala Leu Asp Val Ala Leu Gly His Leu Gly Val
        275                 280                 285
Pro Phe Thr Cys Ile Gly Gln Met Thr Ala Asp Ile Glu Gly Leu Cys
    290                 295                 300
Phe Ile Arg Asp Gly Glu Pro Val Thr Leu Asp Trp Lys Gly Tyr Asp
305                 310                 315                 320
His Phe Ala Thr Pro
                325

<210> SEQ ID NO 111
<211> LENGTH: 876
<212> TYPE: DNA
<213> ORGANISM: Staphylococcus aureus
<220> FEATURE:
<221> NAME/KEY: CDS
<222> LOCATION: (1)..(873)
<223> OTHER INFORMATION: RgsA from S. aureus Newmann encoding a
      phosphatase

<400> SEQUENCE: 111 atg aag aca ggt cga ata gtg aaa tca att agt ggg gta tat caa gta      48
Met Lys Thr Gly Arg Ile Val Lys Ser Ile Ser Gly Val Tyr Gln Val
1               5                   10                  15 gac gtt aat ggc gaa cgt ttc aat aca aaa cca cga gga tta ttt aga      96
Asp Val Asn Gly Glu Arg Phe Asn Thr Lys Pro Arg Gly Leu Phe Arg
                20                  25                  30 aag aaa aaa ttt tca ccg gta gtt ggt gat ata gtg gaa ttt gaa gtt     144
Lys Lys Lys Phe Ser Pro Val Val Gly Asp Ile Val Glu Phe Glu Val
            35                  40                  45 caa aac att aac gaa ggt tat att cat caa gtg ttt gag cgg gaa aat     192
Gln Asn Ile Asn Glu Gly Tyr Ile His Gln Val Phe Glu Arg Glu Asn
        50                  55                  60 gag ttg aaa aga cca cct gta agt aat ata gat aca cta gta att gta     240
Glu Leu Lys Arg Pro Pro Val Ser Asn Ile Asp Thr Leu Val Ile Val
65                  70                  75                  80 atg agt gct gtc gag cca aat ttt tca acg caa tta tta gat cga ttt     288
Met Ser Ala Val Glu Pro Asn Phe Ser Thr Gln Leu Leu Asp Arg Phe
                85                  90                  95 tta gtt att gca cat tcg tat cag tta aat gcg aga att ttg gtg act     336
Leu Val Ile Ala His Ser Tyr Gln Leu Asn Ala Arg Ile Leu Val Thr
                100                 105                 110
```

```
aaa aaa gat aaa aca cca att gaa aag cag ttc gaa ata aat gag ttg      384
Lys Lys Asp Lys Thr Pro Ile Glu Lys Gln Phe Glu Ile Asn Glu Leu
            115                 120                 125 ttg aaa ata tat gaa aat att ggc tat gag act gaa ttt att gga aat      432
Leu Lys Ile Tyr Glu Asn Ile Gly Tyr Glu Thr Glu Phe Ile Gly Asn
        130                 135                 140 gat gat gat cga aaa aaa att gta gaa gct tgg cca gct gga ctt ata      480
Asp Asp Asp Arg Lys Lys Ile Val Glu Ala Trp Pro Ala Gly Leu Ile
145                 150                 155                 160 gta ctt agt ggt caa tca ggt gtc ggt aag tcc act ttc tta aat cat      528
Val Leu Ser Gly Gln Ser Gly Val Gly Lys Ser Thr Phe Leu Asn His
                165                 170                 175 tat cgt cca gaa ctt aat ctt gag aca aat gat ata tca aaa tca tta      576
Tyr Arg Pro Glu Leu Asn Leu Glu Thr Asn Asp Ile Ser Lys Ser Leu
            180                 185                 190 aat cga gga aag cat act aca aga cat gtc gaa cta ttc gaa cgt caa      624
Asn Arg Gly Lys His Thr Thr Arg His Val Glu Leu Phe Glu Arg Gln
        195                 200                 205 aac ggt tat att gca gac aca cct gga ttc agt gct tta gat ttt gat      672
Asn Gly Tyr Ile Ala Asp Thr Pro Gly Phe Ser Ala Leu Asp Phe Asp
210                 215                 220 cat ata gat aaa gat gaa ata aaa gat tat ttt ctt gaa tta aat cga      720
His Ile Asp Lys Asp Glu Ile Lys Asp Tyr Phe Leu Glu Leu Asn Arg
225                 230                 235                 240 tat ggt gaa aca tgt aag ttt agg aat tgt aat cat atc aaa gaa cct      768
Tyr Gly Glu Thr Cys Lys Phe Arg Asn Cys Asn His Ile Lys Glu Pro
                245                 250                 255 aat tgt aat gtt aag cat caa tta gag ata ggg aat att gcg caa ttt      816
Asn Cys Asn Val Lys His Gln Leu Glu Ile Gly Asn Ile Ala Gln Phe
            260                 265                 270 aga tac gac cat tat tta caa cta ttt aat gaa att tca aat aga aag      864
Arg Tyr Asp His Tyr Leu Gln Leu Phe Asn Glu Ile Ser Asn Arg Lys
        275                 280                 285 gtt aga tat taa                                                      876
Val Arg Tyr
    290

<210> SEQ ID NO 112
<211> LENGTH: 291
<212> TYPE: PRT
<213> ORGANISM: Staphylococcus aureus

<400> SEQUENCE: 112

Met Lys Thr Gly Arg Ile Val Lys Ser Ile Ser Gly Val Tyr Gln Val
1               5                   10                  15

Asp Val Asn Gly Glu Arg Phe Asn Thr Lys Pro Arg Gly Leu Phe Arg
            20                  25                  30

Lys Lys Lys Phe Ser Pro Val Val Gly Asp Ile Val Glu Phe Glu Val
        35                  40                  45

Gln Asn Ile Asn Glu Gly Tyr Ile His Gln Val Phe Glu Arg Glu Asn
    50                  55                  60

Glu Leu Lys Arg Pro Val Ser Asn Ile Asp Thr Leu Val Ile Val
65                  70                  75                  80

Met Ser Ala Val Glu Pro Asn Phe Ser Thr Gln Leu Leu Asp Arg Phe
                85                  90                  95

Leu Val Ile Ala His Ser Tyr Gln Leu Asn Ala Arg Ile Leu Val Thr
            100                 105                 110

Lys Lys Asp Lys Thr Pro Ile Glu Lys Gln Phe Glu Ile Asn Glu Leu
```

```
                 115                 120                 125

Leu Lys Ile Tyr Glu Asn Ile Gly Tyr Glu Thr Glu Phe Ile Gly Asn
    130                 135                 140

Asp Asp Asp Arg Lys Lys Ile Val Glu Ala Trp Pro Ala Gly Leu Ile
145                 150                 155                 160

Val Leu Ser Gly Gln Ser Gly Val Gly Lys Ser Thr Phe Leu Asn His
                165                 170                 175

Tyr Arg Pro Glu Leu Asn Leu Gly Thr Asn Asp Ile Ser Lys Ser Leu
            180                 185                 190

Asn Arg Gly Lys His Thr Thr Arg His Val Glu Leu Phe Glu Arg Gln
        195                 200                 205

Asn Gly Tyr Ile Ala Asp Thr Pro Gly Phe Ser Ala Leu Asp Phe Asp
    210                 215                 220

His Ile Asp Lys Asp Glu Ile Lys Asp Tyr Phe Leu Glu Leu Asn Arg
225                 230                 235                 240

Tyr Gly Glu Thr Cys Lys Phe Arg Asn Cys Asn His Ile Lys Glu Pro
                245                 250                 255

Asn Cys Asn Val Lys His Gln Leu Glu Ile Gly Asn Ile Ala Gln Phe
            260                 265                 270

Arg Tyr Asp His Tyr Leu Gln Leu Phe Asn Glu Ile Ser Asn Arg Lys
        275                 280                 285

Val Arg Tyr
    290

<210> SEQ ID NO 113
<211> LENGTH: 786
<212> TYPE: DNA
<213> ORGANISM: Pseudomonas sp.
<220> FEATURE:
<221> NAME/KEY: CDS
<222> LOCATION: (1)..(783)
<223> OTHER INFORMATION: Pseudomonas gene encoding a phosphatase

<400> SEQUENCE: 113 atg tgc cag cag cat ccg cct gcc aac gac caa ctg gac gcg gtg ctg      48
Met Cys Gln Gln His Pro Pro Ala Asn Asp Gln Leu Asp Ala Val Leu
1               5                   10                  15 tgg acc cag acc tcc atc gaa cac gag ctg att tat cgc cag gta ttc      96
Trp Thr Gln Thr Ser Ile Glu His Glu Leu Ile Tyr Arg Gln Val Phe
            20                  25                  30 gcc agc gcc acg cgc cag ctg gac gcc gcg ctg gcc gat ccg acc tgg     144
Ala Ser Ala Thr Arg Gln Leu Asp Ala Ala Leu Ala Asp Pro Thr Trp
        35                  40                  45 gac gcc ctg ccc ttg ccg ccg cgc aac ctc gcc ggg ctg ccg ccg gca     192
Asp Ala Leu Pro Leu Pro Pro Arg Asn Leu Ala Gly Leu Pro Pro Ala
50                  55                  60 gtg gta gtg gat atc gat gaa acc gtg ctc gac aac gtg ccg ctc aac     240
Val Val Val Asp Ile Asp Glu Thr Val Leu Asp Asn Val Pro Leu Asn
65                  70                  75                  80 gcg cgg gac atc atc aac aac cag gtg tat tcc tat gac cgc tgg aac     288
Ala Arg Asp Ile Ile Asn Asn Gln Val Tyr Ser Tyr Asp Arg Trp Asn
                85                  90                  95 acc tgg gtc gac cag gcc aag gcc cag gcg ctg ccc ggc gcc gta gcg     336
Thr Trp Val Asp Gln Ala Lys Ala Gln Ala Leu Pro Gly Ala Val Ala
            100                 105                 110 ttc ctg caa gcg gcc gat aaa aaa ggc atc acc gtc tac tac atc acc     384
Phe Leu Gln Ala Ala Asp Lys Lys Gly Ile Thr Val Tyr Tyr Ile Thr
        115                 120                 125
```

| | | |
|---|---|---|
| aac cgt gaa cac agc cag gtc cag gcc acg gtc gac aac ctg cgc ctg<br>Asn Arg Glu His Ser Gln Val Gln Ala Thr Val Asp Asn Leu Arg Leu<br>130                 135                       140 | | 432 |
| cgc ggt ttc ccg gtg cag cgc aac gaa cag gta ctg gcc gcc agc acc<br>Arg Gly Phe Pro Val Gln Arg Asn Glu Gln Val Leu Ala Ala Ser Thr<br>145                 150                     155                 160 | | 480 |
| ccg acc ggc cac tgc gaa cag gcc ggc tat ggc aag aac tgc cgc cgc<br>Pro Thr Gly His Cys Glu Gln Ala Gly Tyr Gly Lys Asn Cys Arg Arg<br>                 165                       170                 175 | | 528 |
| cag tgg gtg gcc gcg cat gcc cgt gtg ctg atg ctc gcc ggc gac tcg<br>Gln Trp Val Ala Ala His Ala Arg Val Leu Met Leu Ala Gly Asp Ser<br>                      180                       185                 190 | | 576 |
| ctg ggc gac ttc gtg cag gcc gag cac aac acc ctg gcc gac cag cgc<br>Leu Gly Asp Phe Val Gln Ala Glu His Asn Thr Leu Ala Asp Gln Arg<br>                 195                       200                 205 | | 624 |
| aag gca gcc gaa ccg tac ctg gcc tgg ctc ggc caa cgc tgg ttc ctg<br>Lys Ala Ala Glu Pro Tyr Leu Ala Trp Leu Gly Gln Arg Trp Phe Leu<br>210                 215                       220 | | 672 |
| ctg ccc aac cct acg tat ggc aac tgg tac agc gcg ccc tac ggc gac<br>Leu Pro Asn Pro Thr Tyr Gly Asn Trp Tyr Ser Ala Pro Tyr Gly Asp<br>225                 230                     235                 240 | | 720 |
| cag gaa aaa ctg ccc ttt gaa cgc aag cgc cag ctc aag caa cag gcg<br>Gln Glu Lys Leu Pro Phe Glu Arg Lys Arg Gln Leu Lys Gln Gln Ala<br>                      245                       250                 255 | | 768 |
| ctg cct cta gaa aac tag<br>Leu Pro Leu Glu Asn<br>                 260 | | 786 |

```
<210> SEQ ID NO 114
<211> LENGTH: 261
<212> TYPE: PRT
<213> ORGANISM: Pseudomonas sp.

<400> SEQUENCE: 114
```

Met Cys Gln Gln His Pro Pro Ala Asn Asp Gln Leu Asp Ala Val Leu
1                 5                     10                     15

Trp Thr Gln Thr Ser Ile Glu His Glu Leu Ile Tyr Arg Gln Val Phe
                 20                     25                     30

Ala Ser Ala Thr Arg Gln Leu Asp Ala Leu Ala Asp Pro Thr Trp
               35                     40                     45

Asp Ala Leu Pro Leu Pro Pro Arg Asn Leu Ala Gly Leu Pro Pro Ala
 50                       55                     60

Val Val Val Asp Ile Asp Glu Thr Val Leu Asp Asn Val Pro Leu Asn
65                 70                     75                     80

Ala Arg Asp Ile Ile Asn Asn Gln Val Tyr Ser Tyr Asp Arg Trp Asn
                      85                     90                 95

Thr Trp Val Asp Gln Ala Lys Ala Gln Ala Leu Pro Gly Ala Val Ala
                 100                     105                 110

Phe Leu Gln Ala Ala Asp Lys Lys Gly Ile Thr Val Tyr Tyr Ile Thr
               115                     120                 125

Asn Arg Glu His Ser Gln Val Gln Ala Thr Val Asp Asn Leu Arg Leu
 130                      135                     140

Arg Gly Phe Pro Val Gln Arg Asn Glu Gln Val Leu Ala Ala Ser Thr
145                150                     155                 160

Pro Thr Gly His Cys Glu Gln Ala Gly Tyr Gly Lys Asn Cys Arg Arg
                 165                     170                 175

Gln Trp Val Ala Ala His Ala Arg Val Leu Met Leu Ala Gly Asp Ser
                      180                     185                 190

```
Leu Gly Asp Phe Val Gln Ala Glu His Asn Thr Leu Ala Asp Gln Arg
        195                 200                 205

Lys Ala Ala Glu Pro Tyr Leu Ala Trp Leu Gly Gln Arg Trp Phe Leu
    210                 215                 220

Leu Pro Asn Pro Thr Tyr Gly Asn Trp Tyr Ser Ala Pro Tyr Gly Asp
225                 230                 235                 240

Gln Glu Lys Leu Pro Phe Glu Arg Lys Arg Gln Leu Lys Gln Ala
                245                 250                 255

Leu Pro Leu Glu Asn
            260

<210> SEQ ID NO 115
<211> LENGTH: 1404
<212> TYPE: DNA
<213> ORGANISM: Saccharomyces cerevisiae
<220> FEATURE:
<221> NAME/KEY: CDS
<222> LOCATION: (1)..(1401)
<223> OTHER INFORMATION: PHHO3 gene from S. cerevisiae encoding a
      phosphatase (YBR092C)

<400> SEQUENCE: 115 atg ttc aaa tcc gtg gtg tat agc gtc ctg gcg gcc gct ttg gtc aac      48
Met Phe Lys Ser Val Val Tyr Ser Val Leu Ala Ala Ala Leu Val Asn
1               5                   10                  15 gct ggt act att ccg ctg gga gaa ctt gcg gat gtg gcg aaa att ggc      96
Ala Gly Thr Ile Pro Leu Gly Glu Leu Ala Asp Val Ala Lys Ile Gly
            20                  25                  30 acc caa gag gac atc ttc ccg ttc ctc ggc ggc gcc gga ccg tat ttt     144
Thr Gln Glu Asp Ile Phe Pro Phe Leu Gly Gly Ala Gly Pro Tyr Phe
        35                  40                  45 agt ttt ccg ggt gac tac ggg att tcc cgc gac tta cca gaa ggc tgt     192
Ser Phe Pro Gly Asp Tyr Gly Ile Ser Arg Asp Leu Pro Glu Gly Cys
    50                  55                  60 gag atg aaa cag tta caa atg tta gct cgt cat ggc gaa cgc tac cca     240
Glu Met Lys Gln Leu Gln Met Leu Ala Arg His Gly Glu Arg Tyr Pro
65                  70                  75                  80 acc tac tca aag ggg gcg act atc atg aaa acc tgg tat aaa ctc agt     288
Thr Tyr Ser Lys Gly Ala Thr Ile Met Lys Thr Trp Tyr Lys Leu Ser
                85                  90                  95 aac tat acc cgc cag ttt aac ggc agc ctt agc ttc ctt aac gat gac     336
Asn Tyr Thr Arg Gln Phe Asn Gly Ser Leu Ser Phe Leu Asn Asp Asp
            100                 105                 110 tac gag ttt ttt atc cgt gat gat gat gac ctc gaa atg gaa aca acg     384
Tyr Glu Phe Phe Ile Arg Asp Asp Asp Asp Leu Glu Met Glu Thr Thr
        115                 120                 125 ttt gca aac agc gac aat gta ttg aac ccg tat acg ggc gaa atg gat     432
Phe Ala Asn Ser Asp Asn Val Leu Asn Pro Tyr Thr Gly Glu Met Asp
    130                 135                 140 gca aaa cgt cat gca cgc gaa ttc ctt gcg caa tat ggc tat atg ttc     480
Ala Lys Arg His Ala Arg Glu Phe Leu Ala Gln Tyr Gly Tyr Met Phe
145                 150                 155                 160 gaa aat cag act tcg ttt cca atc ttt gcg gcg tcc tct gaa cgc gtt     528
Glu Asn Gln Thr Ser Phe Pro Ile Phe Ala Ala Ser Ser Glu Arg Val
                165                 170                 175 cat gac aca gct caa tac ttt att gat ggt ctg ggg gat cag ttc aac     576
His Asp Thr Ala Gln Tyr Phe Ile Asp Gly Leu Gly Asp Gln Phe Asn
            180                 185                 190 atc agt ctg caa acc gtt agc gaa gcg atg agc gcg ggt gcg aat act     624
Ile Ser Leu Gln Thr Val Ser Glu Ala Met Ser Ala Gly Ala Asn Thr
```

|     |     |     |     |     |     |     |     |     |     |     |     |     |     |     |     |      |
|---|---|---|---|---|---|---|---|---|---|---|---|---|---|---|---|---|
| | | 195 | | | | 200 | | | | | 205 | | | | | |
| ctg | tcc | gct | gga | aac | gct | tgt | cct | ggc | tgg | gac | gag | gat | gcg | aat | gat | 672 |
| Leu | Ser | Ala | Gly | Asn | Ala | Cys | Pro | Gly | Trp | Asp | Glu | Asp | Ala | Asn | Asp | |
| | 210 | | | | 215 | | | | | 220 | | | | | | |
| gac | att | tta | gat | aaa | tac | gat | acc | acc | tac | ctc | gat | gat | att | gct | aag | 720 |
| Asp | Ile | Leu | Asp | Lys | Tyr | Asp | Thr | Thr | Tyr | Leu | Asp | Asp | Ile | Ala | Lys | |
| 225 | | | | | 230 | | | | | 235 | | | | | 240 | |
| cgt | tta | aac | aaa | gaa | aac | aag | ggg | ctg | aat | ctg | acg | tca | aaa | gac | gcc | 768 |
| Arg | Leu | Asn | Lys | Glu | Asn | Lys | Gly | Leu | Asn | Leu | Thr | Ser | Lys | Asp | Ala | |
| | | | | 245 | | | | | 250 | | | | | 255 | | |
| aac | acc | ctg | ttc | gcc | tgg | tgt | gcg | tac | gaa | ctg | aac | gca | cgc | ggc | tac | 816 |
| Asn | Thr | Leu | Phe | Ala | Trp | Cys | Ala | Tyr | Glu | Leu | Asn | Ala | Arg | Gly | Tyr | |
| | | 260 | | | | | 265 | | | | | 270 | | | | |
| agc | gac | gta | tgc | gat | atc | ttt | acc | gaa | gac | gaa | ctt | gtc | cgc | tat | agt | 864 |
| Ser | Asp | Val | Cys | Asp | Ile | Phe | Thr | Glu | Asp | Glu | Leu | Val | Arg | Tyr | Ser | |
| | | | 275 | | | | | 280 | | | | | 285 | | | |
| tac | ggt | caa | gac | ctg | gtt | agc | ttt | tat | cag | gat | ggc | cca | ggg | tac | gat | 912 |
| Tyr | Gly | Gln | Asp | Leu | Val | Ser | Phe | Tyr | Gln | Asp | Gly | Pro | Gly | Tyr | Asp | |
| | 290 | | | | | 295 | | | | | 300 | | | | | |
| atg | att | cgc | agc | gtg | ggt | gcc | aat | ctg | ttc | aac | gcc | acc | ctt | aag | ttg | 960 |
| Met | Ile | Arg | Ser | Val | Gly | Ala | Asn | Leu | Phe | Asn | Ala | Thr | Leu | Lys | Leu | |
| 305 | | | | | 310 | | | | | 315 | | | | | 320 | |
| ctg | aaa | cag | tcg | gag | act | cag | gat | ctg | aaa | gtg | tgg | ctc | tca | ttc | acc | 1008 |
| Leu | Lys | Gln | Ser | Glu | Thr | Gln | Asp | Leu | Lys | Val | Trp | Leu | Ser | Phe | Thr | |
| | | | | 325 | | | | | 330 | | | | | 335 | | |
| cat | gac | acc | gat | att | ctg | aat | tat | ctg | acc | act | gca | ggc | atc | att | gat | 1056 |
| His | Asp | Thr | Asp | Ile | Leu | Asn | Tyr | Leu | Thr | Thr | Ala | Gly | Ile | Ile | Asp | |
| | | | 340 | | | | | 345 | | | | | 350 | | | |
| gac | aag | aac | aac | ctg | acc | gct | gaa | tat | gta | ccg | ttt | atg | ggg | aac | acc | 1104 |
| Asp | Lys | Asn | Asn | Leu | Thr | Ala | Glu | Tyr | Val | Pro | Phe | Met | Gly | Asn | Thr | |
| | | 355 | | | | | 360 | | | | | 365 | | | | |
| ttt | cac | aaa | agc | tgg | tac | gtg | cct | caa | ggg | gcg | cgt | gtg | tat | acg | gaa | 1152 |
| Phe | His | Lys | Ser | Trp | Tyr | Val | Pro | Gln | Gly | Ala | Arg | Val | Tyr | Thr | Glu | |
| | 370 | | | | | 375 | | | | | 380 | | | | | |
| aaa | ttt | cag | tgc | tcg | aac | gat | acc | tat | gtg | cgc | tac | gtc | att | aat | gat | 1200 |
| Lys | Phe | Gln | Cys | Ser | Asn | Asp | Thr | Tyr | Val | Arg | Tyr | Val | Ile | Asn | Asp | |
| 385 | | | | | 390 | | | | | 395 | | | | | 400 | |
| gcc | gtc | gtc | ccc | att | gag | acg | tgc | tct | acc | ggc | cca | ggt | ttt | agt | tgt | 1248 |
| Ala | Val | Val | Pro | Ile | Glu | Thr | Cys | Ser | Thr | Gly | Pro | Gly | Phe | Ser | Cys | |
| | | | | 405 | | | | | 410 | | | | | 415 | | |
| gaa | atc | aac | gac | ttc | tat | gac | tac | gcc | gag | aaa | cgc | gtt | gcc | ggt | acc | 1296 |
| Glu | Ile | Asn | Asp | Phe | Tyr | Asp | Tyr | Ala | Glu | Lys | Arg | Val | Ala | Gly | Thr | |
| | | | 420 | | | | | 425 | | | | | 430 | | | |
| gat | ttt | ctt | aaa | gtg | tgc | aac | gtt | tct | agc | gtt | tct | aat | gtg | act | gaa | 1344 |
| Asp | Phe | Leu | Lys | Val | Cys | Asn | Val | Ser | Ser | Val | Ser | Asn | Val | Thr | Glu | |
| | | 435 | | | | | 440 | | | | | 445 | | | | |
| ctg | acc | ttt | tac | tgg | gat | tgg | aac | acg | acg | cac | tac | aat | gac | aca | ctg | 1392 |
| Leu | Thr | Phe | Tyr | Trp | Asp | Trp | Asn | Thr | Thr | His | Tyr | Asn | Asp | Thr | Leu | |
| | 450 | | | | | 455 | | | | | 460 | | | | | |
| tta | aaa | cag | taa | | | | | | | | | | | | | 1404 |
| Leu | Lys | Gln | | | | | | | | | | | | | | |
| 465 | | | | | | | | | | | | | | | | |

<210> SEQ ID NO 116
<211> LENGTH: 467
<212> TYPE: PRT
<213> ORGANISM: Saccharomyces cerevisiae

<400> SEQUENCE: 116

Met Phe Lys Ser Val Val Tyr Ser Val Leu Ala Ala Ala Leu Val Asn

-continued

```
1               5                   10                  15
Ala Gly Thr Ile Pro Leu Gly Glu Leu Ala Asp Val Ala Lys Ile Gly
                20                  25                  30
Thr Gln Glu Asp Ile Phe Pro Phe Leu Gly Gly Ala Gly Pro Tyr Phe
                35                  40                  45
Ser Phe Pro Gly Asp Tyr Gly Ile Ser Arg Asp Leu Pro Glu Gly Cys
50                              55                  60
Glu Met Lys Gln Leu Gln Met Leu Ala Arg His Gly Glu Arg Tyr Pro
65                  70                  75                  80
Thr Tyr Ser Lys Gly Ala Thr Ile Met Lys Thr Trp Tyr Lys Leu Ser
                85                  90                  95
Asn Tyr Thr Arg Gln Phe Asn Gly Ser Leu Ser Phe Leu Asn Asp Asp
                100                 105                 110
Tyr Glu Phe Phe Ile Arg Asp Asp Asp Leu Glu Met Glu Thr Thr
                115                 120                 125
Phe Ala Asn Ser Asp Asn Val Leu Asn Pro Tyr Thr Gly Glu Met Asp
130                 135                 140
Ala Lys Arg His Ala Arg Glu Phe Leu Ala Gln Tyr Gly Tyr Met Phe
145                 150                 155                 160
Glu Asn Gln Thr Ser Phe Pro Ile Phe Ala Ala Ser Ser Glu Arg Val
                165                 170                 175
His Asp Thr Ala Gln Tyr Phe Ile Asp Gly Leu Gly Asp Gln Phe Asn
                180                 185                 190
Ile Ser Leu Gln Thr Val Ser Glu Ala Met Ser Ala Gly Ala Asn Thr
                195                 200                 205
Leu Ser Ala Gly Asn Ala Cys Pro Gly Trp Asp Glu Asp Ala Asn Asp
                210                 215                 220
Asp Ile Leu Asp Lys Tyr Asp Thr Thr Tyr Leu Asp Asp Ile Ala Lys
225                 230                 235                 240
Arg Leu Asn Lys Glu Asn Lys Gly Leu Asn Leu Thr Ser Lys Asp Ala
                245                 250                 255
Asn Thr Leu Phe Ala Trp Cys Ala Tyr Glu Leu Asn Ala Arg Gly Tyr
                260                 265                 270
Ser Asp Val Cys Asp Ile Phe Thr Glu Asp Glu Leu Val Arg Tyr Ser
                275                 280                 285
Tyr Gly Gln Asp Leu Val Ser Phe Tyr Gln Asp Gly Pro Gly Tyr Asp
                290                 295                 300
Met Ile Arg Ser Val Gly Ala Asn Leu Phe Asn Ala Thr Leu Lys Leu
305                 310                 315                 320
Leu Lys Gln Ser Glu Thr Gln Asp Leu Lys Val Trp Leu Ser Phe Thr
                325                 330                 335
His Asp Thr Asp Ile Leu Asn Tyr Leu Thr Thr Ala Gly Ile Ile Asp
                340                 345                 350
Asp Lys Asn Asn Leu Thr Ala Glu Tyr Val Pro Phe Met Gly Asn Thr
                355                 360                 365
Phe His Lys Ser Trp Tyr Val Pro Gln Gly Ala Arg Val Tyr Thr Glu
370                 375                 380
Lys Phe Gln Cys Ser Asn Asp Thr Tyr Val Arg Tyr Val Ile Asn Asp
385                 390                 395                 400
Ala Val Val Pro Ile Glu Thr Cys Ser Thr Gly Pro Gly Phe Ser Cys
                405                 410                 415
Glu Ile Asn Asp Phe Tyr Asp Tyr Ala Glu Lys Arg Val Ala Gly Thr
                420                 425                 430
```

```
Asp Phe Leu Lys Val Cys Asn Val Ser Ser Val Ser Asn Val Thr Glu
            435                 440                 445

Leu Thr Phe Tyr Trp Asp Trp Asn Thr Thr His Tyr Asn Asp Thr Leu
    450                 455                 460

Leu Lys Gln
465

<210> SEQ ID NO 117
<211> LENGTH: 462
<212> TYPE: DNA
<213> ORGANISM: Escherichia coli
<220> FEATURE:
<221> NAME/KEY: CDS
<222> LOCATION: (1)..(459)
<223> OTHER INFORMATION: NudJ gene from E. coli

<400> SEQUENCE: 117 atg ttt aaa ccg cac gtt acc gtt gct tgc gtg gtg cac gca gaa ggc      48
Met Phe Lys Pro His Val Thr Val Ala Cys Val Val His Ala Glu Gly
1               5                  10                  15 aaa ttt tta gtc gtt gaa gag acg att aat ggt aaa gcg tta tgg aac      96
Lys Phe Leu Val Val Glu Glu Thr Ile Asn Gly Lys Ala Leu Trp Asn
            20                  25                  30 caa cct gcc ggg cat ctg gaa gcc gat gaa acc tta gtg gaa gcc gcc     144
Gln Pro Ala Gly His Leu Glu Ala Asp Glu Thr Leu Val Glu Ala Ala
        35                  40                  45 gcc cgt gaa ctg tgg gaa gaa acc ggc atc agc gcg cag ccg caa cac     192
Ala Arg Glu Leu Trp Glu Glu Thr Gly Ile Ser Ala Gln Pro Gln His
    50                  55                  60 ttt att cgt atg cat cag tgg att gcg cca gat aaa acg ccg ttt ttg     240
Phe Ile Arg Met His Gln Trp Ile Ala Pro Asp Lys Thr Pro Phe Leu
65                  70                  75                  80 cgt ttc ctc ttt gcc att gag ctt gag caa ata tgc ccg acc cag cct     288
Arg Phe Leu Phe Ala Ile Glu Leu Glu Gln Ile Cys Pro Thr Gln Pro
                85                  90                  95 cat gac agc gat atc gac tgc tgc cgt tgg gtc agc gcc gaa gaa att     336
His Asp Ser Asp Ile Asp Cys Cys Arg Trp Val Ser Ala Glu Glu Ile
            100                 105                 110 tta cag gcg tca aat ctt cgt tcg ccg ctg gtg gcg gaa agt att cgt     384
Leu Gln Ala Ser Asn Leu Arg Ser Pro Leu Val Ala Glu Ser Ile Arg
        115                 120                 125 tgt tat caa agc ggg caa cgt tat ccg ctg gag atg att ggc gat ttt     432
Cys Tyr Gln Ser Gly Gln Arg Tyr Pro Leu Glu Met Ile Gly Asp Phe
    130                 135                 140 aac tgg cct ttt aca aag ggt gtc atc taa                             462
Asn Trp Pro Phe Thr Lys Gly Val Ile
145                 150

<210> SEQ ID NO 118
<211> LENGTH: 153
<212> TYPE: PRT
<213> ORGANISM: Escherichia coli

<400> SEQUENCE: 118

Met Phe Lys Pro His Val Thr Val Ala Cys Val Val His Ala Glu Gly
1               5                  10                  15

Lys Phe Leu Val Val Glu Glu Thr Ile Asn Gly Lys Ala Leu Trp Asn
            20                  25                  30

Gln Pro Ala Gly His Leu Glu Ala Asp Glu Thr Leu Val Glu Ala Ala
        35                  40                  45
```

-continued

Ala Arg Glu Leu Trp Glu Glu Thr Gly Ile Ser Ala Gln Pro Gln His
 50                  55                  60

Phe Ile Arg Met His Gln Trp Ile Ala Pro Asp Lys Thr Pro Phe Leu
 65                  70                  75                  80

Arg Phe Leu Phe Ala Ile Glu Leu Glu Gln Ile Cys Pro Thr Gln Pro
                 85                  90                  95

His Asp Ser Asp Ile Asp Cys Cys Arg Trp Val Ser Ala Glu Glu Ile
            100                 105                 110

Leu Gln Ala Ser Asn Leu Arg Ser Pro Leu Val Ala Glu Ser Ile Arg
        115                 120                 125

Cys Tyr Gln Ser Gly Gln Arg Tyr Pro Leu Glu Met Ile Gly Asp Phe
130                 135                 140

Asn Trp Pro Phe Thr Lys Gly Val Ile
145                 150

<210> SEQ ID NO 119
<211> LENGTH: 47
<212> TYPE: DNA
<213> ORGANISM: Artificial Sequence
<220> FEATURE:
<223> OTHER INFORMATION: Description of Artificial Sequence: Synthetic
      oBS194 primer

<400> SEQUENCE: 119
gtcctactca ggagagcgtt caccgacaac tcaggagagc gttcacc         47

<210> SEQ ID NO 120
<211> LENGTH: 48
<212> TYPE: DNA
<213> ORGANISM: Artificial Sequence
<220> FEATURE:
<223> OTHER INFORMATION: Description of Artificial Sequence: Synthetic
      oBS195 primer

<400> SEQUENCE: 120
ctttcgtctt cacctcgagg gaaatcaaaa taggcgtatc acgaggcc        48

<210> SEQ ID NO 121
<211> LENGTH: 26
<212> TYPE: DNA
<213> ORGANISM: Artificial Sequence
<220> FEATURE:
<223> OTHER INFORMATION: Description of Artificial Sequence: Synthetic
      oBS196 primer

<400> SEQUENCE: 121
gatttccctc gaggtgaaga cgaaag                                26

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      oBS197 primer

<400> SEQUENCE: 122
tgtcggtgaa cgctctcctg                                       20

<210> SEQ ID NO 123
<211> LENGTH: 26
<212> TYPE: DNA
<213> ORGANISM: Artificial Sequence
<220> FEATURE:

```
<223> OTHER INFORMATION: Description of Artificial Sequence: Synthetic
      oBS198 primer

<400> SEQUENCE: 123
attattactc gtgtgttgtc agaaag                                            26

<210> SEQ ID NO 124
<211> LENGTH: 41
<212> TYPE: DNA
<213> ORGANISM: Artificial Sequence
<220> FEATURE:
<223> OTHER INFORMATION: Description of Artificial Sequence: Synthetic
      oBS199 primer

<400> SEQUENCE: 124
ctagtattac ctcgctatta gtgacgtaat aggaggtaag c                           41

<210> SEQ ID NO 125
<211> LENGTH: 51
<212> TYPE: DNA
<213> ORGANISM: Artificial Sequence
<220> FEATURE:
<223> OTHER INFORMATION: Description of Artificial Sequence: Synthetic
      oBS200 primer

<400> SEQUENCE: 125
ctattacgtc actaatagcg aggtaatact agatgtgcca gcagcatccg c                51

<210> SEQ ID NO 126
<211> LENGTH: 54
<212> TYPE: DNA
<213> ORGANISM: Artificial Sequence
<220> FEATURE:
<223> OTHER INFORMATION: Description of Artificial Sequence: Synthetic
      oBS201 primer

<400> SEQUENCE: 126
cggaggcctt tctgacaaca cacgagtaat aatctagttt tctagaggca gcgc             54

<210> SEQ ID NO 127
<211> LENGTH: 53
<212> TYPE: DNA
<213> ORGANISM: Artificial Sequence
<220> FEATURE:
<223> OTHER INFORMATION: Description of Artificial Sequence: Synthetic
      oBS202 primer

<400> SEQUENCE: 127
ctattacgtc actaatagcg aggtaatact agatgaagac aggtcgaata gtg              53

<210> SEQ ID NO 128
<211> LENGTH: 56
<212> TYPE: DNA
<213> ORGANISM: Artificial Sequence
<220> FEATURE:
<223> OTHER INFORMATION: Description of Artificial Sequence: Synthetic
      oBS203 primer

<400> SEQUENCE: 128
cggaggcctt tctgacaaca cacgagtaat aatttaatat ctaacctttc tatttg           56

<210> SEQ ID NO 129
<211> LENGTH: 55
<212> TYPE: DNA
<213> ORGANISM: Artificial Sequence
<220> FEATURE:
<223> OTHER INFORMATION: Description of Artificial Sequence: Synthetic
``` oBS210 primer

<400> SEQUENCE: 129
cctattacgt cactaatagc gaggtaatac tagatgttta aaccgcacgt taccg          55

<210> SEQ ID NO 130
<211> LENGTH: 50
<212> TYPE: DNA
<213> ORGANISM: Artificial Sequence
<220> FEATURE:
<223> OTHER INFORMATION: Description of Artificial Sequence: Synthetic
      oBS211 primer

<400> SEQUENCE: 130
ctttctgaca acacacgagt aataatttag atgacaccct ttgtaaaagg                50

<210> SEQ ID NO 131
<211> LENGTH: 37
<212> TYPE: DNA
<213> ORGANISM: Artificial Sequence
<220> FEATURE:
<223> OTHER INFORMATION: Description of Artificial Sequence: Synthetic
      oBS220 primer

<400> SEQUENCE: 131
gtacctataa tgtgtggatg tcccaccgct tacctcc                              37

<210> SEQ ID NO 132
<211> LENGTH: 47
<212> TYPE: DNA
<213> ORGANISM: Artificial Sequence
<220> FEATURE:
<223> OTHER INFORMATION: Description of Artificial Sequence: Synthetic
      oBS221 primer

<400> SEQUENCE: 132
catcaccatc atcaccactg aattattact cgtgtgttgt cagaaag                   47

<210> SEQ ID NO 133
<211> LENGTH: 22
<212> TYPE: DNA
<213> ORGANISM: Artificial Sequence
<220> FEATURE:
<223> OTHER INFORMATION: Description of Artificial Sequence: Synthetic
      oGEN184 primer

<400> SEQUENCE: 133
aaacctcttt atgttgcagt cg                                              22

<210> SEQ ID NO 134
<211> LENGTH: 22
<212> TYPE: DNA
<213> ORGANISM: Artificial Sequence
<220> FEATURE:
<223> OTHER INFORMATION: Description of Artificial Sequence: Synthetic
      oGEN182 primer

<400> SEQUENCE: 134
aaattcgcga gttccactaa ga                                              22

<210> SEQ ID NO 135
<211> LENGTH: 68
<212> TYPE: DNA
<213> ORGANISM: Artificial Sequence
<220> FEATURE:
<223> OTHER INFORMATION: Description of Artificial Sequence: Synthetic
      oGEN227 primer

<400> SEQUENCE: 135
ccgcttacct cctattacgt cactaatagc taaggaggta aatatgtctg caacaaaact    60
gacccgcc    68

<210> SEQ ID NO 136
<211> LENGTH: 52
<212> TYPE: DNA
<213> ORGANISM: Artificial Sequence
<220> FEATURE:
<223> OTHER INFORMATION: Description of Artificial Sequence: Synthetic
      oGEN264 primer

<400> SEQUENCE: 136
cggaggcctt tctgacaaca cacgagtaat aattcatagt ctttgcgagg cg    52

<210> SEQ ID NO 137
<211> LENGTH: 33
<212> TYPE: DNA
<213> ORGANISM: Artificial Sequence
<220> FEATURE:
<223> OTHER INFORMATION: Description of Artificial Sequence: Synthetic
      oGEN265 primer

<400> SEQUENCE: 137
attattactc gtgtgttgtc agaaaggcct ccg    33

<210> SEQ ID NO 138
<211> LENGTH: 31
<212> TYPE: DNA
<213> ORGANISM: Artificial Sequence
<220> FEATURE:
<223> OTHER INFORMATION: Description of Artificial Sequence: Synthetic
      oGEN266 primer

<400> SEQUENCE: 138
attagtgacg taataggagg taagcggtgg g    31

<210> SEQ ID NO 139
<211> LENGTH: 52
<212> TYPE: DNA
<213> ORGANISM: Artificial Sequence
<220> FEATURE:
<223> OTHER INFORMATION: Description of Artificial Sequence: Synthetic
      oBS421 primer

<400> SEQUENCE: 139
cggaggcctt tctgacaaca cacgagtaat aattcaccac caggcgtgga ag    52

<210> SEQ ID NO 140
<211> LENGTH: 60
<212> TYPE: DNA
<213> ORGANISM: Artificial Sequence
<220> FEATURE:
<223> OTHER INFORMATION: Description of Artificial Sequence: Synthetic
      oBS422 primer

<400> SEQUENCE: 140
gcttacctcc tattacgtca ctaatagcta aggaggtaaa tatgcaagtc gacctgctgg    60

<210> SEQ ID NO 141
<211> LENGTH: 90
<212> TYPE: DNA
<213> ORGANISM: Artificial Sequence
<220> FEATURE:
<223> OTHER INFORMATION: Description of Artificial Sequence: Synthetic oBS445 primer

<400> SEQUENCE: 141
cggaacaaag ccgtggatgt ccaacgtcat tgataatggc ccacgcgtgg tatcgccgcc    60
aatgagttgc atatcgtaat aattgagaag                                    90

<210> SEQ ID NO 142
<211> LENGTH: 90
<212> TYPE: DNA
<213> ORGANISM: Artificial Sequence
<220> FEATURE:
<223> OTHER INFORMATION: Description of Artificial Sequence: Synthetic
      oBS446 primer

<400> SEQUENCE: 142
ccagagcgcg ttaaggctcg tcccatcgga acaaagccgt ggatgtccaa cgtcattgat    60
aatggcccac gcgtggtatc gccgccaatg                                    90

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      oBS456 primer

<400> SEQUENCE: 143
catgtggcga gttctccctg                                               20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      oBS457 primer

<400> SEQUENCE: 144
caggtaaacg gtacgcccag                                               20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      oBS521 primer

<400> SEQUENCE: 145
gcaactgtcg atggcgaagc                                               20

<210> SEQ ID NO 146
<211> LENGTH: 19
<212> TYPE: DNA
<213> ORGANISM: Artificial Sequence
<220> FEATURE:
<223> OTHER INFORMATION: Description of Artificial Sequence: Synthetic
      oBS522 primer

<400> SEQUENCE: 146
cctgatcaac cgccaccac                                                19

<210> SEQ ID NO 147
<211> LENGTH: 47
<212> TYPE: DNA

<213> ORGANISM: Escherichia coli
<220> FEATURE:
<221> NAME/KEY: promoter
<222> LOCATION: (1)..(47)
<223> OTHER INFORMATION: apFAB46 promoter

<400> SEQUENCE: 147
aaaaagagta ttgacttcgc atcttttttgt acctataata gattcat    47

<210> SEQ ID NO 148
<211> LENGTH: 37
<212> TYPE: DNA
<213> ORGANISM: Escherichia coli
<220> FEATURE:
<221> NAME/KEY: promoter
<222> LOCATION: (1)..(37)
<223> OTHER INFORMATION: apFAB70 promoter

<400> SEQUENCE: 148
ttgacatcgc atcttttttgt acctataatg tgtggat    37

<210> SEQ ID NO 149
<211> LENGTH: 37
<212> TYPE: DNA
<213> ORGANISM: Escherichia coli
<220> FEATURE:
<221> NAME/KEY: promoter
<222> LOCATION: (1)..(37)
<223> OTHER INFORMATION: apFAB71 promoter

<400> SEQUENCE: 149
ttgacatcgc atcttttttgt acctataata gattcat    37

<210> SEQ ID NO 150
<211> LENGTH: 29
<212> TYPE: DNA
<213> ORGANISM: Escherichia coli
<220> FEATURE:
<221> NAME/KEY: promoter
<222> LOCATION: (1)..(29)
<223> OTHER INFORMATION: pBAD Ara promoter

<400> SEQUENCE: 150
ctgacgcttt ttatcgcaac tctctactg    29

<210> SEQ ID NO 151
<211> LENGTH: 74
<212> TYPE: DNA
<213> ORGANISM: Escherichia coli
<220> FEATURE:
<221> NAME/KEY: promoter
<222> LOCATION: (1)..(74)
<223> OTHER INFORMATION: lac Promoter with lacO operator site

<400> SEQUENCE: 151
agctgtttcc tgtgtgaaat tgttatccgc tcacaattcc acacaacata cgagccggaa    60
gcataaagtg taaa    74

<210> SEQ ID NO 152
<211> LENGTH: 91
<212> TYPE: DNA
<213> ORGANISM: Escherichia coli
<220> FEATURE:
<221> NAME/KEY: terminator
<222> LOCATION: (1)..(91)
<223> OTHER INFORMATION: apFAB378 terminator

<400> SEQUENCE: 152

```
gagttggtag ctcttgatcc ggcaaacaaa ccaccgttgg tagcggtggt ttttttgttt    60
gcaagcagca gattacgcgc agaaaaaaag g                                   91
```

<210> SEQ ID NO 153
<211> LENGTH: 91
<212> TYPE: DNA
<213> ORGANISM: Escherichia coli
<220> FEATURE:
<221> NAME/KEY: terminator
<222> LOCATION: (1)..(91)
<223> OTHER INFORMATION: apFAB377 terminator

<400> SEQUENCE: 153

```
atgaccatct acattactga gctaataaca ggcctgctgg taatcgcagg cctttttatt    60
tgggggagag ggaagtcatg aaaaaactaa c                                   91
```

<210> SEQ ID NO 154
<211> LENGTH: 90
<212> TYPE: DNA
<213> ORGANISM: Escherichia coli
<220> FEATURE:
<221> NAME/KEY: terminator
<222> LOCATION: (1)..(90)
<223> OTHER INFORMATION: apFAB381 terminator

<400> SEQUENCE: 154

```
accctcaaga gaaatgtaa ccaactcact ggctcacctt cacgggtggg cctttcttcg    60
ttccgggcat taaccctcac taacaggaga                                     90
```

<210> SEQ ID NO 155
<211> LENGTH: 31
<212> TYPE: DNA
<213> ORGANISM: Artificial Sequence
<220> FEATURE:
<223> OTHER INFORMATION: Description of Artificial Sequence: Synthetic
      oBS234 primer
<220> FEATURE:
<223> OTHER INFORMATION: Description of Combined DNA/RNA Molecule:
      Synthetic oBS234 primer

<400> SEQUENCE: 155

```
aggcctutct gacaacacac gagtaataat t                                   31
```

<210> SEQ ID NO 156
<211> LENGTH: 26
<212> TYPE: DNA
<213> ORGANISM: Artificial Sequence
<220> FEATURE:
<223> OTHER INFORMATION: Description of Artificial Sequence: Synthetic
      oBS1720 primer

<400> SEQUENCE: 156

```
cgtcactaat agcgaggtaa tactag                                         26
```

<210> SEQ ID NO 157
<211> LENGTH: 42
<212> TYPE: DNA
<213> ORGANISM: Artificial Sequence
<220> FEATURE:
<223> OTHER INFORMATION: Description of Artificial Sequence: Synthetic
      oBS1721 primer

<400> SEQUENCE: 157

```
ctagtattac ctcgctatta gtgacgataa taggaggtaa gc                       42
```

GENETICALLY MODIFIED BACTERIAL CELL FACTORY FOR THIAMINE PRODUCTION

CROSS REFERENCE TO RELATED APPLICATIONS

This application is a 371 National Phase Entry of International Patent Application No. PCT/EP2016/081598 filed on Dec. 16, 2016 which claims benefit under 35 U.S.C. § 119(b) of EP Application No. 15201200.1 filed Dec. 18, 2015, the contents of which are incorporated herein by reference in their entirety.

SEQUENCE LISTING

The sequence listing of the present application has been submitted electronically via EFS-Web as an ASCII formatted sequence listing with a file name "059244-000090USPX SL.txt", creation date of Nov. 29, 2018 and a size of 598,297 bytes. The sequence listing submitted via EFS-Web is part of the specification and is herein incorporated by reference in its entirety.

FIELD OF THE INVENTION

The invention relates to a genetically modified bacterium for production of thiamine; where the bacterium is characterized by a transgene encoding a thiamine monophosphate phosphatase (TMP phosphatase having EC 3.1.3.-) as well as transgenes encoding polypeptides that catalyze steps in the thiamine pathway. The genetically modified bacterium is characterized by enhanced synthesis and release of thiamine into the extracellular environment. The invention further relates to a method for producing thiamine using the genetically modified bacterium of the invention; as well as the use of the genetically modified bacterium for thiamine production.

BACKGROUND OF THE INVENTION

Thiamine, also known as vitamin B 1, is a member of the water-soluble B-complex of vitamins and is a nutritional requirement for mammals. In nature, thiamine exists in multiple phosphorylation states: thiamine, thiamine mono-phosphate (TMP) and thiamine diphosphate (TPP) (there are also traces of thiamine triphosphate found in cells). All living organisms use thiamine, but thiamine and its active form thiamine pyrophosphate (TPP) are only synthesized in bacteria, fungi, and plants. Animals depend on their diet for a source of thiamin, and thus, for humans, it is an essential nutrient. TPP acts in vivo as the coenzyme of enzymes executing several vital metabolic processes such as pentose phosphate pathway and the TCA cycle. Thiamine is on the World Health Organization's List of Essential Medicines that lists the most important medications needed in a basic health system and thiamine deficiency is a widespread health problem. The commercially relevant form of thiamine is un-phosphorylated, since this is the most stable form that can be assimilated and phosphorylated by humans and animals to produce the biologically active cofactor TPP.

The thiamine biosynthetic pathways characterized in bacteria, some protozoans, plants, and fungi, share some common features (FIG. 1). The thiazole and pyrimidine moieties are biosynthesized separately. The pyrimidine moiety, 4-amino-5-hydroxymethyl-2-methylpyrimidine phosphate (HMP-P), is derived from 5-aminoimidazole ribotide (AIR), an intermediate in the de novo purine biosynthetic pathway. In Gram-negative bacteria, conversion of AIR to HMP-P is catalyzed by the thiC gene product. HMP-P is then phosphorylated to HMP-PP by ThiD kinase prior to coupling with the thiazole unit. The thiazole moiety, 5-(2-hydroxyethyl)-4-methylthiazole phosphate (HET-P), is derived from L-tyrosine and 1-deoxy-D-xylulose phosphate (DXP) and cysteine; where the sulfur atom likely derives from L-cysteine. This latter reaction requires expression of at least five genes thiF, thiS, thiG, thiH and thiI.

The pyrimidine and thiazole moieties are then combined to form TMP by the action of thiamine-phosphate synthase (EC 2.5.1.3) encoded by thiE. Thus TMP is the first product of all known thiamine biosynthetic pathways. In E. coli and other Enterobacteriaceae, TMP may be phosphorylated to the cofactor TPP by a thiamine-phosphate kinase (EC 2.7.4.16) encoded by thiL in the presence of ATP. Some bacteria and eukaryotes, rely on the salvage pathway from HMP and HET which requires ThiD, ThiE and ThiM. E. coli uses a salvage enzyme, thiamine kinase, encoded by thiK to convert exogenous thiamine, taken up by the cell, into TMP.

In view of their capacity to synthesize TMP and TPP, micro-organisms can be used as cell factories for the recombinant production of this vitamin. Recombinant production of essential medicines such as the vitamin thiamine requires the use of a suitable host that is capable of producing and exporting thiamine. Un-phosphorylated thiamine (THI) is the desired target for biological production, not only for commercial reasons, but also because thiamine easily crosses cell membranes, in contrast to its phosphorylated forms, and therefore accumulates outside of the production host during fermentation, where it is the most stable form.

The advantages of recombinant Escherichia coli as a cell factory for production of bioproducts are widely recognized due to the fact that: (i) it has unparalleled fast growth kinetics; with a doubling time of about 20 minutes when cultivated in glucose-salts media and under optimal environmental conditions, (ii) it easily achieves a high cell density; where the theoretical density limit of an E. coli liquid culture is estimated to be about 200 g dry cell weight/1 or roughly $1 \times 10^{13}$ viable bacteria/ml. Additionally, there are many molecular tools and protocols at hand for the high-level production of bioproducts in E. coli; heterologous proteins can easily be expressed in E. coli and there are many specialty strains available for the production of specialist end-products.

In most bacteria, TPP is produced by the direct conversion of TMP to TPP, where cell growth requires an intracellular or extracellular supply of TPP. Thus the use of E. coli as a cell factory for thiamine production requires a genetically modified strain that is both viable and at the same time is capable of producing and releasing thiamine into the extracellular environment.

SUMMARY OF THE INVENTION

The invention provides a genetically modified bacterium for production of thiamine; wherein said bacterium is characterized by having seven transgenes encoding, respectively:
a. a polypeptide having thiamine mono-phosphate phosphatase activity (E.C. 3.1.3.-) wherein the amino acid sequence of said polypeptide has at least 80% sequence identity to a sequence selected from the group consisting of SEQ ID No: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72 and 74;

b. a polypeptide having 4-amino-5-hydroxymethyl-2-methylpyrimidine phosphate (HMP-P) synthase activity (E.C. 4.1.99.17);
c. a polypeptide having thiamine phosphate synthase activity (E.C. 2.5.1.3);
d. a polypeptide having ThiS adenylyltransferase activity (E.C. 2.7.7.73); a polypeptide having ThiS sulfur-carrier activity;
e. a polypeptide having thiazole synthase activity (E.C. 2.8.1.10);
f. a polypeptide having 2-iminoacetate synthase activity (E.C. 4.1.99.19), or having glycine oxidase activity (EC 1.4.3.19); and
g. a polypeptide having phosphohydroxymethylpyrimidine kinase activity (E.C. 2.7.4.7),
and wherein the genus of bacterium is selected from the group consisting of *Acetobacter, Azotobacter, Brevibacterium, Burkholderia, Campylobacter, Corynebacterium, Escherichia, Propionibacterium*, and *Streptomyces*.

According to a further embodiment, the genetically modified bacterium of the invention is further characterized by a genetically modified endogenous thiL gene capable of expressing reduced thiamine-phosphate kinase activity (EC 2.7.4.16) as compared to the parent endogenous thiL gene.

According to a further embodiment, the genetically modified bacterium of the invention is further characterized by inactivation or deletion of one or more genes encoding a protein selected from the group: thiamine ABC transporter periplasmic binding protein; thiamine ABC transporter permease; and thiamine ABC transporter ATPase.

The invention further provides a method for producing thiamine comprising the steps of:
introducing a genetically modified bacterium according to any embodiment of the invention into a growth medium to produce a culture;
cultivating the culture; and
recovering thiamine produced by said culture, and optionally purifying the recovered thiamine.

The invention further provides for the use of a transgene encoding a polypeptide having thiamine mono-phosphate phosphatase activity (E.C 3.1.3.-) to enhance thiamine export in a bacterium.

According to one embodiment for the use of the transgene encoding a polypeptide having thiamine mono-phosphate phosphatase activity (E.C 3.1.3.-), the amino acid sequence of said polypeptide has at least 80% sequence identity to a sequence selected from among:
the group consisting of SEQ ID No: 2, 4, 6, 8, 10, 12, 14, 16, 18, 20, 22, 24, 26, 28 and 30;
the group consisting of SEQ ID No: 32, 34, 36, 38, 40, 42, 44, 46, 48, 50, 52, 54, 56, 58, 60, 62, 64 and 66; and
the group consisting of SEQ ID No: 68, 70, 72 and 74.

The invention further provides for the use of a genetically modified bacterium according to any one embodiment of the invention for the production of thiamine.

BRIEF DESCRIPTION OF THE DRAWINGS

FIG. 5 This figure shows an alignment of the protein sequences of 11 TMP phosphatases belonging to clade 1 (*Arabidopsis thaliana* AT5G32470.1 (SEQ ID NO: 2); *Brassica napus* BnaC08g46820D_ embICDY62623.1| (SEQ ID NO: 6); *Citrus sinensis* C17G9.12c-like isoform X1_reflXP_006484613.1| (SEQ ID NO: 16); *Glycine max* LOC100788250 isoform X1_reflXP_003536133.1| (SEQ ID NO: 8); *Jatropha curcas* CGZ_23571 [gblKDP23738.1| (SEQ ID NO: 14); *Nicotiana tomentosiformis* LOC104108252_reflXP_009615535.1 (SEQ ID NO: 10)|; *Oryza sativa* Os08g0566000_reflNP_001062539.1| (SEQ ID NO: 24); *Pyrus x bretschneideri* LOC103968121 isoform X1_reflXP_009379735.1| (SEQ ID NO: 4); *Prunus persica* PRUPE_ppa003431mg_>reflXP_007199656.1| (SEQ ID NO: 18); *Populus trichocarpa* POPTR_0019s03960g_reflXP_002325785.2| (SEQ ID NO:

12); *Zea mays* LOC103653246_ref|XP_008678418.1| (SEQ ID NO: 22). The protein sequences were aligned using the 'geneious alignment' function (standard settings) of the geneious 6.0.6 software (Biomatters Ltd.). The TenA domain is underlined with a dashed line and the HAD domain is underlined with a dotted line. TenA active site residues (based on the crystal structure of representative a representative TenA protein—TenA from *B. subtilis*, PDB ID Number: 1YAF—are marked with * and residues shown to form H-bonds with HMP are marked with +. Conserved residues of a HAD domain are marked with # and the conserved DXD and DXXXD motifs are underlined with a solid line.

Figure 6:
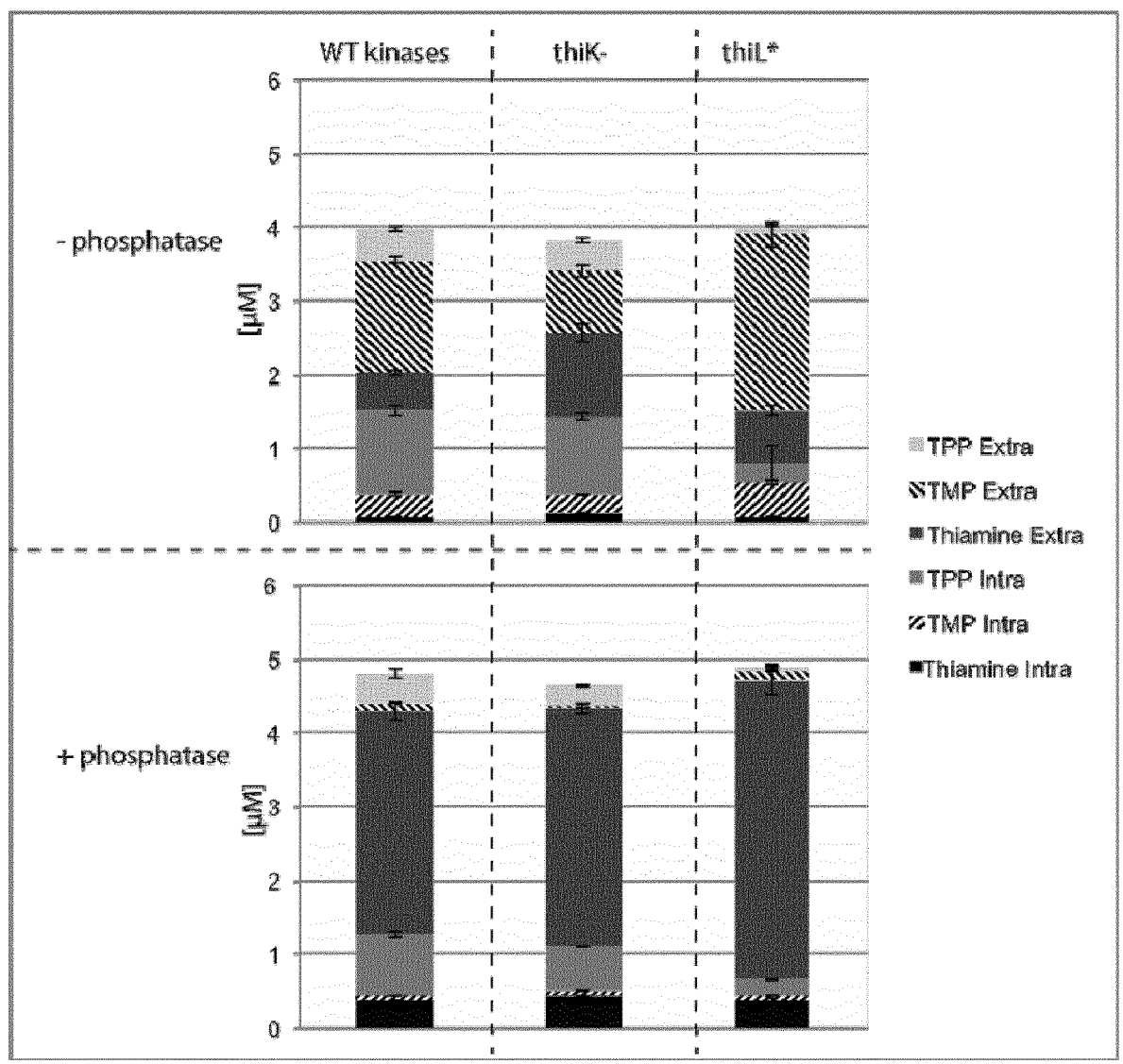

FIG. 6 Bar diagram showing the extracellular and intracellular levels of THI, TMP and TPP detected in cultures of *E. coli* strains with the following genetic modifications: cells deleted for thiK gene (thiK−) in the central bars; cells carrying a mutated (partially inactivated) thiL gene (thiL*) in the right hand bars; and cells with wild-type thiK and thiL genes in the left hand bars. The *E. coli* strains in the lower panel comprise the pBS93 vector encoding the *A. thaliana* TMP phosphatase (At5g32470); and the strains in the upper panel comprise the control vector pBS92. Additionally, all strains comprise the vector pBS140 comprising genes thiMD and thiCEFSGH constitutively expressing enzymes in the thiamine biosynthesis pathway.

Figure 7:
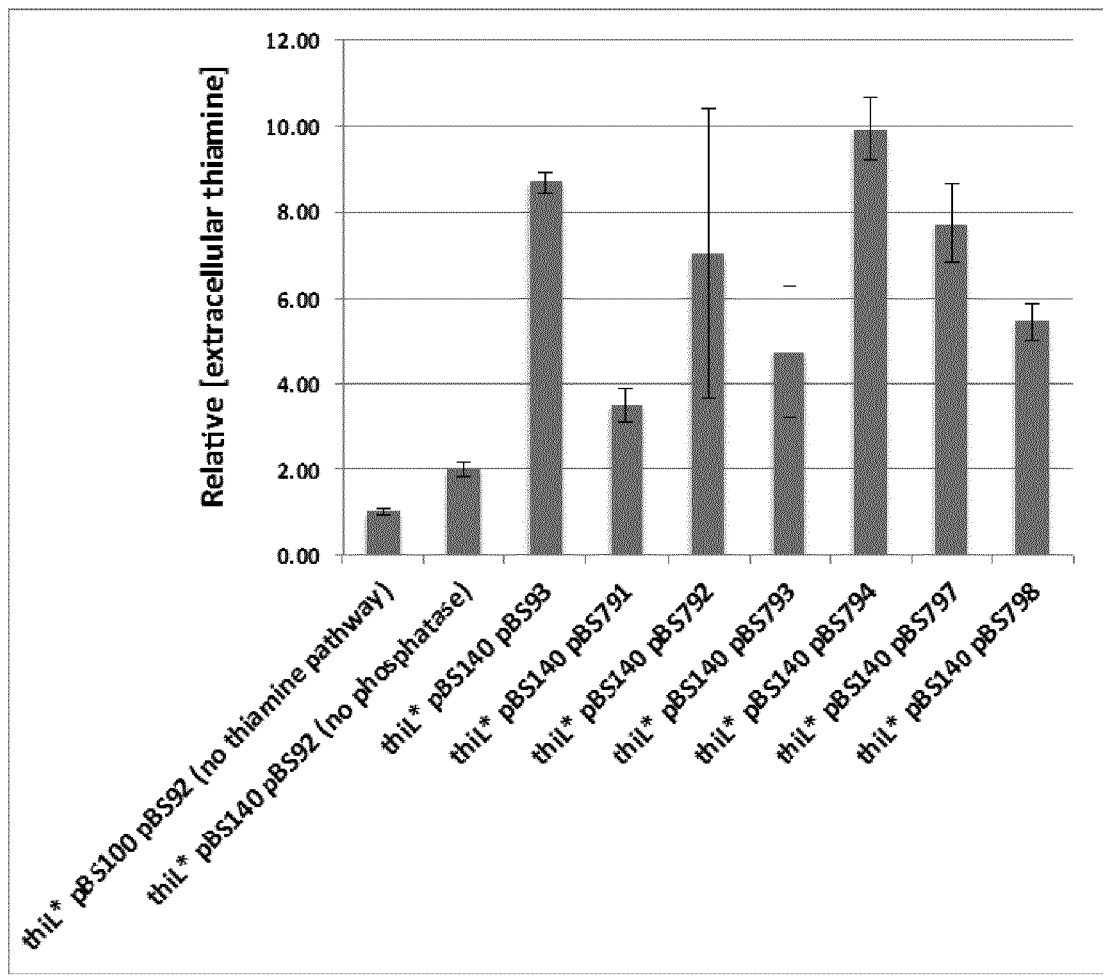

FIG. 7. Bar diagram showing the relative extracellular levels of THI detected in cultures of *E. coli* strains carrying a mutated (partially inactivated) thiL gene (thiL*) and comprising either the vector pBS140 comprising genes thiMD and thiCEFSGH constitutively expressing enzymes in the thiamine biosynthesis pathway or the empty control vector pBS100. Additionally all strains comprise a vector encoding a TMP phosphatase or the corresponding empty control vector pBS92. The phosphatases tested from clade 1 are pBS93: *A. thaliana* TMP phosphatase At5g32470 [SEQ ID No.:2], pBS791: *Jatropha curcas* TMP phosphatase KDP23738.1 [SEQ ID No.:14], and pBS792: *Picea sitchensis* TMP phosphatase ABR16455 [SEQ ID No.:26]. Those tested from clade 2 are pBS793: *Eubacterium ventriosum* TMP phosphatase WP_005362972 [SEQ ID No.:34] and pBS794: *Anaerotruncus colihominis* TMP phosphatase WP_006874980 [SEQ ID No.:32]. And those tested from clade 3 are pBS797: *Desulfitobacterium hafniense* TMP phosphatase WP_018212876 [SEQ ID No.:70] and pBS798: *Syntrophomonas wolfei* TMP phosphatase WP_011640074 [SEQ ID No.:68]. Data shown is the average of triplicates; error bars indicate standard deviation.

ABBREVIATIONS AND TERMS gI number: (genInfo identifier) is a unique integer which identifies a particular sequence, independent of the database source, which is assigned by NCBI to all sequences processed into Entrez, including nucleotide sequences from DDBJ/EMBL/GenBank, protein sequences from SWISS-PROT, PIR and many others.

Amino acid sequence identity: The term "sequence identity" as used herein, indicates a quantitative measure of the degree of homology between two amino acid sequences of substantially equal length. The two sequences to be compared must be aligned to give a best possible fit, by means of the insertion of gaps or alternatively, truncation at the ends of the protein sequences. The sequence identity can be calculated as ((Nref−Ndif)100)/(Nref), wherein Ndif is the total number of non-identical residues in the two sequences when aligned and wherein Nref is the number of residues in one of the sequences. Sequence identity calculations are preferably automated using the BLAST program e.g. the BLASTP program (Pearson W. R and D. J. Lipman (1988)) (www.ncbi.nlm.nih.gov/cgi-bin/BLAST). Multiple sequence alignment is performed with the sequence alignment method ClustalW with default parameters as described by Thompson J., et al 1994, available at world wide web address: ebi.ac.uk/clustalw/.

Preferably, the numbers of substitutions, insertions, additions or deletions of one or more amino acid residues in the polypeptide as compared to its comparator polypeptide is limited, i.e. no more than 1, 2, 3, 4, 5, 6, 7, 8, 9, or 10 substitutions, no more than 1, 2, 3, 4, 5, 6, 7, 8, 9, or 10 insertions, no more than 1, 2, 3, 4, 5, 6, 7, 8, 9, or 10 additions, and no more than 1, 2, 3, 4, 5, 6, 7, 8, 9, or 10 deletions. Preferably the substitutions are conservative amino acid substitutions: limited to exchanges within members of group 1: Glycine, Alanine, Valine, Leucine, Isoleucine; group 2: Serine, Cysteine, Selenocysteine, Threonine, Methionine; group 3: proline; group 4: Phenylalanine, Tyrosine, Tryptophan; Group 5: Aspartate, Glutamate, Asparagine, Glutamine.

Figure 1:
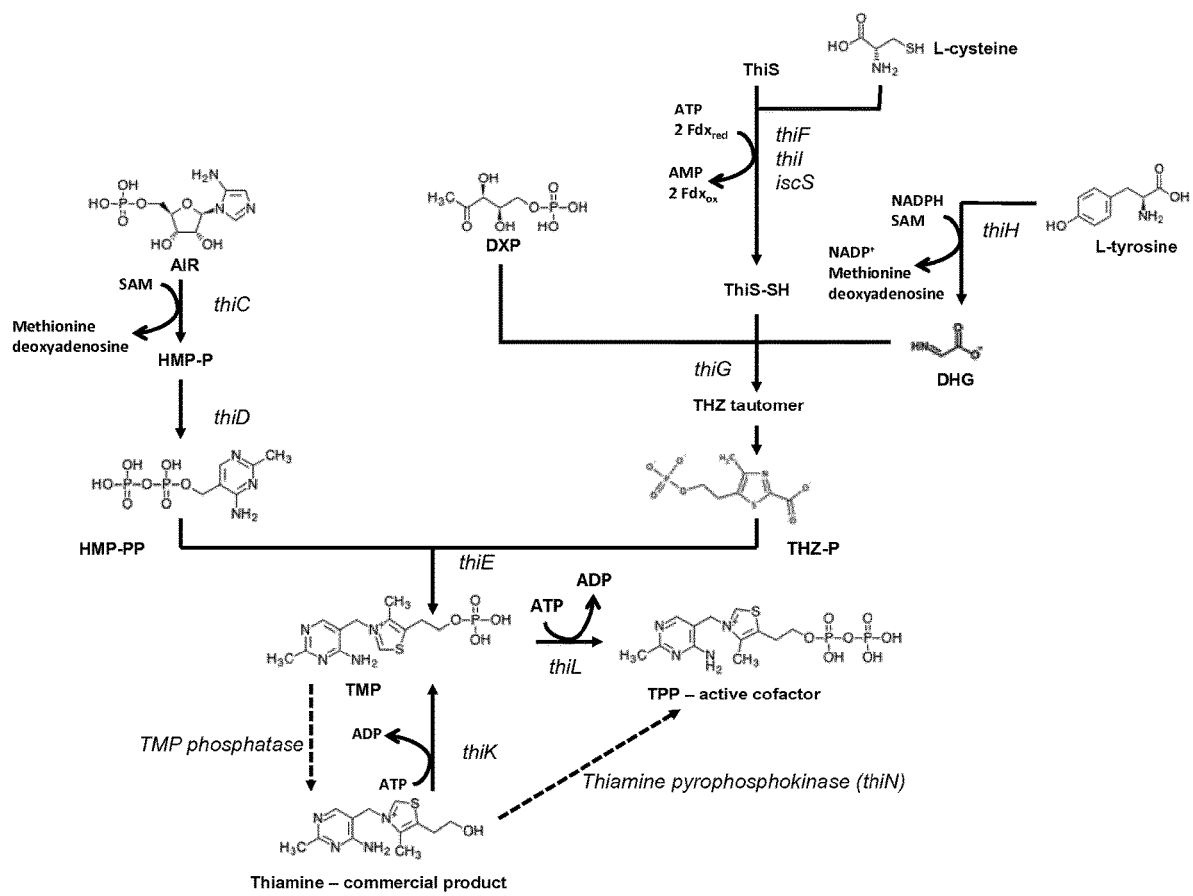
FIG. 1 Cartoon showing intermediates of the thiamine pathway in micro-organisms and the respective enzymatic steps leading to synthesis of thiamine (THI); thiamine monophosphate (TMP) and thiamine diphosphate (TPP). Abbreviation of intermediates: 5-aminoimidazole ribonucleotide (AIR), 4-amino-2-methyl-5-(phosphooxymethyl)pyrimidine (HMP-P), 4-amino-2-methyl-5-(diphosphomethyl) pyrimidine (HMP-PP), 1-deoxy-D-xylulose 5-phosphate (DXP), dehydroglycine (DHG), 4-methyl-5-(2-phosphooxyethyl)thiazole (THZ-P), adenosine triphosphate (ATP), adenosine monophosphate (AMP), S-adenosyl-L-methionine (SAM), reduced nicotinamide adenine dinucleotide phosphate (NADPH), nicotinamide adenine dinucleotide phosphate (NADP+), reduced ferredoxin (Fdx red), oxidized ferredoxin (Fdx ox).

Genetically modified bacterium for production of thiamine, is derived from a member of a genus of bacterium wherein TPP biosynthesis is mediated via the thiL pathway and not the thiN pathway (FIG. 1).

Mutant gene: a mutant gene in the genome of a bacterial cell may exhibit reduced function of the gene and hence where the mutant gene encodes a polypeptide the mutation may results in a loss/reduction of expression of the encoded polypeptide. Alternatively the mutant gene may encode a mutant polypeptide, and where the polypeptide is an enzyme, the mutation may result in a loss of detectable enzymatic activity in the bacterial cell.

Native gene: endogenous gene in a bacterial cell genome, homologous to host micro-organism.

DETAILED DESCRIPTION OF THE INVENTION

Adaptation of *E. coli* for use as a cell factory for thiamine production requires the provision and/or manipulation of enzymes capable of controlling the intracellular phosphorylation state of thiamine. Two approaches can be taken to shift the intracellular equilibrium away from TPP and TMP and towards thiamine.

The first approach involves modification (e.g. down-regulation) of one or more of the kinases that phosphorylate thiamine (e.g. salvage kinase, ThiK in *E. coli*); the kinases that pyro-phosphorylate thiamine (ThiN in *Bacillus subtilis*; commonly found in eukaryotes, but not found in *E. coli*); and the kinases that phosphorylate TMP (thiL in *E. coli*). This approach has been used in *B. subtilis* (WO2004106557).

The second approach that has not previously been described, involves the expression of recombinant enzymes in the cell to dephosphorylate TMP, and optionally TPP in combination with the upregulation of the thiamine biosynthesis pathway. This approach may be further combined with one or more modifications of the first approach. TMP phosphatases and TPP phosphatases suitable for this approach are limited to those that selectively act on TMP and TPP. However, the best-studied phosphatases are promiscuous nucleotide phosphatases (e.g. *E. coli* nudJ encoded phosphatase) that act on both nucleoside di- and triphosphate and the structurally similar TMP and TPP. Such phosphatases are unsuitable, since their non-specific activity will destabilize cellular metabolism.

In some organisms (mostly eukaryotes) TMP is dephosphorylated before being pyrophosphorylated to TPP (see FIG. 1); whereby THI is a key intermediate in TDP and TPP biosynthesis. However, the identity of the responsible phosphatase has long been the subject of speculation, and its encoding gene was described as a missing gene (Goyer et al., 2013). Thiamine metabolism, in vivo, not only requires phosphorylases for the dephosphorylation of TDP and TMP, but also for the disposal of their corrupt forms, oxy- and oxo-thiamin. In a search for TMP phosphatases capable of selectively disposing of toxic forms of thiamine in plants, Goyer et al., 2013 suggested that an *Arabidopsis* protein sequence (At5g32470) was a plausible candidate, because annotation of its sequence predicted a haloacid dehalogenase (HAD) domain fused to a thiaminase 2 (TenA) family protein, which in other organisms TenA proteins were known to serve this selective function for disposal of oxy- and oxo-thiamin. However, the only phosphatase activity detected in extracts of *Arabidopsis* by Komeda Y et al., (1988) corresponded to a protein of 10 kDa, significantly smaller than the 69 kDa protein encoded by the AT5G32470.1 gene.

The present invention relates to the provision of a genetically modified bacterium that is capable of producing and releasing enhanced amounts of thiamine into the extracellular environment as compared to the parent from which was derived.

I a Genetically Modified Bacterium for Production and Export of Thiamine

The present invention provides a genetically modified bacterial cell capable of producing and exporting enhanced levels of thiamine. The bacterial cell of the invention comprises a transgene encoding a thiamine monophosphate phosphatase (TMP phosphatase having EC 3.1.3.-) as well as transgenes encoding polypeptides that catalyze steps in the thiamine pathway. The activity of the polypeptides that catalyze steps in the thiamine pathway enhances the synthesis of both intermediates in the thiamine pathway and products of the thiamine pathway (e.g. TMP and TPP) in the bacterial cell.

Figure 4A:
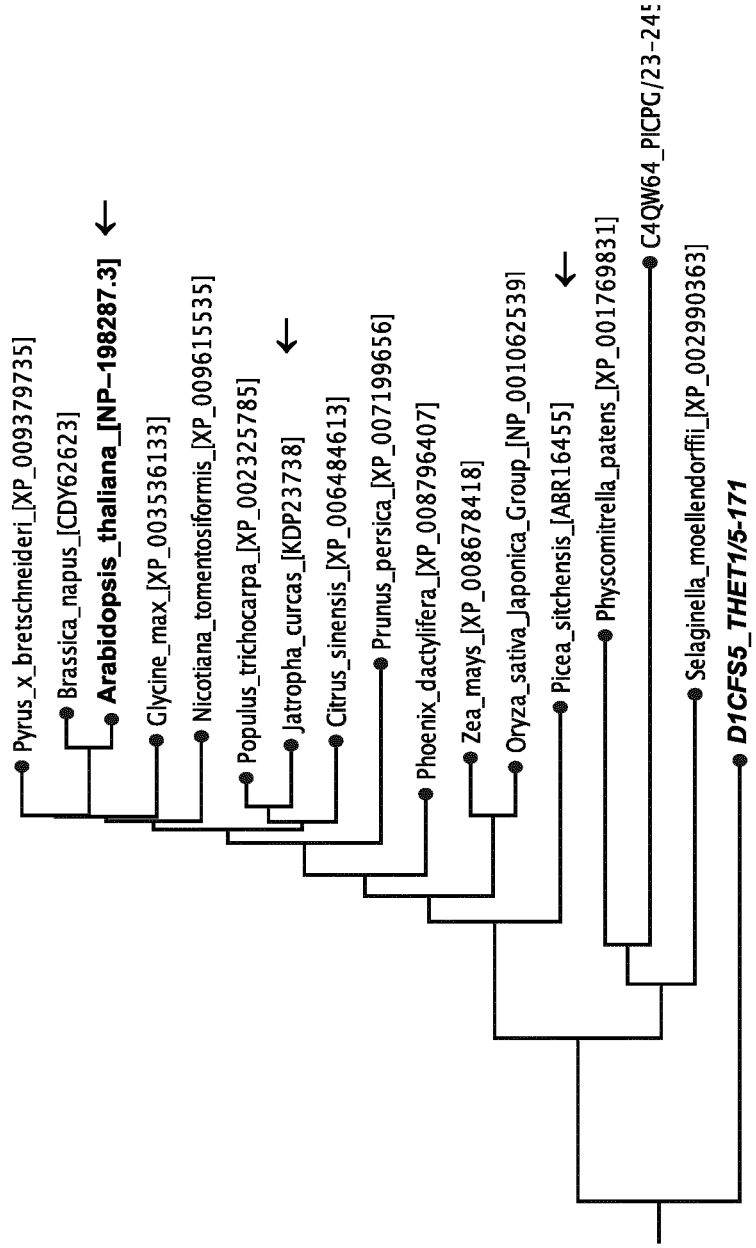
FIG. 4 Phylogenetic tree of TMP phosphatases belonging to (A) clade 1; (B) clade 2 and (C) clade 3 based on alignment of amino acid sequences. Each member of the three clades comprises a haloacid domain (HAD) known to catalyze dephosphorylation of thiamine monophosphate. Clade 1 consists of homologues of At5G32470 and spans the *Viridiplantae* and features a TenA/Teni-4 family domain (PFam: PF03070) at the N-terminus and a HAD in the C-terminal half (see their alignment in FIG. 5). Clade 2 represent bacterial genes often found as fusion with other thiamine genes and include the gene from *Anaerotruncus colihominis* (WP_006874980). Clade 3 represents a clade of bacterial genes that includes *Syntrophomonas wolfei* (WP_011640074.1), which are often found with other thiamine genes. The outgroup leaves are indicated in italics and the representatives of each clade that have been characterized as TMP phosphatases are indicated in bold. Arrows identify genes tested in example 4.4.

A polypeptide having thiamine mono-phosphate phosphatase activity (E.C 3.1.3.-) according to the invention is a member of a family of TMP phosphatase enzymes having a haloacid domain that catalyzes the dephosphorylation of thiamine monophosphate. The members of this family are encoded by genes belonging to three clades (Example 3). The amino acid sequence of the polypeptide having TMP phosphatase activity has at least 70, 75, 80, 85, 90, 95, 96, 98, 100% amino acid sequence identity to a sequence selected from any one of: SEQ ID No.: 2, 4, 6, 8, 10, 12, 14, 16, 18, 20, 22, 24, 26, 28 and 30 encoded by genes of clade 1; SEQ ID No.: 32, 34, 36, 38, 40, 42, 44, 46, 48, 50, 52, 54, 56, 58, 60, 62, 64 and 66 encoded by genes of clade 2; and SEQ ID No.: 68, 70, 72 and 74 encoded by genes of clade 3. The clade 1 gene from *A. thaliana* (AT5G32470.1) and its orthologues listed in FIG. 4A; the Clade 2 genes from *Anaerotruncus colihominis* and *Dorea longicatena* and their orthologues listed in FIG. 4B; and the clade 3 gene from *Syntrophomonas wolfei* and its orthologues listed in FIG. 4C, all encode polypeptides having TMP phosphatase activity (E.C 3.1.3.-).

In one embodiment the amino acid sequence of the polypeptide having TMP phosphatase activity has at least 60, 65, 70, 75, 80, 85, 90, 95, 96, 98, 100% amino acid sequence identity to SEQ ID No.: 2; where the polypeptide is characterized by comprising TenA-like domain, likely important for recognition of thiamine, and a HAD-domain for hydrolysis of the phosphate bond (Example 2). Proteins with this signature structure can be overexpressed in a bacterial cell of the invention in order to shift the thiamine phosphorylation profile towards thiamine.

In one embodiment the amino acid sequence of the polypeptide having TMP phosphatase activity has at least 80, 85, 90, 95, 96, 98, 100% amino acid sequence identity to a sequence selected from any one of: SEQ ID No.: 2, 14, 26, 32, 34, 40, 68 and 70.

In one embodiment the amino acid sequence of the polypeptide having TMP phosphatase activity has at least 80, 85, 90, 95, 96, 98, 100% amino acid sequence identity to a sequence selected from any one of: SEQ ID No.: 2, 14, 26, 32, 34, 68, and 70.

The polypeptides that are encoded by the transgenes in the genetically modified bacterium, and whose activity serves to enhance the synthesis of both intermediates and products of the thiamine pathway, are as follows:

b) a polypeptide having 4-amino-5-hydroxymethyl-2-methylpyrimidine phosphate (HMP-P) synthase activity (E.C. 4.1.99.17); such as a polypeptide with an amino acid sequence having 80, 85, 90, 95 or 100% sequence identity to SEQ ID No.:76, 78, 80 and 82;

c) a polypeptide having thiamine phosphate synthase activity (2.5.1.3), such as a polypeptide with an amino acid sequence having 80, 85, 90, 95 or 100% sequence identity to SEQ ID No.: 84;

d) a polypeptide having ThiS adenylyltransferase activity (2.7.7.73), such as a polypeptide with an amino acid sequence having 80, 85, 90, 95 or 100% sequence identity to SEQ ID No.:86;

e) a polypeptide having ThiS sulfur-carrier activity (immediate sulfur donor in thiazole formation), such as a polypeptide with an amino acid sequence having 80, 85, 90, 95 or 100% sequence identity to SEQ ID No.:88.

f) a polypeptide having thiazole synthase activity (2.8.1.10), such as a polypeptide with an amino acid sequence having 80, 85, 90, 95 or 100% sequence identity to SEQ ID No.:90;

g) a polypeptide having 2-iminoacetate synthase activity (4.1.99.19; also called L-tyrosine 4-methylphenol-lyase) such as a polypeptide with an amino acid sequence having 80, 85, 90, 95 or 100% sequence identity to SEQ ID No.:92; or a polypeptide having Glycine oxidase activity (EC 1.4.3.19) such as a polypeptide with an amino acid sequence having 80, 85, 90, 95 or 100% sequence identity to SEQ ID No.:94, 96 and 98; and h) a polypeptide having phosphohydroxymethylpyrimidine kinase activity (2.7.4.7), such as a polypeptide with an amino acid sequence having 80, 85, 90, 95 or 100% sequence identity to SEQ ID No.:100.

The genetically modified bacterium may additionally be characterized by a genetic modification to reduce the expression of one or more of the three native endogenous thiBPQ genes and thereby reduce thiamine export from the bacterium. The three genes thiB, thiP and thiQ encode a thiamine ABC transporter periplasmic binding protein; a thiamine ABC transporter permease; and a thiamine ABC transporter ATPase, respectively. For example, thiamine export can be reduced by inactivating or deleting (by gene knockout) one or more of the three genes thiB (or thiP or thiQ) in the genome of the bacterium. Preferably, the amino acid sequence of the polypeptide encoded by the inactivated/deleted thiB gene has at least 80% 85, 90, 95 or 100% sequence identity to SEQ ID No.: 102; the polypeptide encoded by the inactivated/deleted thiP gene has at least 80% 85, 90, 95 or 100% sequence identity to SEQ ID No.: 104; and the polypeptide encoded by the inactivated/deleted thiQ gene has at least 80% 85, 90, 95 or 100% sequence identity to SEQ ID No.: 106.

The genetically modified bacterium may additionally be characterized by a further transgene encoding a polypeptide having hydroxyethylthiazole kinase activity (2.7.1.50), such as a polypeptide with an amino acid sequence having 80, 85, 90, 95 or 100% sequence identity to SEQ ID No.:108.

The expression of a transgene encoding a thiamine monophosphate phosphatase (TMP phosphatase having EC 3.1.3.-) in combination with transgenes encoding polypeptides that catalyze steps in the thiamine pathway in the genetically modified bacterium of the invention, not only enhances the production of thiamine compounds, but additionally, it drives the pathway towards the production of un-phosphorylated thiamine (Example 1). As shown in Example 4, levels of extracellular thiamine were increased 6 fold, while total production of thiamine compounds was enhanced by 20%, when compared to cells lacking the transgene encoding TMP phosphatase. The surprisingly high levels of thiamine produced and released into the extracellular medium by the genetically modified bacterium of the invention meet the key requirements for its use as a cell factory for thiamine production.

In a further embodiment, the genetically modified bacterium of the invention is further characterized by a genetically modified endogenous thiL gene that expresses reduced thiamine-phosphate kinase activity (EC 2.7.4.16) as compared to the parent endogenous thiL gene. The genetically modified thiL gene may be mutated to express lower amounts of the encoded polypeptide; or it can be mutated to encode a polypeptide having reduced thiamine-phosphate kinase activity (EC 2.7.4.16). For example, when the amino acid sequence of the encoded polypeptide has at least 80% sequence identity to SEQ ID No.: 110 and with the proviso that the sequence has an amino acid residue substitution G133D (or a G→D substitution in an equivalent position on the basis of sequence alignment); then it will have a reduced thiamine-phosphate kinase activity (EC 2.7.4.16). As shown in Example 4, when genetically modified bacteria comprising transgenes for the thiamine pathway alone, were compared with bacteria further comprising a transgene encoding a TMP phosphatase and a mutant thiL gene (reduced THIL activity), the levels of extracellular thiamine production were increased 7 fold, while total production of thiamine compounds was enhanced by 24%.

The genetically modified bacterium of the invention has a transgene that comprises a promoter operably linked to a coding sequence encoding a thiamine monophosphate phosphatase (TMP phosphatase having EC 3.1.3.-); as well as transgenes encoding polypeptides that catalyze steps in the thiamine pathway. A promoter may be operably linked to each thiamine pathway polypeptide coding sequence; or the respective coding sequences may form an operon that is operably linked to a single promoter.

Suitable promoters include both constitutive promoters (e.g. apFAB46 [SEQ ID No.: 147] apFAB70 [SEQ ID No.: 148], apFAB71 [SEQ ID No.:149]), as well as inducible promoters (e.g pBAD ara promoter [SEQ ID No.:150] when co-expressed with araC gene for regulation (Guzman et al. 1995) or pLac promoter with lacO operator site [SEQ ID No.:151] (Norrander et al. 1983)).

The genetically modified bacterium according to the invention, for the production and export of thiamine, is a member of a genus of bacterium wherein TPP biosynthesis is mediated via the thiL pathway (FIG. 1) and not the thiN pathway. Accordingly the genus of bacterium may be selected from the group consisting of Acetobacter, Azotobacter, Brevibacterium, Burkholderia, Campylobacter, Corynebacterium, Escherichia, Propionibacterium, and Streptomyces. Preferably, the bacterium of the invention is a species of Escherichia, e.g. Escherichia coli.

II a Method for Producing Thiamine Using a Recombinant Microorganism Expressing a Thiamine Mono-Phosphate Phosphatase Thiamine can be produced and exported using microbial cells of the invention (e.g. recombinant bacterial cells) by introducing the cells into a culture medium comprising a carbon source for biosynthesis of one or more of thiamine, TMP and TPP; and finally recovering the thiamine produced by the culture, as illustrated in the Examples.

The bacterial cells of the invention will produce thiamine when supplied with a suitable carbon source including glucose, maltose, galactose, fructose, sucrose, arabinose, xylose, raffinose, mannose, and lactose.

III a Method of Detecting Thiamine Produced and Exported by a Recombinant Microorganism Expressing a Thiamine Mono-Phosphate Phosphatase Methods for detecting and quantifying extracellular and intracellular thiamine produced by a micro-organism of the invention include High Pressure Liquid Chromatography, relative to a thiamine standard. For example, individual thiamine compounds, thiamin, TMP, and TPP can be measured using a modified thiochrome-HPLC assay procedure described previously (Chie et al., 1999). Briefly, 100 μl of culture supernatant or intracellular extracts are added to 200 μl of 4M potassium acetate. The sample is then oxidized by the addition of 100 μl fresh 3.8 mM potassium ferricyanide in 7 M NaOH. The mixture is vigorously mixed and then quenched by addition of 100 μl fresh 0.06% $H_2O_2$ in saturated $KH_2PO_4$. Samples are neutralized with 6M HCl and are transferred to HPLC vials and injected onto a Supelcosil LC-18-T column (15 cm×4.6 mm, 3 μm) (Supeico-Ref. No 58970-U). Elution is made by a 10%-35% methanol ($H_2O$ 50%-25%) gradient in the presence of 40% 0.1 M $K_2HPO_4$ (pH 6.6) and 4 mM tetrabutyl ammonium hydrogen sulfate. Fluorescence is measured at 444 nm after excitation at 365 nm. The chronological order of elution from the column is thiamin, TMP, and TPP. This procedure was utilized to monitor both internal and external thiamine production during fermentation.

Alternatively, direct measurement of thiamine and the intermediates HMP and HET in the fermentation broth can be performed by chromatography of samples on a Phenomenex LUNA C18 column, using an Agilent 1100 HPLC system equipped with a thermostated autosampler and a diode array detector (DAD). The column dimensions are 150×4.6 mm, particle size 5 micron. The column temperature is kept constant at 20 C. The mobile phase is a mixture of 0.4 g pentane sulfonate in water, pH 2 (A) and methanol (B).

IV Methods for Producing a Genetically Modified Bacterium for Production and Export of Thiamine Integration and self-replicating vectors suitable for cloning and introducing one or more gene encoding one or more a polypeptide having an enzymatic activity associated with thiamine synthesis in a bacterium of the invention are commercially available and known to those skilled in the art (see, e.g., Sambrook et al., Molecular Cloning: A Laboratory Manual, Second Edition, Cold Spring Harbor Laboratory Press, 1989). Cells of a bacterium are genetically engineered by the introduction into the cells of heterologous DNA.

Heterologous expression of genes encoding one or more polypeptide having an enzymatic activity associated with thiamine synthesis in a bacterium of the invention is demonstrated in the Example 1 and 3.

A nucleic acid molecule, that encodes one or more polypeptide having an enzymatic activity associated with thiamine synthesis according to the invention, can be introduced into a host cell by means of a self-replicating vector or optionally integrated into the host cell genome using methods and techniques that are standard in the art. For example, nucleic acid molecules can be introduced by standard protocols such as transformation including chemical transformation and electroporation, transduction, particle bombardment, etc. Expressing the nucleic acid molecule encoding the enzymes of the claimed invention also may be accomplished by integrating the nucleic acid molecule into the genome.

Genetic modification of the native endogenous thiL gene in a bacterium of the invention is performed to reduce expression of thiamine-phosphate kinase activity (EC 2.7.4.16) as compared to the parent endogenous thiL gene. For example, the native thiL gene may be mutated to encode a polypeptide having reduced thiamine-phosphate kinase activity (EC 2.7.4.16), as described in Example 4.

Genetic modification of one or more of the native endogenous thiBPQ genes in a bacterium of the invention is performed to reduce re-uptake of extracellular thiamine export into the bacterium. The deletion (knockout) of any one of the three genes thiB (or P or Q) in the genome of the bacterium (e.g. *E. coli* K12 strain), using standard recombineering methods (Datsenko K A, et al.; 2000), is sufficient to reduce thiamine import as compared to a parent bacterium. For example, the thiB::Kan construct (tbpA re-named as thiB) can be PCR amplified from strain JW0067 of the Keio collection (thiP from JW0066; thiQ from JW0065) (Baba et al., 2006). The amplified fragment can be transformed by electroporation into competent host cells (e.g. *E. coli*) carrying the ARed recombinase genes expressed from an inducible promoter (pKD46) (Datsenko K A, et al. 2000). Successful integrants are selected on Kanamycin medium and confirmed by colony PCR. The Kanamycin resistance (kanR) cassette can be eliminated by transforming cells with the temperature-sensitive plasmid pcp20, which expresses the FLP recombinase. Ampicillin-resistant colonies can be isolated at 30° C. and then restreaked non-selectively at 42° C. Loss of KanR can be confirmed by colony PCR.

EXAMPLES

Example 1. Identification of a Thiamine Specific Phosphatase

A key precursor for TDP and TPP biosynthesis in many micro-organisms and plants is THI; which in turn is derived from TMP by the action of a phosphatase.

Five different putative phosphatases, predicted to have phosphatase activity towards the substrates TMP or TPP, were identified based on structure/functional prediction. Nucleic acid molecules, whose nucleotide sequences encoded each phosphatase, were individually cloned into an expression vector giving the following five phosphatase expression vectors (+empty vector control), as shown in Table 1.

TABLE 1

| Vector | Inserted gene | Encoded protein/ SEQ ID NO. |
|---|---|---|
| pBS92 (control) | — | — |
| pBS93 | Synthetic gene encoding *Arabidopsis thaliana* AT5G32470.1 phosphatase codon optimized for expression in *E. coli* | 2 |
| pBS94 | *Staphylococcus aureus* Newmann phosphatase rgsA gene | 112 |
| pBS95 | *Pseudomonas* phosphatase gene identified in a metagenomic screen | 114 |
| pBS96 | *Saccharomyces cerevisiae* pho3 gene (YBR092C) | 116 |
| pBS97 | *E. coli* nudJ gene | 118 |
| pGEN49 | Empty vector used for construction of pBS140 | — |
| pGEN50 | Empty vector used for construction of pBS140 | — |
| pGEN51 | Empty vector used as PCR template for construction of pBS92 | — |
| pBS116 | pGEN49 + thiC operon | 76 |
| pBS117 | pGEN50 + thiM operon | 108 |
| pBS140 | Vector expressing the *E. coli* thiamine pathway genes thiCEFSGHMD | 76, 84, 86, 88, 90, 92, 108, 100 |
| pMA7-sacB | Vector carrying recombinases used for construction of MAGE strains (Lennen et al. 2015) | — | a. Vector construction

Vector pBS92 was constructed using the one-step-isothermal DNA assembly method developed by Gibson et al., (2009). The backbone, carrying the SpecR cassette and the SC101 origin of replication, was amplified from PZS4Int-tetR (see world wide dweb address: expressys.com/main_tools.html) using primers oBS196 and oBS197 and a gene expression cassette comprising an apFAB70 promoter (SEQ ID No.:148) and apFAB381 terminator (SEQ ID No.:154) were synthesized and then amplified using primers pBS194 and oBS195. Purified PCR fragments were assembled by one pot isothermal assembly using the NEB Gibson assembly master mix (# E2611) and standard protocol according to the manufacturer's instructions (Gibson et al., (2009). The assembled vectors were transformed into electro-competent DH10B cells by electroporation and the recovered cells were plated on Luria Broth (LB) Spectinomycin plates.

Vectors pBS93-97 were constructed by amplifying pBS92 with the primer pair oBS198 and oBS199; and the purified PCR product was assembled with the respective phosphatase gene using the NEB Gibson assembly master mix according to the manufacturer's instructions. The phosphatase genes cloned in each vector (Table 1) were amplified as follows:

pBS93: Primers oBS220, oBS221 were used to amplify the synthetic gene encoding *Arabidopsis thaliana* AT5G32470.1 phosphatase which was codon optimized for *E. coli*, and synthesized as two gene blocks;

pBS94: Primers oBS202, oBS203 were used to amplify the rsgA gene from *S. aureus* Newmann genomic DNA;

pBS95: Primers oBS201, oBS200 were used to amplify the coding sequence for an acid phosphatase (EC 3.1.3.2) gene from *Pseudomonas*.

pBS96: Primers: oBS201, oBS202 were used to amplify the *S. cerevisiae* PHO3 gene, which was codon optimized for *E. coli*, and synthesized as one gene block;

pBS97: Primers oBS210, oBS211 were used to amplify the nudJ gene (MG1655) from *E. coli* genomic DNA.

Each of the assembled vectors was transformed into electro-competent DH10B cells by electroporation and the recovered cells were plated on selective LB plates. This host DH10B strain (F-mcrA Δ(mrr-hsdRMS-mcrBC) φ80dlacZΔM15 ΔlacX74 endA1 recA1 deoR Δ(ara,leu)7697 araD139 galU galK nupG rpsL λ-) comprises a chromosomal deletion, resulting in the deletion of three genes (thiBPQ corresponding to EcoGenes: EG11574, EG11573, EG11572) respectively encoding: Thiamine ABC transporter periplasmic binding protein; Thiamine ABC transporter permease; and Thiamine ABC transporter ATPase.

Vector pBS140 was constructed following a two-step hierarchical cloning procedure. First the thiC operon and the thiM operon were assembled into the background vectors pGEN49 (comprising an apFAB46 promoter (SEQ ID No.: 147) and an apFAB377 terminator (SEQ ID No.:153)) and pGEN50 (comprising an apFAB71 promoter (SEQ ID No.: 149)) and an apFAB378 terminator (SEQ ID No.: 152)) respectively, and then the two resulting vectors were combined to form pBS140. The thiC operon was amplified from MG1655 genomic DNA using primers oGEN264 and oGEN227 and the thiM operon was amplified from MG1655 genomic DNA using primers oBS422 and oBS421. Vectors pGEN49 and pGEN50 were amplified with primers oGEN265 and 266 and then assembled with the thiC and thiM operon respectively using one pot isothermal assembly. The resulting vectors were named pBS116 (pGEN49+thiC operon) and pBS117 (pGEN50+thiM operon). The assembled vectors were transformed into electro-competent DH10B cells by electroporation and the recovered cells were plated on LB Kan plates. The sequence of the resulting vectors was confirmed by Sanger sequencing.

The confirmed vector pBS116 was purified and digested for >8 h using SwaI (NEB # R0604). The linearized DNA was gel-purified. Confirmed vector pBS117 was used as a template for PCR with primers oGEN182 and oGEN184. The resulting PCR fragment was gel-purified. The amplified vector and thiM operon were assembled using NEB Gibson assembly master mix, according to the manufacturer's instructions and the mixture was transformed into electro-competent DH10B cells by electroporation and the recovered cells were plated on LB Kan plates. The sequence of the resulting plasmid pBS140 was confirmed by Sanger sequencing.

TABLE 2

List of primers

| Primer name | Sequence | SEQ ID NO.: |
|---|---|---|
| oBS194 | GTCCTACTCAGGAGAGCGTTCACCG ACAACTCAGGAGAGCGTTCACC | 119 |
| oBS195 | CTTTCGTCTTCACCTCGAGGGAAAT CAAAATAGGCGTATCACGAGGCC | 120 |
| oBS196 | GATTTCCCTCGAGGTGAAGACGAAA G | 121 |
| oBS197 | TGTCGGTGAACGCTCTCCTG | 122 |
| oBS198 | ATTATTACTCGTGTGTTGTCAGAAA G | 123 |
| oBS199 | CTAGTATTACCTCGCTATTAGTGAC GTAATAGGAGGTAAGC | 124 |
| oBS200 | CTATTACGTCACTAATAGCGAGGTA ATACTAGATGTGCCAGCAGCATCCG C | 125 |
| oBS201 | CGGAGGCCTTTCTGACAACACACGA GTAATAATCTAGTTTTCTAGAGGCA GCGC | 126 |
| oBS202 | CTATTACGTCACTAATAGCGAGGTA ATACTAGATGAAGACAGGTCGAATA GTG | 127 |
| oBS203 | CGGAGGCCTTTCTGACAACACACGA GTAATAATTTAATATCTAACCTTTC TATTTG | 128 |
| oBS210 | CCTATTACGTCACTAATAGCGAGGT AATACTAGATGTTTAAACCGCACGT TACCG | 129 |
| oBS211 | CTTTCTGACAACACACGAGTAATAA TTTAGATGACACCCTTTGTAAAAGG | 130 |
| oBS220 | GTACCTATAATGTGTGGATGTCCCA CCGCTTACCTCC | 131 |
| oBS221 | CATCACCATCATCACCACTGAATTA TTACTCGTGTGTTGTCAGAAAG | 132 |
| oGEN184 | AAACCTCTTTATGTTGCAGTCG | 133 |
| oGEN182 | AAATTCGCGAGTTCCACTAAGA | 134 |
| oGEN227 | CCGCTTACCTCCTATTACGTCACTA ATAGCTAAGGAGGTAAATATGTCTG CAACAAAACTGACCCGCC | 135 |
| oGEN264 | CGGAGGCCTTTCTGACAACACACGA GTAATAATTCATAGTCTTTGCGAGG CG | 136 |
| oGEN265 | ATTATTACTCGTGTGTTGTCAGAAA GGCCTCCG | 137 |
| oGEN266 | ATTAGTGACGTAATAGGAGGTAAGC GGTGGG | 138 |
| oBS421 | CGGAGGCCTTTCTGACAACACACGA GTAATAATTCACCACCAGGCGTGGA AG | 139 |
| oBS422 | GCTTACCTCCTATTACGTCACTAAT AGCTAAGGAGGTAAATATGCAAGTC GACCTGCTGG | 140 |
| oBS445 | CGGAACAAAGCCGTGGATGTCCAAC GTCATTGATAATGGCCCACGCGTGG TATCGCCGCCAATGAGTTGCATATC GTAATAATTGAGAAG | 141 |
| oBS446 | CCAGAGCGCGTTAAGGCTCGTCCCA TCGGAACAAAGCCGTGGATGTCCAA CGTCATTGATAATGGCCCACGCGTG GTATCGCCGCCAATG | 142 |
| oBS456 | CATGTGGCGAGTTCTCCCTG | 143 |
| oBS457 | CAGGTAAACGGTACGCCCAG | 144 |
| oBS521 | GCAACTGTCGATGGCGAAGC | 145 |
| oBS522 | CCTGATCAACCGCCACCAC | 146 | a. Expression of Putative TMP Phosphatase Genes in Genetically Modified *E. coli* Cells The five candidate TMP phosphatase genes: *A. thaliana* gene (At5g32470); *S. aureus* Newmann phosphatase rgsA gene; *Pseudomonas* phosphatase gene; *S. cerevisiae* pho3 gene (YBRO92C); and an *E. coli* nudJ gene were each expressed in an *E. coli* host strain comprising the vector pBS140. The pBS140 vector comprises the thiamine pathway genes thiMD and thiCEFSGH; whose expression in the host cells leads to overexpression of the thiamine biosynthesis pathway.

Cells of transformed *E. coli* host strains expressing each of the candidate phosphatase genes (and control *E. coli* host strains) were first pre-cultured in 400 µL Modified MOPS medium (comprising antibiotics for vector maintenance) in deep 96-well cultivation plates at 37 degrees, shaking at 300 rpm overnight; and cultures produced were then used to inoculate the same volume of medium to an OD600 nm of 0.0015. These cultures were grown for 24 hours under the same conditions; and then used for thiamine analysis. OD600 nm was measured using a plate reader, and then converted to the corresponding OD600 nm in a cuvette.

a. Extraction and Detection of TPP, TMP and Thiamine Produced by Genetically Modified *E. coli* Cells Extracellular and intracellular TPP, TMP and thiamine in each culture was recovered and extracted as follows: 0.4 mL of each culture was harvested at 4° C. by centrifugation in the cultivation plate at 4000×g for 5 minutes. All remaining steps were performed on ice. 40 µL of supernatant was gently removed for analysis of extracellular TPP, TMP and thiamine. After decanting the remaining supernatant; the culture plate was inverted to remove residual medium and then vortexed. 100 µL ice-cold HPLC grade methanol was added to each well of the culture plate; and the cells were vortexed again. After incubation on ice for a minimum of 20 minutes cell debris was pelleted by centrifugation at 4000×g for 5 minutes. The supernatant was used as intracellular extract for further analysis.

In order to detect TPP, TMP and thiamine using a fluorescence detector, the thiamine compounds produced by each culture were derivatized into thiochromes, which are strongly fluorescent. All steps are performed at room temperature. 40 µl volumes of the extracellular and intracellular extracts was added to 80 µl of 4M potassium acetate and mixed by pipetting. 40 µl of freshly prepared 3.8 mM potassium ferricyanide in 7M NaOH was added and mixed. The reaction was quenched by addition of 40 µl freshly prepared 0.06% $H_2O_2$ in saturated $KH_2PO_4$. The extracts were neutralized by addition of 47 µL 6M HCl and then analyzed by HPLC as described below. All derivatized compounds were quantified using fluorescence standard curves of freshly prepared of TPP, TMP and thiamine standards that were derivatized to thiachromes in parallel with the analyzed extracts.

HPLC was used to quantitate the intracellular and extracellular content of thiamine; TMP and TPP in each culture by a method adapted from the method described by Schyns G et al., (2005).

Column: Hypersil Gold, 3 µm particle size, dimensions: 150×2.1 mm (Thermo product number: 25003-152130) with guard column of the same material.

Buffer A: 10 mM $K_2HPO_4$ pH: 7, 4 mM t-butyl ammonium hydrogen sulfate

Buffer B: Methanol

Buffer C: Distilled water

Gradient: Constant concentration of Buffer A at 40%. 0-2 min: constant concentration of B at 10%; 2-6 min: gradient of B from 10-30%; 6-8 min: constant concentration of B at 30%; 8-8.1 min: gradient of B from 30-10%; 8.1-12 min: constant concentration of B at 10%.

Flow rate 0.8 mL/min

Injection volume: 24 for intracellular samples, 5 uL for extracellular samples.

Figure 2:
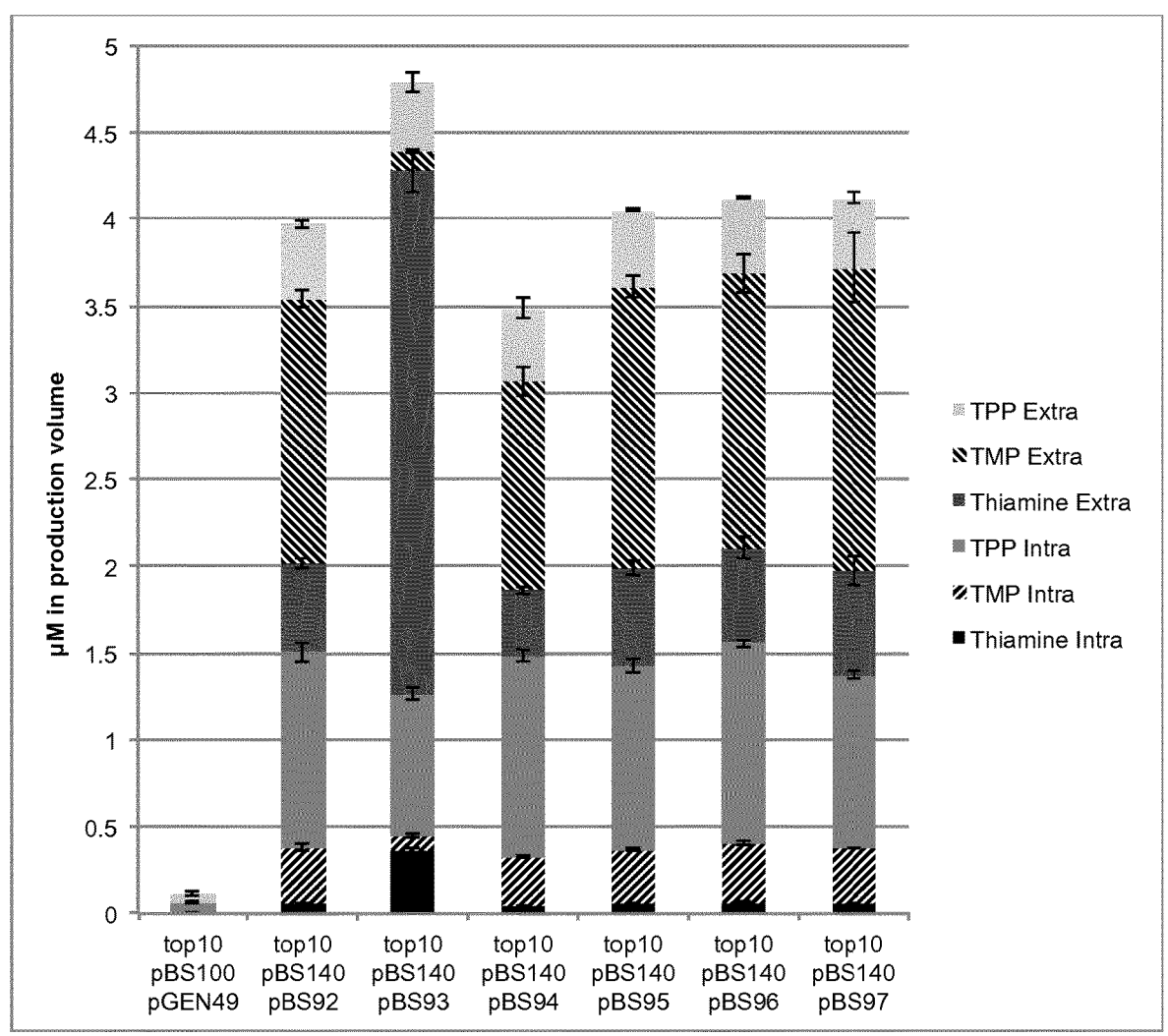
FIG. 2 Bar diagram showing the extracellular and intracellular levels of THI, TMP and TPP detected in cultures of genetically modified *E. coli* strains transformed with a vector expressing one of 5 different phosphatase genes: pBS93 with the *A. thaliana* gene (At5g32470); pBS94 with the *S. aureus* Newmann phosphatase rgsA gene; pBS95 with the *Pseudomonas* phosphatase gene; pBS96 with the *S. cerevisiae* pho3 gene (YBRO92C); and pBS97 with the an *E. coli* nudJ gene, as compared to a strain comprising pBS92, a control vector. Additionally each strain comprises the vector pBS140 comprising genes thiMD and thiCEF-SGH constitutively expressing enzymes in the thiamine biosynthesis pathway; to be compared with the control strain transformed with empty vector (pGEN49) lacking the genes encoding the pathway enzymes. The intracellular concentrations are calculated using the entire culture volume, i.e. the indicated level is the effective concentration if the intracellular metabolite had been released into the culture volume.

Order of elution: thiamine, TMP, TPP. Detection using fluorescence detector with with λexcitation: 365 nm and Remission: 444 nm.

a. *A. thaliana* Protein AT5G32470.1 Expressed in Genetically Modified *E. coli* Cells Exhibits TMP Phosphatase Activity The composition of the thiamine compounds produced by cells of genetically modified *E. coli*, engineered to overexpress the thiamine pathway, and expressing one of five different phosphatase genes is shown in FIG. 2. The only cells showing a significant shift in thiamine phosphorylation profile towards un-phosphorylated thiamine relative to that of cells comprising the control vector pBS92, were those expressing a gene encoding *A. thaliana* protein AT5G32470.1. TMP was not detectable in these cells; the amount of TPP was slightly reduced; on which basis it can be deduced that the *A. thaliana* protein AT5G32470.1 has TMP phosphatase activity, and may also have TPP activity. The TMP phosphatase activity in cells expressing the *A. thaliana* TMP phosphatase resulted in a striking increase in both total extracellular thiamine compound production, and in extracellular un-phosphorylated thiamine, which accounted for 80% of total thiamine compounds detected in the culture.

Thiamine compounds were barely detectable in cultures of *E. coli* cells transformed with the empty vectors (pGEN49 and pBS92) that neither expressed a TMP phosphatase, nor thiamine pathway enzymes. A comparison of the levels of thiamine compounds produced by cells expressing thiamine pathway enzymes alone or together with TMP phosphatase, reveals their synergistic effect on thiamine compound production.

Example 2 Alignment and Structural Annotation of the *A. thaliana* Protein (AT5G32470.1)

Sequence alignment and structural annotation of the *A. thaliana* protein (AT5G32470.1) reveals two structural and functional domains. The first domain is a TenA-like domain located between amino acids 85-292, which based on alignment with the *Bacillus subtilis* protein TenA, is assigned responsibility for the recognition of phosphorylated thiamine substrates. The crystal structure of *B. subtilis* protein TenA has been solved alone and in complex with the thiamine precursor HMP (Toms et al. 2005). *B. subtilis* TenA is an aminopyrimidine aminohydrolase that catalyzes the hydrolysis of 4-amino-5-aminomethyl-2-methylpyrimidine to 4-amino-5-hydroxymethyl-2-methylpyrimidine (HMP). Since HMP corresponds to half of the thiamine molecule, the thiamine binding site residues in the *A. thaliana* protein, are predicted to correspond to the HMP binding sites in *B. subtilis* TenA. A sequence alignment shows that key residues, which form H-bond contacts to HMP and that line the active site, are conserved between *B. subtilis* TenA and AT5G32470.1 (which are identified in FIG. 5). *B. subtilis* TenA is capable of hydrolyzing thiamine, albeit at a much slower rate than HMP, strengthening the argument that the TenA domain is responsible for thiamine binding.

A second domain in the *A. thaliana* protein belongs to a conserved family of haloacid dehalogenase-like hydrolase domains (HAD-like superfamily) (see world wide web address: ncbi.nlm.nih.gov/Structure/cdd/cddsrv.cgi?uid=277525). This superfamily includes carbon hydrolases and phosphate hydrolases. Members of the HAD-like domain superfamily are known to catalyze a nucleophilic substitution reaction at the carbon or phosphorus in question. A hallmark of this HAD domain (PFAM code PF00702) is the presence of several conserved residues that are part of the of the Rossmann fold (Burroughs, A. M. et al., 2006). A conserved aspartate at the end of sheet 1, a conserved serine or threonine at the end of sheet 2, a lysine on a structure called C2 cap and a conserved aspartate on sheet 4, that together function in catalysis. Accordingly, the HAD-like domain in the *A. thaliana* protein (FIG. 5) was assigned phosphate hydrolase activity. These conserved functional domains allow the identification of polypeptides having TMP phosphatase activity.

Example 3 Identification and Structural Annotation of TMP Phosphatase Protein Families Members of the TMP phosphatase protein family, capable of enhancing thiamine levels in a bacterial cell, were identified on the basis of sequence, structural and functional homology, employing the following criteria and tools:

Four genes were empirically known to encode enzymes with a thiamine monophosphate hydrolysing activity, either promiscuous or physiological. The three genes were the AT5G32470.1 gene, first identified herein as a phosphatase, and three recently reported genes (Hasnain et al. 2016). Sequences that were homologous to these genes, as well as belonging to either the group of TenA-HAD fusion proteins, or alternatively being fused to a thiamine pathway gene or present in operons comprising thiamine pathway genes, was taken as a strong indicator of conservation of their function as encoding a TMP phosphatase. Sequences encoding a haloacid domain, which is a characteristic feature of proteins that catalyse dephosphorylations, was taken as a further indicator of TMP phosphatase function. The PF012710 seed dataset was used as a base dataset for HAD protein diversity. In the case of proteins composed of multiple domains the extra domains were removed based on a preliminary alignment with known HAD domain sequences. The datasets of genes of interest were chosen manually and the headers changed with a small Python script. The genes were then aligned with the Pfam dataset and outgroups chosen accordingly for each group. The sequences were independently aligned for each group with Muscle and were trimmed with Gblocks under permissive settings and the resulting alignments used for tree inference by Maximum likelihood under a WAG model with a CAT distribution.

Figure 3:
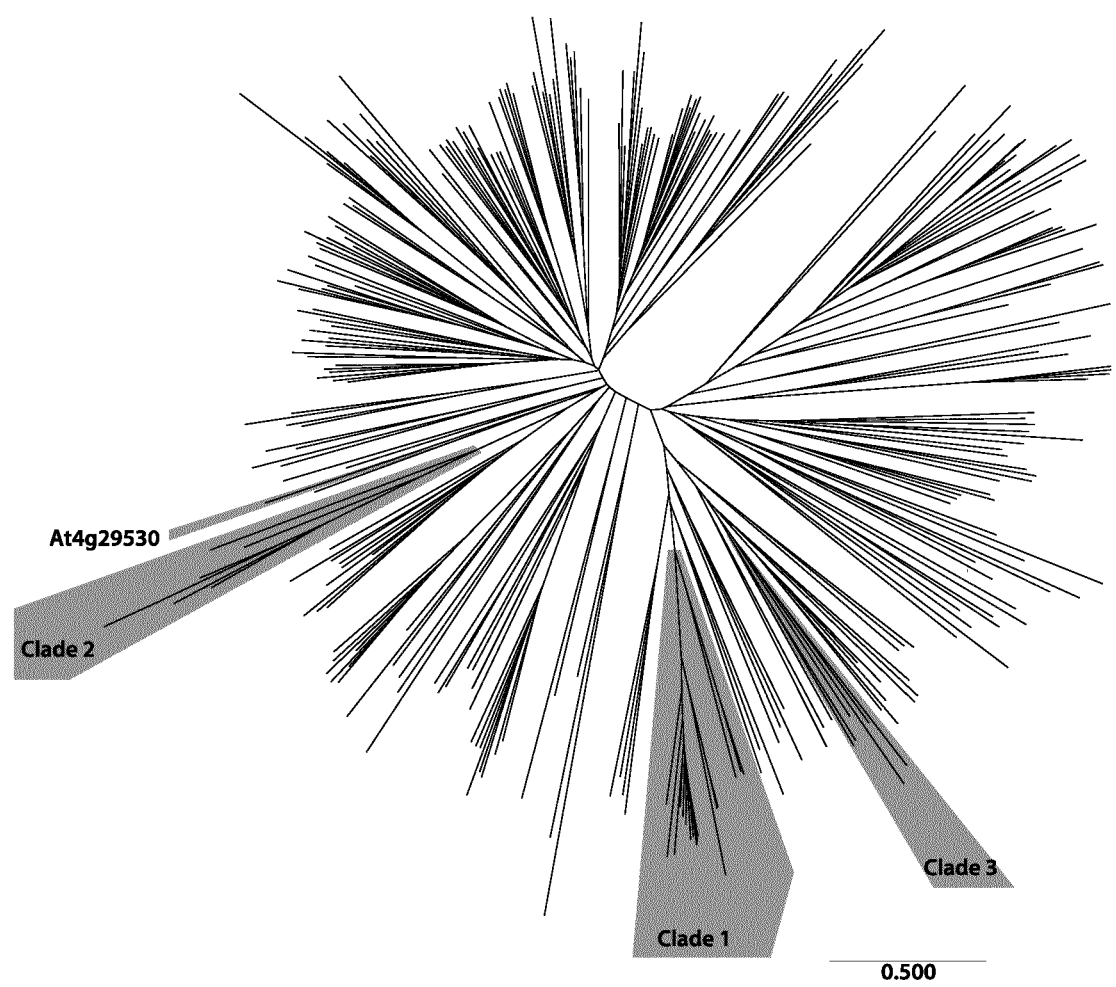
FIG. 3 Neighbor joining tree showing distribution of TMP phosphatases in 3 clades based on alignment of amino acid sequences. Distance scale bar indicates changes/amino acid residue. Clade 1 comprises the *A. thaliana* gene (At5g32470); Clade 2 comprises an *Anaerotruncus colihominis* gene (WP_006874980) (Hasnain et al. 2016); Clade 3 comprises a *Syntrophomonas wolfei* gene (WP_011640074.1) (Hasnain et al. 2016).

The characterized TMP phosphatase haloacid domain proteins that catalyze the dephosphorylation of thiamine monophosphate fall into three clades (FIG. 3), indicative of their parallel independent evolution.

Figure 5:
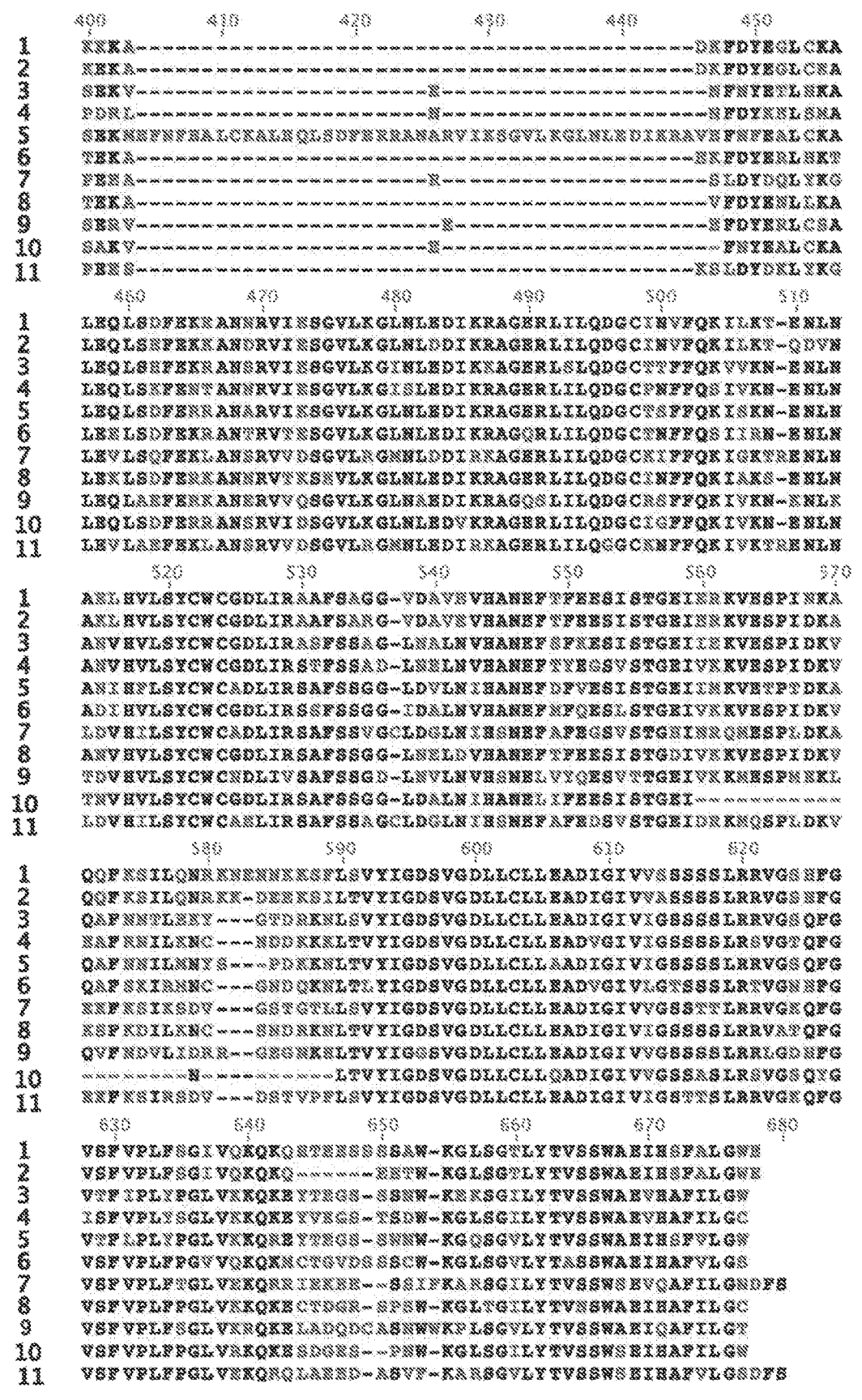

Clade 1 comprises homologues of At5G32470 and spans the *Viridiplantae* (FIG. 4A), and its members all feature a TenA/Teni-4 family domain (PFam: PF03070) at the N-terminus (FIG. 5). The members of this clade comprise the proteins: Arabidopsis thaliana NP-198287.3 (AT5G32470.1) [SEQ ID No.:2]; *Pyrus* x *bretschneideri* XP_009379735.1 [SEQ ID No.:4]; *Brassica napus* CDY62623.1 [SEQ ID No.:6]; *Glycine max* XP_003536133.1 [SEQ ID No.:8]; *Nicotiana tomentosiformis* XP_009615535.1 [SEQ ID No.:10]; *Populus trichocarpa* XP_002325785.2 [SEQ ID No.:12]; *Jatropha curcas* KDP23738.1[SEQ ID No.:14]; *Citrus sinensis* XP_006484613.1 [SEQ ID No.:16]; *Prunus persica* XP_007199656.1 [SEQ ID No.:18]; *Phoenix_dactylifera*_XP_008796407 [SEQ ID No.:20]; *Zea mays* XP_008678418.1 [SEQ ID No.:22]; *Oryza sativa* NP_001062539.1 [SEQ ID No.:24]; *Picea_sitchensis* ABR16455 [SEQ ID No.:26]; *Physcomitrella_patens*_XP_001769831 [SEQ ID No.:28]; and *Selaginella_moellendoiffii*_XP_002990363 [SEQ ID No.:30].

Figure 4B:
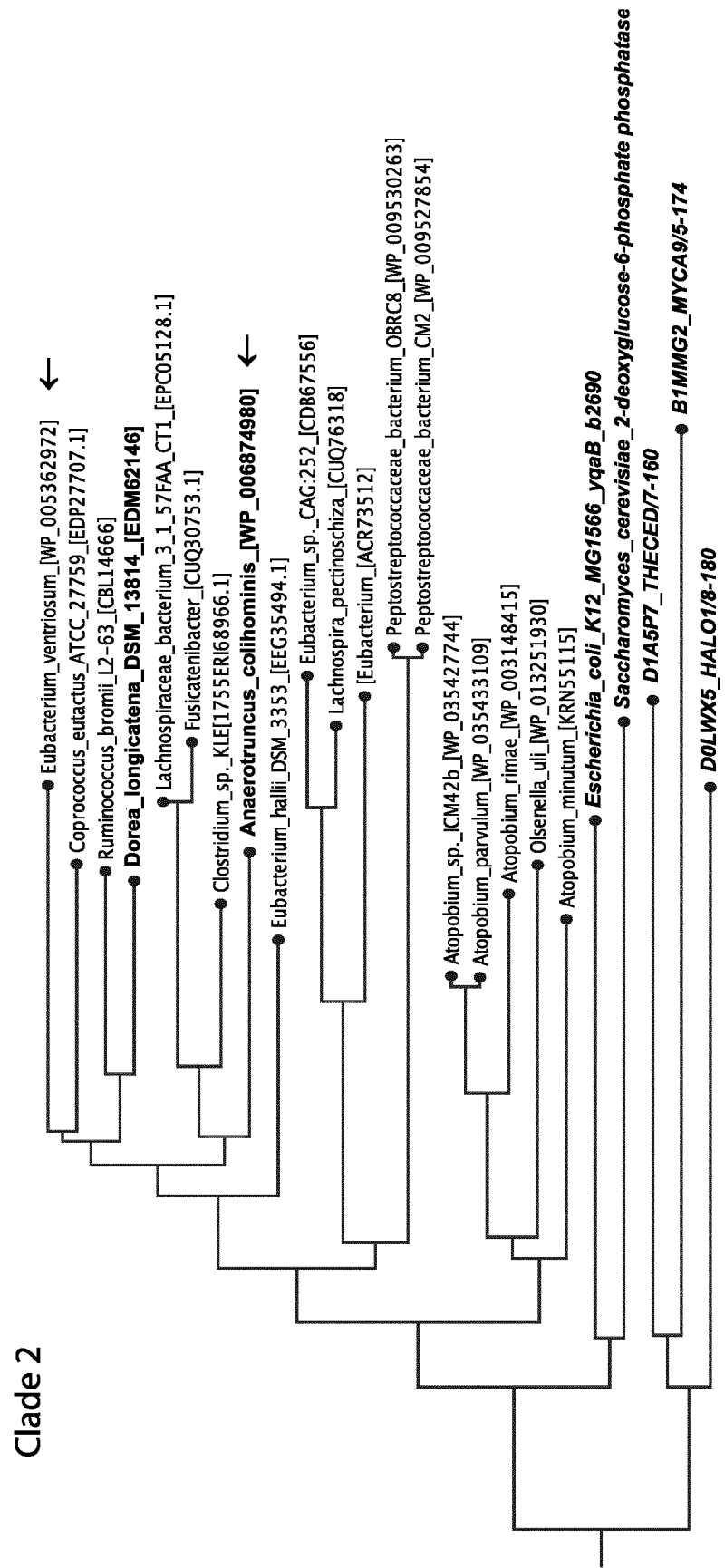
Figure 4C:
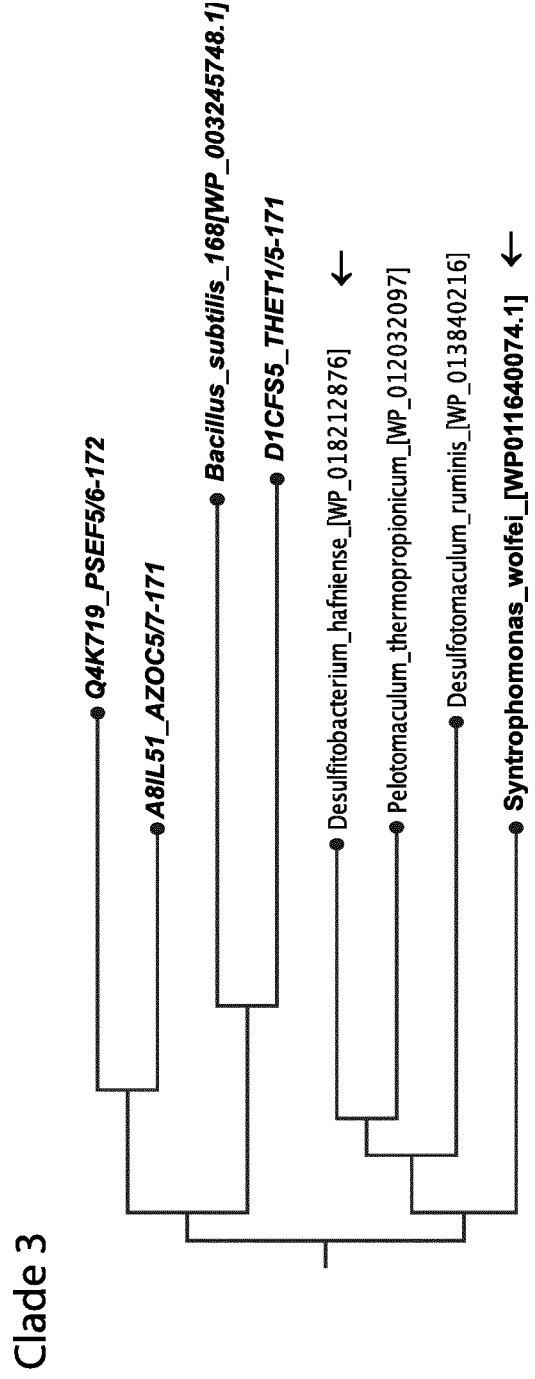

Clade 2 comprises bacterial genes, many of which are fused with thiamine pathway genes (FIG. 4B). Clade 2 includes an *Anaerotruncus colihominis* gene (WP_006874980) characterized as a TMP phosphatase (Hasnain et al. 2016). The members of this clade comprise the proteins: *Anaerotruncus_colihominis*_WP_006874980 [SEQ ID No.:32]; *Eubacterium_ventriosum*_WP_005362972 [SEQ ID No.:34]; *Coprococcus eutactus_*(ATCC_27759)_EDP27707 [SEQ ID No.:36]; *Ruminococcus_bromii*_L2-63 CBL14666 [SEQ ID No.: 38]; *Dorea_longicatena_*(DSM_13814)_EDM62146 [SEQ ID No.:40]; Lachnospiraceae bacterium EPC05128 [SEQ ID No.:42]; *Fusicatenibacter*_CUQ30753 [SEQ ID No.:44]; *Clostridium*_sp. ERI68966 [SEQ ID No.:46]; *Eubacterium_hallii*_EEG35494 [SEQ ID No.:48]; *Eubacterium_*sp._CDB67556 [SEQ ID No.:50]; *Lachnospira_pectinoschiza*_CUQ76318 [SEQ ID No.:52]; *Peptostreptococcaceae_bacterium*_WP_009530263 [SEQ ID No.:54]; *Peptostreptococcaceae_bacterium*_WP_009527854 [SEQ ID No.:56]; *Atopobium_*sp._WP_035427744 [SEQ ID No.: 58]; *Atopobium_parvulum*_WP_035433109 [SEQ ID No.: 60]; *Atopobium_rimae*_WP_003148415 [SEQ ID No.:62]; *Olsenella_uli*_WP_013251930 [SEQ ID No.:64]; and *Atopobium_minutum*_KRN55115 [SEQ ID No.:66].

Clade 3 comprises another group of bacterial genes, many of which map adjacent to thiamine pathway genes (FIG. 4C); and includes a characterized TMP phosphatase encoded by a *Syntrophomonas wolfei* gene (WP_011640074.1) (Hasnain et al. 2016). The members of this clade comprise the proteins: *Syntrophomonas_wolfei*_WP_011640074 [SEQ ID No.:68]; *Desulfitobacterium_hafniense*_WP_018212876 [SEQ ID No.:70]; *Pelotomaculum_thermopropionicum*_WP_012032097 [SEQ ID No.:72]; and *Desulfotomaculum_ruminis*_WP_013840216 [SEQ ID No.:74].

Example 4 Genetically Modified *E. coli* Strains Engineered for Enhanced Thiamine Production In order to drive the equilibrium further towards un-phosphorylated thiamine (THI) in a thiamine production strain, the expression of a TMP phosphatase was combined with mutations in the endogenous thiamine or TMP kinases genes, thiK and thiL. Since TPP is essential for cell growth, and since the only enzyme in *E. coli* capable of producing TPP from TMP is encoded by the thiL gene, full thiL knockout strains are not viable unless provided with a supply of TPP which is un-economic. Instead, kinase activity expressed in the host cells was decreased by introducing a point mutation (codon 133 from GGT to GAC) into the thiL gene causing G133D substitution in the encoded enzyme. This point mutation was known to decrease kinase activity encoded by the mutant thiL927 gene in *Salmonella typhimurium* (Webb E, et al., 1997). This mutation was introduced into cells of the *E. coli* host strain using Multiplex Automated Genome Engineering (MAGE).

4.1 Construction of a thiK⁻ Knockout Strain (BS131)

The thiK gene was knocked out in the *E. coli* host strain DH10B to produce strain BS131 by using λ-RED recombineering methods (Datsenko K et al., 2000) by the follow steps: A thiK::Kan construct was PCR amplified from strain DA/1092 of the Keio collection (Baba T, et al., 2006). Although the amplified thiK gene was originally named ycfN, in the Keio database, this corresponds to thiK (Melnick J. et al., 2004). The amplified fragment was transformed by electroporation into competent cells of *E. coli* DH10B carrying the ARed recombinase genes expressed from an inducible promoter (pKD46) Datsenko et al, 2000). Successful integrants were selected on Kanamycin medium and confirmed by colony PCR using primers oBS521 and oBS522. The Kanamycin resistance cassette was eliminated by transforming cells with the temperature-sensitive plasmid pcp20, which expresses the FLP recombinase. Ampicillin-resistant colonies were isolated at 30° C. and then re-streaked non-selectively at 42° C. Loss of KanR was confirmed by colony PCR with primers oBS521 and oBS522.

4.2 Construction of thiL G133D (thiL* Strain (BS182))

The thiL gene was partially inactivated by mutation in the *E. coli* host strain DH10B to produce strain BS182 using MAGE comprising the transient overexpression of DNA adenine methylase, as described by Lennen et al (2015). Briefly: the pMA7sacB plasmid was introduced into cells of the *E. coli* DH10B strain. The resulting strain was grown under inducing conditions (0.2% arabinose) to mid-log phase and electrocompetent cells were prepared using standard conditions. The competent cells were electroporated with a 1:1 mixture of oligos oBS445 and oBS446, which both introduce a mutation in the genomic copy of the thiL gene encoding a G133D substitution mutation. After rescue this procedure was repeated once more before cells were plated and successful mutants were identified by sequencing with primers oBS456 and 457.

4.3 Thiamine Production is Enhanced in Genetically Modified *E. coli* Having Reduced Thiamine Kinase Activity (thiL*) Combined with Expression of the *A. thaliana* Phosphatase (AT5G32470.1)

The thiK– knockout *E. coli* strain, BS131, and the mutated ThiL* *E. coli* strain, BS182, as well as the parent strain DH10B, were each transformed with the pBS140 vector comprising the thiamine pathway genes thiMD and thiCEFSGH, either alone, or in combination with the pBS93 vector encoding the *A. thaliana* TMP phosphatase (AT5G32470.1). These genetically modified strains were cultivated as described in Example 1.2, and the thiamine phosphorylation profile and thiamine content of all resulting cultures was determined by HPLC as described in Example 1.3.

As seen in FIG. 5 (and Table 3), the expression of the *A. thaliana* TMP phosphatase alone converts most of the intra- and extra-cellular TMP to thiamine. Mutation of thiL alone significantly decreases the amount of TPP relative to TMP and thiamine. A combination of these two genetic modifications results in almost all of the cellular thiamine being converted to the dephosphorylated state (90% of total, compare with 14% for wild-type kinase strains). This corresponds to a 6.8 fold increase in the amount of THI produced. Furthermore, the amount of extracellular thiamine is also greatly increased, (7 fold) a very desirable for ease of downstream processing of the product. Finally the overall titer of THI+TMP+TPP is also increased by 24%. In strains expressing the *A. thaliana* TMP phosphatase, the intracellular levels of thiamine compounds are consistently reduced; which in turn may reduce potential feedback inhibition on the thiamine pathway, thereby accounting for the enhanced total thiamine compound production. The thiK– deletion, however, only slightly enhances the production of THI when combined with expression of the *A. thaliana* TMP phosphatase. Accordingly, the dephosphorylation of thiamine catalyzed by the TMP phosphatase appears to outcompete the phosphorylation of thiamine catalyzed by the thiamine kinase (ThiK), such that deletion of ThiK gene has a lesser effect.

TABLE 3

Production of thiamine compounds in genetically modified *E. coli* strains

| E. coli Strain | Genome modification/ vectors | Production of THI + TMP + TPP [μM] | Production of THI [μM] | Production of extracellular THI + TMP + TPP [μM] | Production of extracellular THI [μM] |
|---|---|---|---|---|---|
| BS167 | Wt strain pBS140 pBS92 | 3.97 | 0.57 | 2.46 | 0.51 |
| BS168 | Wt strain pBS140 pBS93 | 4.79 | 3.39 | 3.53 | 3.02 |
| BS233 | thiL* pBS140 pBS92 | 4.02 | 0.78 | 3.22 | 0.71 |
| BS234 | thiL* pBS140 pBS93 | 4.91 | 4.43 | 4.26 | 4.05 |

4.4 Construction of Vectors for Expression of Members of the TMP Phosphatase Protein Family Genes encoding members of clades 1, 2 and 3 of the TMP phosphatase protein family (see FIG. 4) were cloned into expression vectors, for expression in a bacterial cell. Vectors pBS791-798 were constructed by amplifying the empty vector, pBS92 (see Example 1.1) with the primer pair oBS198 and oBS1721 (Tables 2 and 4). The phosphatase genes were each synthesized by Gen9, Inc. along with 3' and 5' regions that overlap with vector pBS92 and were supplied in a cloning vector. Each gene was then amplified with primer pair oBS1720, oBS234 (Table 4) having binding sites flanking the gene in the supplied vector. The purified PCR product comprising the respective phosphatase gene was then assembled with the amplified pBS92 backbone using the NEB Gibson assembly master mix according to the manufacturer's instructions.

Each of the assembled vectors was transformed into electro-competent DH10B cells by electroporation and the recovered cells were plated on selective LB plates. The fully assembled plasmids (Table 5) were then isolated from the resulting strains.

TABLE 4

List of primers

| Primer name | Sequence | SEQ ID No.: |
|---|---|---|
| oBS234 | AGGCCTUTCTGACAACACACGAGTAATAATT | 155 |
| oBS1720 | CGTCACTAATAGCGAGGTAATACTAG | 156 |
| oBS1721 | CTAGTATTACCTCGCTATTAGTGACGATAATAGGAGGTAAGC | 157 |

TABLE 5

| Vector | Inserted gene | Encoded protein/ SEQ ID No. |
|---|---|---|
| pBS791 | *Jatropha curcas* TMP phosphatase KDP23738.1, codon optimized for expression in *E. coli* | 14 |
| pBS792 | *Picea sitchensis* TMP phosphatase ABR16455, codon optimized for expression in *E. coli* | 26 |
| pBS793 | *Eubacterium ventriosum* TMP phosphatase WP_005362972, codon optimized for expression in *E. coli* | 34 |
| pBS794 | *Anaerotruncus colihominis* TMP phosphatase WP_006874980, codon optimized for expression in *E. coli* | 32 |
| pBS797 | *Desulfitobacterium hafniense* TMP phosphatase WP_018212876, codon optimized for expression in *E. coli* | 70 |
| pBS798 | *Syntrophomonas wolfei* TMP phosphatase WP_011640074, codon optimized for expression in *E. coli* | 68 |

4.5 Extracellular Thiamine Production is Enhanced in Genetically Modified *E. coli* Having Reduced Thiamine Kinase Activity (thiL*) Combined with Expression of Members of the TMP Phosphatase Protein Family Representative genes from clade 1, 2 and 3, identified in Example 3 (FIGS. 3, 4, 5) that were predicted to increase the thiamine production of a thiamine cell factory, were expressed in a production strain to demonstrate their ability to enhance extracellular thiamine levels. The mutated ThiL* *E. coli* strain, BS182 was transformed with the pBS140 vector comprising the thiamine pathway genes thiMD and thiCEFSGH or control vector pBS100, either in combination with control vector pBS92, or in combination with the pBS93 vector encoding the *A. thaliana* TMP phosphatase (AT5G32470.1), or with one of the TMP phosphatase encoding vectors described in Table 4.

These genetically modified strains were cultivated as described in Example 1.2. The supernatant of the cultures was collected after 24 hours and the extracellular thiamine levels were measured by LCMS by MS Omics ApS using the following protocol: All samples were filtered through a 0.2 µM filter and the samples were analysed using a slightly modified version of the acidic protocol (positive ionization) described by Paglia et al., (Waters application note). For quality control, a mixed pooled sample (QC sample) was created by taking a small aliquot from each sample. Every four-to-five aliquots of the QC sample were analysed. To minimize matrix effects the samples were dilutes 50 times. For quantification, a mixture of the blank media samples was created and the standards were prepared in this mixture. Quantification was performed using the sum of three ions (122.0716, 265.112 and 144.0473 Da).

The resulting extracellular thiamine titers were normalized to the thiamine titers of the non-producing strain control strain (thiL* pBS100 pBS92) and results are shown in FIG. 7. As shown in FIG. 6, the expression of the *A. thaliana* TMP phosphatase (pBS93) greatly increases the extracellular thiamine titer. As seen in FIG. 7, expression of all of the representative TMP phosphatases from clade 1, 2 and 3 (PBS791, 792, 793, 794, 797 and 798) in the production strain significantly increased the production of extracellular THI, in therefore share the same properties as the *A. thaliana* TMP phosphatase.

REFERENCES

The references cited herein in the specification and Examples are incorporated herein in their entirety by reference.

Baba T, Ara T, Hasegawa M, et al. (2006) Construction of *Escherichia coli* K-12 in-frame, single-gene knockout mutants: the Keio collection. Mol Syst Biol.; 2:2006.0008

Burroughs, A. M. et al., 2006. Evolutionary Genomics of the HAD Superfamily: Understanding the Structural Adaptations and Catalytic Diversity in a Superfamily of Phosphoesterases and Allied Enzymes. J. Mol. Biol., 361, pp. 1003-1034.

Datsenko K A, Wanner B L. (2000) One-step inactivation of chromosomal genes in *Escherichia coli* K-12 using PCR products. Proc Natl Acad Sci USA.; 97(12):6640-5.

Gibson D G, Young L, Chuang R-Y, Venter J C, Hutchison C a, Smith H O., (2009) Enzymatic assembly of DNA molecules up to several hundred kilobases. Nat Methods., 6(5):343-5.

Goyer A, Hasnain G, Frelin O, Ralat M a, Gregory J F, Hanson A D. (2013) A cross-kingdom Nudix enzyme that pre-empts damage in thiamin metabolism. Biochem J. 454(3):533-42.

Guzman, L., Belin, D. & Carson, M. J., 1995. Tight Regulation, Modulation, and High-Level Expression by Vectors Containing the Arabinose P BAD Promoter. Journal of bacteriology, 177(14):4121-4130.

Hasnain G., et al., (2016) Bacterial and plant HAFD enzymes catalyze a missing phosphatase step in thiamine diphosphatase biosynthesis. Biochemical Journal, 473 (2) 157-166

Komeda Y, Tanaka M, Nishimune T. (1988) A th-1 Mutant of *Arabidopsis thaliana* is Defective for a Thiamin-Phosphate-Synthesizing Enzyme: Thiamin Phosphate Pyrophosphorylase. Plant Physiol. 88(2):248-50.

Lennen, R. M. et al., (2015) Transient overexpression of DNA adenine methylase enables efficient and mobile genome engineering with reduced off-target effects. Nucleic acids research, pp. 1-14.

Melnick J, Lis E, Park J-H, et al. (2004) Identification of the two missing bacterial genes involved in thiamine salvage: thiamine pyrophosphokinase and thiamine kinase. J Bacteriol.: 186(11):3660-2

NorranderJ, Tomas Kempe, Joachim Messing, 1983. Construction of improved M13 vectors using oligodeoxynucleotide-directed mutagenesis, Gene, 26(1), pp. 101-106.

Paglia, G., James Langridge, J., Astarita G., Development of a Metabolomic Assay for the Analysis of Polar Metabolites Using HILIC UPLC/QTof MS, Waters Application Note: Library number: APNT134726984 (2013) (at world wide web address: waters.com/waters/library.htm?lid=134726984&locale=en_DK Schyns G, Geng Y, Barbosa T M, Henriques A, Perkins J B. (2005) Isolation and Characterization of New Thiamine-Deregulated Mutants of *Bacillus subtilis*. J Bacteriol.; 187(23):8127-8136.

Webb E, Downs D. (1997) Characterization of thiL, Encoding Thiamin-monophosphate Kinase, in *Salmonella typhimurium*. J Biol Chem.; 272(25):15702-15707

The invention claimed is:

1. A genetically modified bacterium for production of un-phosphorylated thiamine; wherein said bacterium is characterized by having transgenes encoding:
   a) a polypeptide having thiamine mono-phosphate phosphatase activity (E.C. 3.1.3), wherein the amino acid sequence of said polypeptide has at least 80% sequence identity to a sequence selected from the group consisting of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72 and 74;
   b) a polypeptide having 4-amino-5-hydroxymethyl-2-methylpyrimidine phosphate (HMP-P) synthase activity (E.C. 4.1.99.17);
   c) a polypeptide having thiamine phosphate synthase activity (E.C.2.5.1.3);
   d) a polypeptide having ThiS adenylyltransferase activity (E.C.2.7.7.73);
   e) a polypeptide having ThiS sulfur-carrier activity;
   f) a polypeptide having thiazole synthase activity (E.C.2.8.1.10);
   g) a polypeptide having 2-iminoacetate synthase activity (E.C.4.1.99.19) or having glycine oxidase activity (E.C.1.4.3.19); and
   h) a polypeptide having phosphohydroxymethylpyrimidine kinase activity (E.C.2.7.4.7), wherein the genus of the bacterium is *Escherichia*.

2. The genetically modified bacterium according to claim 1, further characterized by a genetically modified endogenous thiL gene capable of expressing reduced thiamine-phosphate kinase activity (E.C.2.7.4.16) as compared to the parent endogenous thiL gene.

3. The genetically modified bacterium according to claim 2, wherein the genetically modified endogenous thiL gene encodes a polypeptide having reduced thiamine-phosphate kinase activity (E.C.2.7.4.16) as compared to the polypeptide encoded by the wild-type parent endogenous thiL gene.

4. The genetically modified bacterium according to claim 2, wherein the amino acid sequence of the polypeptide having thiamine-phosphate kinase activity (E.C. 2.7.4.16) has at least 80% sequence identity to SEQ ID NO: 110 with the proviso that the sequence has amino acid residue substitution G133D.

5. The genetically modified micro-organism according to claim 1, wherein said bacterium is characterized by inactivation or deletion of one or more gene encoding a protein selected from the group: thiamine ABC transporter periplasmic binding protein, thiamine ABC transporter permease, and thiamine ABC transporter ATPase.

6. The genetically modified micro-organism according to claim 1, wherein said bacterium is characterized by an additional transgene encoding a polypeptide having hydroxyethylthiazole kinase activity (E.C.2.7.1.50).

7. The genetically modified bacterium according to claim 6, wherein the amino acid sequence of the polypeptide having hydroxyethylthiazole kinase activity (E.C.2.7.1.50) has at least 80% sequence identity SEQ ID NO:108.

8. The genetically modified bacterium according to claim 1, wherein the amino acid sequence of the polypeptide having thiamine mono-phosphate phosphatase activity (E.C 3.1.3) has at least 80% sequence identity to a sequence selected from the group consisting of SEQ ID NO: 2, 4, 6, 8, 10, 12, 14, 16, 18, 20, 22, 24, 26, 28 and 30.

9. The genetically modified bacterium according to claim 1, wherein the amino acid sequence of:
   a) the polypeptide having 4-amino-5-hydroxymethyl-2-methylpyrimidine phosphate (HMP-P) synthase activity (E.C. 4.1.99.17) has at least 80% sequence identity to a sequence selected from the group SEQ ID NO: 76, 78, 80 and 82;
   b) the polypeptide having thiamine phosphate synthase activity (E.C.2.5.1.3) has at least 80% sequence identity SEQ ID NO:84;
   c) the polypeptide having ThiS adenylyltransferase activity (E.C.2.7.7.73) has at least 80% sequence identity SEQ ID NO: 86;
   d) the polypeptide having ThiS sulfur-carrier activity has at least 80% sequence identity SEQ ID NO88;
   e) the polypeptide having thiazole synthase activity (E.C.2.8.1.10) has at least 80% sequence identity SEQ ID NO:90;
   f) the polypeptide having 2-iminoacetate synthase activity (E.C.4.1.99.19) has at least 80% sequence identity SEQ ID NO:92 and the polypeptide having glycine oxidase activity (E.C.1.4.3.19) has at least 80% sequence identity to a sequence selected from the group SEQ ID NO: 94, 96 and 98; and
   g) the polypeptide having phosphohydroxymethylpyrimidine kinase activity (E.C.2.7.4.7) has at least 80% sequence identity SEQ ID NO:100.

10. The genetically modified bacterium according to claim 1, wherein the amino acid sequence of the polypeptide having thiamine mono-phosphate phosphatase activity (E.C 3.1.3) has at least 80% sequence identity to a sequence selected from the group SEQ ID NO: 2, 14, 26, 32, 34, 40, 68 and 70.

11. A method for producing un-phosphorylated thiamine comprising the steps of:
   a) introducing a genetically modified bacterium according to any one of claims 1-10 into a growth medium to produce a culture;
   b) cultivating the culture; and
   c) recovering thiamine produced by said culture, and optionally purifying the recovered thiamine.

12. A method for producing un-phosphorylated thiamine comprising the steps of:
   a) introducing a genetically modified *Escherichia* bacterium comprising a transgene encoding a polypeptide having thiamine mono-phosphate phosphatase activity (E.C3.1.3) into a growth medium to produce a culture;
   b) cultivating the culture; and
   c) recovering thiamine produced by said culture, and optionally purifying the recovered thiamine.

13. The method of claim 12, wherein the polypeptide having thiamine mono-phosphate phosphatase activity (E.C 3.1.3) has an amino acid sequence at least 80% sequence identity to a sequence selected from among:
   a) the group consisting of SEQ ID NO: 2, 4, 6, 8, 10, 12, 14, 16, 18, 20, 22, 24, 26, 28 and 30;
   b) the group consisting of SEQ ID NO: 32, 34, 36, 38, 40, 42, 44, 46, 48, 50, 52, 54, 56, 58, 60, 62, 64 and 66; and
   c) the group consisting of SEQ ID NO: 68, 70, 72 and 74.

14. The method of claim 13, wherein the *Escherichia* bacterium is a genetically modified bacterium characterized by having transgenes encoding:
   a) a polypeptide having thiamine mono-phosphate phosphatase activity (E.C 3.1.3);
   b) a polypeptide having 4-amino-5-hydroxymethyl-2-methylpyrimidine phosphate (HMP-P) synthase activity (E.C. 4.1.99.17);
   c) a polypeptide having thiamine phosphate synthase activity (E.C.2.5.1.3);
   d) a polypeptide having ThiS adenylyltransferase activity (E.C.2.7.7.73);

e) a polypeptide having ThiS sulfur-carrier activity;
f) polypeptide having thiazole synthase activity (E.C.2.8.1.10);
g) a polypeptide having 2-iminoacetate synthase activity (E.C.4.1.99.19) or having glycine oxidase activity (E.C.1.4.3.19); and
h) a polypeptide having phosphohydroxymethylpyrimidine kinase activity (E.C.2.7.4.7).

15. The method of claim 12, wherein the *Escherichia* bacterium is a genetically modified bacterium characterized by comprising transgenes encoding:
a) a polypeptide having thiamine mono-phosphate phosphatase activity (E.C 3.1.3);
b) a polypeptide having 4-amino-5-hydroxymethyl-2-methylpyrimidine phosphate (HMP-P) synthase activity (E.C. 4.1.99.17);
c) a polypeptide having thiamine phosphate synthase activity (E.C.2.5.1.3);
d) a polypeptide having ThiS adenylyltransferase activity (E.C.2.7.7.73);
e) a polypeptide having ThiS sulfur-carrier activity;
f) a polypeptide having thiazole synthase activity (E.C.2.8.1.10);
g) a polypeptide having 2-iminoacetate synthase activity (E.C.4.1.99.19) or having glycine oxidase activity (E.C. 1.4.3.19); and
h) a polypeptide having phosphohydroxymethylpyrimidine kinase activity (E.C.2.7.4.7).

16. A method for the-production of un-phosphorylated thiamine, comprising culturing a genetically modified bacterium according to claim 1 in a growth media for a sufficient time to produce un-phosphorylated thiamine.

\* \* \* \* \*

UNITED STATES PATENT AND TRADEMARK OFFICE
CERTIFICATE OF CORRECTION

PATENT NO. : 10,696,992 B2
APPLICATION NO. : 16/063373
DATED : June 30, 2020
INVENTOR(S) : Luisa Gronenberg et al.

Page 1 of 1

It is certified that error appears in the above-identified patent and that said Letters Patent is hereby corrected as shown below:

On the Title Page

Item [73], delete:
"Biosynthia"
Insert:
-- Biosyntia --.

Signed and Sealed this
Thirtieth Day of March, 2021

Drew Hirshfeld
*Performing the Functions and Duties of the*
*Under Secretary of Commerce for Intellectual Property and*
*Director of the United States Patent and Trademark Office*